US012440457B2

(12) United States Patent
Mehra et al.

(10) Patent No.: US 12,440,457 B2
(45) Date of Patent: *Oct. 14, 2025

(54) METHODS OF TREATING SUICIDALITY

(71) Applicant: Seelos Therapeutics, Inc., New York, NY (US)

(72) Inventors: Raj Mehra, New York, NY (US); Timothy Whitaker, New York, NY (US)

(73) Assignee: Seelos Therapeutics, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/133,176

(22) Filed: Apr. 11, 2023

(65) Prior Publication Data

US 2023/0241008 A1 Aug. 3, 2023

Related U.S. Application Data

(63) Continuation of application No. 17/792,208, filed as application No. PCT/US2021/014748 on Jan. 22, 2021.

(60) Provisional application No. 63/079,791, filed on Sep. 17, 2020, provisional application No. 62/964,598, filed on Jan. 22, 2020.

(51) Int. Cl.
*A61K 31/135* (2006.01)
*A61K 9/00* (2006.01)
*A61K 45/06* (2006.01)
*A61P 25/24* (2006.01)

(52) U.S. Cl.
CPC .......... *A61K 31/135* (2013.01); *A61K 9/0043* (2013.01); *A61K 45/06* (2013.01); *A61P 25/24* (2018.01); *A61K 2300/00* (2013.01)

(58) Field of Classification Search
CPC ........................................................ A61P 25/24
See application file for complete search history.

(56) References Cited

U.S. PATENT DOCUMENTS 3,760,077 A 9/1973 Thompson et al.
4,017,619 A 4/1977 Burnap
5,352,683 A 10/1994 Mayer et al.
5,384,331 A 1/1995 Kogan et al.
(Continued)

FOREIGN PATENT DOCUMENTS

EP 1103256 5/2001
GB 1330878 9/1973
(Continued)

OTHER PUBLICATIONS

Dadiomov, The effects of ketamine on suicidality across various formulations and study settings, Mental Health Clinician, 2019, 9(1), pp. 48-60 (Year: 2019).*
(Continued)

*Primary Examiner* — Renee Claytor
*Assistant Examiner* — Andrew P Lee
(74) *Attorney, Agent, or Firm* — Fish & Richardson P.C.

(57) ABSTRACT

The present disclosure relates to compositions comprising racemic ketamine, or a pharmaceutically acceptable salt thereof, for use in treating psychiatric disorders such as suicidality, suicidal ideation, major depressive disorder, treatment-resistant depression, and post-traumatic stress disorder.

26 Claims, 54 Drawing Sheets

| Analyte | Parameter (unit) | Racemic Ketamine 30 mg IN, Day 1 | | | | | | | |
|---|---|---|---|---|---|---|---|---|---|
| | | N | Mean | SD | Min | Median | Max | Geometric Mean | Geometric CV% |
| Ketamine | $AUC_{0-t}$ (h*ng/mL) | 12 | 130.66 | 42.73 | 71.83 | 119.16 | 203.62 | 124.65 | 32.71 |
| | $AUC_{0-inf}$ (h*ng/mL) | 12 | 141.5 | 43.57 | 86.31 | 131.74 | 215.22 | 135.75 | 30.5 |
| | $C_{max}$(ng/mL) | 12 | 42.79 | 15.82 | 17.86 | 40.24 | 82.05 | 40.26 | 38.32 |
| | Cl/F(L/h) | 12 | 229.9 | 65.85 | 139.39 | 227.72 | 347.6 | 220.99 | 30.5 |
| | $V_d$/F(L) | 12 | 1346.52 | 362.2 | 619.69 | 1381.46 | 2066.45 | 1296.83 | 30.64 |
| **Analyte** | **Parameter (unit)** | **N** | **Mean** | **SD** | **CV** | | **Min** | **Median** | **Max** |
| Ketamine | $t_{1/2}$(h) | 12 | 4.37 | 1.85 | 42.4 | - | 2.88 | 3.43 | 7.91 |
| | $\lambda_z$(/h) | 12 | 0.1808 | 0.0582 | 32.1747 | - | 0.0876 | 0.2028 | 0.2403 |
| **Analyte** | **Parameter (unit)** | **N** | | **Min** | **Max** | **Median** | **Q1** | **Q3** | |
| Ketamine | $T_{max}$(h) | 12 | - | 0.453 | 1.069 | 0.507 | 0.463 | 0.798 | - |

| Analyte | Parameter (unit) | Racemic Ketamine 75 mg IN, Day 1 | | | | | | | |
|---|---|---|---|---|---|---|---|---|---|
| | | N | Mean | SD | Min | Median | Max | Geometric Mean | Geometric CV% |
| Ketamine | $AUC_{0-t}$ (h*ng/mL) | 12 | 353.64 | 71.97 | 244.27 | 343.48 | 484.06 | 346.89 | 20.82 |
| | $AUC_{0-inf}$ (h*ng/mL) | 12 | 371 | 74.16 | 256.48 | 356.49 | 508.38 | 364.17 | 20.46 |
| | $C_{max}$(ng/mL) | 12 | 89.88 | 24.96 | 42.18 | 95.24 | 133 | 86.31 | 31.8 |
| | Cl/F(L/h) | 12 | 209.88 | 43.04 | 147.53 | 210.44 | 292.43 | 205.95 | 20.46 |
| | $V_d$/F(L) | 12 | 1949.57 | 503.34 | 1276.59 | 1992.01 | 2856.06 | 1890.12 | 26.58 |
| **Analyte** | **Parameter (unit)** | **N** | **Mean** | **SD** | **CV** | | **Min** | **Median** | **Max** |
| Ketamine | $t_{1/2}$(h) | 12 | 6.39 | 0.67 | 10.53 | - | 5.61 | 6.32 | 7.93 |
| | $\lambda_z$(/h) | 12 | 0.1095 | 0.0108 | 9.8883 | - | 0.0874 | 0.1098 | 0.1235 |
| **Analyte** | **Parameter (unit)** | **N** | | **Min** | **Max** | **Median** | **Q1** | **Q3** | |
| Ketamine | $T_{max}$(h) | 12 | - | 0.482 | 1.57 | 0.805 | 0.671 | 0.819 | - |

(56) References Cited

U.S. PATENT DOCUMENTS

| | | | |
|---|---|---|---|
| 5,543,434 | A | 8/1996 | Weg |
| 5,578,567 | A | 11/1996 | Cardinaux |
| 5,604,244 | A | 2/1997 | Desantis, Jr. et al. |
| 5,654,281 | A | 8/1997 | Mayer et al. |
| 5,679,714 | A | 10/1997 | Weg |
| 5,683,709 | A | 11/1997 | Yamada et al. |
| 5,688,830 | A | 11/1997 | Berger et al. |
| 5,817,699 | A | 10/1998 | Flores et al. |
| 5,834,465 | A | 11/1998 | Olnev |
| 5,854,217 | A | 12/1998 | Maccecchini |
| 5,897,858 | A | 4/1999 | Haslwanter et al. |
| 5,919,826 | A | 7/1999 | Caruso |
| 5,989,582 | A | 11/1999 | Weq |
| 6,001,876 | A | 12/1999 | Singh |
| 6,015,797 | A | 1/2000 | Camborde et al. |
| 6,017,961 | A | 1/2000 | Flores et al. |
| 6,028,080 | A | 2/2000 | Ackerman et al. |
| 6,124,282 | A | 9/2000 | Sellers et al. |
| 6,197,830 | B1 | 3/2001 | Frame |
| 6,200,990 | B1 | 3/2001 | Namil et al. |
| 6,248,741 | B1 | 6/2001 | Wheeler et al. |
| 6,248,789 | B1 | 6/2001 | Weg |
| 6,329,429 | B1 | 12/2001 | Schrier et al. |
| 6,441,001 | B1 | 8/2002 | Watson et al. |
| 6,441,047 | B2 | 8/2002 | Desantis |
| 6,509,028 | B2 | 1/2003 | Williams et al. |
| 6,576,636 | B2 | 6/2003 | Webb et al. |
| 6,602,902 | B2 | 8/2003 | Shashoua et al. |
| 6,627,771 | B1 | 9/2003 | Belliotti et al. |
| 6,638,981 | B2 | 10/2003 | Williams et al. |
| 6,642,256 | B2 | 11/2003 | Kornberg et al. |
| 6,649,187 | B2 | 11/2003 | Hussain et al. |
| 6,667,331 | B2 | 12/2003 | Duplantier et al. |
| 6,787,532 | B2 | 9/2004 | Biggadike et al. |
| 6,824,791 | B2 | 11/2004 | Mathiowitz et al. |
| 6,825,203 | B2 | 11/2004 | Pasternak et al. |
| 6,878,751 | B1 | 4/2005 | Donnelly et al. |
| 6,902,734 | B2 | 6/2005 | Giles-Komar et al. |
| 6,989,445 | B2 | 1/2006 | Dantanarayana et al. |
| 7,071,233 | B2 | 7/2006 | Squires |
| 7,273,889 | B2 | 9/2007 | Mermelstein et al. |
| 7,299,949 | B2 | 11/2007 | Greiner-Perth |
| 7,784,460 | B2 | 8/2010 | Djupesland et al. |
| 8,146,589 | B2 | 4/2012 | Djupesland |
| 8,785,500 | B2 | 7/2014 | Charney et al. |
| 8,875,711 | B2 | 11/2014 | Sather et al. |
| 8,985,116 | B2 | 3/2015 | Doshi et al. |
| 9,244,712 | B2 | 1/2016 | Cola-Robles et al. |
| 9,555,950 | B2 | 1/2017 | La Maner et al. |
| 9,592,207 | B2 | 3/2017 | Charney et al. |
| 10,099,019 | B2 | 10/2018 | Shahal et al. |
| 10,179,216 | B2 | 1/2019 | Djupesland et al. |
| 10,525,218 | B2 | 1/2020 | Djupesland et al. |
| 10,549,052 | B2 | 2/2020 | Shahaf et al. |
| 2002/0004484 | A1 | 1/2002 | Pasternak et al. |
| 2002/0094974 | A1 | 7/2002 | Castelhano et al. |
| 2002/0119912 | A1 | 8/2002 | Fogel |
| 2002/0192288 | A1 | 12/2002 | Williams et al. |
| 2002/0198209 | A1 | 12/2002 | Woodward et al. |
| 2004/0039352 | A1 | 2/2004 | Bergeson et al. |
| 2004/0106681 | A1 | 6/2004 | Rao et al. |
| 2004/0122090 | A1 | 6/2004 | Lipton |
| 2004/0138298 | A1 | 7/2004 | Mermelstein et al. |
| 2004/0266808 | A1 | 12/2004 | Kamen et al. |
| 2005/0148673 | A1 | 7/2005 | Harbut et al. |
| 2005/0209218 | A1 | 9/2005 | Meyerson et al. |
| 2005/0222270 | A1 | 10/2005 | Olney et al. |
| 2007/0287753 | A1 | 12/2007 | Charney et al. |
| 2008/0268071 | A1 | 10/2008 | Gant et al. |
| 2009/0054923 | A1 | 2/2009 | Benson |
| 2011/0038807 | A1 | 2/2011 | Papolos |
| 2012/0000459 | A1 | 1/2012 | Djupesland |
| 2012/0017902 | A1 | 1/2012 | Berger et al. |
| 2013/0143843 | A1 | 6/2013 | Turdi et al. |
| 2013/0245560 | A1 | 9/2013 | Guillen Garcia et al. |
| 2014/0018295 | A1 | 1/2014 | Djupesland |
| 2014/0256821 | A1 | 9/2014 | Charney et al. |
| 2015/0190268 | A1 | 7/2015 | Creps |
| 2016/0074340 | A1 | 3/2016 | Caers et al. |
| 2017/0020383 | A1 | 1/2017 | Papania et al. |
| 2017/0151397 | A1 | 6/2017 | Djupesland |
| 2017/0216540 | A1 | 8/2017 | Djupesland |
| 2018/0235906 | A1 | 8/2018 | Weg |
| 2018/0256836 | A1 | 9/2018 | Hoekman et al. |
| 2018/0256867 | A1 | 9/2018 | Levin |
| 2018/0272085 | A1 | 9/2018 | Djupesland et al. |
| 2018/0361085 | A1 | 12/2018 | Malhotra et al. |
| 2019/0054016 | A1 | 2/2019 | Djupesland |
| 2019/0070372 | A1 | 3/2019 | Farina et al. |
| 2019/0083722 | A1 | 3/2019 | Djupesland et al. |
| 2019/0117916 | A1 | 4/2019 | Armistead et al. |
| 2019/0117918 | A1 | 4/2019 | Djupesland et al. |
| 2019/0143054 | A1 | 5/2019 | Levin |
| 2019/0269867 | A1 | 9/2019 | Djupesland |
| 2019/0290863 | A1 | 9/2019 | Djupesland et al. |
| 2019/0290864 | A1 | 9/2019 | Djupesland et al. |
| 2019/0314588 | A1 | 10/2019 | Beck |
| 2019/0350879 | A1 | 11/2019 | Gary |
| 2019/0358078 | A1 | 11/2019 | Akihiro |
| 2019/0358417 | A1 | 11/2019 | Brouet et al. |
| 2020/0023146 | A1 | 1/2020 | Djupesland et al. |
| 2020/0054843 | A1 | 2/2020 | Levin |
| 2020/0060972 | A1 | 2/2020 | Malcolm et al. |
| 2020/0206012 | A1 | 7/2020 | Akihiro |
| 2020/0206441 | A1 | 7/2020 | Papania et al. |
| 2020/0206547 | A1 | 7/2020 | Hellman et al. |
| 2022/0054435 | A1 | 2/2022 | Mermelstein et al. |
| 2022/0160655 | A1 | 5/2022 | Weg |
| 2023/0064327 | A1 | 3/2023 | Mehra et al. |
| 2024/0261236 | A1 | 8/2024 | Mehra et al. |
| 2024/0261237 | A1 | 8/2024 | Mehra et al. |

FOREIGN PATENT DOCUMENTS

| | | |
|---|---|---|
| JP | H10500664 | 1/1998 |
| JP | 2002539245 | 11/2002 |
| JP | 2009530385 | 8/2009 |
| JP | 2010500664 | 1/2010 |
| JP | 2010525081 | 7/2010 |
| JP | 2010534674 | 11/2010 |
| WO | WO 1995022965 | 8/1995 |
| WO | WO 1997007750 | 3/1997 |
| WO | WO 1998051282 | 11/1998 |
| WO | WO 2000024396 | 5/2000 |
| WO | WO 2000056301 | 9/2000 |
| WO | WO 2004028522 | 4/2004 |
| WO | WO 2007111880 | 10/2007 |
| WO | WO 2008134525 | 11/2008 |
| WO | WO 2009015236 | 1/2009 |
| WO | WO 2011020061 | 2/2011 |
| WO | WO 2014031975 | 2/2014 |
| WO | WO 2014169272 | 10/2014 |
| WO | WO 2016109427 | 7/2016 |
| WO | WO 2016172672 | 10/2016 |
| WO | WO 2020178653 | 9/2020 |
| WO | WO 2021026232 | 2/2021 |
| WO | WO 2021150985 | 7/2021 |
| WO | WO 2022241214 | 11/2022 |
| WO | WO 2022241315 | 11/2022 |

OTHER PUBLICATIONS

[No Author Listed] "Benzalkonium Chloride: Summary Report," Committee for Veterinary Medicinal Products, EMEA, Dec. 1997, 3 pages.

Ahuja, "Analgesic Effect of Intrathecal Ketamine in Rats," Br J Anaesth, 1983, 55:991-995.

Al-Harbi, "Treatment-resistant depression: therapeutic trends, challenges, and future directions," Patient Prefer. Adherence, 2012, 6:369-388.

Allergan, "ACULAR LS (ketorolac tromethamine ophthalmic solution) 0.4%," NDA 21-528, May 2003, 5 pages.

(56) References Cited

OTHER PUBLICATIONS

Atkinson et al., "Inhibition of platelet aggregation by ketamine hydrochloride," Thrombosis Res., Oct. 15, 1985, 40:227-234.
Ball et al., "Venlafaxine: in vitro inhibition of CYP2D6 dependent imipramine and desipramine metabolism; comparative studies with selected SSRIs, and effects on human hepatic CYP3A4r, CYP2C9 and CYP1A2," Br J Clin Pharmacol, 1997, 43:619-626.
Battacharya et al., "Subcutaneous infusion of ketamine and morphine for relief of postoperative pain: a double-blind comparative study", Ann. Acad. Med. Singapore 1994, 23:456-9.
Baudouin et al., "Short term comparative study of topical 2% carteolol with and without benzalkonium chloride in healthy volunteers," Br J Ophthalmol, 1998, 82(1):39-42.
Beck et al., "The Impact of Event Scale-Revised: Psychometric properties in a sample of motor vehicle accident survivors," Journal of Anxiety Disorders, vol. 22, p. 187-198, 2008.
Berman et al., "Antidepressant effects of ketamine in depressed patients," Soc. Of Biol., Psych, 2000, 47:4:351-354.
Blake et al., "The Development of a Clinician-Administered PTSD Scale," Journal of Traumatic Stress, 1995, 8(1):75-90.
Bookwalter, "Pain management with ketamine: a case study," Plastic Surgical Nursing, 1994, 14:43-44.
Bowdle et al., "Psychedelic effects of ketamine in healthy volunteers," Anesthesiology, 1998, 88:82-88.
Brock-Utne et al., "Intrathecal ketamine with preservative-histological effects on spinal nerve roots of baboons," S Afr Med J, 1982, 61(12):440-441.
Burcusa et al., "Risk for Recurrence in Depression," Clin. Psychol. Rev., Dec. 2007, 27(8):959-985.
Burstein, "Preservative cytotoxic threshold for benzalkonium chloride and chlorhexidine digluconate in cat and rabbit corneas," Invest Ophthalmol Vis Sci, 1980, 19(3):308-313.
Caraceni et al., "An international survey of cancer pain characteristics and syndromes," Pain, 1999, 82:263-274.
Carr et al., "Safety and efficacy of intranasal ketamine for the treatment of breakthrough pain in patients with chronic pain: a randomized, double-blind, placebo-controlled, crossover study," Pain, 2004, 108(1): 17-27.
Chen et al., "Mechanisms of ketamine-involved regulation of cytochrome P450 gene expression," Expert Opin Drug Metab Toxicol., Mar. 2010, 6(3):273-81.
Clark et al., "Effective treatment of severe cancer pain of the head using low-dose ketamine in an opioid-tolerant patient," J Pain Symptom Manage, 1995, 10(4):310-314.
Clements et al. "Bioavailability, pharmacokinetics, and analgesic activity of ketamine in humans," J Pharm Sci., May 1982, 71(5):539-542.
clinicaltrials.gov, View of NCT00749203 on Mar. 26, 2012, URL <https://clinicaltrials.gov/ct2/show/NCT00749203?term-NCT00749203&draw=2&ra nk=1>, 4 pages.
Clinton et al., "Effects of phenytoin, ketamine, and atropine methyl nitrate in preventing neuromuscular toxicity of acetylcholinesterase inhibitors soman and diisopropylphosphorofluoridate," J Toxicol Environ Health, 1998, 24(4):439-449.
Coates et al., "Ketamine and its preservative, benzethonium chloride, both inhibit human recombinant a7 and a4132 neuronal nicotinic acetylcholine receptors in Xenopus oocytes," Br J Pharmacol, 2001, 134(4):871-879.
Collingridge et al., "The NMDA Receptor," Oxford University Press, 1994, 2 pages.
Cooper et al., "Strategies to mitigate dissociative and psychotomimetic effects of ketamine in the treatment of major depressive episodes: a narrative review," The world Journal of Biological Psychiatry, Aug. 31, 2017, 18(6):410-423.
creative-developments.co.com [online], "Creative Cosmetic Developments (Cosmetics) Limited: Surfactants 1999," 1999, retrieved from URL <www.creative-developments.co.uk>, 4 pages.
Dadiomov et al., "The effects of ketamine on suicidality across various formulations and study settings," MHC, 2019, 9:1:48-60.
Dalgarno et al., "Illicit use of ketamine in Scotland," J Psycho Drugs, Apr.-Jun. 1996, 28(2):191-199.
Darbin et al., "Effects of seizure severity and seizure repetition on postictal cardiac arrhythmia following maximal electroshock," Exp Neurol, 2003, 181(2): 327-331.
De Conno et al., "Pain measurement in cancer patients: a comparison if six methods," Pain, 1994, 57(2):161-166.
Dich-Nielsen et al., "Intramuscular low-dose ketamine versus pethidine for postoperative pain treatment after thoracic surgery," Acta Anaesthesiol Scand, 1992, 36(6):583-587.
Durieux et al., "Synergistic inhibition of muscarinic signaling by ketamine stereoisomers and the preservative benzethonium chloride," Anesthesiology, 1997, 86(6):1326-1333.
Ebert et al., "Norketamine, the main metabolite of ketamine, is a non-competitive NMDA receptor antagonist in the rat cortex and spinal cord.," Eur J Pharmacol., Aug. 20, 1997, 333(1):99-104.
Eide et al., "Relief of post-herpetic neuralgia with the N-methyl-D-aspartic acid receptor antagonist ketamine: a double-blind, cross-over comparison with morphine and placebo," Pain, 1994, 58(3):347-354.
Enarson et al., "Clinical experience with oral ketamine," J Pain Symptom Manage, May 1999, 17(5):384-386.
Errando et al., "Subarachnoid ketamine in swine-pathological findings after repeated doses: Acute toxicity study," Rea Anesth Pain Med, 1999, 24(2):146-52.
Extended European Search Report in European Appln. No. 21156344.0, dated Jul. 26, 2021, 12 pages.
Farooq et al., "Tackling nonadherence in psychiatric disorders: current opinion," Neuropsychiatr Dis Treat., Jun. 12, 2014, 10:1069-77.
Fava et al., "Double blind, placebo-controlled, dose-ranging trial of intravenous ketamine as adjunctive therapy in treatment resistant depression (TRD)," Mol. Psych, Apr. 14, 2019, 25:7:1592-1603.
Feder, et al., "Efficacy of intravenous ketamine for treatment of chronic posttraumatic stress disorder: a randomized clinical trial," JAMA Psychiatry, Jun. 2014, 71(6):681-688.
Fine, "Low-dose ketamine in the management of opioid nonresponsive terminal cancer pain," J Pain Symptom Manage, 1999, 17(4):296-300.
Fitzgibbon et al., "Low dose ketamine as an analgesic adjuvant in difficult pain syndromes: a strategy for conversion from parenteral to oral ketamine," J Pain Symptom Manage., Feb. 2002, 23:165-170.
Fix et al., "Neuronal Vacuolization and Necrosis Induced by the Noncompetitive N-methyl-d-aspartate (NMDA) Antagonist MK(+)801 (Dizocilpine Maleate): A Light and Electron Microscopic Evaluation of the Rat Retrosplenial Cortex," Experimental Neurology, 1993, 123: 204-215.
Fix et al., "Integrated evaluation of central nervous system lesions: stains for neurons, astrocytes, and microglia reveal the spatial and temporal features of MK-801-induced neuronal necrosis in the rat cerebral cortex," Toxicol Pathol, 1996, 24(3):291-304.
Fogelman et al., "O- and N-demethylation of venlafaxine in vitro by human liver microsomes and by microsomes from cDNA-transfected cells: effect of metabolic inhibitors and SSRI antidepressants," Neuropsychopharmacology, 1999, 20(5):480-90.
Foster et al., "Taking apart NMDA receptors," Nature, 1897, 329(6138):395-396.
Garman, "Artifacts in routinely immersion fixed nervous tissue," Toxicol. Pathol., 1990, 18:149-153.
Gebhardt, "Pharmacology and clinical results with peridural and intrathecal administration of ketamine," Anaesthesist, 1994, 43 Suppl 2:S34-40 (German).
Ghasemi et al., "Measurement Scales of Suicidal Ideation and Attitudes: A Systematic Review Article," Health Promot. Perspect., Oct. 25, 2015, 5(3):156-168.
Ghoneim et al., "Ketamine: behavioral effects of subanesthetic doses," J Clin Psychopharmacol, Apr. 1985, 5(2):70-77.
Grant et al. "Pharmacokinetics and analgesic effects of I.M. and oral ketamine," Br J Anaesth., Aug. 1981, 53(8):805-810.
Guha Thakurta et al., "Rapid response with Ketamine on suicidal cognition in resistant depression," Indian J Psychol Med., Apr. 2012, 34(2):170-175.

(56) References Cited

OTHER PUBLICATIONS

Gurnani et al., "Analgesia for acute musculoskeletal trauma: low-dose subcutaneous infusion of ketamine," Anaesth Intensive Care, 24(1):32-36 (1996).
Haddad, "Newer antidepressants and the discontinuation syndrome," J Clin Psychiatry, 1997, 58(suppl 7):17-22.
Hartvig et al., "Central nervous system effects of subdissociative doses of (S)-ketamine are related to plasma and brain concentrations measured with positron emission tomography in healthy volunteers," Clin Pharmacol Ther., Aug. 1995, 58(2):165-173.
health.harvard.edu [online], "Ketamine for major depression: New tool, new questions," May 22, 2019, retrieved on Mar. 30, 2023, retrieved from URL <https://www.health.harvard.edu/blog/ketamine-for-major-depression-new-tool-new-questions-2019052216673>, 7 pages.
Heresco-Levy et al., "Pilot controlled trial of D-serine for the treatment of post-traumatic stress disorder," Int J Neuropsychopharmacol, 2009, 12(9): 1275-1282.
Hidinger et al., "Intravenous analgesia with ketamine for emergency patients," Anaesthsist 1987, 140-142.
Hindmarch et al., "Pharmacodynamics of milnacipran in young and elderly volunteers," Br. J. Clin. Pharmcol., 2000, 49:2:118-125.
Hirota et al., "Ketamine: it's mechanism of action and unusual clinical uses (editorial)," Br J Anesth., Oct. 1996, 77:441-444.
Hool, "Anaesthesia in pregnancy for non-obstetric surgery," Anesthesia Tutorial of the Week, Jun. 28, 2010, ATOTW 185, 9 pages.
https://www.who.int, [online] "World Health Organization," Dec. 1998, retrieved Apr. 28, 2023, retrieved from URL <https://www.who.int/>, 14 pages.
Hummel et al., "Exploratory assessment of dose proportionality: review of current approaches and proposal for a practical criterion," Pharmaceut. Statist., Apr. 3, 2008, 8: 38-49.
Humphries et al., "Superiority of oral ketamine as an analgesic and sedative for wound care procedures in the pediatric patient with burns," J Burn Care Rehabil, 1997, 18(1 Pt 1):34-36.
International Preliminary Report on Patentability in International Appln. No. PCT/US2021/014748, mailed Aug. 4, 2022, 7 pages.
International Search Report and Written Opinion in Appln. No. PCT/US2021/014748, dated May 20, 2021, 9 pages.
International Search Report and Written Opinion in Appln. No. PCT/US2022/029192, mailed Aug. 31, 2022, 17 pages.
International Search Report and Written Opinion in Appln. No. PCT/US2022/029453, mailed Sep. 23, 2022, 21 pages.
International Search Report and Written Opinion in International Appln. No. PCT/US03/31073, dated Mar. 3, 2004, 4 pages.
International Search Report and Written Opinion in International Appln. No. PCT/US2013/056424, dated Jan. 10, 2014, 18 pages.
Invitation to Pay Additional Fees in Appln. No. PCT/US2022/029453, mailed Aug. 2, 2022, 16 pages.
Irwin et al., "Oral ketamine for the rapid treatment of depression and anxiety in patients receiving hospice care," J Palliat Med, 13(7):903-908 (2010).
Jahromi et al., "Comparison of the effects of intranasal midazolam versus different doses of intranasal ketamine on reducing preoperative pediatric anxiety: a prospective randomized clinical trial," J Anesth, 2012, 26(6): 878-882.
Jansen, "A review of the nonmedical use of ketamine: use, users and consequences," J Psycho Drug, Oct.-Dec. 2000, 32:419-433.
Japanese Office Action in Appln. No. 2015-528691 dated Mar. 25, 2019, 15 pages, English translation.
Japanese Office Action in Appln. No. 2015-528691 dated Aug. 19, 2019, 10 pages, English translation.
Japanese Office Action in Appln. No. 2018-124196, May 7, 2019, 9 pages, English translation.
Jevtovic-Todorovic et al., "A comparative evaluation of the neurotoxic properties of ketamine and nitrous oxide," Brain Res, Jan. 2001, 895(1-2):264-267.
Kapur et al., "Oral ketamine: a promising treatment for restless leg syndrome," Anesth Analg., Jun. 2002, 94:1558-1559.
Karpinski et al., "Subpial vacuolar myelopathy after intrathecal ketamine: report of a case," Pain, 1997, 73(1):103-105.
Kaube et al., "Aura in some patients with familial hemiplegic migraine can be stopped by intranasal ketamine," Neurology, Jul. 12, 2000, 55(1):139-141.
Kennedy, "Core symptoms of major depressive disorder: relevance to diagnosis and treatment," Dialogues Clin. Neurosci., 2008, 10:3: 271-277.
Khorramzadeh et al., "The use of ketamine in psychiatry," Psychosomatics, 1973, 14(6): 344-346.
Kim et al., "Enhancing a sedation score to include truly noxious stimulation: the Extended Observer's Assessment of Alertness and Sedation (EOAA/S)," Br J Anaesth, Oct. 2015, 115(4):569-577.
Klonsky et al., "Suicide, Suicide Attempts, and Suicidal Ideation," Annu. Rev. Clin. Psychol., Jan. 11, 2016, 12:307-330.
Knox et al., "Acute phantom limb pain controlled by ketamine.," Anaesth Intensive Care, 1995, 23(5):620-622.
Kryshtalskyj et al., "Use of low-dose ketamine hydrochloride in outpatient oral surgery," Oral Surg Oral Med Oral Pathol, 1990, 69(4):413-419.
Krystal, et al., "Subanesthetic effects of the noncompetitive NMDA antagonist, ketamine, in humans," Arch. Gen. Psychiatry, 1994, 51:199-214.
Kuboyama et al., "Nasal lesions induced by intranasal administration of benzalkonium chloride in rats," J Toxicol Sci, 1997, 22:153-160.
Kudoh et al., "Small-Dose Ketamine Improves the Postoperative State of Depressed Patients," Anesth Analg, Jul. 2002, 95(1): 114-118.
Kupfer, "The pharmacological management of depression," Dialogues Clin. Neurosci., 2005, 7(3):191-205.
Lahti et al., "Effects of Ketamine in Normal and Schizophrenic Volunteers," Neuropsychopharmacol, 2001, 25(4): 455-467.
Lapidus et al., "Randomized Controlled Trial of Intranasal Ketamine in Major Depressive Disorder," Biological Psychiatry, Dec. 1, 2004, 76(12):970-976.
Lauretti et al., "Oral ketamine and transdermal nitroglycerin as analgesic adjuvants to oral morphine therapy for cancer pain management," Anesthesiology, 1999, 90:1528-1533.
Lee et al., "Duration of occupancy of opiate receptors by naltrexone," J Nuc Med., Jul. 1998, 29(7):1207-1211.
Leung et al., "Comparative pharmacology in the rat of ketamine and its two principal metabolites, norketamine and (Z)-6-hydroxynorketamine," J. Med. Chem., Nov. 1986, 29(11):2396-2399.
Li et al., "Ketamine: 50 Years of Modulating the Mind," Front. Hum. Neurosci., Nov. 29, 2016, 10:1-15.
Li et al., "The CYP2B6*6 allele significantly alters the N-demethylation of ketamine enantiomers in vitro," Drug Metab Dispos., Jun. 2013, 41(6):1264-72.
Lin et al. "Association of hearing impairment with brain vol. changes in older adults," Neuroimage, Apr. 15, 2014, 90:84-92.
Lin, et al., "Test Review: The Profile of Mood States 2nd Edition," JPA, 2014, 32:3: 273-277.
Loo et al., "Sedation for the conduct of lumbar epidural anaesthesia: A study using subanaesthetic dose of ketamine in combination with midazolam," Ann Acad Med Singap, 1997, 26(2):200-204.
Luckenbaugh et al., "Do the dissociative side effects of ketamine mediate its antidepressant effects?" J. Affect. Disord., Apr. 2014, 159:56-61.
Lundy et al., "Differential effects of ketamine isomers on neuronal and extraneuronal catecholamine uptake mechanisms," Anesthesiology, Mar. 1986, 64(3):359-363.
Malhotra et al., "NMDA receptor function and human cognition: the effects of ketamine in healthy volunteers," Neuropsychopharmacology, May 1996, 14:301-307.
Malinovsky et al., "Is ketamine or its preservative responsible for neurotoxicity in the rabbit?" Anesthesiology, 1993, 78:109-115.
Malinovsky et al., "Ketamine and midazolam neurotoxicity in the rabbit," Anesthesiology, 1991, 75(1):91-97.
Martin, "Juvenile Bipolar Disorder: Intranasal Ketamine Effective, Well-Tolerated," Psychiatry Advisor, Sep. 21, 2017, 4 pages.

(56) References Cited

OTHER PUBLICATIONS

Masaaki et al., "Cytotoxicity of surfactants to the FHM-sp cell line," Fisheries Science, Oct. 22, 2002, 68:1124-1128.
Mathers et al., "Projections of global mortality and burden of disease from 2002 to 2030," PLoS Med., Nov. 2006, 3(11):e442, 20 pages.
Mathisen et al., "Effect of ketamine, an NMDA receptor inhibitor, in acute and chronic orofacial pain," Pain, 1995, 61(2):215-220.
Mayer et al., "Excitatory amino acid receptors, second messengers and regulation of intracellular Ca2+ in mammalian neurons," Trends Pharmacol Sci, 1990, 11(6):254-260.
McGhee et al., "The correlation between ketamine and post-traumatic stress disorder in burned service members," J Trauma, 64(2 Supp): S195-199; Discussion S, 2008, 197-8.
medd.upenn.edu [online], "Columbia-Suicide Severity Rating Scale (C-SSRS)," Nov. 21, 2011, retrieved from URL <www.med.upenn.edu/cbti/assets/user-content/documents/Columbia-Suicide%20Severity%20Rating%20Scales%20(C-SSRS).pdf>, 5 pages.
Meltzer et al., "Clozapine treatment for suicidality in schizophrenia," Arch Gen Psychiatry, 2003, 60(1):82-91.
Mercadante et al., "Long-term ketamine subcutaneous continuous infusion in neuropathic cancer pain," J Pain Symptom Manage, 1995, 10(7):564-568.
Mikkelsen et al., "Effect of oral ketamine on secondary hyperalgesia, thermal and mechanical pain thresholds, and sedation in humans," Reg Anesth Pain Med., Sep.-Oct. 2000, 25(5):452-458.
Moaddel et al., "Sub-anesthetic concentrations of (R,S)-ketamine metabolites inhibit acetylcholine-evoked currents in $\alpha$7 nicotinic acetylcholine receptors," Eur. J. Pharmacol., Jan. 5, 2013, 698(1-3):228-234.
Mohebbi et al., "Patient centric measures for a patient centric era: Agreement and convergent between ratings on The Patient Global Impression of Improvement (PGI-I) scale and the Clinical Global Impressions—Improvement (CGI-S) scale in bipolar and major depressive disorder," Eur Psychiatry, Sep. 2018, 53:17-22.
Moore et al., "Urine concentrations of ketamine and norketamine following illegal consumption," J Anal Toxicol, Oct. 2001, 25(7):583-588.
Murrough et al., "Rapid and longer-term antidepressant effects of repeated ketamine infusions in treatment-resistant major depression," Biol Psychiatry, Aug. 15, 2013, 74(4):250-256.
Musazzi, et al., "What acute stress protocols can tell us about PTSD and stress-related neuropsychiatric disorders," Frontiers in Pharmacology, Jul. 2018, 9:758, 13 pages.
Naguib et al., "Epidural ketamine for postoperative analgesia," Can Anaesth Soc J, 1986, 33(1):16-21.
Obach et al., "Sertraline is metabolized by multiple cytrochrome P450 enzymes, monoamine oxidases, and glucuronyl transferases in human: an in vitro study," Drug Met and Disp., Feb. 2005, 33(2):262-270.
Oda et al. "Patient anxiety scores after low-dose ketamine or fentanyl for epidural catheter placement." Canadian journal of anaesthesia 47.9 (2000): 910-913.
Olney et al., "NMDA Antagonist Neurotoxicity: Mechanism and Prevention," Science, 1991, 254(5037):1515-1518.
Olney et al., "Pathological changes induced in cerebrocortical neurons by phencyclidine and related drugs," Science, 1989, 244(4910):1360-1362.
Papolos et al., "Clinical experience using intranasal ketamine in the longitudinal treatment of juvenile bipolar disorder with fear of harm phenotype," Journal of Affective Disorders, Aug. 30, 2017, 225:545-551.
Papolos et al., "Clinical experience using intranasal ketamine in the treatment of pediatric bipolar disorder/fear of harm phenotype," Journal of Affective Disorders, May 1, 2013, 147(1-3):431-436.
Perumal, et al., "Midazolam premedication for Ketamine-induced emergence phenomenon: A prospective observational study," J. Res. Pharm. Pract., Apr.-Jun. 2015, 4(2):89-93.
Pfizer Canada ULC, "Product Monograph—Zoloft (sertraline hydrochloride)," Submission Control No. 231452, Nov. 25, 2019, 57 pages.
Pham, et al., "Common Neurotransmission Recruited in (R,S)-Ketamine and (2R,6R)-Hydroxynorketamine-Induced Sustained Antidepressant-like Effects," Biol. Psychiatry, 2018, 84:1:e3-e6.
Physicians' Desk Reference, 1986 Edition, Product Information, Cover page and pp. 1356-1358 Product Information Brochure, "Acular LS," 2003.
Pomarol-Clotet et al., "Psychological effects of ketamine in healthy volunteers. Phenomenological study," Br J Psychiatry, Aug. 2006, 189:173-179.
Posner et al., "Columbia-Suicide Severity Rating Scale C-SSRS) Since last Visit," The Research Foundation for Mental Hygiene, Inc., Jan. 14, 2009, 3 pages.
Posner et al., "Columbia-Suicide Severity Rating Scale (C-SSRS) Baseline," The Research Foundation for Mental Hygiene, Inc., Jan. 1, 2009, 3 pages.
Rapaport et al., "Quality-of-Life Impairment in Depressive and Anxiety Disorders," Am. J. Psychiatry, Jun. 2005, 162(6):1171-1178.
Reich et al., "Ketamine: an update on the first twenty-five years of clinical experience," Can J Anaesth., Mar. 1989, 36(2):186-197.
Reinstatler, "Ketamine as a potential treatment for suicidal ideation: a systematic review of the literature," Drugs in R&D, Feb. 10, 2015, 15(1):37-43.
Roelofse et al., "A double blind randomized comparison of oral trimeprazine-methadone and ketamine-midazolam for sedation of pediatric dental patients for oral surgical procedures," Anesth Prag, 1998, 45(1):3-11.
Rostamnejadi et al., "A study on oral ketamine premedication effect on anxiety of parental separation in 2-7 y/o children for elective surgery," Arak Medical University Journal, 2002, 5:3(20).
Sackheim, "The definition and meaning of treatment-resistant depression," J. Clin. Psychiatry, 2001, 62:16:10-17.
Saegusa et al., "Pharmacologic analysis of ketamine-induced cardiac actions in isolated, blood perfused canine atriam," J Cardiovasc Pharmacology, Mar. 1986, 8(2):414-419.
Sancora et al., "Ketamine: Promising path or false prophecy in the development of novel therapeutics for mood disorders?" Neuropsychopharmacology, 2015, 40:259-267.
Schatzberg, "A word to the wise about ketamine," Am. J. Psych., Mar. 2014, 171:3.
Schmid et al., "Use and efficacy of low-dose ketamine in the management of acute postoperative pain: a review of current techniques and outcomes," Pain, 1999, 82(2):111-125.
Schmued, "Fluoro-Jade B: a high affinity fluorescent marker for the localization of neuronal degeneration," Brain Research, 2000, 874:123-130.
Schmued, "Fluoro-Jade: Novel Fluorochromes for Detecting Toxicant-Induced Neuronal Degeneration," Toxicologic Pathology, 2000, 28:91-99.
Semahegn et al., "Psychotropic medication non-adherence and associated factors among adult patients with major psychiatric disorders: a protocol for a systematic review," System. Rev., Jan. 22, 2018, 7(10), 5 pages.
Shahar et al., "Morphological alterations in cultured neuromuscular tissue induced by two anesthetic agents," Neurochem Res, Jul. 6, 1989, 14(10):1017-1024.
Sheehan et al., "Is There Value in Asking the Question "Do you think you would be better off dead?" in Assessing Suicidality? A Case Study," Innov. Clin. Neurosci., Sep. 2014, 11(9-10):182-190.
Sheehan et al., "Status Update on the Sheehan-Suicidality Tracking Scale (S-STS) 2014," Innov. Clin. Neurosci., 2014, 11:(9-10)93-140.
Sheehan et al., "Suicidality Assessment and Documentation for Healthcare Providers: A Brief, Practical Guide," Harm Research Press. Apr. 2016, 9 pages.
Sheehan et al., "Suicidality: A Roadmap for Assessment and Treatment," Harm Research Press, Nov. 2015, 10 pages.
Sheehan et al., "The Mini-International Neuropsychiatric Interview (M.I.N.I.): the development and validation of a structured diagnos-

(56) References Cited

OTHER PUBLICATIONS tic psychiatric interview for DSM-IV and ICD-10," J. Clin Psychiatry, 1998, 59(suppl 20): 22-33.
Shibuya et al., "Unilateral Atrophy of the Optic Nerve Associated with Retrograde and Anterograde Degenerations in the Visual Pathways in Sic: Wistar Rats", J Vet Med Sci. 55:905-912, 1993.
Shioiri, "About the pathology of anxiety disorders: Stress-induced fear circuitry disorders," Psychiatria et neurologia Japonica, 2010, 112(8):797-805, English translation.
Smith, "Inappropriate Prescribing," Amer. Psychol. Assoc., Jun. 2012, 4(6):36.
Stein et al., "Posttraumatic stress disorder in the primary care medical setting," Gen. Hosp. Psychiatry, Jul.-Aug. 2000, 22(4):261-269.
Sternberg, "High-speed scanning in human memory," Science, Aug. 5, 1996,153(3736):652-654.
Stone et al., "Relationship between ketamine-induced psychotic symptoms and NMDA receptor occupancy-a [123] CNS-1262 SPET study," Psychopharmacology, Jan. 5, 2008, 197:401-408.
Supplementary European Search Report, dated Feb. 19, 2016, issued in European Application No. EP 13831683, 10 pages.
Switzer, "Application of Silver Degeneration Stains for Neurotoxicity Testing," Toxicol. Pathol., 28: 70-83, 2000.
Switzer, "Silver Staining Methods: Their Role in Detecting Neurotoxicity," New York Acad. Sci., 1993, 679: 341-348.
Takamiya et al., "Posttraumatic stress symptoms in mothers and fathers of childhood cancer survivors," J Fam Psychol., 2004, 18:493-504 (English abstract).
Thase, "Effects of venlafaxine on blood pressure: a meta-analysis of original data from 3744 depressed patients," J Clin Psychiatry, 1998, 59(10):502-8.
Torrice, "Ketamine is revolutionizing antidepressant research, but we still don't know how it works," Neuroscience, Jan. 15, 2020, 89(3), 8 pages.
U.S. Department of Health and Human Services, "Guidance for Industry: Drug Interaction Studies—Study Design, Data Analysis, Implications for Dosing, and Labeling Recommendations (Draft Guidance)," Docket No. FDA-2006-D-0036, Feb. 2012, 79 pages.
Upjohn Canada ULC, "Product Monograph—Effexor XR (Venlafaxine Hydrochloride Extended Release Capsules)," Submission Control No. 237819, May 13, 2020, 76 pages.
Van Laere et al., "Equivalent dynamic human brain NK1-receptor occupancy following single-dose i.v. fosaprepitant vs. oral aprepitant as assessed by PET imaging," Clin Pharmacol Ther., Aug. 2012, 92(2):243-250.
Vick, "Treatment of central post-stroke pain with oral ketamine," Pain, May 2001, 92(1-2):311-313.
Walsky et al., "Evaluation of 227 drugs for in vitro inhibition of cytrochrome P450 2B6," J Clin Pharmacol., Jan. 2007, 46:1426-1438.
Wang et al., "Effects of propofol and ketamine as combined anesthesia for electroconvulsive therapy in patients with depressive disorder," J ECT, 2012, 28(2):128-132.
Weathers et al., "The Clinician-Administered PTSD Scale for DSM-5 (CAPS-5): Development and initial psychometric evaluation in military veterans" Psychol. Assess., May 11, 2018; 30(3):383-395.
Weber et al., "Premedication with nasal s-ketamine and midazolam provided good conditions for induction of anesthesia in preschool children," Can J. Anaesth., May 2003, 50:470-475.
Weiner et al., "Ketamine abusers presenting to the emergency department: a case series," J Emerg Med., May 2000, 18(4):447-451.
Weksler et al., "Nasal ketamine for paediatric premedication," Can J Anaesth, 1993, 40(2): 119-121.
White et al., "Ketamine—its pharmacology and therapeutic uses," Anesthesiology, Feb. 1982, 56:119-136.
wikipedia.com [online], "Benzalkonium Chloride," retrieved on Jul. 18, 2019, retrieved from URL <https://en.wikipedia.org/wiki/Benzalkonium_chloride>, 11 pages.
Williams et al., "Opioid Receptor Antagonism Attenuates Antidepressant Effects of Ketamine," Am J Psychiatry, Dec. 1, 2018, 175(12):1205-1215.
Wlaz et al., "Low doses of the glycine/NMDA receptor antagonist R-(+)-HA-966 but not D-cycloserine induce paroxysmal activity in limbic brain regions of kindled rats," Eur J Neurosci, 1994, 6(11):1710-1719.
www.accessdata.fda.gov., [online] "Highlights of prescribing information," upon information and belief, available no later than Feb. 11, 2020, retrieved from URL<https://www.accessdata.fda.gov/drugsatfda_docs/label/2020/211243s0031bl.pdf > 41 pages.
Zanos et al., "NMDAR inhibition-independent antidepressant actions of ketamine metabolites," Nat., 2016, 533, 481-486.
Zanos, et al., "Ketamine and ketamine metabolite pharmacology: Insights into therapeutic mechanisms," Pharmacol. Rev., 2018, 70:3:621-660.
Zawertailo, "Variations in CYP2D6 activity affect the pharmacokinetics and dynamics of dextromethorphan in humans," Thesis for the degree of Doctor of Philosophy, University of Toronto, Department of Pharmacology, 2002, 293 pages.
Zeppetella et al., "Prevalence and characteristics of breakthrough pain in cancer patients admitted to a hospice," J. Pain Symptom Manage., 2000, 20(2):87-92.
Paul et al., "Comparison of racemic ketamine and S-ketamine in treatment-resistant major depression: Report of two cases," The World Journal of Biological Psychiatry, Aug. 2009, 10(3):241-244.
dvcipm.org [online], "Local Anesthetics," Jan. 12, 2009, retrieved Aug. 8, 2023, retrieved from URL<http://www.dvcipm.org/site/assets/files/1083/chapt3.pdf>, 5 pages.
Akil et al., "Treatment Resistant Depression: A Multi-Scale, Systems Biology Approach, " Neuroscience and Biobehavioral Reviews, Jan. 2018, 84:272-288.
Baldessarini et al., "Bipolar depression: a major unsolved challenge," Int J Bipolar Disord., Jan. 2020,8(1):1-13.
Banerjee et al., "Towards a better diagnosis and treatment of Rett syndrome: a model synaptic disorder, " Brai, Jan. 2019: 142:239-248.
Beghi, "The Epidemiology of Epilepsy," Neuroepidemiology, Dec. 2019, 54:185-191.
Busner et al., "The Clinical Global Impressions Scale: Applying a Research Tool in Clinical Practice," Psychiatry, Jul. 2007, 4(7):28-37.
Caraci et al., "New antipsychotic drugs for the treatment of agitation and psychosis in Alzheimer's disease: focus on brexpiprazole and pimavanserin [version 1; peer review: 2 approved]," F1000Research 2020, Jul. 2020, 9(Faculty Rev):686, 9 pages.
Colloca et al., "Neuropathic pain," Nat Rev Dis Primers, Mar. 2017, 3:17002, 45 pages.
Crosby et al., "Defining clinically meaningful change in health-related quality of life," Journal of Clinical Epidemiology, May 2003, 56(5):395-407.
Dundar et al., "Pharmacological treatment of acute agitation associated with psychotic and bipolar disorder: a systematic review and meta-analysis," Hum. Psychopharmacol Clin Exp, May 2016, 31:268-285.
empr.com [online], "Intranasal racemic ketamine fast-tracked for acute suicidal ideation and behavior in MDD," Nov. 2019, retrieved on Feb. 14, 2024, retrieved from URL<https://www.empr.com/home/news/drugs-in-the-pipeline/intranasal-racemic-ketamine-fast-tracked-for-acute-suicidal-ideation-and-behavior-in-mdd/>, 4 pages.
en.wikipedia.org [online], "Profile of Mood States (POMS)," Oct. 2023, retrieved on Nov. 10, 2023, retrieved from URL<https://en.wikipedia.org/wiki/Profile_of_mood_states>, 2 pages.
eprovide.mapi-trust.org [online], "Clinician Administered Dissociative States Scale (CADSS)," Mar. 2023, retrieved on Nov. 13, 2023, retrieved from URL<https://eprovide.mapi-trust.org/instruments/clinician-administered-dissociative-states-scale>, 7 pages.
eprovide.mapi-trust.org [online], "Modified Observer's Assessment of Alertness/Sedation Scale (MOAA/S)," Jun. 2023, retrieved on Nov. 13, 2023, retrieved from URL< https://eprovide.mapi-trust.org/instruments/modified-observer-s-assessment-of-alertness-sedation-scale>, 3 pages.

(56) References Cited

OTHER PUBLICATIONS eprovide.mapi-trust.org [online], "Sheehan—Suicidality Tracking Scale (S-STS)," Aug. 2023, retrieved on Nov. 13, 2023, retrieved from URL<https://eprovide.mapi-trust.org/instruments/sheehan-suicidality-tracking-scale>, 8 pages.
Field et al., "Prenatal Depression Effects and Interventions: A Review," Infant Behavior & Development, Dec. 2010, 33:409-418.
Frieder et al., "Pharmacotherapy of Postpartum Depression: Current Approaches and Novel Drug Development," CNS Drugs, Feb. 2019, 33(3):265-282, 18 pages.
International Preliminary Report on Patentability in International Appln. No. PCT/US2022/029192, mailed Nov. 23, 2023, 10 pages.
International Preliminary Report on Patentability in International Appln. No. PCT/US2022/029453, mailed Nov. 23, 2023, 12 pages.
Kessing et al., "Course of illness in depressive and bipolar disorders, Naturalistic study, 1994-1999," Br J Psychiatry, 2004, 185:372-377.
Kessing et al., "Rate and predictors of conversion from unipolar to bipolar disorder: A systematic review and meta-analysis," Bipolar Disorders, Aug. 2017,19(5):324-335.
McIntyre et al., "Bipolar depression: the clinical characteristics and unmet needs of a complex disorder," Current Medical Research And Opinion, Aug. 2019, 35(11):1993-2005.
mdapp.co [online], "Montgomery-Åsberg Depression Rating Scale (MADRS)," Jul. 2020, retrieved on Nov. 10, 2023, retrieved from URL< https://www.mdapp.co/montgomery-asberg-depression-rating-scale-madrs-score-calculator-497/>, 8 pages.
Mills et al., "Chronic pain: a review of its epidemiology and associated factors in population-based studies," British Journal of Anaesthesia, Mar. 2019, 123(2): e273-e283.
Otte et al., "Major Depressive Disorder," Nature Reviews, Sep. 2016, 2, 20 pages.
pcl.psychiatry.uw.edu [online], "Columbia Suicide Severity Rating Scale (C-SSRS)," Jan. 2009, retrieved on Nov. 10, 2023, retrieved from URL <https://pcl.psychiatry.uw.edu/wp-content/uploads/2021/12/C-SSRS.pdf>, 5 pages.
Rakofsky et al., "Mood Disorders," Continuum (Minneap Minn) Behavioral Neurology And Psychiatry, Jun. 2018, 24(3):804-827.
Shmuely et al., "The heart of epilepsy: Current views and future concepts," Seizure, Jan. 2017, 44:176-183.
Spravato, "Highlights of Prescribing Information," FDA label, Feb. 11, 2020, 41 pages.
Allen et al., "Managing the agitated psychotic patient: a reappraisal of the evidence," J Clin Psychiatry, Dec. 30, 2000, 61 Suppl 14:11-20.
Anand et al., "Ketamine versus ECT for nonpsychotic treatment-resistant major depression," New England Journal of Medicine, Jun. 22, 2023, 388(25):2315-25.
Baldessarini et al., "Antidepressant-associated mood-switching and transition from unipolar major depression to bipolar disorder: a review," J Affect Disorders, May 15, 2013, 148(1):129-35.
Baldessarini et al., "Duration of initial antidepressant treatment and subsequent relapse of major depression," J Clin Psychopharmacology, Feb. 2015, 35(1):75-6.
Baldessarini et al., "First-episode types in bipolar disorder: predictive associations with later illness," Acta Psychiatr Scand, May 2014, 129(5):383-92.
Baldessarini et al., "Suicidal risk factors in major affective disorders," The British Journal of Psychiatry, Jul. 2019, 215:621-626.
Barbuti et al., "Antidepressant-induced hypomania/mania in patients with major depression: Evidence from the BRIDGE-II-MIX study," J Affect Disorders, Sep. 2017, 219:187-192.
Bernet et al., "Relationship of childhood maltreatment to the onset and course of major depression in adulthood," Depression and Anxiety, 1999, 9(4):169-74.
Bipolar Disorder: The NICE Guideline on the Assessment and Management of Bipolar Disorder in Adults, Children and Young People in Primary and Secondary Care. London: The British Psychological Society and The Royal College of Psychiatrists, Sep. 2014, 390 pages.
Brown et al., "Treatment of acute psychotic agitation: gaps in the evidence base," Advances in psychiatric treatment, Mar. 2011, 17(2):101-3.
Bschor et al., "Are bipolar disorders underdiagnosed in patients with depressive episodes? Results of the multicenter BRIDGE screening study in Germany," Journal of Affective Disorders, Dec. 15, 2012, 142(1-3):45-52.
CG25: Violence. The Short-Term Management of Disturbed/Violent Behaviour in in-Patient Psychiatric Settings and Emergency Departments, Royal College of Nursing, Feb. 2005, 135 pages.
Citrome et al., "Do guidelines for severe mental illness promote physical health and well-being?," Journal of Psychopharmacology, Nov. 2005, 19(6_suppl):102-9.
Conway et al., "Recent Trial Data from Nitrous Oxide Effects in Treatment-Resistant Depression," Biological Psychiatry, May 19, 2017, 81(10):S170.
Cuellar et al., "Distinctions between bipolar and unipolar depression," Clinical Psychology Review, May 2005, 25(3):307-39.
Declaration of Dr. Raj Mehra, dated Oct. 1, 2024, 22 pages.
Diego et al., "Maternal psychological distress, prenatal cortisol, and fetal weight," Psychosom Medicine, Sep. 2006, 68(5):747-53.
Drancourt et al., "Duration of untreated bipolar disorder: missed opportunities on the long road to optimal treatment," Acta Psychiatr Scandinavica, Feb. 2013, 127(2):136-44.
Dunlop et al., "Noninvasive brain stimulation treatments for addiction and major depression," Ann N Y Acad Sciences, Apr. 2017, 1394(1):31-54.
Fava et al., "Can long-term treatment with antidepressant drugs worsen the course of depression?," J Clin Psychiatry, Feb. 2003, 64(2):123-33.
Field et al., "Cortisol: the culprit prenatal stress variable," Int J Neuroscience, Aug. 2008, 118(8):1181.
Field et al., "Prenatal cortisol, prematurity and low birthweight," Infant Behavior & Development, Apr. 2006, 29(2):268-75.
Field et al., "Prenatal depression effects on the fetus and the newborn," Infant Behavior & Development, May 1, 2004, 27(2):216-29.
Field et al., "Stability of mood states and biochemistry across pregnancy," Infant Behav Dev, Apr. 2006, 29(2):262-7.
Field et al., "Prenatal maternal cortisol, fetal activity and growth," The International journal of neuroscience, Mar. 1, 2005, 115(3):423-9.
Forte et al., "Long-term morbidity in bipolar-I, bipolar-II, and unipolar major depressive disorders," Journal of Affective Disorders, Jun. 1, 2015, 178(6):71-78.
Gomathi et al., "Drug Studies on Rett Syndrome: From Bench to Bedside," J Autism Dev Disorders, Aug. 2020, 50(8):2740-2764.
Jellinger et al., "Neuropathology of Rett syndrome," Am J Med Genet Suppl, Jan. 1986, 1:259-88.
Li et al., "Presence of depressive symptoms during early pregnancy and the risk of preterm delivery: a prospective cohort study," Hum Reproduction, Jan. 2009, 24(1):146-53.
Lindenmayer et al., "The pathophysiology of agitation," J Clin Psychiatry, Jan. 1, 2000, 61:5-10.
Maina et al., "Impact of maternal psychological distress on fetal weight, prematurity and intrauterine growth retardation," Journal of Affective Disorders, Dec. 1, 2008, 111:214-220.
Marcus et al., "Depression during pregnancy: rates, risks and consequences—Motherisk Update 2008," Can J Clin Pharmacology, Jan. 22, 2009, 16(1):e15-22.
McGirr et al., "Safety and efficacy of adjunctive second generation antidepressant therapy with a mood-stabilizer or an atypical antipsychotic in acute bipolar depression: systematic review and meta-analysis of randomized placebo-controlled trials," Lancet Psychiatry, Dec. 2016, 3(12):1138-1146.
Nanni et al., "Childhood maltreatment predicts unfavorable course of illness and treatment outcome in depression: a meta-analysis," Am J Psychiatry, Feb. 2012, 169(2):141-51.
Nordstrom et al., "Inhaled loxapine for acute agitation in schizophrenia and bipolar disorder," Future Neurology, Sep. 2009, 4(5):539-45.
Ösby et al., "Excess mortality in bipolar and unipolar disorder in Sweden," Arch Gen Psychiatry, Sep. 2001, 58(9):844-50.

(56) References Cited

OTHER PUBLICATIONS

Ösby et al., "Mortality trends in cardiovascular causes in schizophrenia, bipolar and unipolar mood disorder in Sweden 1987-2010," Eur J Pub Health, Oct. 1, 2016, 26(5):867-871.
Pacchiarotti et al., "International Society for Bipolar Disorders (ISBD) Task-Force report on antidepressant use in bipolar disorders," Am J Psychiatry, Nov. 2013, 170(11):1249-1262.
Post et al., "Early-onset bipolar disorder and treatment delay are risk factors for poor outcome in adulthood, " J Clin Psychiatry, Jul. 15, 2010, 71(7):864-72.
Psychosis and Schizophrenia in Adults: Treatment and Management: Updated Edition 2014, London: National Institute for Health and Care Excellence (UK), 2014, 685 pages.
Sachs et al., "A review of agitation in mental illness: burden of illness and underlying pathology," J Clin Psychiatry, Jan. 1, 2006, 67(Suppl 10):5-12.
Schleifer et al., "Management of acute agitation in psychosis: an evidence-based approach in the USA," Advances in psychiatric treatment, Mar. 2011, 17(2):91-100.
Shen et al., "Analysis of Misdiagnosis of Bipolar Disorder in An Outpatient Setting," Shanghai Arch Psychiatry, Apr. 25, 2018, 30(2):93-101.
Sjostrom et al., "Maternal anxiety in late pregnancy and fetal hemodynamics," European Journal of Obstetrics, Gynecology, and Reproductive Biology, Aug. 1997, 74:149-155.
Stensland et al., "Diagnosis of unipolar depression following initial identification of bipolar disorder: a common and costly misdiagnosis," J Clin Psychiatry, May 2008, 69(5):749-58.
Teixeira et al., "Association between material anxiety in pregnancy and increased uterine artery resistance index: cohort based study," British Medical Journal, Jan. 16, 1999, 318:153-157.
Tondo et al., "Bipolar disorders following initial depression: modeling predictive clinical factors," J Affect Disorders, Oct. 1, 2014, 167(10):44-49.
Tondo et al., "Characteristics of depressive and bipolar disorder patients with mixed features," Acta Psychiatr Scandinavica, Sep. 2018, 138(3):243-252.
Tondo et al., "Mania associated with antidepressant-treatment: comprehensive meta-analytic review," Acta Psychiatr Scandinavica, Jun. 2010, 121(6):404-414.
Trede et al., "Manic-depressive illness: evolution in Kraepelin's textbook," Harv Rev Psychiatry, May-Jun. 2005, 13(3):155-78.
Van den Bergh et al., "Antenatal maternal anxiety and stress and the neurobehavioural development of the fetus and child: links and possible mechanisms. A review. ," Neuroscience and Biobehavioral Reviews, Apr. 2005, 29(2):237-58.
Vöhringer et al., "Discriminating between bipolar disorder and major depressive disorder," Psychiatric Clinics of North America, Mar. 1, 2016, 39(1):1-0.
Weinstock et al., "The potential influence of maternal stress hormones on development and mental health of the offspring," Brain, Behavior, and Immunity, Jul. 2005, 19(4):296-308.
Williams et al., "Childhood trauma predicts antidepressant response in adults with major depression: data from the randomized international study to predict optimized treatment for depression," Transl Psychiatry, May 3, 2016, 6(5):e799.

* cited by examiner

| Analyte | Parameter (unit) | Racemic Ketamine 30 mg IN, Day 1 | | | | | | | |
|---|---|---|---|---|---|---|---|---|---|
| | | N | Mean | SD | Min | Median | Max | Geometric Mean | Geometric CV% |
| Ketamine | $AUC_{0-t}$ (h*ng/mL) | 12 | 130.66 | 42.73 | 71.83 | 119.16 | 203.62 | 124.65 | 32.71 |
| | $AUC_{0-inf}$ (h*ng/mL) | 12 | 141.5 | 43.57 | 86.31 | 131.74 | 215.22 | 135.75 | 30.5 |
| | $C_{max}$(ng/mL) | 12 | 42.79 | 15.82 | 17.86 | 40.24 | 82.05 | 40.26 | 38.32 |
| | Cl/F(L/h) | 12 | 229.9 | 65.85 | 139.39 | 227.72 | 347.6 | 220.99 | 30.5 |
| | $V_d$/F(L) | 12 | 1346.52 | 362.2 | 619.69 | 1381.46 | 2066.45 | 1296.83 | 30.64 |
| **Analyte** | **Parameter (unit)** | **N** | **Mean** | **SD** | **CV** | | **Min** | **Median** | **Max** |
| Ketamine | $t_{1/2}$(h) | 12 | 4.37 | 1.85 | 42.4 | - | 2.88 | 3.43 | 7.91 |
| | $\lambda_z$(/h) | 12 | 0.1808 | 0.0582 | 32.1747 | - | 0.0876 | 0.2028 | 0.2403 |
| **Analyte** | **Parameter (unit)** | **N** | | **Min** | **Max** | **Median** | **Q1** | **Q3** | |
| Ketamine | $T_{max}$(h) | 12 | - | 0.453 | 1.069 | 0.507 | 0.463 | 0.798 | - |

FIG. 1A

| Analyte | Parameter (unit) | Racemic Ketamine 75 mg IN, Day 1 | | | | | | | |
|---|---|---|---|---|---|---|---|---|---|
| | | N | Mean | SD | Min | Median | Max | Geometric Mean | Geometric CV% |
| Ketamine | $AUC_{0-t}$ (h*ng/mL) | 12 | 353.64 | 71.97 | 244.27 | 343.48 | 484.06 | 346.89 | 20.82 |
| | $AUC_{0-inf}$ (h*ng/mL) | 12 | 371 | 74.16 | 256.48 | 356.49 | 508.38 | 364.17 | 20.46 |
| | $C_{max}$(ng/mL) | 12 | 89.88 | 24.96 | 42.18 | 95.24 | 133 | 86.31 | 31.8 |
| | Cl/F(L/h) | 12 | 209.88 | 43.04 | 147.53 | 210.44 | 292.43 | 205.95 | 20.46 |
| | $V_d$/F(L) | 12 | 1949.57 | 503.34 | 1276.59 | 1992.01 | 2856.06 | 1890.12 | 26.58 |
| **Analyte** | **Parameter (unit)** | **N** | **Mean** | **SD** | **CV** | | **Min** | **Median** | **Max** |
| Ketamine | $t_{1/2}$(h) | 12 | 6.39 | 0.67 | 10.53 | - | 5.61 | 6.32 | 7.93 |
| | $\lambda_z$(/h) | 12 | 0.1095 | 0.0108 | 9.8883 | - | 0.0874 | 0.1098 | 0.1235 |
| **Analyte** | **Parameter (unit)** | **N** | | **Min** | **Max** | **Median** | **Q1** | **Q3** | |
| Ketamine | $T_{max}$(h) | 12 | - | 0.482 | 1.57 | 0.805 | 0.671 | 0.819 | - |

FIG. 1B

| Analyte | Parameter (unit) | Racemic Ketamine 90 mg IN, Day 1 | | | | | | | |
|---|---|---|---|---|---|---|---|---|---|
| | | N | Mean | SD | Min | Median | Max | Geometric Mean | Geometric CV% |
| Ketamine | $AUC_{0-t}$ (h*ng/mL) | 12 | 431.26 | 132.44 | 225.05 | 438.76 | 658.96 | 411.49 | 33.72 |
| | $AUC_{0-inf}$ (h*ng/mL) | 11 | 434.54 | 127.81 | 232.94 | 461.26 | 661.41 | 416.34 | 32.28 |
| | $C_{max}$(ng/mL) | 12 | 115.01 | 44.24 | 68.89 | 101.45 | 207.05 | 107.75 | 38.75 |
| | Cl/F(L/h) | 11 | 226.53 | 75.99 | 136.07 | 195.12 | 386.37 | 216.17 | 32.28 |
| | $V_d$/F(L) | 11 | 1874.63 | 703.79 | 915.59 | 1690.2 | 3253.33 | 1762.02 | 38.2 |
| **Analyte** | **Parameter (unit)** | **N** | **Mean** | **SD** | **CV** | | **Min** | **Median** | **Max** |
| Ketamine | $t_{1/2}$(h) | 11 | 6.06 | 2.01 | 33.17 | - | 2.5 | 6.97 | 8.1 |
| | $\lambda_z$(/h) | 11 | 0.1352 | 0.0715 | 52.9232 | - | 0.0856 | 0.0994 | 0.2768 |
| **Analyte** | **Parameter (unit)** | **N** | | **Min** | **Max** | **Median** | **Q1** | **Q3** | |
| Ketamine | $T_{max}$(h) | 12 | - | 0.456 | 1.058 | 0.798 | 0.483 | 1.031 | - |

FIG. 1C

| Analyte | Parameter (unit) | Racemic Ketamine 30 mg IN, Day 4 | | | | | | | |
|---|---|---|---|---|---|---|---|---|---|
| | | N | Mean | SD | Min | Median | Max | Geometric Mean | Geometric CV% |
| Ketamine | $AUC_{0-t}$ (h*ng/mL) | 11 | 142.01 | 72.64 | 81.97 | 119.54 | 334.85 | 129.99 | 43.16 |
| | $AUC_{0-inf}$ (h*ng/mL) | 11 | 153.27 | 74.31 | 93.28 | 130.67 | 349.73 | 141.38 | 41.25 |
| | $C_{max}$(ng/mL) | 11 | 43.46 | 25.07 | 22.46 | 31.82 | 97.72 | 38.72 | 49.77 |
| | Cl/F(L/h) | 11 | 225.92 | 74.91 | 85.78 | 229.58 | 321.62 | 212.2 | 41.25 |
| | $V_d$/F(L) | 11 | 1136.99 | 336.69 | 672.56 | 1161.74 | 1672.84 | 1089.84 | 31.85 |
| **Analyte** | **Parameter (unit)** | **N** | **Mean** | **SD** | **CV** | | **Min** | **Median** | **Max** |
| Ketamine | $t_{1/2}$(h) | 11 | 3.66 | 1.01 | 27.61 | - | 2.65 | 3.51 | 6.33 |
| | $\lambda_z$(/h) | 11 | 0.1994 | 0.0421 | 21.1283 | - | 0.1096 | 0.1976 | 0.2617 |
| **Analyte** | **Parameter (unit)** | **N** | | **Min** | **Max** | **Median** | **Q1** | **Q3** | |
| Ketamine | $T_{max}$(h) | 11 | - | 0.457 | 1.074 | 0.796 | 0.467 | 1.031 | - |

FIG. 2A

| Analyte | Parameter (unit) | Racemic Ketamine 75 mg IN, Day 4 | | | | | | | |
|---|---|---|---|---|---|---|---|---|---|
| | | N | Mean | SD | Min | Median | Max | Geometric Mean | Geometric CV% |
| Ketamine | $AUC_{0-t}$ (h*ng/mL) | 11 | 360.79 | 66.68 | 273.63 | 352.27 | 491.87 | 355.35 | 18.39 |
| | $AUC_{0-inf}$ (h*ng/mL) | 11 | 377.91 | 68.35 | 287.79 | 364.18 | 516.74 | 372.47 | 17.9 |
| | $C_{max}$(ng/mL) | 11 | 94.07 | 25.58 | 50.96 | 98.92 | 131.82 | 90.62 | 30.17 |
| | Cl/F(L/h) | 11 | 204.23 | 35.66 | 145.14 | 205.94 | 260.6 | 201.36 | 17.9 |
| | $V_d$/F(L) | 11 | 1831.88 | 490.58 | 1310.56 | 1753.1 | 2929.72 | 1778.71 | 25.28 |
| **Analyte** | **Parameter (unit)** | **N** | **Mean** | **SD** | **CV** | | **Min** | **Median** | **Max** |
| Ketamine | $t_{1/2}$(h) | 11 | 6.18 | 0.95 | 15.44 | - | 5.04 | 6.16 | 8.65 |
| | $\lambda_z$(/h) | 11 | 0.1142 | 0.0153 | 13.3946 | - | 0.0801 | 0.1126 | 0.1376 |
| **Analyte** | **Parameter (unit)** | **N** | | **Min** | **Max** | **Median** | **Q1** | **Q3** | |
| Ketamine | $T_{max}$(h) | 11 | - | 0.454 | 1.048 | 0.799 | 0.463 | 0.826 | - |

FIG. 2B

| Analyte | Parameter (unit) | Racemic Ketamine 90 mg IN, Day 4 | | | | | | | |
|---|---|---|---|---|---|---|---|---|---|
| | | N | Mean | SD | Min | Median | Max | Geometric Mean | Geometric CV% |
| Ketamine | $AUC_{0-t}$ (h*ng/mL) | 12 | 362.86 | 82.8 | 224.97 | 365.98 | 510.78 | 353.81 | 24.22 |
| | $AUC_{0-inf}$ (h*ng/mL) | 12 | 382.93 | 92.55 | 234.97 | 383.21 | 554.33 | 372.36 | 25.47 |
| | $C_{max}$(ng/mL) | 12 | 96.3 | 22.41 | 66.77 | 93.57 | 150.05 | 94.11 | 22.4 |
| | Cl/F(L/h) | 12 | 248.93 | 64.9 | 162.36 | 234.86 | 383.03 | 241.7 | 25.47 |
| | $V_d$/F(L) | 12 | 2052.17 | 726.37 | 1148.75 | 1858.59 | 3755.69 | 1943.63 | 35.31 |
| **Analyte** | **Parameter (unit)** | **N** | **Mean** | **SD** | **CV** | | **Min** | **Median** | **Max** |
| Ketamine | $t_{1/2}$(h) | 12 | 5.96 | 1.94 | 32.62 | - | 2.45 | 6.66 | 8.1 |
| | $\lambda_z$(/h) | 12 | 0.1362 | 0.0698 | 51.1992 | - | 0.0831 | 0.1041 | 0.2768 |
| **Analyte** | **Parameter (unit)** | **N** | | **Min** | **Max** | **Median** | **Q1** | **Q3** | |
| Ketamine | $T_{max}$(h) | 12 | - | 0.456 | 1.533 | 0.803 | 0.468 | 0.93 | - |

FIG. 2C

| Analyte | Parameter (unit) | Racemic Ketamine 30 mg IN, Day 8 | | | | | | | |
|---|---|---|---|---|---|---|---|---|---|
| | | N | Mean | SD | Min | Median | Max | Geometric Mean | Geometric CV% |
| Ketamine | $AUC_{0-t}$ (h*ng/mL) | 10 | 150.29 | 55.01 | 101.03 | 145.96 | 296.68 | 143.61 | 30.53 |
| | $AUC_{0-inf}$ (h*ng/mL) | 10 | 160.46 | 55.21 | 105.34 | 159.49 | 305.43 | 153.93 | 29.41 |
| | $C_{max}$(ng/mL) | 10 | 42.95 | 12.85 | 25.21 | 40.9 | 70.24 | 41.31 | 30.01 |
| | Cl/F(L/h) | 10 | 201.58 | 50.96 | 98.22 | 188.12 | 284.79 | 194.9 | 29.41 |
| | $V_d$/F(L) | 10 | 1215.59 | 566.59 | 704.84 | 958.75 | 2271.55 | 1119.6 | 42.69 |
| **Analyte** | **Parameter (unit)** | **N** | **Mean** | **SD** | **CV** | | **Min** | **Median** | **Max** |
| Ketamine | $t_{1/2}$(h) | 10 | 4.38 | 2.17 | 49.69 | - | 2.58 | 3.42 | 8.27 |
| | $\lambda_z$(/h) | 10 | 0.188 | 0.0692 | 36.7908 | - | 0.0838 | 0.2034 | 0.2692 |
| **Analyte** | **Parameter (unit)** | **N** | | **Min** | **Max** | **Median** | **Q1** | **Q3** | |
| Ketamine | $T_{max}$(h) | 10 | - | 0.453 | 1.964 | 0.631 | 0.463 | 1.029 | - |

FIG. 3A

| Analyte | Parameter (unit) | Racemic Ketamine 75 mg IN, Day 8 | | | | | | | |
|---|---|---|---|---|---|---|---|---|---|
| | | N | Mean | SD | Min | Median | Max | Geometric Mean | Geometric CV% |
| Ketamine | $AUC_{0-t}$ (h*ng/mL) | 11 | 359.21 | 77.45 | 268.99 | 352.21 | 522.83 | 352.07 | 21.03 |
| | $AUC_{0-inf}$ (h*ng/mL) | 11 | 375.98 | 79.39 | 289.09 | 369.17 | 548.27 | 368.86 | 20.46 |
| | $C_{max}$(ng/mL) | 11 | 101.74 | 30.33 | 48.87 | 97.21 | 151.79 | 97.26 | 33.51 |
| | Cl/F(L/h) | 11 | 207.04 | 40.21 | 136.8 | 203.16 | 259.44 | 203.33 | 20.46 |
| | $V_d$/F(L) | 11 | 1714.83 | 457.34 | 1253.34 | 1533.67 | 2616.63 | 1663.71 | 25.81 |
| **Analyte** | **Parameter (unit)** | **N** | **Mean** | **SD** | **CV** | | **Min** | **Median** | **Max** |
| Ketamine | $t_{1/2}$(h) | 11 | 5.8 | 1.27 | 21.86 | - | 3.35 | 6.06 | 8.45 |
| | $\lambda_z$(/h) | 11 | 0.1254 | 0.0318 | 25.4019 | - | 0.082 | 0.1144 | 0.207 |
| **Analyte** | **Parameter (unit)** | **N** | | **Min** | **Max** | **Median** | **Q1** | **Q3** | |
| Ketamine | $T_{max}$(h) | 11 | - | 0.451 | 1.966 | 0.803 | 0.471 | 1.034 | - |

FIG. 3B

| Analyte | Parameter (unit) | Racemic Ketamine 90 mg IN, Day 8 | | | | | | | |
|---|---|---|---|---|---|---|---|---|---|
| | | **N** | **Mean** | **SD** | **Min** | **Median** | **Max** | **Geometric Mean** | **Geometric CV%** |
| Ketamine | $AUC_{0-t}$ (h*ng/mL) | 12 | 382.85 | 94.82 | 243.04 | 378.03 | 594.03 | 372.38 | 25.03 |
| | $AUC_{0-inf}$ (h*ng/mL) | 12 | 405.4 | 105.39 | 254.58 | 403.17 | 657.92 | 393.65 | 25.62 |
| | $C_{max}$(ng/mL) | 12 | 113.22 | 41.89 | 51.81 | 111.42 | 191.72 | 105.81 | 41.04 |
| | Cl/F(L/h) | 12 | 235.32 | 59.19 | 136.79 | 223.26 | 353.52 | 228.63 | 25.62 |
| | $V_d$/F(L) | 12 | 1890.32 | 767.91 | 957.38 | 1643.55 | 3374.55 | 1760.23 | 40.54 |
| **Analyte** | **Parameter (unit)** | **N** | **Mean** | **SD** | **CV** | | **Min** | **Median** | **Max** |
| Ketamine | $t_{1/2}$(h) | 12 | 5.72 | 2.07 | 36.2 | - | 2.68 | 6.12 | 8.47 |
| | $\lambda_z$(/h) | 12 | 0.1407 | 0.0621 | 44.1486 | - | 0.0819 | 0.1133 | 0.259 |
| **Analyte** | **Parameter (unit)** | **N** | | **Min** | **Max** | **Median** | **Q1** | **Q3** | |
| Ketamine | $T_{max}$(h) | 12 | - | 0.457 | 1.975 | 0.639 | 0.477 | 1.035 | - |

FIG. 3C

| Analyte | Parameter (unit) | Racemic Ketamine 30 mg IN, Day 1 | | | | | | | |
|---|---|---|---|---|---|---|---|---|---|
| | | N | Mean | SD | Min | Median | Max | Geometric Mean | Geometric CV% |
| Norketamine | $AUC_{0-t}$ (h*ng/mL) | 12 | 430.29 | 98.68 | 258.13 | 444.95 | 595.1 | 419.31 | 24.59 |
| | $AUC_{0-inf}$ (h*ng/mL) | 12 | 481.36 | 114.82 | 266.15 | 479.21 | 675.33 | 467.63 | 26.36 |
| | $C_{max}$(ng/mL) | 12 | 74.08 | 21.72 | 43.45 | 71.04 | 109.22 | 71.16 | 30.48 |
| **Analyte** | **Parameter (unit)** | **N** | **Mean** | **SD** | **CV** | | **Min** | **Median** | **Max** |
| Norketamine | $t_{1/2}$(h) | 12 | 7.68 | 1.53 | 19.89 | - | 5.1 | 7.66 | 11.09 |
| | $\lambda_z$(/h) | 12 | 0.0937 | 0.0191 | 20.3552 | - | 0.0625 | 0.0905 | 0.136 |
| **Analyte** | **Parameter (unit)** | **N** | | **Min** | **Max** | **Median** | **Q1** | **Q3** | |
| Norketamine | $T_{max}$(h) | 12 | - | 1.02 | 2.968 | 1.493 | 1.042 | 1.758 | - |

FIG. 4A

| Analyte | Parameter (unit) | Racemic Ketamine 75 mg IN, Day 1 | | | | | | | |
|---|---|---|---|---|---|---|---|---|---|
| | | N | Mean | SD | Min | Median | Max | Geometric Mean | Geometric CV% |
| Norketamine | $AUC_{0-t}$ (h*ng/mL) | 12 | 1139.94 | 271.22 | 698.77 | 1075.34 | 1606.09 | 1110.26 | 24.53 |
| | $AUC_{0-inf}$ (h*ng/mL) | 12 | 1279.47 | 319.04 | 742.88 | 1193.89 | 1874.83 | 1242.82 | 25.86 |
| | $C_{max}$(ng/mL) | 12 | 166.74 | 40.21 | 79.02 | 162.77 | 236.56 | 161.49 | 28.49 |
| **Analyte** | **Parameter (unit)** | **N** | **Mean** | **SD** | **CV** | | **Min** | **Median** | **Max** |
| Norketamine | $t_{1/2}$(h) | 12 | 7.57 | 1.16 | 15.36 | - | 5.71 | 7.65 | 9.17 |
| | $\lambda_z$(/h) | 12 | 0.0938 | 0.0155 | 16.536 | - | 0.0756 | 0.0906 | 0.1214 |
| **Analyte** | **Parameter (unit)** | **N** | | **Min** | **Max** | **Median** | **Q1** | **Q3** | |
| Norketamine | $T_{max}$(h) | 12 | - | 0.821 | 5.99 | 2.466 | 1.955 | 3.468 | - |

FIG. 4B

| Analyte | Parameter (unit) | Racemic Ketamine 90 mg IN, Day 1 | | | | | | | |
|---|---|---|---|---|---|---|---|---|---|
| | | N | Mean | SD | Min | Median | Max | Geometric Mean | Geometric CV% |
| Norketamine | $AUC_{0-t}$ (h*ng/mL) | 12 | 1414.51 | 314.81 | 899.58 | 1390.35 | 2063.12 | 1382.95 | 22.54 |
| | $AUC_{0-inf}$ (h*ng/mL) | 12 | 1606.36 | 411.89 | 926.51 | 1611.16 | 2380.41 | 1557.04 | 26.91 |
| | $C_{max}$(ng/mL) | 12 | 224.61 | 59.36 | 149.89 | 214.18 | 363.43 | 218.05 | 25.49 |
| **Analyte** | **Parameter (unit)** | **N** | **Mean** | **SD** | **CV** | | **Min** | **Median** | **Max** |
| Norketamine | $t_{1/2}$(h) | 12 | 7.64 | 2.16 | 28.3 | - | 4.99 | 7.49 | 12.42 |
| | $\lambda_z$(/h) | 12 | 0.0973 | 0.0263 | 27.0644 | - | 0.0558 | 0.0925 | 0.1389 |
| **Analyte** | **Parameter (unit)** | **N** | | **Min** | **Max** | **Median** | **Q1** | **Q3** | |
| Norketamine | $T_{max}$(h) | 12 | - | 0.811 | 3.982 | 2.468 | 1.802 | 3.465 | - |

FIG. 4C

| Analyte | Parameter (unit) | Racemic Ketamine 30 mg IN, Day 4 | | | | | | | |
|---|---|---|---|---|---|---|---|---|---|
| | | N | Mean | SD | Min | Median | Max | Geometric Mean | Geometric CV% |
| Norketamine | $AUC_{0-t}$ (h*ng/mL) | 11 | 493 | 100.82 | 335.16 | 470.9 | 704.27 | 484 | 20.25 |
| | $AUC_{0-inf}$ (h*ng/mL) | 11 | 550.6 | 133.9 | 345.91 | 534.33 | 851.44 | 536.68 | 23.93 |
| | $C_{max}$(ng/mL) | 11 | 78.19 | 20.2 | 50.33 | 77.11 | 117.48 | 75.84 | 26.55 |
| **Analyte** | **Parameter (unit)** | **N** | **Mean** | **SD** | **CV** | | **Min** | **Median** | **Max** |
| Norketamine | $t_{1/2}$(h) | 11 | 7.37 | 1.37 | 18.6 | - | 5.1 | 7.61 | 9.87 |
| | $\lambda_z$(/h) | 11 | 0.0972 | 0.019 | 19.5667 | - | 0.0703 | 0.0911 | 0.1358 |
| **Analyte** | **Parameter (unit)** | **N** | | **Min** | **Max** | **Median** | **Q1** | **Q3** | |
| Norketamine | $T_{max}$(h) | 11 | - | 0.799 | 2.956 | 1.464 | 1.054 | 1.945 | - |

FIG. 5A

| Analyte | Parameter (unit) | Racemic Ketamine 75 mg IN, Day 4 | | | | | | | |
|---|---|---|---|---|---|---|---|---|---|
| | | N | Mean | SD | Min | Median | Max | Geometric Mean | Geometric CV% |
| Norketamine | $AUC_{0-t}$ (h*ng/mL) | 11 | 1252.32 | 266.55 | 813.9 | 1185.38 | 1603.73 | 1225.66 | 22.31 |
| | $AUC_{0-inf}$ (h*ng/mL) | 11 | 1416.35 | 306 | 956.15 | 1306.91 | 1801.15 | 1385.8 | 22.34 |
| | $C_{max}$(ng/mL) | 11 | 181.87 | 50.55 | 129.13 | 156.92 | 275.5 | 176.23 | 26.04 |
| **Analyte** | **Parameter (unit)** | **N** | **Mean** | **SD** | **CV** | | **Min** | **Median** | **Max** |
| Norketamine | $t_{1/2}$(h) | 11 | 7.82 | 1.35 | 17.33 | - | 5.6 | 7.6 | 10.2 |
| | $\lambda_z$(/h) | 11 | 0.0912 | 0.0161 | 17.6688 | - | 0.068 | 0.0912 | 0.1238 |
| **Analyte** | **Parameter (unit)** | **N** | | **Min** | **Max** | **Median** | **Q1** | **Q3** | |
| Norketamine | $T_{max}$(h) | 11 | - | 1.039 | 3.974 | 1.96 | 1.515 | 2.959 | - |

FIG. 5B

| Analyte | Parameter (unit) | Racemic Ketamine 90 mg IN, Day 4 | | | | | | | |
|---|---|---|---|---|---|---|---|---|---|
| | | N | Mean | SD | Min | Median | Max | Geometric Mean | Geometric CV% |
| Norketamine | $AUC_{0-t}$ (h*ng/mL) | 12 | 1432.56 | 322.05 | 1105.21 | 1315.43 | 2032.22 | 1402.76 | 21.14 |
| | $AUC_{0-inf}$ (h*ng/mL) | 12 | 1606.19 | 398.26 | 1144.01 | 1477.93 | 2358.23 | 1565.09 | 23.64 |
| | $C_{max}$(ng/mL) | 12 | 223.53 | 51.72 | 153.62 | 210.52 | 328.86 | 218.35 | 22.68 |
| **Analyte** | **Parameter (unit)** | **N** | **Mean** | **SD** | **CV** | | **Min** | **Median** | **Max** |
| Norketamine | $t_{1/2}$(h) | 12 | 7.38 | 1.6 | 21.63 | - | 4.99 | 7.51 | 9.77 |
| | $\lambda_z$(/h) | 12 | 0.0984 | 0.0231 | 23.4925 | - | 0.0709 | 0.0924 | 0.139 |
| **Analyte** | **Parameter (unit)** | **N** | | **Min** | **Max** | **Median** | **Q1** | **Q3** | |
| Norketamine | $T_{max}$(h) | 12 | - | 1.496 | 3.985 | 1.948 | 1.518 | 2.955 | - |

FIG. 5C

| Analyte | Parameter (unit) | Racemic Ketamine 30 mg IN, Day 8 | | | | | | | |
|---|---|---|---|---|---|---|---|---|---|
| | | N | Mean | SD | Min | Median | Max | Geometric Mean | Geometric CV% |
| Norketamine | $AUC_{0-t}$ (h*ng/mL) | 10 | 540.73 | 63.79 | 447.13 | 529.59 | 640.84 | 537.36 | 11.83 |
| | $AUC_{0-inf}$ (h*ng/mL) | 10 | 604.42 | 75.97 | 501.94 | 589.1 | 730.21 | 600.16 | 12.57 |
| | $C_{max}$(ng/mL) | 10 | 84.23 | 22.63 | 60.95 | 78.1 | 130.58 | 81.77 | 25.55 |
| **Analyte** | **Parameter (unit)** | **N** | **Mean** | **SD** | **CV** | | **Min** | **Median** | **Max** |
| Norketamine | $t_{1/2}$(h) | 10 | 7.62 | 0.98 | 12.9 | - | 5.67 | 7.67 | 8.79 |
| | $\lambda_z$(/h) | 10 | 0.0925 | 0.0134 | 14.4624 | - | 0.0789 | 0.0903 | 0.1223 |
| **Analyte** | **Parameter (unit)** | **N** | | **Min** | **Max** | **Median** | **Q1** | **Q3** | |
| Norketamine | $T_{max}$(h) | 10 | - | 0.77 | 2.948 | 1.277 | 0.995 | 1.964 | - |

FIG. 6A

| Analyte | Parameter (unit) | Racemic Ketamine 75 mg IN, Day 8 | | | | | | | |
|---|---|---|---|---|---|---|---|---|---|
| | | N | Mean | SD | Min | Median | Max | Geometric Mean | Geometric CV% |
| Norketamine | $AUC_{0-t}$ (h*ng/mL) | 11 | 1353.04 | 296.74 | 837.89 | 1464.65 | 1762.41 | 1321.13 | 23.78 |
| | $AUC_{0-inf}$ (h*ng/mL) | 11 | 1543 | 337.72 | 967.79 | 1556.23 | 2049.78 | 1507.97 | 23.13 |
| | $C_{max}$(ng/mL) | 11 | 195.99 | 38.55 | 124.6 | 201 | 250.66 | 192.22 | 21.48 |
| **Analyte** | **Parameter (unit)** | **N** | **Mean** | **SD** | **CV** | | **Min** | **Median** | **Max** |
| Norketamine | $t_{1/2}$(h) | 11 | 7.63 | 1.46 | 19.18 | - | 5.27 | 7.65 | 9.86 |
| | $\lambda_z$(/h) | 11 | 0.0942 | 0.02 | 21.2093 | - | 0.0703 | 0.0906 | 0.1316 |
| **Analyte** | **Parameter (unit)** | **N** | | **Min** | **Max** | **Median** | **Q1** | **Q3** | |
| Norketamine | $T_{max}$(h) | 11 | - | 1.126 | 2.966 | 1.954 | 1.534 | 1.967 | - |

FIG. 6B

| Analyte | Parameter (unit) | Racemic Ketamine 90 mg IN, Day 8 | | | | | | | |
|---|---|---|---|---|---|---|---|---|---|
| | | N | Mean | SD | Min | Median | Max | Geometric Mean | Geometric CV% |
| Norketamine | $AUC_{0-t}$ (h*ng/mL) | 12 | 1525.79 | 321.87 | 1148.56 | 1465.32 | 2159.52 | 1497.08 | 20.24 |
| | $AUC_{0-inf}$ (h*ng/mL) | 12 | 1741.54 | 411.15 | 1185.03 | 1707.91 | 2466.86 | 1698.69 | 23.55 |
| | $C_{max}$(ng/mL) | 12 | 226.67 | 47.57 | 165.98 | 215.83 | 332.19 | 222.39 | 20.35 |
| **Analyte** | **Parameter (unit)** | **N** | **Mean** | **SD** | **CV** | | **Min** | **Median** | **Max** |
| Norketamine | $t_{1/2}$(h) | 12 | 7.46 | 1.81 | 24.3 | - | 5.03 | 7.66 | 11.13 |
| | $\lambda_z$(/h) | 12 | 0.098 | 0.0236 | 24.1146 | - | 0.0623 | 0.0908 | 0.1379 |
| **Analyte** | **Parameter (unit)** | **N** | | **Min** | **Max** | **Median** | **Q1** | **Q3** | |
| Norketamine | $T_{max}$(h) | 12 | - | 0.833 | 3.984 | 1.543 | 1.514 | 2.473 | - |

FIG. 6C

| Analyte | Parameter (unit) | Racemic Ketamine 30 mg IN, Day 1 | | | | | | | |
|---|---|---|---|---|---|---|---|---|---|
| | | N | Mean | SD | Min | Median | Max | Geometric Mean | Geometric CV% |
| Hydroxynorketamine | $AUC_{0-t}$ (h*ng/mL) | 12 | 530.42 | 131.13 | 301.86 | 513.65 | 771.9 | 514.82 | 26.5 |
| | $AUC_{0-inf}$ (h*ng/mL) | 12 | 689.17 | 196.21 | 405.08 | 673.9 | 1066.8 | 663.59 | 29.63 |
| | $C_{max}$(ng/mL) | 12 | 41.81 | 12.92 | 19.89 | 40.73 | 71.91 | 40.02 | 32.17 |
| **Analyte** | **Parameter (unit)** | **N** | **Mean** | **SD** | **CV** | | **Min** | **Median** | **Max** |
| Hydroxynorketamine | $t_{1/2}$(h) | 12 | 10.67 | 2.19 | 20.49 | - | 5.93 | 11.46 | 13.24 |
| | $\lambda_z$(/h) | 12 | 0.0684 | 0.0188 | 27.5138 | - | 0.0524 | 0.0605 | 0.1169 |
| **Analyte** | **Parameter (unit)** | **N** | | **Min** | **Max** | **Median** | **Q1** | **Q3** | |
| Hydroxynorketamine | $T_{max}$(h) | 12 | - | 1.961 | 4 | 2.973 | 1.981 | 3.969 | - |

FIG. 7A

| Analyte | Parameter (unit) | Racemic Ketamine 75 mg IN, Day 1 | | | | | | | |
|---|---|---|---|---|---|---|---|---|---|
| | | N | Mean | SD | Min | Median | Max | Geometric Mean | Geometric CV% |
| Hydroxynorketamine | $AUC_{0-t}$ (h*ng/mL) | 12 | 1240.73 | 316.14 | 833.31 | 1207.45 | 1665.37 | 1202.77 | 26.79 |
| | $AUC_{0-inf}$ (h*ng/mL) | 12 | 1682 | 445.65 | 1105.86 | 1724 | 2362.18 | 1626.96 | 27.68 |
| | $C_{max}$(ng/mL) | 12 | 89.36 | 28.07 | 52.79 | 83.71 | 145.3 | 85.44 | 32.09 |
| **Analyte** | **Parameter (unit)** | **N** | **Mean** | **SD** | **CV** | | **Min** | **Median** | **Max** |
| Hydroxynorketamine | $t_{1/2}$(h) | 12 | 11.44 | 2.58 | 22.57 | - | 8.56 | 10.67 | 17.92 |
| | $\lambda_z$(/h) | 12 | 0.063 | 0.0123 | 19.5036 | - | 0.0387 | 0.065 | 0.081 |
| **Analyte** | **Parameter (unit)** | **N** | | **Min** | **Max** | **Median** | **Q1** | **Q3** | |
| Hydroxynorketamine | $T_{max}$(h) | 12 | - | 2.946 | 7.982 | 3.971 | 2.998 | 5.99 | - |

FIG. 7B

| Analyte | Parameter (unit) | Racemic Ketamine 90 mg IN, Day 1 | | | | | | | |
|---|---|---|---|---|---|---|---|---|---|
| | | N | Mean | SD | Min | Median | Max | Geometric Mean | Geometric CV% |
| Hydroxynorketamine | $AUC_{0-t}$ (h*ng/mL) | 12 | 1978.45 | 471.48 | 1331.48 | 1831.16 | 2842.61 | 1929.66 | 23.46 |
| | $AUC_{0-inf}$ (h*ng/mL) | 12 | 2628.39 | 580.6 | 1815.8 | 2715.17 | 3668.03 | 2569.54 | 22.62 |
| | $C_{max}$(ng/mL) | 12 | 151.87 | 48.76 | 76.55 | 140.1 | 233.13 | 144.7 | 33.78 |
| **Analyte** | **Parameter (unit)** | **N** | **Mean** | **SD** | **CV** | | **Min** | **Median** | **Max** |
| Hydroxynorketamine | $t_{1/2}$(h) | 12 | 11.05 | 3.15 | 28.51 | - | 6.91 | 9.91 | 15.7 |
| | $\lambda_z$(/h) | 12 | 0.0673 | 0.0181 | 26.8883 | - | 0.0441 | 0.07 | 0.1003 |
| **Analyte** | **Parameter (unit)** | **N** | | **Min** | **Max** | **Median** | **Q1** | **Q3** | |
| Hydroxynorketamine | $T_{max}$(h) | 12 | - | 0.811 | 7.973 | 3.956 | 2.962 | 4.98 | - |

FIG. 7C

| Analyte | Parameter (unit) | Racemic Ketamine 30 mg IN, Day 4 | | | | | | | |
|---|---|---|---|---|---|---|---|---|---|
| | | N | Mean | SD | Min | Median | Max | Geometric Mean | Geometric CV% |
| Hydroxynorketamine | $AUC_{0-t}$ (h*ng/mL) | 11 | 524.62 | 165.38 | 311.65 | 474.82 | 778.65 | 501.56 | 32.25 |
| | $AUC_{0-inf}$ (h*ng/mL) | 11 | 704.71 | 242.31 | 398.88 | 702.53 | 1149.11 | 667.11 | 36.19 |
| | $C_{max}$(ng/mL) | 11 | 40.72 | 17.23 | 22.48 | 34.96 | 81.58 | 37.97 | 39.4 |
| **Analyte** | **Parameter (unit)** | **N** | **Mean** | **SD** | **CV** | | **Min** | **Median** | **Max** |
| Hydroxynorketamine | $t_{1/2}$(h) | 11 | 11.44 | 2.74 | 23.94 | - | 6.33 | 11.12 | 14.99 |
| | $\lambda_z$(/h) | 11 | 0.0645 | 0.019 | 29.4037 | - | 0.0463 | 0.0623 | 0.1095 |
| **Analyte** | **Parameter (unit)** | **N** | | **Min** | **Max** | **Median** | **Q1** | **Q3** | |
| Hydroxynorketamine | $T_{max}$(h) | 11 | - | 1.551 | 3.99 | 2.959 | 2.947 | 3.964 | - |

FIG. 8A

| Analyte | Parameter (unit) | Racemic Ketamine 75 mg IN, Day 4 | | | | | | | |
|---|---|---|---|---|---|---|---|---|---|
| | | N | Mean | SD | Min | Median | Max | Geometric Mean | Geometric CV% |
| Hydroxynorketamine | $AUC_{0-t}$ (h*ng/mL) | 11 | 1314.05 | 268.67 | 942.32 | 1369.35 | 1684.18 | 1287.63 | 21.75 |
| | $AUC_{0-inf}$ (h*ng/mL) | 11 | 1814.08 | 338.04 | 1299.52 | 1746.14 | 2349.09 | 1784.92 | 19.21 |
| | $C_{max}$(ng/mL) | 11 | 95.68 | 24.89 | 54.42 | 96.43 | 132.02 | 92.47 | 28.77 |
| **Analyte** | **Parameter (unit)** | **N** | **Mean** | **SD** | **CV** | | **Min** | **Median** | **Max** |
| Hydroxynorketamine | $t_{1/2}$(h) | 11 | 12.24 | 3.67 | 29.95 | - | 8.35 | 11.44 | 22.26 |
| | $\lambda_z$(/h) | 11 | 0.06 | 0.0132 | 21.9713 | - | 0.0311 | 0.0606 | 0.083 |
| **Analyte** | **Parameter (unit)** | **N** | | **Min** | **Max** | **Median** | **Q1** | **Q3** | |
| Hydroxynorketamine | $T_{max}$(h) | 11 | - | 2.946 | 5.982 | 3.945 | 2.947 | 3.971 | - |

FIG. 8B

| Analyte | Parameter (unit) | Racemic Ketamine 90 mg IN, Day 4 | | | | | | | |
|---|---|---|---|---|---|---|---|---|---|
| | | N | Mean | SD | Min | Median | Max | Geometric Mean | Geometric CV% |
| Hydroxynorketamine | $AUC_{0-t}$ (h*ng/mL) | 12 | 1947.96 | 532.94 | 1188.89 | 1886.4 | 3033.65 | 1883.73 | 27.49 |
| | $AUC_{0-inf}$ (h*ng/mL) | 12 | 2545.05 | 641.47 | 1770.61 | 2340.73 | 3668.86 | 2473.23 | 25.29 |
| | $C_{max}$(ng/mL) | 12 | 154.08 | 54.71 | 71.73 | 149.58 | 254.76 | 145 | 38.45 |
| **Analyte** | **Parameter (unit)** | **N** | **Mean** | **SD** | **CV** | | **Min** | **Median** | **Max** |
| Hydroxynorketamine | $t_{1/2}$(h) | 12 | 10.78 | 2.64 | 24.5 | - | 7.84 | 10.21 | 15.17 |
| | $\lambda_z$(/h) | 12 | 0.0677 | 0.0155 | 22.8751 | - | 0.0457 | 0.068 | 0.0884 |
| **Analyte** | **Parameter (unit)** | **N** | | **Min** | **Max** | **Median** | **Q1** | **Q3** | |
| Hydroxynorketamine | $T_{max}$(h) | 12 | - | 2.941 | 5.978 | 3.953 | 2.971 | 3.983 | - |

FIG. 8C

| Analyte | Parameter (unit) | Racemic Ketamine 30 mg IN, Day 8 | | | | | | | |
|---|---|---|---|---|---|---|---|---|---|
| | | N | Mean | SD | Min | Median | Max | Geometric Mean | Geometric CV% |
| Hydroxynorketamine | $AUC_{0-t}$ (h*ng/mL) | 10 | 497.63 | 174.77 | 305.35 | 468.96 | 806.33 | 472.1 | 34.85 |
| | $AUC_{0-inf}$ (h*ng/mL) | 10 | 669.74 | 244.12 | 378.23 | 679.66 | 1075.82 | 629.81 | 38.67 |
| | $C_{max}$(ng/mL) | 10 | 36.51 | 11.6 | 22.43 | 34.85 | 57.25 | 34.98 | 31.23 |
| **Analyte** | **Parameter (unit)** | **N** | **Mean** | **SD** | **CV** | | **Min** | **Median** | **Max** |
| Hydroxynorketamine | $t_{1/2}$(h) | 10 | 11.41 | 2.4 | 21.06 | - | 8.23 | 11 | 16.6 |
| | $\lambda_z$(/h) | 10 | 0.063 | 0.0123 | 19.4417 | - | 0.0417 | 0.0631 | 0.0842 |
| **Analyte** | **Parameter (unit)** | **N** | | **Min** | **Max** | **Median** | **Q1** | **Q3** | |
| Hydroxynorketamine | $T_{max}$(h) | 10 | - | 1.023 | 4.049 | 3.95 | 2.95 | 3.959 | - |

FIG. 9A

| Analyte | Parameter (unit) | Racemic Ketamine 75 mg IN, Day 8 | | | | | | | |
|---|---|---|---|---|---|---|---|---|---|
| | | N | Mean | SD | Min | Median | Max | Geometric Mean | Geometric CV% |
| Hydroxynorketamine | $AUC_{0-t}$ (h*ng/mL) | 11 | 1264.63 | 338.58 | 663.15 | 1278.43 | 1853.57 | 1219.24 | 30 |
| | $AUC_{0-inf}$ (h*ng/mL) | 11 | 1767.83 | 354.53 | 1192.95 | 1894.53 | 2305.7 | 1733.57 | 21.36 |
| | $C_{max}$(ng/mL) | 11 | 94.11 | 23.15 | 57.91 | 91.2 | 133.99 | 91.4 | 26.28 |
| **Analyte** | **Parameter (unit)** | **N** | **Mean** | **SD** | **CV** | | **Min** | **Median** | **Max** |
| Hydroxynorketamine | $t_{1/2}$(h) | 11 | 11.95 | 3.4 | 28.43 | - | 9.13 | 11.23 | 20.51 |
| | $\lambda_z$(/h) | 11 | 0.0613 | 0.0133 | 21.6639 | - | 0.0338 | 0.0617 | 0.0759 |
| **Analyte** | **Parameter (unit)** | **N** | | **Min** | **Max** | **Median** | **Q1** | **Q3** | |
| Hydroxynorketamine | $T_{max}$(h) | 11 | - | 1.963 | 3.975 | 2.966 | 2.951 | 3.971 | - |

FIG. 9B

| Analyte | Parameter (unit) | Racemic Ketamine 90 mg IN, Day 8 | | | | | | | |
|---|---|---|---|---|---|---|---|---|---|
| | | N | Mean | SD | Min | Median | Max | Geometric Mean | Geometric CV% |
| Hydroxynorketamine | $AUC_{0-t}$ (h*ng/mL) | 12 | 1868.21 | 384.62 | 1084.85 | 1882.49 | 2478.69 | 1828.12 | 22.75 |
| | $AUC_{0-inf}$ (h*ng/mL) | 12 | 2432.59 | 492.85 | 1694.08 | 2446.31 | 3247.7 | 2386.27 | 20.84 |
| | $C_{max}$(ng/mL) | 12 | 153.28 | 52.99 | 66.69 | 154.48 | 248.77 | 144.17 | 39.29 |
| **Analyte** | **Parameter (unit)** | **N** | **Mean** | **SD** | **CV** | | **Min** | **Median** | **Max** |
| Hydroxynorketamine | $t_{1/2}$(h) | 12 | 10.03 | 2.79 | 27.78 | - | 6.42 | 9.48 | 15.55 |
| | $\lambda_z$(/h) | 12 | 0.0738 | 0.0191 | 25.8744 | - | 0.0446 | 0.0732 | 0.108 |
| **Analyte** | **Parameter (unit)** | **N** | | **Min** | **Max** | **Median** | **Q1** | **Q3** | |
| Hydroxynorketamine | $T_{max}$(h) | 12 | - | 1.948 | 5.991 | 3.956 | 3.451 | 3.989 | - |

FIG. 9C

| DAY 1 | Racemic Ketamine 60 mg IN + placebo IV | | | | | Ketamine IV 0.3 mg/kg (dose equivalent to 60 mg IN) + placebo IN | | | | |
|---|---|---|---|---|---|---|---|---|---|---|
| Parameter (unit) | N | Geometric Mean | SD | Min | Max | N | Geometric Mean | SD | Min | Max |
| $AUC_{0-t}$ (h*ng/mL) | 12 | 271.15 | 91.91 | 127.92 | 449.82 | 12 | 319.48 | 43.91 | 244.99 | 371.32 |
| $AUC_{0-inf}$ (h*ng/mL) | 12 | 284.96 | 93.6 | 142.56 | 468.36 | 12 | 334.89 | 46.32 | 257.56 | 400.9 |
| $C_{max}$ (ng/mL) | 12 | 69.02 | 23.8 | 49.78 | 127.1 | 12 | 134.31 | 35.91 | 93.99 | 206.84 |
| Cl/F (L/h) | 12 | 210.55 | 78.02 | 128.11 | 420.87 | 12 | 71.51 | 11.49 | 55.15 | 89.11 |
| $V_d$/F (L) | 12 | 1415.11 | 430.47 | 832.66 | 2208.16 | 12 | 509.68 | 158.17 | 257.19 | 802.41 |
| $F_{abs}$ (%) | 12 | 33.96 | 8 | 18.9 | 46.02 | | - | - | - | - |
| | N | Mean | SD | Min | Max | N | Mean | SD | Min | Max |
| $t_{1/2}$(h) | 12 | 4.84 | 1.29 | 2.59 | 6.49 | 12 | 5.2 | 1.61 | 2.56 | 8.02 |
| λz(/h) | 12 | 0.1559 | 0.0541 | 0.1069 | 0.2676 | 12 | 0.1489 | 0.0577 | 0.0864 | 0.2707 |
| | N | Median | Min | Max | | N | Median | Min | Max | |
| $T_{max}$(h) | 12 | 0.679 | 0.361 | 1.544 | - | 12 | 0.254 | 0.126 | 0.378 | - |

FIG. 10A

| DAY 4 | Racemic Ketamine 60 mg IN + placebo IV | | | | | Ketamine IV 0.3 mg/kg (dose equivalent to 60 mg IN) + placebo IN | | | | |
|---|---|---|---|---|---|---|---|---|---|---|
| **Parameter (unit)** | **N** | **Geometric Mean** | **SD** | **Min** | **Max** | **N** | **Geometric Mean** | **SD** | **Min** | **Max** |
| $AUC_{0-t}$ (h*ng/mL) | 11 | 279.04 | 64.7 | 196.13 | 397.24 | 12 | 302.49 | 49.39 | 209.02 | 392.31 |
| $AUC_{0-inf}$ (h*ng/mL) | 11 | 292.39 | 65.72 | 205.25 | 407.95 | 12 | 316.69 | 51.96 | 219.78 | 406.95 |
| $C_{max}$ (ng/mL) | 11 | 74.68 | 14.46 | 56.59 | 99.79 | 12 | 107.22 | 33.77 | 68.31 | 184.73 |
| Cl/F (L/h) | 11 | 205.21 | 47.31 | 147.08 | 292.33 | 12 | 75.62 | 11.64 | 56.47 | 104.42 |
| $V_d$/F (L) | 11 | 1445.64 | 556.74 | 837.58 | 2587.67 | 12 | 522.82 | 155.92 | 279.97 | 751.74 |
| $F_{abs}$ (%) | 12 | 36.77 | 6.4 | 28.56 | 52.97 | | - | - | - | - |
| **Parameter (unit)** | **N** | **Mean** | **SD** | **Min** | **Max** | **N** | **Mean** | **SD** | **Min** | **Max** |
| $t_{1/2}$(h) | 11 | 5.08 | 1.35 | 2.62 | 6.33 | 12 | 5.06 | 1.57 | 2.49 | 7.11 |
| λz(/h) | 11 | 0.1491 | 0.0538 | 0.1095 | 0.2647 | 12 | 0.1546 | 0.0639 | 0.0974 | 0.2783 |
| **Parameter (unit)** | **N** | **Median** | **Min** | **Max** | | **N** | **Median** | **Min** | **Max** | |
| $T_{max}$(h) | 11 | 0.674 | 0.593 | 0.732 | - | 12 | 0.358 | 0.124 | 0.371 | - |

FIG. 10B

| DAY 8 | Racemic Ketamine 60 mg IN + placebo IV | | | | | Ketamine IV 0.3 mg/kg (dose equivalent to 60 mg IN) + placebo IN | | | | |
|---|---|---|---|---|---|---|---|---|---|---|
| Parameter (unit) | N | Geometric Mean | SD | Min | Max | N | Geometric Mean | SD | Min | Max |
| $AUC_{0-t}$ (h*ng/mL) | 11 | 280.19 | 64.54 | 184.63 | 410.68 | 12 | 312.53 | 41.23 | 242.05 | 369.73 |
| $AUC_{0-inf}$ (h*ng/mL) | 11 | 293.55 | 64.6 | 192.54 | 419.61 | 12 | 328.98 | 43.99 | 255.79 | 387.23 |
| $C_{max}$ (ng/mL) | 11 | 68.73 | 16 | 50.27 | 93.69 | 12 | 112.8 | 28.97 | 63.49 | 157.08 |
| Cl/F (L/h) | 11 | 204.39 | 49.55 | 142.99 | 311.63 | 12 | 72.79 | 11.09 | 55.63 | 89.72 |
| $V_d$/F (L) | 11 | 1443.57 | 497.26 | 777.08 | 2463.35 | 12 | 491.55 | 197.42 | 218.76 | 804.96 |
| $F_{abs}$ (%) | 11 | 35.4 | 4.81 | 25.6 | 42.05 | | - | - | - | - |
| | N | Mean | SD | Min | Max | N | Mean | SD | Min | Max |
| $t_{1/2}$(h) | 11 | 5.05 | 1.24 | 2.74 | 6.79 | 12 | 5 | 1.74 | 2.69 | 7.32 |
| λz(/h) | 11 | 0.147 | 0.0457 | 0.1022 | 0.253 | 12 | 0.1596 | 0.0669 | 0.0947 | 0.2577 |
| | N | Median | Min | Max | | N | Median | Min | Max | |
| $T_{max}$(h) | 11 | 0.68 | 0.364 | 1.561 | - | 12 | 0.145 | 0.12 | 0.364 | - |

FIG. 10C

| DAY 1 | Racemic Ketamine 60 mg IN + placebo IV Analyte: Norketamine | | | | | Ketamine IV 0.3 mg/kg (dose equivalent to 60 mg IN) + placebo IN Analyte: Norketamine | | | | |
|---|---|---|---|---|---|---|---|---|---|---|
| Parameter (unit) | N | Geometric Mean | SD | Min | Max | N | Geometric Mean | SD | Min | Max |
| $AUC_{0-t}$ (h*ng/mL) | 12 | 916.10 | 324.6 | 512.57 | 1387.63 | 12 | 450.56 | 120.69 | 260.24 | 669.09 |
| $AUC_{0-inf}$ (h*ng/mL) | 12 | 1016.76 | 356.96 | 571.31 | 1568.07 | 12 | 527.63 | 165.05 | 278.20 | 819.97 |
| $C_{max}$ (ng/mL) | 12 | 127.26 | 39.28 | 77.45 | 200.80 | 12 | 48.85 | 11.53 | 33.71 | 70.09 |
| $F_{abs}$ (%) | 12 | 76.91 | 15.08 | 54.06 | 105.17 | - | - | - | - | - |
| | N | Mean | SD | Min | Max | N | Mean | SD | Min | Max |
| $t_{1/2}$(h) | 12 | 6.80 | 0.97 | 5.30 | 7.88 | 12 | 8.48 | 1.71 | 6.01 | 11.32 |
| λz(/h) | 12 | 0.1042 | 0.0166 | 0.0879 | 0.1309 | 12 | 0.0851 | 0.0182 | 0.0613 | 0.1153 |
| | N | Median | Min | Max | | N | Median | Min | Max | |
| $T_{max}$(h) | 12 | 1.560 | 1.509 | 2.841 | - | 12 | 1.510 | 0.609 | 2.853 | - |

FIG. 11A

| DAY 4 | Racemic Ketamine 60 mg IN + placebo IV Analyte: Norketamine | | | | | Ketamine IV 0.3 mg/kg (dose equivalent to 60 mg IN) + placebo IN Analyte: Norketamine | | | | |
|---|---|---|---|---|---|---|---|---|---|---|
| **Parameter (unit)** | **N** | **Geometric Mean** | **SD** | **Min** | **Max** | **N** | **Geometric Mean** | **SD** | **Min** | **Max** |
| $AUC_{0-t}$ (h*ng/mL) | 11 | 1044.26 | 252.75 | 744.00 | 1601.85 | 12 | 472.00 | 115.66 | 255.75 | 678.76 |
| $AUC_{0-inf}$ (h*ng/mL) | 11 | 1165.75 | 284.80 | 804.87 | 1769.65 | 12 | 568.49 | 154.71 | 275.01 | 832.04 |
| $C_{max}$ (ng/mL) | 11 | 144.52 | 30.80 | 114.49 | 228.13 | 12 | 46.50 | 16.44 | 26.51 | 83.01 |
| $F_{abs}$ (%) | 11 | 84.07 | 12.64 | 67.21 | 111.94 | - | - | - | - | - |
| | **N** | **Mean** | **SD** | **Min** | **Max** | **N** | **Mean** | **SD** | **Min** | **Max** |
| $t_{1/2}$(h) | 11 | 7.13 | 0.96 | 5.54 | 8.18 | 12 | 9.19 | 2.01 | 6.07 | 12.51 |
| λz(/h) | 11 | 0.0989 | 0.0145 | 0.0847 | 0.1252 | 12 | 0.0792 | 0.0192 | 0.0554 | 0.1142 |
| | **N** | **Median** | **Min** | **Max** | | **N** | **Median** | **Min** | **Max** | |
| $T_{max}$(h) | 11 | 1.548 | 0.696 | 3.936 | - | 12 | 1.110 | 0.603 | 2.856 | - |

FIG. 11B

| DAY 8 | Racemic Ketamine 60 mg IN + placebo IV<br>Analyte: Norketamine | | | | | Ketamine IV 0.3 mg/kg (dose equivalent to 60 mg IN) + placebo IN<br>Analyte: Norketamine | | | | |
|---|---|---|---|---|---|---|---|---|---|---|
| **Parameter (unit)** | **N** | **Geometric Mean** | **SD** | **Min** | **Max** | **N** | **Geometric Mean** | **SD** | **Min** | **Max** |
| $AUC_{0-t}$ (h*ng/mL) | 11 | 1048.16 | 305.24 | 605.48 | 1595.10 | 12 | 520.04 | 104.28 | 327.28 | 690.36 |
| $AUC_{0-inf}$ (h*ng/mL) | 11 | 1173.89 | 334.12 | 688.74 | 1769.16 | 12 | 632.68 | 139.02 | 352.78 | 887.65 |
| $C_{max}$ (ng/mL) | 11 | 141.00 | 23.96 | 94.57 | 186.75 | 12 | 47.43 | 9.52 | 35.30 | 64.51 |
| $F_{abs}$ (%) | 11 | 75.17 | 9.92 | 63.38 | 88.63 | - | - | - | - | - |
| | **N** | **Mean** | **SD** | **Min** | **Max** | **N** | **Mean** | **SD** | **Min** | **Max** |
| $t_{1/2}$(h) | 11 | 7.20 | 0.90 | 5.75 | 8.40 | 12 | 9.49 | 2.37 | 6.27 | 14.11 |
| λz(/h) | 11 | 0.0977 | 0.0127 | 0.0825 | 0.1206 | 12 | 0.0774 | 0.0198 | 0.0491 | 0.1106 |
| | **N** | **Median** | **Min** | **Max** | | **N** | **Median** | **Min** | **Max** | |
| $T_{max}$(h) | 11 | 1.538 | 0.707 | 2.860 | - | 12 | 1.119 | 0.593 | 2.848 | - |

FIG. 11C

| DAY 1 | Racemic Ketamine 60 mg IN + placebo IV Analyte: Hydroxynorketamine | | | | | Ketamine IV 0.3 mg/kg (dose equivalent to 60 mg IN) + placebo IN Analyte: Hydroxynorketamine | | | | |
|---|---|---|---|---|---|---|---|---|---|---|
| Parameter (unit) | N | Geometric Mean | SD | Min | Max | N | Geometric Mean | SD | Min | Max |
| $AUC_{0-t}$ (h*ng/mL) | 12 | 894.11 | 205.64 | 708.00 | 1358.57 | 12 | 424.24 | 96.50 | 278.03 | 600.00 |
| $AUC_{0-inf}$ (h*ng/mL) | 12 | 1182.22 | 270.01 | 877.97 | 1693.91 | 12 | 627.53 | 153.65 | 405.56 | 945.67 |
| $C_{max}$ (ng/mL) | 12 | 66.39 | 17.58 | 46.58 | 102.91 | 12 | 25.57 | 7.47 | 15.91 | 40.41 |
| $F_{abs}$ (%) | 12 | 75.19 | 17.17 | 49.24 | 107.72 | - | - | - | - | - |
| | N | Mean | SD | Min | Max | N | Mean | SD | Min | Max |
| $t_{1/2}$(h) | 12 | 10.94 | 2.20 | 8.17 | 16.13 | 12 | 13.85 | 3.54 | 9.27 | 21.04 |
| $\lambda z$(/h) | 12 | 0.0655 | 0.0118 | 0.0430 | 0.0848 | 12 | 0.0529 | 0.0124 | 0.0329 | 0.0748 |
| | N | Median | Min | Max | | N | Median | Min | Max | |
| $T_{max}$(h) | 12 | 3.902 | 1.509 | 8.028 | - | 12 | 3.927 | 2.817 | 7.945 | - |

FIG. 12A

| DAY 4 | Racemic Ketamine 60 mg IN + placebo IV Analyte: Hydroxynorketamine | | | | | Ketamine IV 0.3 mg/kg (dose equivalent to 60 mg IN) + placebo IN Analyte: Hydroxynorketamine | | | | |
|---|---|---|---|---|---|---|---|---|---|---|
| **Parameter (unit)** | **N** | **Geometric Mean** | **SD** | **Min** | **Max** | **N** | **Geometric Mean** | **SD** | **Min** | **Max** |
| $AUC_{0-t}$ (h*ng/mL) | 11 | 940.26 | 233.03 | 698.54 | 1485.54 | 12 | 425.86 | 91.11 | 279.75 | 623.66 |
| $AUC_{0-inf}$ (h*ng/mL) | 11 | 1303.53 | 308.68 | 941.36 | 2082.75 | 12 | 687.69 | 157.17 | 483.85 | 1045.14 |
| $C_{max}$ (ng/mL) | 11 | 66.90 | 20.83 | 41.97 | 116.18 | 12 | 24.80 | 6.13 | 15.59 | 35.40 |
| $F_{abs}$ (%) | 11 | 74.57 | 9.57 | 60.41 | 92.00 | - | - | - | - | - |
| | **N** | **Mean** | **SD** | **Min** | **Max** | **N** | **Mean** | **SD** | **Min** | **Max** |
| $t_{1/2}$(h) | 11 | 12.20 | 2.08 | 9.21 | 15.94 | 12 | 16.30 | 4.01 | 9.54 | 23.32 |
| λz(/h) | 11 | 0.0584 | 0.0100 | 0.0435 | 0.0753 | 12 | 0.0453 | 0.0127 | 0.0297 | 0.0727 |
| | **N** | **Median** | **Min** | **Max** | | **N** | **Median** | **Min** | **Max** | |
| $T_{max}$(h) | 11 | 3.911 | 1.523 | 3.936 | - | 12 | 3.927 | 2.853 | 7.951 | - |

FIG. 12B

| DAY 8 | Racemic Ketamine 60 mg IN + placebo IV Analyte: Hydroxynorketamine | | | | | Ketamine IV 0.3 mg/kg (dose equivalent to 60 mg IN) + placebo IN Analyte: Hydroxynorketamine | | | | |
|---|---|---|---|---|---|---|---|---|---|---|
| **Parameter (unit)** | **N** | **Geometric Mean** | **SD** | **Min** | **Max** | **N** | **Geometric Mean** | **SD** | **Min** | **Max** |
| **$AUC_{0-t}$ (h*ng/mL)** | 11 | 885.67 | 191.68 | 647.79 | 1236.82 | 12 | 414.61 | 75.15 | 281.39 | 509.22 |
| **$AUC_{0-inf}$ (h*ng/mL)** | 11 | 1239.35 | 268.20 | 831.38 | 1757.25 | 12 | 661.42 | 144.50 | 438.67 | 1027.38 |
| **$C_{max}$ (ng/mL)** | 11 | 64.07 | 18.60 | 43.56 | 107.74 | 12 | 25.39 | 6.61 | 16.34 | 35.89 |
| **$F_{abs}$ (%)** | 11 | 73.01 | 10.13 | 61.05 | 89.18 | - | - | - | - | - |
| | **N** | **Mean** | **SD** | **Min** | **Max** | **N** | **Mean** | **SD** | **Min** | **Max** |
| **$t_{1/2}$(h)** | 11 | 12.54 | 2.05 | 10.09 | 16.56 | 12 | 15.8 | 3.77 | 10.96 | 22.80 |
| **$\lambda z$(/h)** | 11 | 0.0565 | 0.0086 | 0.0419 | 0.0687 | 12 | 0.0462 | 0.0107 | 0.0304 | 0.0633 |
| | **N** | **Median** | **Min** | **Max** | | **N** | **Median** | **Min** | **Max** | |
| **$T_{max}$(h)** | 11 | 3.92 | 2.845 | 3.949 | - | 12 | 3.927 | 2.831 | 8.026 | - |

FIG. 12C

Montgomery-Asberg Depression Rating Scale (MADRS) Total Score (Range 0 – 60)

| | Day 1 | | | | | | | | | |
|---|---|---|---|---|---|---|---|---|---|---|
| | **Baseline*** | **4 Hrs** | **24 Hours (Day 2)** | **Day 3** | **Day 4*** | **Day 5** | **Day 6** | **Day 7** | **Day 8*** | **Day 9** |
| Subject 1 | 35 | 18 | 8[1,2] | 12[1,2] | 9[1,2] | 2[1,2] | 2[1,2] | na | 7[1,2] | na |
| Subject 2 | 38 | 35 | 15[2] | 7[1,2] | 13[2] | 10[1,2] | 11[1,2] | na | 16[2] | na |
| **Mean** | **36.5** | **26.5** | **11.5[1,2]** | **9.5[1,2]** | **11.0[1,2]** | **6.0[1,2]** | **6.5[1,2]** | **na** | **11.5[1,2]** | **na** |

* Dosing Day
[1] Meets Definition of MADRS Remission; MADRS Total ≤ 12
[2] Meets Definition of MADRS Response; MADRS Total ≤ 50% of Baseline
na = not applicable

FIG. 13A

| Clinical Global Impression of Severity for Suicide Ideation and Behavior (CGIS-SI/B) (Range 1 – 5) | | | | | | | | | | |
|---|---|---|---|---|---|---|---|---|---|---|
| | Day 1 | | | | | | | | | |
| | Baseline* | 4 Hrs | 24 Hours (Day 2) | Day 3 | Day 4* | Day 5 | Day 6 | Day 7 | Day 8* | Day 9 |
| Subject 1 | 4 | 1 | 1 | 1 | 1 | 1 | 1 | 1 | 1 | 1 |
| Subject 2 | 4 | 4 | 2 | 1 | 1 | 1 | 1 | 1 | 1 | 1 |
| **Mean** | **4.0** | **2.5** | **1.5** | **1.0** | **1.0** | **1.0** | **1.0** | **1.0** | **1.0** | **1.0** |

* Dosing Day
Scores range from 1 = Not At All Suicidal to 5 = Among The Most Extremely Suicidal

FIG. 14A

Sheehan – Suicidality Tracking Scale (S-STS)
Clinically Meaningful Change Measure (CMCM) (Range 0 – 52)

| | Day 1 | | | | | | | | | |
|---|---|---|---|---|---|---|---|---|---|---|
| | Baseline* | 4 Hrs | 24 Hours (Day 2) | Day 3 | Day 4* | Day 5 | Day 6 | Day 7 | Day 8* | Day 9 |
| Subject 1 | 18 | 0 | 0 | 0 | 0 | 0 | 0 | 0 | 0 | 0 |
| Subject 2 | 22 | 18 | 3 | 0 | 0 | 0 | 0 | 0 | 0 | 0 |
| **Mean** | **20.0** | **9.0** | **1.5** | **0.0** | **0.0** | **0.0** | **0.0** | **0.0** | **0.0** | **0.0** |

* Dosing Day

FIG. 15A

Patient Global Impression of Severity for Suicide Ideation and Behavior (PGIS-SI/B) (Range 1 – 5)

| | Day 1 | | | | | | | | | |
|---|---|---|---|---|---|---|---|---|---|---|
| | **Baseline*** | **4 Hrs** | **24 Hours (Day 2)** | **Day 3** | **Day 4*** | **Day 5** | **Day 6** | **Day 7** | **Day 8*** | **Day 9** |
| Subject 1 | 3 | 2 | 1 | 1 | 1 | 1 | 1 | 1 | 1 | 1 |
| Subject 2 | 4 | 4 | 1 | 1 | 1 | 1 | 1 | 1 | 1 | 1 |
| **Mean** | **3.5** | **3.0** | **1.0** | **1.0** | **1.0** | **1.0** | **1.0** | **1.0** | **1.0** | **1.0** |

* Dosing Day
Scores range from 1 = Not Present to 5 = Extremely Severe

FIG. 16A

| Clinical Global Impression of Change in Suicide Ideation and Behavior (CGIC-SI/B) (Range 1 – 7) | | | | | | | | | | |
|---|---|---|---|---|---|---|---|---|---|---|
| | Day 1 | | | | | | | | | |
| | **Baseline*** | **4 Hrs** | **24 Hours (Day 2)** | **Day 3** | **Day 4*** | **Day 5** | **Day 6** | **Day 7** | **Day 8*** | **Day 9** |
| Subject 1 | na | 1 | 1 | 1 | 1 | 1 | 1 | 1 | na | na |
| Subject 2 | na | na | 1 | 1 | 1 | 1 | 1 | 1 | 1 | na |
| **Mean** | **na** | **1.0** | **1.0** | **1.0** | **1.0** | **1.0** | **1.0** | **1.0** | **1.0** | **na** |

* Dosing Day
Scores range from 1= Very Much Improved to 7 = Very Much Worse
na = not applicable

FIG. 17

Patient Global Impression of Change in Suicide Ideation and Behavior (PGIC-SI/B) (Range 1 – 5)

| | Day 1 | | | | | | | | | |
|---|---|---|---|---|---|---|---|---|---|---|
| | **Baseline*** | **4 Hrs** | **24 Hours (Day 2)** | **Day 3** | **Day 4*** | **Day 5** | **Day 6** | **Day 7** | **Day 8*** | **Day 9** |
| Subject 1 | na | 2 | 1 | 1 | 1 | 1 | 1 | 1 | 1 | 1 |
| Subject 2 | na | 3 | 2 | 1 | 2 | 1 | 1 | 1 | 1 | 1 |
| **Mean** | **na** | **2.5** | **1.5** | **1.0** | **1.5** | **1.0** | **1.0** | **1.0** | **1.0** | **1.0** |

* Dosing Day
Scores range from 1= Very Much Improved to 7 = Very Much Worse
na = not applicable

FIG. 18

| Montgomery-Asberg Depression Rating Scale (MADRS) Item 10 Score (Range 0 – 6) | | | | | | | | | | |
|---|---|---|---|---|---|---|---|---|---|---|
| | Day 1 | | | | | | | | | |
| | Baseline* | 4 Hrs | 24 Hours (Day 2) | Day 3 | Day 4* | Day 5 | Day 6 | Day 7 | Day 8* | Day 9 |
| Subject 1 | 5 | 1 | 0[3] | 0[3] | 0[3] | 0[3] | 0[3] | na | 0[3] | na |
| Subject 2 | 5 | 4 | 0[3] | 0[3] | 0[3] | 0[3] | 0[3] | na | 0[3] | na |
| **Mean** | **5.0** | **2.5[3]** | **0.0[3]** | **0.0[3]** | **0.0[3]** | **0.0[3]** | **0.0[3]** | **na** | **0.0[3]** | **na** |

* Dosing Day
3 Meets definition of MADRS Item 10 Response; score < 3
na = not applicable

FIG. 19A

Sheehan – Suicidality Tracking Scale (S-STS)
Clinically Meaningful Change Measure (CMCM)
Risk of Suicide at This Time (Range 0 – 9)

| | Day 1 | | | | | | | | | |
|---|---|---|---|---|---|---|---|---|---|---|
| | **Baseline*** | **4 Hrs** | **24 Hours (Day 2)** | **Day 3** | **Day 4*** | **Day 5** | **Day 6** | **Day 7** | **Day 8*** | **Day 9** |
| Subject 1 | 7 | 5 | 3 | 3 | 3 | 4 | 2 | 1 | 2 | 2 |
| Subject 2 | 7 | 7 | 3 | 2 | 1 | 1 | 1 | 2 | 2 | 0 |
| **Mean** | **7.0** | **6.0** | **3.0** | **2.5** | **2.0** | **2.5** | **1.5** | **1.5** | **2.0** | **1.0** |

* Dosing Day
Scores range from 0 = No Apparent Risk to 10 = Severe

FIG. 20A

Sheehan – Suicidality Tracking Scale (S-STS)
Clinically Meaningful Change Measure (CMCM)
Risk of Suicide at Within the Next 7 Days (Range 1 - 10)

| | Day 1 | | | | | | | | | |
|---|---|---|---|---|---|---|---|---|---|---|
| | **Baseline*** | **4 Hrs** | **24 Hours (Day 2)** | **Day 3** | **Day 4*** | **Day 5** | **Day 6** | **Day 7** | **Day 8*** | **Day 9** |
| Subject 1 | 5 | 4 | 2 | 0 | 1 | 1 | 1 | 0 | 0 | 0 |
| Subject 2 | 7 | 6 | 1 | 0 | 1 | 0 | 0 | 0 | 0 | 0 |
| **Mean** | **6.0** | **5.0** | **1.5** | **0.0** | **1.0** | **0.5** | **0.5** | **0.0** | **0.0** | **0.0** |

* Dosing Day
Scores range from 1 = None Apparent to 10 = Extreme

FIG. 21A

Modified Observer's Assessment of Alertness/Sedation (MOAA/S) (Range 0 – 5)

| | | Time Relative to Dosing | | | | | | | | | | |
|---|---|---|---|---|---|---|---|---|---|---|---|---|
| **Subject** | **Day** | **PreDose** | **15 min** | **30 min** | **45 min** | **60 min** | **75 min** | **90 min** | **2 hours** | **4 hours** | **6 hours** | **24 hours** |
| **1** | 1 | 5 | 4 | 5 | 5 | 5 | 5 | 5 | 5 | 5 | 5 | 5 |
| | 4 | 5 | 5 | 5 | 5 | 5 | 5 | 5 | 5 | 5 | 5 | na |
| | 8 | 5 | 5 | 5 | 5 | 5 | 5 | 5 | 5 | 5 | na | na |
| **2** | 1 | 5 | 5 | 5 | 5 | 5 | 5 | 5 | 5 | 5 | 5 | 5 |
| | 4 | 5 | 5 | 5 | 5 | 5 | 5 | 5 | 5 | 5 | 5 | na |
| | 8 | 5 | 5 | 5 | 5 | 5 | 5 | 5 | 5 | 5 | na | na |

Scores range from 0 = Does Not Respond to Noxious Stimulant to 5 = Responds Readily To Name Spoken In Normal Tone
na = not applicable

FIG. 22

Clinician Administered Dissociative States Scale (CADSS) (Range 0 – 92)

| | | Time Relative to Dosing | | | | | | |
|---|---|---|---|---|---|---|---|---|
| **Subject** | **Day** | **PreDose** | **40 min** | **1 hour** | **2 hours** | **4 hours** | **6 hours** | **24 hours** |
| **1** | 1 | 0 | 0 | 0 | 0 | -- | 0 | 0 |
| | 4 | 0 | 0 | 0 | 0 | 0 | 0 | na |
| | 8 | 0 | 0 | 0 | 0 | 0 | na | na |
| **2** | 1 | 0 | 3 | 0 | 0 | 0 | 0 | 0 |
| | 4 | 0 | 2 | 0 | 0 | 0 | 0 | Na |
| | 8 | 0 | 0 | 0 | 0 | 0 | na | na |

Scores based on 23 questions for which response ranges from 0 = Not at All to 4 = Extreme
na = not applicable

FIG. 23

| Columbia Suicide Severity Rating Scale (C-SSRS) | | | |
|---|---|---|---|
| **Subject** | **Day** | **Suicidal Ideation** | **Suicidal Behavior** |
| 1 | Baseline | YES for ‘Wish to be dead’<br>YES for ‘Non-specific active suicidal thoughts | NO for all responses |
| | 24 Hours (Day 2) | NO for all responses | NO for all responses |
| | 3 | NO for all responses | NO for all responses |
| | 4 | NO for all responses | NO for all responses |
| | 5 | NO for all responses | NO for all responses |
| | 6 | NO for all responses | NO for all responses |
| | 7 | NO for all responses | NO for all responses |
| | 8 | NO for all responses | NO for all responses |
| | 9 | NO for all responses | NO for all responses |
| 2 | Baseline | YES for ‘Wish to be dead’<br>YES for ‘Non-specific active suicidal thoughts | NO for all responses |
| | 24 Hours (Day 2) | YES for ‘Wish to be dead’<br>NO for ‘Non-specific active suicidal thoughts | NO for all responses |
| | 3 | NO for all responses | NO for all responses |
| | 4 | NO for all responses | NO for all responses |
| | 5 | NO for all responses | NO for all responses |
| | 6 | NO for all responses | NO for all responses |
| | 7 | NO for all responses | NO for all responses |
| | 8 | NO for all responses | NO for all responses |
| | 9 | NO for all responses | NO for all responses |

FIG.24

METHODS OF TREATING SUICIDALITY

CROSS-REFERENCE TO RELATED APPLICATIONS

This application is a continuation of U.S. application Ser. No. 17/792,208, filed on Jul. 12, 2022, which is a national stage application under 35 U.S.C. § 371 of International Application No. PCT/US2021/014748 having an International Filing Date of Jan. 22, 2021, which claims priority to U.S. Provisional Application No. 63/079,791, filed on Sep. 17, 2020 and U.S. Provisional Application No. 62/964,598, filed on Jan. 22, 2020, which is incorporated by reference herein in its entirety.

TECHNICAL FIELD

The present disclosure relates to compositions and methods for treating psychiatric disorders such as suicidality, suicidal ideation, major depressive disorder, treatment-resistant depression, and post-traumatic stress disorder.

BACKGROUND

Depression is among the most disabling of all medical disorders and is a major public health problem. It frequently appears early in life, can occur chronically throughout life, and can adversely affect the prognosis of other medical illnesses such as cardiovascular and neurological conditions.

While antidepressant medications and cognitive behavioral therapy can be effective for some individuals with depression, up to 20% do not respond to these interventions, and many of those who do respond, eventually relapse. Similarly, an estimated 50% of depressed individuals are only partially (inadequately) treated by available clinical interventions. See Al Harbi, Patient Prefer. Adherence, Vol. 6, pp. 369-388 (2012). In the NIMH Sequenced Treatment Alternatives to Relieve Depression (STAR*D) study, approximately half of patients treated with a first-line antidepressant therapy had reduction of symptoms to at least half of the original intensity and only approximately one-third of patients achieved remission (Chan 2013). While these patients may eventually recover, many require a trial and error approach to therapy, and many will ultimately develop treatment resistant depression over time. See, e.g., Sackheim, J. Clin. Psychiatry, Vol. 62, Suppl. 16, pp. 10-17 (2001). This can lead to even more serious conditions such as suicidal ideation and suicidality. Suicide remains a clear, present and increasing public health problem, despite being a potentially preventable tragedy. The incidence of suicide is particularly high in individuals with undiagnosed or inadequately treated psychiatric disorders.

The treatment of discovery of tricyclic antidepressants and monoamine oxidase inhibitors revolutionized the treatment of depression. However, even recently developed medications for treating depression take weeks to months to achieve their full effects and may not be efficacious for all subjects at any safe dose. For example, most antidepressants require an average of 6 weeks to begin to have an effect on depressive symptoms. Some patients do not respond to antidepressant medications at all, and for others, only some types seem to work to ameliorate symptoms. In the meantime, individuals continue to suffer from depression, have a risk of self-harm, and experience a negative impact in their personal and professional lives. See, e.g., Burcusa and Iacono, Clin. Psychol. Rev. Vol. 27, No. 8, pp. 959-985 (2007). Providing rapid-onset and sustained antidepressant effects would have a substantial impact on public health.

SUMMARY

The details of one or more embodiments are set forth in the description below. Other features, objects, and advantages of the invention will be apparent from the description and from the claims.

Some embodiments provide a method for treating suicidality in a subject in need thereof, comprising intranasally administering a therapeutically effective amount of racemic ketamine, or a pharmaceutically acceptable salt thereof, to the subject.

Some embodiments provide a method for treating suicidal ideation in a subject in need thereof, comprising intranasally administering a therapeutically effective amount of racemic ketamine, or a pharmaceutically acceptable salt thereof, to the subject.

Some embodiments provide a method for treating major depressive disorder in a subject in need thereof, comprising intranasally administering a therapeutically effective amount of racemic ketamine, or a pharmaceutically acceptable salt thereof, to the subject.

Some embodiments provide a method for reducing one or more side effects of ketamine in a subject in need thereof, the method comprising intranasally administering a therapeutically effective amount of racemic ketamine, or a pharmaceutically acceptable salt thereof, to the subject.

In some embodiments, the subject has been previously diagnosed with and/or is currently suffering from, post-traumatic stress disorder. In some embodiments, the subject has been previously diagnosed with and/or is currently suffering from, major depressive disorder.

DESCRIPTION OF THE FIGURES

Abbreviations

N: Number of observations; SD: Standard Deviation; Min: Minimum; Max: Maximum; IN: Intranasal.

FIGS. 1A-1C are tables describing pharmacokinetic parameters for ketamine on Day 1 in Part A of the study described in Example 1 for 30 mg racemic ketamine (FIG. 1A), 75 mg racemic ketamine (FIG. 1B), or 90 mg racemic ketamine (FIG. 1C).

FIGS. 2A-2C are tables describing pharmacokinetic parameters for ketamine on Day 4 in Part A of the study described in Example 1 for 30 mg racemic ketamine (FIG. 2A), 75 mg racemic ketamine (FIG. 2B), or 90 mg racemic ketamine (FIG. 2C).

FIGS. 3A-3C are tables describing pharmacokinetic parameters for ketamine on Day 8 in Part A of the study described in Example 1 for 30 mg racemic ketamine (FIG. 3A), 75 mg racemic ketamine (FIG. 3B), or 90 mg racemic ketamine (FIG. 3C).

FIGS. 4A-4C are tables describing pharmacokinetic parameters for norketamine on Day 1 in Part A of the study described in Example 1 for 30 mg racemic ketamine (FIG. 4A), 75 mg racemic ketamine (FIG. 4B), or 90 mg racemic ketamine (FIG. 4C).

FIGS. 5A-5C are tables describing pharmacokinetic parameters for norketamine on Day 4 in Part A of the study described in Example 1 for 30 mg racemic ketamine (FIG. 5A), 75 mg racemic ketamine (FIG. 5B), or 90 mg racemic ketamine (FIG. 5C).

FIGS. 6A-6C are tables describing pharmacokinetic parameters for norketamine on Day 8 in Part A of the study described in Example 1 for 30 mg racemic ketamine (FIG. 6A), 75 mg racemic ketamine (FIG. 6B), or 90 mg racemic ketamine (FIG. 6C).

FIGS. 7A-7C are tables describing pharmacokinetic parameters for hydroxynorketamine on Day 1 in Part A of the study described in Example 1 for 30 mg racemic ketamine (FIG. 7A), 75 mg racemic ketamine (FIG. 7B), or 90 mg racemic ketamine (FIG. 7C).

FIGS. 8A-8C are tables describing pharmacokinetic parameters for hydroxynorketamine on Day 4 in Part A of the study described in Example 1 for 30 mg racemic ketamine (FIG. 8A), 75 mg racemic ketamine (FIG. 8B), or 90 mg racemic ketamine (FIG. 8C).

FIGS. 9A-9C are tables describing pharmacokinetic parameters for hydroxynorketamine on Day 8 in Part A of the study described in Example 1 for 30 mg racemic ketamine (FIG. 9A), 75 mg racemic ketamine (FIG. 9B), or 90 mg racemic ketamine (FIG. 9C).

FIGS. 10A-10C are tables describing pharmacokinetic parameters for ketamine on Day 1 (FIG. 10A), Day 4 (FIG. 10B), or Day 8 (FIG. 10C) in Part B of the study described in Example 1 for racemic ketamine 60 mg IN+placebo IV and ketamine IV 0.3 mg/kg racemic ketamine (dose equivalent to 60 mg IN)+placebo IN.

FIGS. 11A-11C are tables describing pharmacokinetic parameters for norketamine on Day 1 (FIG. 11A), Day 4 (FIG. 11B), or Day 8 (FIG. 11C) in Part B of the study described in Example 1 for racemic ketamine 60 mg IN+placebo IV and ketamine IV 0.3 mg/kg racemic ketamine (dose equivalent to 60 mg IN)+placebo IN.

FIGS. 12A-12C are tables describing pharmacokinetic parameters for hydroxynorketamine on Day 1 (FIG. 12A), Day 4 (FIG. 12B), or Day 8 (FIG. 12C) in Part B of the study described in Example 1 for racemic ketamine 60 mg IN+placebo IV and ketamine IV 0.3 mg/kg racemic ketamine (dose equivalent to 60 mg IN)+placebo IN.

FIGS. 13A-13B are a table (FIG. 13A) and a graph (FIG. 13B) describing the MADRS depressions scores for Subject 1 and Subject 2 from Day 1 to Day 9 described in Example 3 of the study.

FIGS. 14A-14B are a table (FIG. 14A) and a graph (FIG. 14B) describing the CGIS-SI/B suicide ideation scores for Subject 1 and Subject 2 from Day 1 to Day 9 described in Example 3 of the study.

FIGS. 15A-15B are a table (FIG. 15A) and a graph (FIG. 15B) describing the S-STS suicidality scores for Subject 1 and Subject 2 from Day 1 to Day 9 described in Example 3 of the study.

FIGS. 16A-16B are a table (FIG. 16A) and a graph (FIG. 16B) describing the PGIS-SI/B suicide ideation scores for Subject 1 and Subject 2 from Day 1 to Day 9 described in Example 3 of the study.

FIG. 17 is a table describing the CGIC-SI/B suicide ideation scores for Subject 1 and Subject 2 from Day 1 to Day 8 described in Example 3 of the study.

FIG. 18 is a table describing the PGIC-SI/B scores for Subject 1 and Subject 2 from Day 1 to Day 9 described in Example 3 of the study.

FIGS. 19A-19B are a table (FIG. 19A) and a graph (FIG. 19B) describing the MADRS item 10 scores for Subject 1 and Subject 2 from Day 1 to Day 9 described in Example 3 of the study.

FIGS. 20A-20B are a table (FIG. 20A) and a graph (FIG. 20B) describing the STS CMCM ("risk of suicide at this time") scores for Subject 1 and Subject 2 from Day 1 to Day 9 described in Example 3 of the study.

FIGS. 21A-21B are a table (FIG. 21A) and a graph (FIG. 21B) describing the STS CMCM ("risk of suicide at within the next 7 day") scores for Subject 1 and Subject 2 from Day 1 to Day 9 described in Example 3 of the study.

FIG. 22 is a table describing the MOAA/S alertness/sedation scores for Subject 1 and Subject 2 from pre-dose to 24 hours on Day 1 and Day 4 described in Example 3 of the study.

FIG. 23 is a table describing the CADSS dissociation scores from Subject 1 and Subject 2 from pre-dose to 24 hours on Day 1 and Day 4 described in Example 3 of the study.

FIG. 24 is a table describing the C-SSRS scores for S from Day 1 to Day 9 for Subject 1 and Day 1 to Day 4 for Subject 2 described in Example 3 of the study.

DETAILED DESCRIPTION

Definitions

Figure 13B:
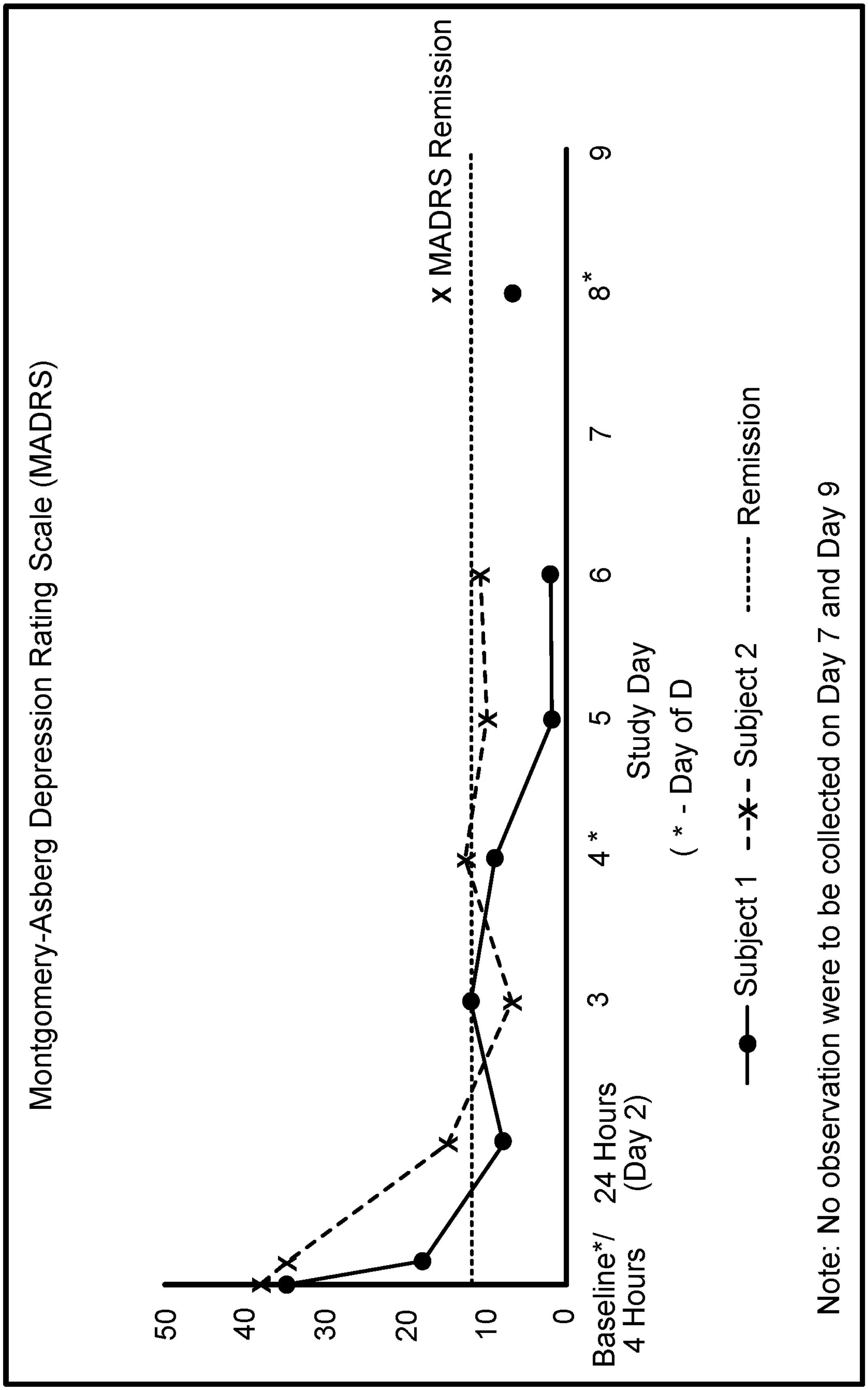

In order that the present disclosure can be more readily understood, certain terms are first defined. As used in this application, except as otherwise expressly provided herein, each of the following terms shall have the meaning set forth below. Additional definitions are set forth throughout the application.

Unless defined otherwise, all technical and scientific terms used herein have the same meaning as commonly understood by one of ordinary skill in the art to which this disclosure is related. For purposes of the present disclosure, the following terms are defined.

Units, prefixes, and symbols are denoted in their Système International de Unites (SI) accepted form. Numeric ranges are inclusive of the numbers defining the range. The headings provided herein are not limitations of the various aspects of the disclosure, which can be had by reference to the specification as a whole. Accordingly, the terms defined immediately below are more fully defined by reference to the specification in its entirety.

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

The term "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

The terms "about" and "approximately" as used herein shall generally mean an acceptable degree of error for the quantity measured given the nature or precision of the measurements. Typical, exemplary degrees of error are within 10% or within 5% of a given value or range of values. Any reference to "about X" specifically indicates at least the values X, 0.95X, 0.96X, 0.97X, 0.98X, 0.99X, 1.01X, 1.02X, 1.03X, 1.04X, and 1.05X. Thus, "about X" is intended to provide written description support for a claim limitation of, e.g., "0.98×." The terms "about" and "approximately," particularly in reference to a given quantity, encompass and describe the given quantity itself.

When "about" is applied to the beginning of a numerical range, it applies to both ends of the range. Thus, "from about 5 to 20%" is equivalent to "from about 5% to about 20%." When "about" is applied to the first value of a set of values, it applies to all values in that set. Thus, "about 5, 10, or 15 mg" is equivalent to "about 5, about 10, or about 15 mg."

"Racemic ketamine" refers to a 1:1 mixture of the two enantiomers of ketamine: (R)-2-(2-chlorophenyl)-2-(methylamino)cyclohexanone and (S)-2-(2-chlorophenyl)-2-(methylamino)cyclohexanone.

An "equivalent dose" refers to an equivalent dose of an active agent based on bioavailability. An equivalent dose based on bioavailability can be determined by comparing the extent and rate of drug absorption of two or more dosages (e.g., dosages formulated as an intranasal formulation and as an intravenous formulation, respectively) of an active agent, for example, by determining the area under the blood or plasma concentration-time curve (AUC) and/or the maximum concentration ($C_{max}$), respectively. Accordingly, as used herein, an equivalent dose based on bioavailability is present when the two dosages each exhibit an AUC and/or $C_{max}$ within about 80% to about 125% of one another.

"Suicidal ideation" refers to a psychiatric disorder where the subject experiences, for example, one or more of a wish to be dead, non-specific active suicidal thoughts, active ideation without intent, active ideation with some intent to act, and active ideation with a specific plan or intent. The presence and frequency of these thoughts and/or experiences can be evaluated using several psychiatric tests known in the art, such as the Columbia Suicide Severity Rating Scale. See, e.g., Ghasemi, et al., Health Promot. Perspect., Vol. 5, No. 3, pp. 156-168 (2015), which is incorporated herein by reference in its entirety.

"Suicidality" refers to a subject experiencing suicidal ideation that takes active step(s) towards committing suicide, including, for example, a suicide attempt. See, e.g., Klonsky, et al., Annu. Rev. Clin. Psychol. Vol. 12, pp. 307-330 (2016), which is incorporated herein by reference in its entirety.

"Treatment" or "therapy" of a subject refers to any type of intervention or process performed on, or the administration of an active agent to, the subject with the objective of reversing, alleviating, ameliorating, inhibiting, or slowing down, the onset, progression, development, severity, or recurrence of a symptom, complication, condition, or biochemical indicia associated with a disease. In some embodiments, "treatment" includes resolution of a particular disorder, including a reduction in one or more symptoms of the disorder and/or a reduction in in the severity of one or more symptoms associated with the disorder.

"Administering" or "administration" refer to the physical introduction of a therapeutic agent to a subject, using any of the various methods and delivery systems known to those skilled in the art. Routes of administration can include oral, intravenous, intranasal, intramuscular, subcutaneous, intraperitoneal, spinal or other parenteral routes of administration, for example by injection or infusion (e.g., intravenous infusion). Administration can also be performed, for example, once, a plurality of times, and/or over one or more extended periods.

A "subject" includes any human or non-human animal. The term "non-human animal" includes, but is not limited to, vertebrates such as non-human primates, sheep, dogs, and rodents such as mice, rats, and guinea pigs. In some embodiments, the subject is a human.

An "effective amount" or "therapeutically effective amount" of a therapeutic agent is any amount of the drug that, when used alone or in combination with one or more additional therapies, slowing down the onset of a psychiatric disorder or promotes regression of the disorder evidenced by a decrease in severity of disorder symptoms, an increase in frequency and duration of disorder symptom-free periods, or a ameliorating an impairment or disability due to the disorder affliction. The ability of one or more additional therapies to promote disorder regression can be evaluated using a variety of methods known to the skilled practitioner, such as in human subjects during clinical trials, in animal model systems predictive of efficacy in humans, or by assaying the activity of the agent in in vitro assays.

As used herein, a measure of a treatment effect is "clinically meaningful" based on the practical importance of a treatment effect. For example, whether the treatment effect has a real genuine, palpable, and/or noticeable effect on the subject (e.g., a lack of clinically meaningful effect occurs when the difference in the subject is small enough that it may be considered similar, such as prior to and after administration of a treatment as provided herein). One skilled in the art would recognize whether a particular effect is "clinically meaningful." For example, a subject having a baseline score indicating severe depression and/or suicidality (using any of the scales described herein) and a post-treatment score indicating remission of the severe depression and/or suicidality would be a clinically meaningful effect.

As used herein, "$AUC_{0-t}$" refers to the area under the plasma concentration-time curve from time=0 to the time at which the last measurable concentration occurs. In some embodiments, the last measurable concentration occurs at t=32 hours (e.g., $AUC_{0-t}=AUC_{0-32}$).

A subject that is "not responsive" refers to a subject that has been, or is currently being, treated with one or more therapies that are not providing a clinically meaningful change towards the desired outcome (e.g., subjects that are not responsive includes patients that are refractory to a particular treatment). For example, a subject may exhibit no measurable change in response to therapy. A non-responsive subject could also, for example, exhibit a positive change in a depression scale score, but the change is not clinically meaningful.

As used herein, a psychiatric evaluation or side effect profile test score that is "substantially similar" or "substantially the same" as a reference score, corresponds to the same score, with a skilled artisan understanding that particular test scores may vary to a reasonable extent (such as ±10%) while still describing a given value, due to, for example, experimental error, routine subject-to-subject evaluation, and routine statistical analysis.

The phrase "pharmaceutically acceptable" indicates that the substance or composition must be compatible chemically and/or toxicologically, with the other ingredients comprising a formulation, and/or the mammal being treated therewith.

As used herein, the term "pharmaceutically acceptable carrier" refers to a substance that aids the administration of an active agent to a cell, an organism, or a subject. "Pharmaceutically acceptable carrier" refers to a carrier or excipient that can be included in the compositions of the disclosure and that causes no significant adverse toxicological effect on the subject. Non-limiting examples of pharmaceutically acceptable carriers include water, NaCl, normal saline solutions, lactated Ringer's, normal sucrose, normal glucose, binders, fillers, disintegrants, lubricants, coatings, sweeteners, flavors and colors, liposomes, dispersion media, microcapsules, cationic lipid carriers, isotonic and absorption delaying agents, and the like. The carrier may also be substances for providing the formulation with stability, sterility and isotonicity (e.g., antimicrobial preservatives, antioxidants, chelating agents and buffers), for preventing the action of microorganisms (e.g. antimicrobial and antifungal agents, such as parabens, chlorobutanol, phenol, sorbic acid and the like) or for providing the formulation with an edible flavor etc. In some instances, the carrier is an agent that facilitates the delivery of a small molecule drug or antibody to a target cell or tissue. One of skill in the art will recognize that other pharmaceutical carriers are useful in the present disclosure.

As used in the methods described herein, the term "reducing" refers to a reduction in the indicated parameter relative to the baseline measurement (or measurements) of the same parameter in the subject taken prior to the initiation of administration with racemic ketamine, or a pharmaceutically acceptable salt thereof, or a reduction in the indicated parameter relative to the baseline measurement (or measurements) of the same parameter. In some embodiments, the same parameter is measured in a healthy subject (for example, a subject that does not have a psychiatric disorder as described herein). In some embodiments, the same parameter is measured relative to another treatment modality (for example, the standard of care treatment for a psychiatric disorder as described herein).

Similarly, the term "increasing," as used herein, refers to an increase in the indicated parameter relative to the baseline measurement (or measurements) of the same parameter in the subject taken prior to the initiation of administration with racemic ketamine, or a pharmaceutically acceptable salt thereof, or an increase in the indicated parameter relative to the baseline measurement (or measurements) of the same parameter. In some embodiments, the same parameter is measured in a healthy subject (for example, a subject that does not have a psychiatric disorder as described herein). In some embodiments, the same parameter is measured relative to another treatment modality (for example, the standard of care treatment for a psychiatric disorder as described herein).

The term "synergy" or "synergistic" is used herein to mean that the effect of the combination of the two therapeutic agents of the combination therapy is greater than the sum of the effect of each agent when administered alone. A "synergistic amount" or "synergistically effective amount" is an amount of the combination of the two combination partners that results in a synergistic effect, as "synergistic" is defined herein. Determining a synergistic interaction between two combination partners, the optimum range for the effect and absolute dose ranges of each component for the effect may be definitively measured by administration of the combination partners over different w/w (weight per weight) ratio ranges and doses to subjects in need of treatment. However, the observation of synergy in in vitro models or in vivo models can be predictive of the effect in humans and other species and in vitro models or in vivo models exist, as described herein, to measure a synergistic effect. Exemplary synergistic effects includes, but are not limited to, enhanced therapeutic efficacy, decreased dose at equal or increased level of efficacy, reduced or delayed development of drug resistance, and simultaneous enhancement or equal therapeutic actions (e.g., the same therapeutic effect as at least one of the therapeutic agents) and reduction of unwanted drug effects (e.g., side effects and adverse events) of at least one of the therapeutic agents.

For example, a synergistic ratio of two therapeutic agents can be identified by determining a synergistic effect in, for example, an art-accepted in vivo model (e.g., an animal model) of depression (e.g., despair-based, reward-based, or anxiety-based mouse models).

As described herein, any concentration range, percentage range, ratio range, or integer range is to be understood to include the value of any integer within the recited range and, when appropriate, fractions thereof (such as one tenth and one hundredth of an integer), unless otherwise indicated.

Unless otherwise stated, any reference to an amount of ketamine in this disclosure is based on the free equivalent weight of ketamine. For example, 30 mg of ketamine refers to 30 mg of ketamine in the free form or an equivalent amount of a salt form of ketamine (e.g., ketamine hydrochloride).

Various aspects of the disclosure are described in further detail herein.

Introduction

Depression is characterized by depressed mood and a markedly diminished interest or pleasure in activities. Other symptoms may include significant weight loss or weight gain, decrease or increase in appetite, insomnia or hypersomnia, psychomotor agitation or retardation, fatigue or loss of energy, feelings of worthlessness or excessive or inappropriate guilt, diminished ability to think or concentrate or indecisiveness, recurrent thoughts of death, suicidal ideation or suicidal attempts. See Kennedy, Dialogues Clin. Neurosci., Vol. 10, No. 3, pp. 271-2'77 (2008). A variety of somatic symptoms may also be present. Though depressive feelings are common, depressive disorder is diagnosed only when the symptoms reach a threshold and last at least two weeks. Depression can vary in severity from mild to very severe. It is most often episodic but can be recurrent or chronic. More than 50% of those who initially suffer a single major depressive episode eventually develop another. Unfortunately, current pharmacological interventions for depression take weeks to months to achieve their full therapeutic effect, and many subjects are, or will become, resistant to these therapies. See, e.g, Kupfer, Dialogues Clin. Neurosci., Vol. 7, No. 3, pp. 191-205 (2005).

Ketamine has been used as an intravenous, short-acting anesthetic in both humans and animals. In addition to analgesia, ketamine produces a state of "dissociative anesthesia," and is also used recreationally to induce these effects. See, e.g., Li and Vlisides, Front. Hum. Neurosci., Vol. 10, Article 612, pp. 1-15 (2016); and the Spravato® ((S)-ketamine) Package Insert dated Feb. 11, 2020; www.accessdata.fda.gov/drugsatfda_docs/label/2020/211243s003lbl.pdf, which is hereby incorporated by reference in its entirety.

At low doses, ketamine produces mild sedation and euphoria, while at higher doses, individuals experience dissociative effective similar to phencyclidine hydrochloride (PCP). Other somatic effects of ketamine include vertigo, difficulties with balance, nausea, vomiting, sweating, tremor, dystonic movements, respiratory depression, and sleep apnea. See Zanos, et al., Pharmacol. Rev., Vol. 70, No. 3, pp. 621-660 (2018). The most frequently observed adverse events following administration of ketamine are manifested in psychic emergence phenomena, as such floating sensations, vivid dreams, hallucinations, hypertonus, and delirium. These effects can continue for up to 24 hours after administration. See Perumal, et al., J. Res. Pharm. Pract., Vol. 4, No. 2, pp. 89-93 (2015).

After administration, ketamine is demethylated to form norketamine, and both ketamine and norketamine can be hydroxylated, forming hydroxyphenylketamine, 6-hydroxyketamine, hydroxyphenylnorketamine, and 6-hydroxynorketamine (also referred to herein as hydroxynorketamine). The structures of these (racemic) compounds are shown below.

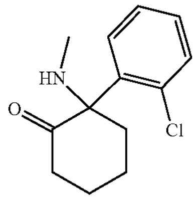

Ketamine

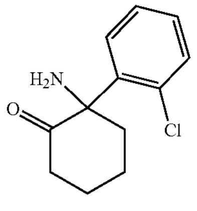

Norketamine

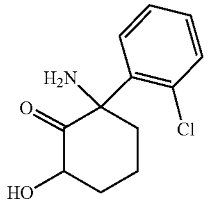

6-hydronorketamine
("hydroxynorketamine")

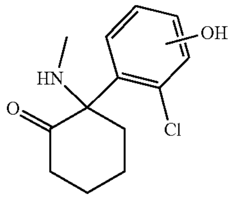

Hydroxyphenylketamine

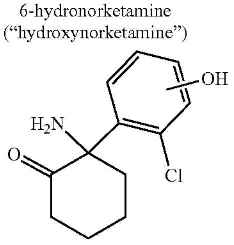

Hydroxyphenylnorketamine

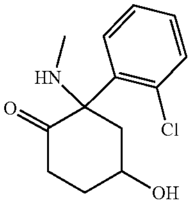

4-hydroxyketamine

Each of these metabolites has a unique receptor binding profile and pharmacological activity. See, e.g., Zanos, et al., Pharmacol. Rev., Vol. 70, No. 3, pp. 621-660 (2018). For example, racemic ketamine binds to the NMDA receptor with a $K_i$ of about 1.06 (S)-norketamine and (R)-norketamine have $K_i$s of about 2.25 μM and 26.46 μM respectively, and (2S,6S)-hydroxynorketamine and (2R,6R)-hydroxynorketamine have $K_i$s of about 21.19 μM and over 100 μM, respectively. See Moaddel, et al., Eur. J. Pharmacol., Vol. 698, pp. 228-234 (2013). Ketamine and norketamine both have anesthetic activity, and subjects administered ketamine or norketamine exhibit increased movement during the anesthetic recovery phase. In contrast, the same dose of 6-hydroxynorketamine provides no anesthetic or locomotor activity. See Leung and Baillie, J. Med. Chem., Vol. 29, pp. 2396-2399 (1986). However, like ketamine, 6-hydroxynorketamine does exhibit antidepressant properties. See Pham, et al., Biol. Psychiatry, Vol. 84, No. 1, pp. e3-e6 (2018).

The present application is based, in part, on the surprising discovery that intranasal administration of racemic ketamine provides advantageous properties relative to intravenous administration of racemic ketamine or intranasal administration of (R)- or (S)-ketamine (e.g., at least about 95% (R)-ketamine, or at least about 95% (S)-ketamine). Moreover, leveraging the different physiological and psychological effects of each enantiomer of ketamine, and the corresponding metabolites may provide beneficial treatments, including treatments with reduced negative side effects, for various psychiatric disorders.

Formulations

Some embodiments provide a pharmaceutical composition comprising about 5% (w/v) to about 20% (w/v) of racemic ketamine, or a pharmaceutically acceptable salt thereof, and a pharmaceutically acceptable carrier; wherein the composition is formulated for intranasal administration.

In some embodiments, the pharmaceutical composition comprises an aqueous solution of about 7.5% (w/v) to about 15% (w/v) of racemic ketamine, or a pharmaceutically acceptable salt thereof, for example, about 7.5%, about 8%, about 8.5%, about 9%, about 9.5%, about 10%, about 10.5%, about 11%, about 11.5%, about 12%, about 12.5%, about 13%, about 13.5%, about 14%, about 14.5%, about 15%, or any value in between. In some embodiments, the pharmaceutical composition comprises an aqueous solution of about 7.5% (w/v) of racemic ketamine, or a pharmaceutically acceptable salt thereof. In some embodiments, the pharmaceutical composition comprises an aqueous solution of about 15% (w/v) of racemic ketamine, or a pharmaceutically acceptable salt thereof.

In some embodiments, the formulation provides about 30 mg to about 90 mg of racemic ketamine, or a pharmaceutically acceptable salt thereof, per dose. For example, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, or any value in between. In some embodiments, the formulation provides about 45 mg to about 75 mg of racemic ketamine, or a pharmaceutically acceptable salt thereof, per dose. In some embodiments, the formulation provides about 60 mg to about 90 mg of racemic ketamine, or a pharmaceutically acceptable salt thereof, per dose. In some embodiments, the formulation provides about 30 mg, about 60 mg, about 75 mg, or about 90 mg of racemic ketamine, or a pharmaceutically acceptable salt thereof, per dose. In some embodiments, the formulation provides about 30 mg of racemic ketamine, or a pharmaceutically acceptable salt thereof, per dose. In some embodiments, the formulation provides about 60 mg of racemic ketamine, or a pharmaceutically acceptable salt thereof, per dose. In some embodiments, the formulation provides about 75 mg of racemic ketamine, or a pharmaceutically acceptable salt thereof, per dose. In some embodiments, the formulation provides about 90 mg of racemic ketamine, or a pharmaceutically acceptable salt thereof, per dose.

In some embodiments, the formulation provides a total amount of about 30 mg to about 90 mg of racemic ketamine, or a pharmaceutically acceptable salt thereof, over two doses (e.g., two spray discharges of an intranasal delivery device). For example, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, or any value in between. In some embodiments, the formulation provides a total amount of about 45 mg to about 75 mg of racemic ketamine, or a pharmaceutically acceptable salt thereof, over two doses. In some embodiments, the formulation provides a total amount of about 60 mg to about 90 mg of racemic ketamine, or a pharmaceutically acceptable salt thereof, per dose. In some embodiments, the formulation provides a total amount of about 30 mg, about 60 mg, about 75 mg, or about 90 mg of racemic ketamine, or a pharmaceutically acceptable salt thereof, over two doses. In some embodiments, the formulation provides about 60 mg of racemic ketamine, or a pharmaceutically acceptable salt thereof, over two doses. In some embodiments, the formulation provides about 75 mg of racemic ketamine, or a pharmaceutically acceptable salt thereof, over two doses. In some embodiments, the formulation provides about 90 mg of racemic ketamine, or a pharmaceutically acceptable salt thereof, over two doses.

In some embodiments, the composition further comprises a preservative. Exemplary preservatives include, but are not limited to parabens (e.g., alkyl parabens), benzyl alcohol, chlorobutanol, benzoic acid, sorbic acid, propylene glycol, quaternary ammonium salts (e.g., benzalkonium chloride and benzethonium chloride). In some embodiments, the preservative is benzalkonium chloride. In some embodiments, the racemic ketamine is in the form of a pharmaceutically acceptable salt, such as the hydrochloride salt. In some embodiments, the composition further comprises about 0.01 mg/mL to about 0.04 mg/mL benzalkonium chloride. In some embodiments, the composition further comprises about 0.02 mg/mL benzalkonium chloride.

In some embodiments, the composition further comprises one or more excipients selected from the group consisting of surfactants, antioxidants, buffers, and absorption enhancing agents.

Exemplary surfactants include, but are not limited to ionic, nonionic, and amphoteric surface active agents. For example, Tweens, PEGs, sorbitan esters, and ethoxylated fatty acids. In some embodiments, the composition further comprises a surfactant in an amount of about 1% to about 10% surfactant (w/v).

Exemplary antioxidants include, but are not limited to tocopherols, butyl hydroxytoluene, sodium metabisulfite, potassium metabisulfite, and ascorbyl palmitate. In some embodiments, the composition further comprises an antioxidant in an amount of about 0.001% to about 5% (w/w).

Exemplary absorption enhancing agents include, but are not limited to chitosan, caproic acid salts, and cyclopentadecalactone. In some embodiments, the composition further comprises an absorption enhancing agent in an amount of about 1% to about 10% (w/w).

Exemplary buffers include, but are not limited to citrate, phosphate, acetate, lactate, fumarate, tartrate, malate, and amino acid-based buffers. In some embodiments, the composition further comprises a buffer in an amount of about 0.1% to about 5% (w/w).

In some embodiments, the pharmaceutically acceptable carrier is water or saline.

In some embodiments, the formulation is as described in Table 1.

TABLE 1

| Component | Function | Product Concentration (per mL) | Single Spray (per 0.1 mL) |
|---|---|---|---|
| Ketamine hydrochloride* | Active Ingredient | 150 mg/mL | 15 mg |
| Benzalkonium chloride | Antimicrobial preservative | 0.02 mg/mL | 0.002 mg |
| Sodium hydroxide or HCl acid solution | Adjust pH | q.s | q.s |
| Purified Water | Aqueous Medium | q.s. to 1.0 mL | q.s. to 0.1 mL |

*1 mg of Ketamine = 1.15 mg Ketamine hydrochloride

At 15 mg per single spray, the formulation described in Table 1 provides a dose of 30 mg at 2 sprays, a dose of 60 mg at 4 sprays, and a dose of 90 mg at 6 sprays.

In some embodiments, the formulation is as described in Table 2.

TABLE 2

| Component | Function | Product Concentration (per mL) | Single Spray (per 0.1 mL) |
|---|---|---|---|
| Ketamine hydrochloride* | Active Ingredient | 75 mg/mL | 7.5 mg |
| Benzalkonium chloride | Antimicrobial preservative | 0.02 mg/mL | 0.002 mg |
| Sodium hydroxide or HCl acid solution | Adjust pH | q.s | q.s |
| Purified Water | Aqueous Medium | q.s. to 1.0 mL | q.s. to 0.1 mL |

*1 mg of Ketamine = 1.15 mg Ketamine hydrochloride

At 7.5 mg per single spray, the formulation described in Table 2 provides a dose of 30 mg at 4 sprays, a dose of 60 mg at 8 sprays, and a dose of 90 mg at 12 sprays.

Methods of Treatment

Some embodiments provide a method for a treating psychiatric disorder (e.g., suicidality, suicidal ideation, major depressive disorder, treatment-resistant depression, or post-traumatic stress disorder) in a subject in need thereof, comprising intranasally administering a therapeutically effective amount of racemic ketamine, or a pharmaceutically acceptable salt thereof, to the subject.

Some embodiments provide a method for treating suicidality in a subject in need thereof, comprising intranasally administering a therapeutically effective amount of racemic ketamine, or a pharmaceutically acceptable salt thereof, to the subject.

Some embodiments provide a method for treating suicidal ideation in a subject in need thereof, comprising intranasally administering a therapeutically effective amount of racemic ketamine, or a pharmaceutically acceptable salt thereof, to the subject.

Some embodiments provide a method for treating major depressive disorder in a subject in need thereof, comprising intranasally administering a therapeutically effective amount of racemic ketamine, or a pharmaceutically acceptable salt thereof, to the subject.

In some embodiments described herein, the psychiatric disorder resolves faster relative to the resolution observed after administration of an equivalent dose of intravenous racemic ketamine, or a pharmaceutically acceptable salt thereof. For example, in some embodiments, the suicidality, suicidal ideation, major depressive disorder, treatment resistant depression, or post-traumatic stress disorder of the subject resolves faster. In some embodiments, the psychiatric disorder resolves from about 1.2× faster to about 10× faster relative to the resolution observed after administration of an equivalent dose of intravenous racemic ketamine, or a pharmaceutically acceptable salt thereof, such as 1.2×, 1.4×, 1.6×, 1.8×, 2×, 2.5×, 3×, 3.5×, 4×, 4.5×, 5×, 5.5×, 6×, 6.5×, 7×, 7.5×, 8×, 8.5×, 9×, 9.5×, 10× faster, or any value in between.

In some embodiments described herein, the psychiatric disorder resolves faster relative to the resolution observed following administration of an equivalent dose of (S)-ketamine (e.g., intranasal (S)-ketamine), or a pharmaceutically acceptable salt thereof. For example, in some embodiments, the suicidality, suicidal ideation, major depressive disorder, treatment resistant depression, or post-traumatic stress disorder of the subject resolves faster. In some embodiments, the psychiatric disorder resolves from about 1.2× faster to about 10× faster relative to the resolution observed following administration of an equivalent dose of (S)-ketamine, or a pharmaceutically acceptable salt thereof, such as 1.2×, 1.4×, 1.6×, 1.8×, 2×, 2.5×, 3×, 3.5×, 4×, 4.5×, 5×, 5.5×, 6×, 6.5×, 7×, 7.5×, 8×, 8.5×, 9×, 9.5×, 10× faster, or any value in between.

In some embodiments described herein, the subject compliance with treatment for a psychiatric disorder is improved relative to an equivalent dose of intravenous racemic ketamine, or a pharmaceutically acceptable salt thereof. In some embodiments described herein, the subject compliance with treatment for a psychiatric disorder is improved relative to an equivalent dose of (S)-ketamine, or a pharmaceutically acceptable salt thereof. For example, the subject compliance with treatment for suicidality, suicidal ideation, major depressive disorder, treatment-resistant depression, or post-traumatic stress disorder is improved.

Many methods can be used to measure suicidality and/or suicidal ideation in a subject. Non-limiting examples include the Mini International Psychiatric Interview Version 7.02 for Suicidality Disorders (MINI), Clinical Global Impression (CGI), Patient Global Impression (PGI), the Columbia-Suicide Severity Rating Scale (CSSRS), the Montgomery-Åsberg Depression Rating Scale (MADRS), and the Sheehan Suicide Tracking Scale Clinically Meaningful Change Measure (STS-CMCM). See, e.g., Ghasemi et al., Health Promot. Perspect., Vol. 5, No. 3, pp. 156-168 (2015), which is incorporated by reference herein in its entirety.

The MINI for Suicidality Disorders for DSM-5 is a semi-structured clinical interview that can be administered (e.g., at screening) to confirm a primary diagnosis of MDD, to evaluate current suicidal ideation and behavior (SIB), and to assess for comorbid neuropsychiatric disorders. The MINI can inform and complement a full psychiatric intake examination when administered by a qualified and trained. See, e.g., Sheehan et al. J. Clin Psychiatry, 1998; 59(suppl 20): 22-33; Sheehan and Giddens (2015). Suicidality: A Roadmap for Assessment and Treatment. (1st ed.). Tampa, FL: Harm Research Press. November 2015 (Available from: HarmResearch.org) ISBN: 978-0-9969729-0-1; and Sheehan and Giddens. (2016). Suicidality Assessment and Documentation for Healthcare Providers: A Brief, Practical Guide. (1st ed.). Tampa, FL: Harm Research Press. April 2016. (Available from: HarmResearch.org) ISBN: 978-0-9969729-1-8).

The S-STS CMCM (version 01/01/19) is a clinician-rated outcome measure which assesses SIB on a standard 22-item scale, as well as multiple patient and clinician-rated items. The first 16 items are rated on a Likert-type scale ranging from "not at all" (0) to "extremely" (4), where select scoring (i.e., 4 specific items are scored based on the highest score on 2 of those items) yields a total score ranging from 0 to 52. The final 6 items are used only when the patient misses a visit and is unable to complete the scale; if that missed visit is due to attempted or completed suicide, the possible maximum score is 100. The CMCM also yields 5 different single-item global assessments: 1) subject-rated likelihood of a suicide attempt; 2) subject-rated treatment needed; 3) clinician global severity of suicidal impulses, thoughts, and behaviors; 4) clinician judgment of suicide risk at this time and level of management needed for suicidality; and 5) clinician judgment of subject's likelihood of making a suicide attempt or of dying by suicide in the next 7 days.

In some embodiments, the S-STS CMCM total score of the subject is decreased by about 15 points to about 25 points 24 hours after intranasal administration of racemic ketamine. In some embodiments, the S-STS CMCM total score is decreased by about 15 points to about 20 points, about 17 points to about 22 points, or about 20 points to about 25 points.

The CGIS-SI/B scale is a 5-item clinician-rated measure of suicidality-specific symptom severity. Clinicians rate the most severe level of suicidality experienced by the subject during the specified recall period (e.g., at screening, at baseline, or before intranasal administration of racemic ketamine as described herein), with response reported on a 5-point Likert-type scale ranging from 1 (not at all suicidal) to 5 (among the most extremely suicidal). The clinician can subsequently rate how much a subject's suicidality changed compared with their condition at baseline also on a 5 point Likert-type scale ranging from 1 (very much improved) to 5 (very much worse). See, e.g., Meltzer et al. Arch Gen Psychiatry. 2003; 60(1):82-91.

In some embodiments, the CGIS-SI/B score of the subject is 4 or greater prior to intranasal administration of the racemic ketamine, or a pharmaceutically acceptable salt thereof. In some embodiments, the CGIS-SI/B score is 4 or greater, about 5 minutes to about 24 hours prior to intranasal administration of the racemic ketamine, or a pharmaceutically acceptable salt thereof. For example, about 5 minutes to 1 hour, about 5 minutes to 6 hours, about 5 minutes to 12 hours, about 5 minutes to 18 hours, about 18 hours to 24 hours, about 12 hours to 24 hours, or about 6 hours to 24 hours prior to intranasal administration of the racemic ketamine, or a pharmaceutically acceptable salt thereof. In some embodiments, the CGIS-SI/B score of the subject is 4, 5, 6, or 7, about 1 hour to about 4 hours, about 1.5 hours to about 5 hours, about 2 hours to about 6 hours, or about 5 hours to about 10 hours, prior to intranasal administration of the racemic ketamine, or a pharmaceutically acceptable salt thereof.

In some embodiments, the CGIS-SI/B score decreases by 1 to 4 (e.g., by 1 to 4 units) after intranasal administration of the racemic ketamine, or a pharmaceutically acceptable salt thereof. In some embodiments, the CGIS-SI/B score decreases by 1 to 3 (e.g., 1 to 3 units) after intranasal administration of the racemic ketamine, or a pharmaceutically acceptable salt thereof. In some embodiments, the CGIS-SI/B score decreases by 1 to 2 (e.g., 1 to 2 units) after intranasal administration of the racemic ketamine, or a pharmaceutically acceptable salt thereof. In some embodiments, the CGIS-SI/B score of the subject is decreased by 3 or 4 points 24 hours after intranasal administration of racemic ketamine, or a pharmaceutically acceptable salt thereof. In some embodiments, the CGIS-SI/B score of the subject is decreased by 3 points. In some embodiments, the CGIS-SI/B score of the subject is decreased by 4 points.

In some embodiments, the CGIS-SI/B score is 3 or greater (e.g., 3, 4, or 5) prior to intranasal administration of the racemic ketamine, or a pharmaceutically acceptable salt thereof, and decreases by 1 to 4 after intranasal administration of the racemic ketamine, or a pharmaceutically acceptable salt thereof. In some embodiments, the CGIS-SI/B score is 4 or greater (e.g., 4 or 5) prior to intranasal administration of the racemic ketamine, or a pharmaceutically acceptable salt thereof, and decreases by 1 to 4, e.g., by 1, 2, 3, or 4, after intranasal administration of the racemic ketamine, or a pharmaceutically acceptable salt thereof. In some embodiments, the CGIS-SI/B score is 2 to 5 (e.g., 2, 3, 4, or 5) prior to intranasal administration of the racemic ketamine, or a pharmaceutically acceptable salt thereof, and decreases by 1 to 4, e.g., by 1, 2, 3, or 4 after intranasal administration of the racemic ketamine, or a pharmaceutically acceptable salt thereof. In some embodiments, the CGIS-SI/B score of the subject is 2, 3, 4, or 5 at about 5 minutes to about 24 hours prior to intranasal administration of the racemic ketamine, or a pharmaceutically acceptable salt thereof, and decreases by 1, 2, 3, or 4, about 5 minutes to about 24 hours after intranasal administration of the racemic ketamine, or a pharmaceutically acceptable salt thereof. In some embodiments, the CGIS-SI/B score of the subject is 2, 3, 4, 5 at about 1 hour to about 4 hours, about 1.5 hours to about 5 hours, about 2 hours to about 6 hours, or about 5 hours to about 10 hours, prior to intranasal administration of the racemic ketamine, or a pharmaceutically acceptable salt thereof, and decreases by 1, 2, 3, or 4, about 1 hour to about 4 hours, about 1.5 hours to about 5 hours, about 2 hours to about 6 hours, or about 5 hours to about 10 hours, after intranasal administration of the racemic ketamine, or a pharmaceutically acceptable salt thereof.

In some embodiments, a first CGIS-SI/B score is determined about 1 hour to about 12 hours prior to intranasal administration of the racemic ketamine, or a pharmaceutically acceptable salt thereof and a second CGIS-SI/B score is determined about 1 hour to about 24 hours after to intranasal administration of the racemic ketamine, or a pharmaceutically acceptable salt thereof. In some embodiments, the first CGIS-SI/B score from the subject is determined about 4 hours to about 8 hours prior to intranasal administration of the racemic ketamine, or a pharmaceutically acceptable salt thereof. In some embodiments, the second CGIS-SI/B score from the subject is determined about 4 hours to about 24 hours after intranasal administration of the racemic ketamine, or a pharmaceutically acceptable salt thereof. In some embodiments, the first CGIS-SI/B score and the second CGIS-SI/B score are determined at equivalent times before, and after, administration of the racemic ketamine, or a pharmaceutically acceptable salt thereof, such as 4 hours. In some embodiments, the first CGIS-SI/B score and the second CGIS-SI/B score are determined at different times before, and after, administration of the racemic ketamine, or a pharmaceutically acceptable salt thereof, such as 4 hours before, and 12 hours after, administration of the racemic ketamine, or a pharmaceutically acceptable salt thereof.

The PGIS-SI/B is a 5-point, subject-rated scale for assessing a subject's view of the general severity of their illness, which is rated on a single-item Likert-type scale ranging from 1 (not at all suicidal) to 5 (extremely suicidal). The PGIS-SI/B and PGIC-SI/B scales can be administered at various time points (e.g., before intranasal administration of racemic ketamine as described herein or after one or more doses of the racemic ketamine). See, e.g., Mohebbi et al. Eur Psychiatry. 2018; 53:17-22.

In some embodiments, the PGIS-SI/B score of the subject is 3 or greater prior to intranasal administration of the racemic ketamine, or a pharmaceutically acceptable salt thereof. In some embodiments, the PGIS-SI/B score is 3 or greater, about 5 minutes to about 24 hours prior to intranasal administration of the racemic ketamine, or a pharmaceutically acceptable salt thereof. For example, about 5 minutes to 1 hour, about 5 minutes to 6 hours, about 5 minutes to 12 hours, about 5 minutes to 18 hours, about 18 hours to 24 hours, about 12 hours to 24 hours, or about 6 hours to 24 hours prior to intranasal administration of the racemic ketamine, or a pharmaceutically acceptable salt thereof. In some embodiments, the PGIS-SI/B score of the subject is 3, 4, or 5, about 1 hour to about 4 hours, about 1.5 hours to about 5 hours, about 2 hours to about 6 hours, or about 5 hours to about 10 hours, prior to intranasal administration of the racemic ketamine, or a pharmaceutically acceptable salt thereof.

In some embodiments, the PGIS-SI/B score decreases by 1 to 4 (e.g., by 1 to 4 units) after intranasal administration of the racemic ketamine, or a pharmaceutically acceptable salt thereof. In some embodiments, the PGIS-SI/B score decreases by 1 to 3 (e.g., 1 to 3 units) after intranasal administration of the racemic ketamine, or a pharmaceutically acceptable salt thereof. In some embodiments, the PGIS-SI/B score decreases by 1 to 2 (e.g., 1 to 2 units) after intranasal administration of the racemic ketamine, or a pharmaceutically acceptable salt thereof.

In some embodiments, the PGIS-SI/B score is 3 or greater (e.g., 3, 4, or 5) prior to intranasal administration of the racemic ketamine, or a pharmaceutically acceptable salt thereof, and decreases by 1 to 6 after intranasal administration of the racemic ketamine, or a pharmaceutically acceptable salt thereof. In some embodiments, the PGIS-SI/B score is 4 or greater (e.g., 4 or 5) prior to intranasal administration of the racemic ketamine, or a pharmaceutically acceptable salt thereof, and decreases by 1 to 4, e.g., by 1, 2, 3, or 4, after intranasal administration of the racemic ketamine, or a pharmaceutically acceptable salt thereof. In some embodiments, the PGIS-SI/B score is 3 to 5 (e.g., 3, 4, or 5) prior to intranasal administration of the racemic ketamine, or a pharmaceutically acceptable salt thereof, and decreases by 1 to 4, e.g., by 1, 2, 3, or 4 after intranasal administration of the racemic ketamine, or a pharmaceutically acceptable salt thereof. In some embodiments, the PGIS-SI/B score of the subject is 2, 3, 4, or 5, about 5 minutes to about 24 hours prior to intranasal administration of the racemic ketamine, or a pharmaceutically acceptable salt thereof, and decreases by 1, 2, 3, or 4, about 5 minutes to about 24 hours after intranasal administration of the racemic ketamine, or a pharmaceutically acceptable salt thereof. In some embodiments, the PGIS-SI/B score of the subject is 2, 3, 4, or 5 between about 1 hour to about 4 hours, about 1.5 hours to about 5 hours, about 2 hours to about 6 hours, or about 5 hours to about 10 hours, prior to intranasal administration of the racemic ketamine, or a pharmaceutically acceptable salt thereof, and decreases by 1, 2, 3, or 4, about 1 hour to about 4 hours, about 1.5 hours to about 5 hours, about 2 hours to about 6 hours, or about 5 hours to about 10 hours, after intranasal administration of the racemic ketamine, or a pharmaceutically acceptable salt thereof. In some embodiments, the PGIS-SI/B score of the subject is decreased by 3 or 4 points 24 hours after intranasal administration of racemic ketamine. In some embodiments, the PGIS-SI/B score of the subject is decreased by 3 points. In some embodiments, the PGIS-SI/B score of the subject is decreased by 4 points.

In some embodiments, a first PGIS-SI/B score is determined about 1 hour to about 12 hours prior to intranasal administration of the racemic ketamine, or a pharmaceutically acceptable salt thereof and a second PGIS-SI/B score is determined about 1 hour to about 24 hours after to intranasal administration of the racemic ketamine, or a pharmaceutically acceptable salt thereof. In some embodiments, the first PGIS-SI/B score from the subject is determined about 4 hours to about 8 hours prior to intranasal administration of the racemic ketamine, or a pharmaceutically acceptable salt thereof. In some embodiments, the second PGIS-SI/B score from the subject is determined about 4 hours to about 24 hours after intranasal administration of the racemic ketamine, or a pharmaceutically acceptable salt thereof. In some embodiments, the first PGIS-SI/B score and the second PGIS-SI/B score are determined at equivalent times before, and after, administration of the racemic ketamine, or a pharmaceutically acceptable salt thereof, such as 4 hours. In some embodiments, the first PGIS-SI/B score and the second PGIS-SI/B score are determined at different times before, and after, administration of the racemic ketamine, or a pharmaceutically acceptable salt thereof, such as 4 hours before, and 12 hours after, administration of the racemic ketamine, or a pharmaceutically acceptable salt thereof.

In some embodiments, the CSSRS is used to measure suicidality and/or suicidal ideation in a subject. The CSSRS can assess both suicidal behavior and ideation in a subject. For example, the CSSRS can assess the lethality of suicide attempts and other features of suicidal ideation such as frequency, duration, controllability, reasons for ideation, and deterrents, all of which can be significantly predictive of completed suicide. See, e.g., www.med.upenn.edu/cbti/assets/user-content/documents/Columbia-Suicide %20Severity %20Rating %20Scales %20(C-SSRS).pdf. In some embodiments, the CSSRS can be used to provide a summary of suicidal ideation and behavior in a subject.

The CSSRS provides several questions directed to suicidal ideation that the subject answers with a "yes" or a "no." Such questions are directed to a wish to be dead; nonspecific active suicidal thoughts; active suicidal ideation with any methods (not a plan) without intent to act; active suicidal ideation with some intent to act; without a specific plan; and active suicidal ideation with specific plan and intent. Additionally, the CSSRS includes features that are rated by the subject to help assess the intensity of ideation. Such features include asking about the frequency (e.g., less than one a week, once a week, 2-5 times a week, daily or almost daily, and many times each day); duration (e.g., fleeting, less than an hour, 1-4 hours, 4-8 hours, more than 8 hours); controllability (e.g., easily able to control thoughts, can control thoughts with little difficulty, can control thoughts with some difficulty, can control thoughts with a lot of difficulty, unable to control thoughts, and does not attempt to control thoughts); deterrents (e.g., deterrents definitely stopped you from attempting suicide, deterrents probably stopped you, uncertain deterrent stopped you, deterrent most likely did not stop you, and deterrents definitely did not stop you); and reasons for ideation (e.g., completely to get attention, mostly to get attention, equally to get attention and to end/stop pain, mostly to end/stop pain, and completely to end/stop pain). The CSSRS can also include questions directed to suicidal behavior and an actual suicide attempt such as asking about if an attempt was made; asking if anything was done to cause harm to one's self, and asking if the subject has done anything dangerous where he or she could have died.

In some embodiments, the CSSRS score is 3 or greater prior to intranasal administration of the racemic ketamine, or a pharmaceutically acceptable salt thereof. For example, the subject answers "yes" to 3, 4, 5, 6, or 7 questions prior to intranasal administration of the racemic ketamine, or a pharmaceutically acceptable salt thereof. In some embodiments, the subject answers "yes" to 4, 5, 6 or 7 questions on the CSSRS as described herein, about 5 minutes to about 24 hours prior to intranasal administration of the racemic ketamine, or a pharmaceutically acceptable salt thereof. For example, about 5 minutes to 1 hour, about 5 minutes to 6 hours, about 5 minutes to 12 hours, about 5 minutes to 18 hours, about 18 hours to 24 hours, about 12 hours to 24 hours, or about 6 hours to 24 hours prior to intranasal administration of the racemic ketamine, or a pharmaceutically acceptable salt thereof. In some embodiments, the subject answers "yes" to 3, 4, 5, 6, or 7 questions on the CSSRS described herein, about 1 hour to about 4 hours, about 1.5 hours to about 5 hours, about 2 hours to about 6 hours, or about 5 hours to about 10 hours, prior to intranasal administration of the racemic ketamine, or a pharmaceutically acceptable salt thereof.

In some embodiments, the CSSRS score decreases by 1 to 7 (e.g., by 1 to 7 units) after intranasal administration of the racemic ketamine, or a pharmaceutically acceptable salt thereof. For example, the subject answers "yes" to 1, 2, 3, 4, 5, 6, or 7 fewer questions after intranasal administration of the racemic ketamine, or a pharmaceutically acceptable salt thereof. In some embodiments, the CSSRS decreases by 1 to 5 (e.g., 1 to 5 units) after intranasal administration of the racemic ketamine, or a pharmaceutically acceptable salt thereof. In some embodiments, the CSSRS decreases by 1 to 3 (e.g., 1 to 3 units) after intranasal administration of the racemic ketamine, or a pharmaceutically acceptable salt thereof.

In some embodiments, the CSSRS score is 3 or greater (e.g., 3, 4, 5, 6, or 7) prior to intranasal administration of the racemic ketamine, or a pharmaceutically acceptable salt thereof, and decreases by 1 to 7 after intranasal administration of the racemic ketamine, or a pharmaceutically acceptable salt thereof. For example, the subject answers "yes" to 3, 4, 5, 6, or 7 questions prior to intranasal administration of the racemic ketamine, or a pharmaceutically acceptable salt thereof, and answers "yes" to 1, 2, 3, 4, 5, 6, or 7 fewer questions after intranasal administration of the racemic ketamine, or a pharmaceutically acceptable salt thereof. In some embodiments, the CSSRS score is 6 or greater (e.g., 6 or 7) prior to intranasal administration of the racemic ketamine, or a pharmaceutically acceptable salt thereof, and decreases by 1 to 7, e.g., by 1, 2, 3, 4, 5, 6, or 7, after intranasal administration of the racemic ketamine, or a pharmaceutically acceptable salt thereof. In some embodiments, the CSSRS score is 3 to 5 (e.g., 3, 4, or 5) prior to intranasal administration of the racemic ketamine, or a pharmaceutically acceptable salt thereof, and decreases by 1 to 5, e.g., by 1, 2, 3, 4, or 5, after intranasal administration of the racemic ketamine, or a pharmaceutically acceptable salt thereof. In some embodiments, the subject answers "yes" to 3, 4, 5, 6 or 7 questions on the CSSRS as described herein, about 5 minutes to about 24 hours prior to intranasal administration of the racemic ketamine, or a pharmaceutically acceptable salt thereof, and answers "yes" to 1, 2, 3, 4, 5, 6, or 7 fewer questions 5 minutes to about 24 hours after intranasal administration of the racemic ketamine, or a pharmaceutically acceptable salt thereof. For example, the subject answers "yes" to 3, 4, 5, 6 or 7 questions on the CSSRS, about 5 minutes to 1 hour, about 5 minutes to 6 hours, about 5 minutes to 12 hours, about 5 minutes to 18 hours, about 18 hours to 24 hours, about 12 hours to 24 hours, or about 6 hours to 24 hours prior to intranasal administration of the racemic ketamine, or a pharmaceutically acceptable salt thereof, and answers "yes" to 1, 2, 3, 4, 5, 6, or 7 fewer questions, about 5 minutes to 1 hour, about 5 minutes to 6 hours, about 5 minutes to 12 hours, about 5 minutes to 18 hours, about 18 hours to 24 hours, about 12 hours to 24 hours, or about 6 hours to 24 hours after intranasal administration of the racemic ketamine, or a pharmaceutically acceptable salt thereof. In some embodiments, the subject answers "yes" to 3, 4, 5, 6, or 7 questions on the CSSRS described herein, about 1 hour to about 4 hours, about 1.5 hours to about 5 hours, about 2 hours to about 6 hours, or about 5 hours to about 10 hours, prior to intranasal administration of the racemic ketamine, or a pharmaceutically acceptable salt thereof, and answers "yes" to 1, 2, 3, 4, 5, 6, or 7 fewer questions, about 1 hour to about 4 hours, about 1.5 hours to about 5 hours, about 2 hours to about 6 hours, or about 5 hours to about 10 hours, after intranasal administration of the racemic ketamine, or a pharmaceutically acceptable salt thereof.

In some embodiments, a first CSSRS score is determined about 1 hour to about 12 hours prior to intranasal administration of the racemic ketamine, or a pharmaceutically acceptable salt thereof; and a second CSSRS score is determined about 1 hour to about 24 hours after to intranasal administration of the racemic ketamine, or a pharmaceutically acceptable salt thereof. In some embodiments, the first CSSRS score from the subject is determined about 4 hours to about 8 hours prior to intranasal administration of the racemic ketamine, or a pharmaceutically acceptable salt thereof. In some embodiments, the second CSSRS score from the subject is determined about 4 hours to about 8 hours after intranasal administration of the racemic ketamine, or a pharmaceutically acceptable salt thereof. In some embodiments, the first CSSRS score and the second CSSRS score are determined at equivalent times before, and after, administration of the racemic ketamine, or a pharmaceutically acceptable salt thereof, such as 4 hours. In some embodiments, the first CSSRS score and the second CSSRS score are determined at different times before, and after, administration of the racemic ketamine, or a pharmaceutically acceptable salt thereof, such as 4 hours before, and 12 hours after, administration of the racemic ketamine, or a pharmaceutically acceptable salt thereof.

Two versions of the CSSRS can be used: a Baseline version, which can assess lifetime and twelve month suicidal ideation and behavior in a subject, and a "Since Last Visit" version, which can assess suicidal thoughts or behaviors the subject may have had since the last time the CSSRS was administered to the subject. For example, a subject should only respond "yes" to being asked about making a suicide attempt in the "Since Last Visit" version, if the attempt was made after the Baseline version of the CSSRS was administered. In some embodiments, a subject is administered the Baseline version of the CSSRS prior to intranasal administration of racemic ketamine as described herein. For example, the Baseline version of the CSSRS can be administered about 1 hour to about 6 months prior to intranasal administration of racemic ketamine as described herein. In some embodiments, the Baseline version of the CSSRS is administered about 1 hour to about 6 hours, about 1 hour to about 1 day, about 1 hour to about 1 week, about 1 hour to about 1 month, about 1 hour about 3 months, about 3 months to about 6 months, about 1 month to about 6 months, about 1 week to about 5 months, or about 1 day to about 6 months prior to intranasal administration of racemic ketamine as described herein.

In some embodiments, occurrence of suicidal ideation after baseline is defined as having answered "yes" to at least 1 of the 5 suicidal ideation subcategories (i.e., wish to be dead; nonspecific active suicidal thoughts; active suicidal ideation with any methods without intent to act; active suicidal ideation with some intent to act; and active suicidal ideation with specific plan and intent) at a CSSRS administration after the Baseline CSSRS. In some embodiments, occurrence of suicidal behavior after baseline is defined as having answered "yes" to at least 1 of the 4 suicidal behavior sub-categories (i.e., actual attempt, interrupted attempt, aborted attempt, and preparatory acts or behavior) at a CSSRS administration after the Baseline CSSRS. In some embodiments, a trained rater with complete the CSSRS based on responses from the subject.

In some embodiments, the Since Last Visit version of the CSSRS is administered to the subject after intranasal administration of the racemic ketamine, or a pharmaceutically acceptable salt thereof, as described herein. In some embodiments, the CSSRS is administered to the subject, about 5 minutes to about 24 hours after intranasal administration of the racemic ketamine, or a pharmaceutically acceptable salt thereof, to the subject. For example, about 5 minutes to 1 hour, about 5 minutes to 6 hours, about 5 minutes to 12 hours, about 5 minutes to 18 hours, about 18 hours to 24 hours, about 12 hours to 24 hours, or about 6 hours to 24 hours after intranasal administration of the racemic ketamine, or a pharmaceutically acceptable salt thereof, to the subject. In some embodiments, the CSSRS is administered to the subject, about 5 minutes to 1 hour, about 5 minutes to 6 hours, about 5 minutes to 12 hours, about 5 minutes to 18 hours, about 18 hours to 24 hours, about 12 hours to 24 hours, or about 6 hours to 24 hours after intranasal administration of the racemic ketamine, or a pharmaceutically acceptable salt thereof, to the subject.

In some embodiments, CSSRS score is about 0 to about 2 after intranasal administration of racemic ketamine, or a pharmaceutically acceptable salt thereof, as described herein. For example, the subject answers "yes" to 0, 1, or 2 questions on the CSSRS after intranasal administration of racemic ketamine as described herein. In some embodiments, the CSSRS score of the subject is as described herein about 5 minutes to about 24 hours after intranasal administration of the racemic ketamine, or a pharmaceutically acceptable salt thereof. For example, about 5 minutes to 1 hour, about 5 minutes to 6 hours, about 5 minutes to 12 hours, about 5 minutes to 18 hours, about 18 hours to 24 hours, about 12 hours to 24 hours, or about 6 hours to 24 hours after intranasal administration of the racemic ketamine, or a pharmaceutically acceptable salt thereof. In some embodiments, the subject answers "yes" to 0, 1, or 2 questions on the CSSRS, about 1 hour to about 4 hours, about 2 to about 12 hours, about 1.5 hours to about 5 hours, about 2 hours to about 6 hours, about 4 to about 8 hours, about 5 hours to about 10 hours, or about 45 minutes to about 24 hours after intranasal administration of the racemic ketamine, or a pharmaceutically acceptable salt thereof. In some embodiments, the CSSRS is the Since Last Visit version of the CSSRS.

In some embodiments, the subject has an intensity of ideation on the CSSRS of about 0 to about 5 after intranasal administration of the racemic ketamine, or a pharmaceutically acceptable salt thereof. For example, the intensity of ideation of the subject can be 0, 1, 2, 3, 4, or 5 after intranasal administration of the racemic ketamine, or a pharmaceutically acceptable salt thereof. In some embodiments, the intensity of ideation of the subject is as described herein about 5 minutes to about 24 hours after intranasal administration of the racemic ketamine, or a pharmaceutically acceptable salt thereof. For example, about 5 minutes to 1 hour, about 5 minutes to 6 hours, about 5 minutes to 12 hours, about 5 minutes to 18 hours, about 18 hours to 24 hours, about 12 hours to 24 hours, or about 6 hours to 24 hours after intranasal administration of the racemic ketamine, or a pharmaceutically acceptable salt thereof. In some embodiments, the intensity of ideation of the subject is as described herein, about 1 hour to about 4 hours, about 1.5 hours to about 5 hours, about 2 hours to about 6 hours, or about 5 hours to about 10 hours, after intranasal administration of the racemic ketamine, or a pharmaceutically acceptable salt thereof. In some embodiments, the Since Last Version of the CSSRS is administered after intranasal administration of the racemic ketamine, or a pharmaceutically acceptable salt thereof.

In some embodiments, CSSRS score is reduced by about 1 to about 7 after intranasal administration of the racemic ketamine, or a pharmaceutically acceptable salt thereof. For example, the subject can answer “yes” to 1, 2, 3, 4, 5, 6 or 7 fewer questions after intranasal administration of the racemic ketamine, or a pharmaceutically acceptable salt thereof, relative to the number of questions the subject answered “yes” to on the CSSRS prior to intranasal administration of the racemic ketamine, or a pharmaceutically acceptable salt thereof. In some embodiments, the subject answers “yes” to 1, 2, 3, 4, 5, 6 or 7 fewer questions on the CSSRS as described herein, about 5 minutes to about 24 hours after intranasal administration of the racemic ketamine, or a pharmaceutically acceptable salt thereof. For example, about 5 minutes to 1 hour, about 5 minutes to 6 hours, about 5 minutes to 12 hours, about 5 minutes to 18 hours, about 18 hours to 24 hours, about 12 hours to 24 hours, or about 6 hours to 24 hours after intranasal administration of the racemic ketamine, or a pharmaceutically acceptable salt thereof. In some embodiments, the subject answers “yes” to 1, 2, 3, 4, 5, 6 or 7 fewer questions on the CSSRS described herein, about 1 hour to about 4 hours, about 1.5 hours to about 5 hours, about 2 hours to about 6 hours, or about 5 hours to about 10 hours, after intranasal administration of the racemic ketamine, or a pharmaceutically acceptable salt thereof (e.g., relative to prior to intranasal administration of the racemic ketamine, or a pharmaceutically acceptable salt thereof). In some embodiments, the Since Last Version of the CSSRS is administered after intranasal administration of the racemic ketamine, or a pharmaceutically acceptable salt thereof. In some embodiments, the Baseline version of the CSSRS is administered prior to intranasal administration of the racemic ketamine, or a pharmaceutically acceptable salt thereof.

In some embodiments, the subject has a lower intensity of ideation on the CSSRS after intranasal administration of the racemic ketamine, or a pharmaceutically acceptable salt thereof. For example, the intensity of ideation of the subject can be reduced by about 1 to about 25 after intranasal administration of the racemic ketamine, or a pharmaceutically acceptable salt thereof, relative to the intensity of ideation of the subject prior to intranasal administration of the racemic ketamine, or a pharmaceutically acceptable salt thereof. In some embodiments, the intensity of ideation of the subject can be reduced by about 1 to about 5, about 1 to about 10, about 1 to about 15, about 1 to about 20, about 20 to about 25, about 15 to about 25, about 10 to about 25, or about 5 to about 25 after intranasal administration of the racemic ketamine, or a pharmaceutically acceptable salt thereof, relative to the intensity of ideation of the subject prior to intranasal administration of the racemic ketamine, or a pharmaceutically acceptable salt thereof. In some embodiments, the intensity of ideation of the subject as described herein is reduced about 5 minutes to about 24 hours after intranasal administration of the racemic ketamine, or a pharmaceutically acceptable salt thereof. For example, about 5 minutes to 1 hour, about 5 minutes to 6 hours, about 5 minutes to 12 hours, about 5 minutes to 18 hours, about 18 hours to 24 hours, about 12 hours to 24 hours, or about 6 hours to 24 hours after intranasal administration of the racemic ketamine, or a pharmaceutically acceptable salt thereof. In some embodiments, the intensity of ideation of the subject is reduced as described herein, about 1 hour to about 4 hours, about 1.5 hours to about 5 hours, about 2 hours to about 6 hours, or about 5 hours to about 10 hours, after intranasal administration of the racemic ketamine, or a pharmaceutically acceptable salt thereof (e.g., relative to prior to intranasal administration of the racemic ketamine, or a pharmaceutically acceptable salt thereof). In some embodiments, the Since Last Version of the CSSRS is administered after intranasal administration of the racemic ketamine, or a pharmaceutically acceptable salt thereof. In some embodiments, the Baseline version of the CSSRS is administered prior to intranasal administration of the racemic ketamine, or a pharmaceutically acceptable salt thereof.

In some embodiments, the CSSRS score in a subject administered intranasal racemic ketamine, or a pharmaceutically acceptable salt thereof, is about 1 to about 7 points less than a subject administered an equivalent dose of intravenous racemic ketamine, or a pharmaceutically acceptable salt thereof, or (S)-ketamine, or a pharmaceutically acceptable salt thereof.

In some embodiments, the CSSRS score in a subject administered intranasal racemic ketamine, or a pharmaceutically acceptable salt thereof, improves at a faster rate than a subject administered an equivalent dose of intravenous racemic ketamine, or a pharmaceutically acceptable salt thereof, or (S)-ketamine, or a pharmaceutically acceptable salt thereof. For example, the CSSRS score improves at a rate of 0.25 points/hr, 0.5 points/hr, 0.75 points/hr, 1 point/hr, 1.25 points/hr, 1.5 points/hr, 1.75 points/hr, 2 points/hr, 2.25 points/hr, 2.5 points/hr, 2.75 points/hr, 3 points/hr, 3.25 points/hr, 3.5 points/hr, 3.75 points/hr, 4 points/hr, or any value in between, faster than a subject administered an equivalent dose of intravenous racemic ketamine, or a pharmaceutically acceptable salt thereof, or (S)-ketamine, or a pharmaceutically acceptable salt thereof.

The Montgomery-Åsberg Depression Rating Scale (MADRS) is a diagnostic questionnaire that can be used to measure the severity of a depressive episode in a subject. In some embodiments, the MADRS can be used to measure suicidal ideation. For example, the MADRS includes 10 items directed to the following: 1) apparent sadness (e.g., representing despondency, gloom and despair that is more than just ordinary transient low spirits that is reflected in speech, facial expression, and posture); 2) reported sadness (e.g., representing reports of depressed mood, regardless of whether it is reflected in appearance or not and can include low spirits, despondency or the feeling of being beyond help and without hope); 3) inner tension (e.g., representing feelings of ill-defined discomfort, edginess, inner turmoil, mental tension mounting to either panic, dread or anguish); 4) reduced sleep (e.g., representing the experience of reduced duration or depth of sleep compared to the subject's own normal pattern when well); 5) reduced appetite (e.g., representing the feeling of a loss of appetite compared with when-well); 6) concentration difficulties (e.g., representing difficulties in collecting one's thoughts mounting to an incapacitating lack of concentration); 7) lassitude (e.g., representing difficulty in getting started or slowness in initiating and performing everyday activities); 8) inability to feel (e.g., representing the subjective experience of reduced interest in the surroundings, or activities that normally give pleasure, and the ability to react with adequate emotion to circumstances or people is reduced); 9) pessimistic thoughts (e.g., representing thoughts of guilt, inferiority, self-reproach, sinfulness, remorse and ruin); and 10) suicidal thoughts (e.g., representing the feeling that life is not worth living, that a natural death would be welcome, suicidal thoughts, and preparations for suicide). Each item is rated from 0 to 6, with 0 reflecting that the subject is not at all as described by the item and 6 reflecting that the subject is extremely like what is described by the item. For example, for apparent sadness, a score of 0 can indicate that the subject does not display any sadness, whereas a score of 6 can indicate that the subject looks miserable all the time, e.g., the subject is extremely despondent. As another example, for suicidal thoughts, a score of 0 can indicate that the subject enjoys life or takes it as it comes; a score of 2 can indicate that the subject is weary of life and may have fleeting suicidal thoughts; a score of 4 can indicate that the subject feels he or she would probably be better off dead (e.g., suicidal thoughts are common, and suicide is considered as a possible solution, but without specific plans or intention); and a score of 6 can indicate that the subject has explicit plans for suicide when there is an opportunity (e.g., the subject has made active preparations for suicide). Thus, the total score, after summation of each score for each item, is on a scale of 0 to 60. In some embodiments, a total score on the MADRS of about 0 to about 6 for the subject reflects the subject does not have symptoms related to depression; a score of about 7 to about 9 reflects that the subject has mild depression; a score of about 20 to about 34 reflects that the subject has moderate depression; and a score of about 34 to about 60 reflects that the subject has severe depression.

In some embodiments, the total MADRS score of the subject is about 10 to about 60 prior to intranasal administration of racemic ketamine, or a pharmaceutically acceptable salt thereof, as described herein. For example, about 10 to about 20, about 10 to about 30, about 10 to about 40, about 10 to about 50, about 50 to about 60, about 40 to about 60, about 30 to about 60, or about 20 to about 60 prior to intranasal administration of racemic ketamine as described herein. In some embodiments, the total MADRS score of the subject is about 10, about 15, about 20, about 25, about 30, about 35, about 40, about 45, about 50, about 55, or about 60 prior to intranasal administration of racemic ketamine as described herein. In some embodiments, the total MADRS score of the subject is measured about 5 minutes to about 24 hours prior to intranasal administration of the racemic ketamine, or a pharmaceutically acceptable salt thereof. For example, about 5 minutes to 1 hour, about 5 minutes to 6 hours, about 5 minutes to 12 hours, about 5 minutes to 18 hours, about 18 hours to 24 hours, about 12 hours to 24 hours, or about 6 hours to 24 hours prior to intranasal administration of the racemic ketamine, or a pharmaceutically acceptable salt thereof. In some embodiments, the total MADRS score of the subject is as described herein, about 1 hour to about 4 hours, about 1.5 hours to about 5 hours, about 2 hours to about 6 hours, about 5 hours to about 10 hours, or about 45 minutes to about 24 hours prior to intranasal administration of the racemic ketamine, or a pharmaceutically acceptable salt thereof.

In some embodiments, the total MADRS score of the subject is about 0 to about 6 after intranasal administration of racemic ketamine, or a pharmaceutically acceptable salt thereof, as described herein. For example, about 0 to about 2, about 0 to about 3, about 0 to about 4, about 0 to about 5, about 5 to about 6, about 4 to about 6, about 3 to about 6, about 2 to about 6, or about 1 to about 6 after intranasal administration of racemic ketamine as described herein. In some embodiments, the total MADRS score of the subject is 0, 1, 2, 3, 4, 5, or 6 after intranasal administration of racemic ketamine as described herein. In some embodiments, the total MADRS score of the subject is measured at about 5 minutes to about 24 hours after intranasal administration of the racemic ketamine, or a pharmaceutically acceptable salt thereof. For example, about 5 minutes to 1 hour, about 5 minutes to 6 hours, about 5 minutes to 12 hours, about 5 minutes to 18 hours, about 18 hours to 24 hours, about 12 hours to 24 hours, or about 6 hours to 24 hours after intranasal administration of the racemic ketamine, or a pharmaceutically acceptable salt thereof. In some embodiments, the total MADRS score of the subject is as described herein, about 1 hour to about 4 hours, about 1.5 hours to about 5 hours, about 2 hours to about 6 hours, about 5 hours to about 10 hours, or about 45 minutes to about 24 hours after intranasal administration of the racemic ketamine, or a pharmaceutically acceptable salt thereof.

In some embodiments, the total MADRS score of the subject is about 10 to about 60 prior to intranasal administration of racemic ketamine, or a pharmaceutically acceptable salt thereof, and the total MADRS score of the subject is about 0 to about 6 after intranasal administration of racemic ketamine, or a pharmaceutically acceptable salt thereof. For example, about 10 to about 20, about 10 to about 30, about 10 to about 40, about 10 to about 50, about 50 to about 60, about 40 to about 60, about 30 to about 60, or about 20 to about 60 prior to intranasal administration of racemic ketamine as described herein and about 0 to about 2, about 0 to about 3, about 0 to about 4, about 0 to about 5, about 5 to about 6, about 4 to about 6, about 3 to about 6, about 2 to about 6, or about 1 to about 6 after intranasal administration of racemic ketamine as described herein. In some embodiments, the total MADRS score of the subject is about 10, about 15, about 20, about 25, about 30, about 35, about 40, about 45, about 50, about 55, or about 60 prior to intranasal administration of racemic ketamine as described herein and the total MADRS score of the subject is 0, 1, 2, 3, 4, 5, or 6 after intranasal administration of racemic ketamine as described herein. In some embodiments, the total MADRS score of the subject is measured at about 5 minutes to about 24 hours prior to intranasal administration of the racemic ketamine, or a pharmaceutically acceptable salt thereof. For example, about 5 minutes to 1 hour, about 5 minutes to 6 hours, about 5 minutes to 12 hours, about 5 minutes to 18 hours, about 18 hours to 24 hours, about 12 hours to 24 hours, or about 6 hours to 24 hours prior to intranasal administration of the racemic ketamine, or a pharmaceutically acceptable salt thereof, and about 5 minutes to 1 hour, about 5 minutes to 6 hours, about 5 minutes to 12 hours, about 5 minutes to 18 hours, about 18 hours to 24 hours, about 12 hours to 24 hours, or about 6 hours to 24 hours after intranasal administration of the racemic ketamine, or a pharmaceutically acceptable salt thereof. In some embodiments, the total MADRS score of the subject is as described herein about 1 hour to about 4 hours, about 1.5 hours to about 5 hours, about 2 hours to about 6 hours, about 5 hours to about 10 hours, or about 45 minutes to about 24 hours prior to intranasal administration of the racemic ketamine, or a pharmaceutically acceptable salt thereof, and about 1 hour to about 4 hours, about 1.5 hours to about 5 hours, about 2 hours to about 6 hours, about 5 hours to about 10 hours, or about 45 minutes to about 24 hours after intranasal administration of the racemic ketamine, or a pharmaceutically acceptable salt thereof.

In some embodiments, the total MADRS score of the subject is reduced by about 1 to about 60 after intranasal administration of the racemic ketamine, or a pharmaceutically acceptable salt thereof. For example, the total MADRS score of the subject can be reduced by about 1 to about 60 after intranasal administration of the racemic ketamine, or a pharmaceutically acceptable salt thereof, relative to prior to intranasal administration of the racemic ketamine, or a pharmaceutically acceptable salt thereof. In some embodiments, the total MADRS score of the subject is reduced by about 1 to about 50, about 1 to about 40, about 1 to about 30, about 1 to about 20, about 1 to about 10, about 50 to about 60, about 40 to about 60, about 30 to about 60, about 20 to about 60, or about 10 to about 60 after intranasal administration of the racemic ketamine, or a pharmaceutically acceptable salt thereof. In some embodiments, the total MADRS score of the subject is reduced as described herein about 5 minutes to about 24 hours after intranasal administration of the racemic ketamine, or a pharmaceutically acceptable salt thereof. For example, about 5 minutes to 1 hour, about 5 minutes to 6 hours, about 5 minutes to 12 hours, about 5 minutes to 18 hours, about 18 hours to 24 hours, about 12 hours to 24 hours, or about 6 hours to 24 hours after intranasal administration of the racemic ketamine, or a pharmaceutically acceptable salt thereof. In some embodiments, the total MADRS score of the subject is reduced as described herein about 1 hour to about 4 hours, about 1.5 hours to about 5 hours, about 2 hours to about 6 hours, or about 5 hours to about 10 hours, after intranasal administration of the racemic ketamine, or a pharmaceutically acceptable salt thereof (e.g., relative to prior to intranasal administration of the racemic ketamine, or a pharmaceutically acceptable salt thereof). In some embodiments, the MADRS total score of the subject is decreased by about 20 points to about 30 points 24 hours after intranasal administration of racemic ketamine, or a pharmaceutically acceptable salt thereof, for example, about 20-25 points, about 22-27 points, or about 25-30 points.

In some embodiments, item 10, e.g., suicidal thoughts, of the MADRS can be used to measure suicidal ideation. In some embodiments, the score for item 10 on the MADRS for the subject is 0 or 1 after intranasal administration of racemic ketamine, or a pharmaceutically acceptable salt thereof, as described herein. In some embodiments, the score for item 10 on the MADRS for the subject is as described herein about 5 minutes to about 24 hours after intranasal administration of the racemic ketamine, or a pharmaceutically acceptable salt thereof. For example, about 5 minutes to 1 hour, about 5 minutes to 6 hours, about 5 minutes to 12 hours, about 5 minutes to 18 hours, about 18 hours to 24 hours, about 12 hours to 24 hours, or about 6 hours to 24 hours after intranasal administration of the racemic ketamine, or a pharmaceutically acceptable salt thereof. In some embodiments, the score for item 10 on the MADRS for the subject is as described herein about 1 hour to about 4 hours, about 1.5 hours to about 5 hours, about 2 hours to about 6 hours, about 5 hours to about 10 hours, or about 45 minutes to about 24 hours after intranasal administration of the racemic ketamine, or a pharmaceutically acceptable salt thereof.

In some embodiments, the score for item 10 on the MADRS for the subject is reduced by 1 to 6 after intranasal administration of the racemic ketamine, or a pharmaceutically acceptable salt thereof. For example, the score for item 10 on the MADRS for the subject can be reduced by 1 to 6 after intranasal administration of the racemic ketamine, or a pharmaceutically acceptable salt thereof, relative to prior to intranasal administration of the racemic ketamine, or a pharmaceutically acceptable salt thereof. In some embodiments, the score for item 10 on the MADRS for the subject is reduced by 1 to 5, 1 to 4, 1 to 3, 1 to 2, 5 to 6, 4 to 6, 3 to 6, or 2 to 6 after intranasal administration of the racemic ketamine, or a pharmaceutically acceptable salt thereof. In some embodiments, the score for item 10 on the MADRS for the subject is reduced as described herein about 5 minutes to about 24 hours after intranasal administration of the racemic ketamine, or a pharmaceutically acceptable salt thereof. For example, about 5 minutes to 1 hour, about 5 minutes to 6 hours, about 5 minutes to 12 hours, about 5 minutes to 18 hours, about 18 hours to 24 hours, about 12 hours to 24 hours, or about 6 hours to 24 hours after intranasal administration of the racemic ketamine, or a pharmaceutically acceptable salt thereof. In some embodiments, the score for item 10 on the MADRS for the subject is reduced as described herein about 1 hour to about 4 hours, about 1.5 hours to about 5 hours, about 2 hours to about 6 hours, or about 5 hours to about 10 hours, after intranasal administration of the racemic ketamine, or a pharmaceutically acceptable salt thereof (e.g., relative to prior to intranasal administration of the racemic ketamine, or a pharmaceutically acceptable salt thereof).

In some embodiments, the MADRS item 10 score of the subject is reduced by 4, 5, or 6 points 24 hours after intranasal administration of racemic ketamine. In some embodiments, the MADRS Item 10 score of the subject is reduced by 4 points. In some embodiments, the MADRS Item 10 score of the subject is reduced by 5 points. In some embodiments, the MADRS Item 10 score of the subject is reduced by 6 points.

In some embodiments, a subject is administered the MADRS prior to intranasal administration of racemic ketamine as described herein. For example, the MADRS can be administered to the subject about 1 hour to about 6 months prior to intranasal administration of racemic ketamine as described herein. In some embodiments, the MADRS is administered to the subject about 1 hour to about 6 hours, about 1 hour to about 1 day, about 1 hour to about 1 week, about 1 hour to about 1 month, about 1 hour about 3 months, about 3 months to about 6 months, about 1 month to about 6 months, about 1 week to about 5 months, or about 1 day to about 6 months prior to intranasal administration of racemic ketamine as described herein.

The STS-CMCM is a diagnostic questionnaire that can be used to measure a change in suicidal ideation and behavior in a subject. The STS-CMCM can also provide a comprehensive description of suicidal ideation and behavior. See, e.g., Sheehan et al., Innov. Clin. Neurosci. Vol. 11, No. 9-10, pp. 93-140 (2014). The STS-CMCM includes 4 parts. The first part can include a 16 item scale that assesses the seriousness of suicidality phenomena on a scale of 0 to 4, ranging from "not at all" (0) to "extremely" (4). The second part presents the subject with a series of additional items to rate including 1) a series of risk or protective items that might be important aggravating or relieving factors in the subject's suicidal ideation and behaviors; 2) a series of 11-point (0-10) discretized visual analog (DISCAN) scales; and 3) items related to a global severity of suicidal impulses, thoughts, and behaviors rating and an opportunity for the subject to provide a self-assessment of treatment needs. The DISCAN scales can include the subject rating their ability and willingness to cope with their suicidality, their ability and willingness to "stay safe," the extent to which their suicidality is deliberate, the extent to which it is impulsive, the extent to which it has impacted the quality of their lives, and the extent to which it has impaired their work, social, or family lives. The third part includes a rating from a clinician regarding his or her judgment of the subject's suicide risk and a judgment of level of management required for the subject's suicidal ideation and behavior. The third part can also include a global assessment of suicidality based on all the information collected in the earlier sections of the scale with additional input from others and from any additional probe questions the clinician deems necessary to complete the assessment. The fourth section part can be completed by the clinician if the subject misses a follow up appointment and is unavailable, which allows completion of the scale.

In some embodiments, the STS-CMCM score of the subject is reduced by at least 2 after intranasal administration of the racemic ketamine, or a pharmaceutically acceptable salt thereof. For example, the STS-CMCM score of the subject can be reduced by at least 2, at least 3, at least 4, or at least 5 after intranasal administration of the racemic ketamine, or a pharmaceutically acceptable salt thereof, relative to prior to intranasal administration of the racemic ketamine, or a pharmaceutically acceptable salt thereof. In some embodiments, the STS-CMCM score of the subject is reduced as described herein about 5 minutes to about 24 hours after intranasal administration of the racemic ketamine, or a pharmaceutically acceptable salt thereof. For example, about 5 minutes to 1 hour, about 5 minutes to 6 hours, about 5 minutes to 12 hours, about 5 minutes to 18 hours, about 18 hours to 24 hours, about 12 hours to 24 hours, or about 6 hours to 24 hours after intranasal administration of the racemic ketamine, or a pharmaceutically acceptable salt thereof. In some embodiments, the STS-CMCM score of the subject is reduced as described herein about 1 hour to about 4 hours, about 1.5 hours to about 5 hours, about 2 hours to about 6 hours, or about 5 hours to about 10 hours, after intranasal administration of the racemic ketamine, or a pharmaceutically acceptable salt thereof (e.g., relative to prior to intranasal administration of the racemic ketamine, or a pharmaceutically acceptable salt thereof). In some embodiments, a subject is administered the STS-CMCM prior to intranasal administration of racemic ketamine as described herein. For example, the STS-CMCM can be administered to the subject about 1 hour to about 6 months prior to intranasal administration of racemic ketamine as described herein. In some embodiments, the STS-CMCM is administered to the subject about 1 hour to about 6 hours, about 1 hour to about 1 day, about 1 hour to about 1 week, about 1 hour to about 1 month, about 1 hour about 3 months, about 3 months to about 6 months, about 1 month to about 6 months, about 1 week to about 5 months, or about 1 day to about 6 months prior to intranasal administration of racemic ketamine as described herein.

In some embodiments described herein, when the subject is being administered one or more additional therapies, the subject does not experience a clinically significant weight gain relative to the administration of the one or more additional therapies in the absence of intranasal administration of racemic ketamine, or a pharmaceutically acceptable salt thereof. Clinically significant weight gain refers to an increase in body mass of at least about 5% over the course of treatment, for example, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 30%, about 35%, about 40%, about 45%, about 50%, about 55%, about 60%, about 65%, about 70%, about 75%, about 80%, about 85%, about 90%, about 95%, about 100%, or any value in between.

In some embodiments, the methods described herein provide one or more synergistic effects when the racemic ketamine, or a pharmaceutically acceptable salt thereof, is administered in combination with one or more additional therapies.

In some embodiments, the efficacy of the intranasal racemic ketamine, or a pharmaceutically acceptable salt thereof, and the one or more additional therapies, is greater than the sum of the efficacy of each individual agent when administered alone. For example, in some embodiments, the change in the CSSRS score after administration of the intranasal racemic ketamine, or a pharmaceutically acceptable salt thereof, compared to prior to administration of the intranasal racemic ketamine, or a pharmaceutically acceptable salt thereof, is greater than the change in the CSSRS score after administration of the intranasal racemic ketamine, or a pharmaceutically acceptable salt thereof, and the one or more additional therapies compared to prior to administration of the intranasal racemic ketamine, or a pharmaceutically acceptable salt thereof, and the one or more additional therapies. In some embodiments, the efficacy of the ketamine, or a pharmaceutically acceptable salt thereof, is increased. In some embodiments, the efficacy of the one or more additional therapies is increased. In some embodiments, the efficacy of both the intranasal racemic ketamine, or a pharmaceutically acceptable salt thereof, and the one or more additional therapies are increased. In some embodiments, the efficacy of the one or more additional therapies administered with the intranasal racemic ketamine, or a pharmaceutically acceptable salt thereof, is increased relative to the efficacy observed following administration with an equivalent dose of intravenous racemic ketamine, or a pharmaceutically acceptable salt thereof. In some embodiments, the efficacy of the one or more additional therapies administered with the intranasal racemic ketamine, or a pharmaceutically acceptable salt thereof, is increased relative to the efficacy observed following administration with an equivalent dose of (S)-ketamine, or a pharmaceutically acceptable salt thereof.

In some embodiments, the dose of the intranasal racemic ketamine, or a pharmaceutically acceptable salt thereof, and/or the one or more additional therapies, required to provide a therapeutic effect is reduced relative to the dose of each individual agent when administered alone. In some embodiments, the dose of the one or more additional therapies required to provide a therapeutic effect is reduced relative to the dose administering with an equivalent dose of intravenous racemic ketamine, or a pharmaceutically acceptable salt thereof. In some embodiments, the dose of the one or more additional therapies required to provide a therapeutic effect is reduced relative to the dose administering with an equivalent dose of (S)-ketamine, or a pharmaceutically acceptable salt thereof. In some embodiments, the dose of the ketamine, or a pharmaceutically acceptable salt thereof, is reduced. In some embodiments, the dose of the one or more additional therapies is reduced. In some embodiments, the dose of both the intranasal racemic ketamine, or a pharmaceutically acceptable salt thereof, and the one or more additional therapies are reduced. For example, the dose of intranasal racemic ketamine, or a pharmaceutically acceptable salt thereof, can be reduced by about 5% to about 95%, or any value in between, such as about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%. Similarly, the dose of the one or more additional therapies can be reduced by about 5% to about 95%, or any value in between, such as about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%.

In some embodiments, the onset of resistance to treatment with the intranasal racemic ketamine, or a pharmaceutically acceptable salt thereof, and the one or more additional therapies, is delayed relative to the onset of resistance to treatment with each individual agent when administered alone. In some embodiments, the onset of resistance to treatment with the one or more additional therapies is delayed relative to the onset of resistance to treatment when administered with intravenous racemic ketamine, or a pharmaceutically acceptable salt thereof. In some embodiments, the onset of resistance to treatment with the one or more additional therapies is delayed relative to the onset of resistance to treatment when administered with (S)-ketamine, or a pharmaceutically acceptable salt thereof.

In some embodiments, one or more side effects of the intranasal racemic ketamine, or a pharmaceutically acceptable salt thereof, and/or the one or more additional therapies, required to provide a therapeutic effect is reduced relative to the side effects of each individual agent when administered alone. In some embodiments, one or more side effects of the ketamine, or a pharmaceutically acceptable salt thereof, is reduced. In some embodiments, one or more side effects of the one or more additional therapies is reduced. In some embodiments, one or more side effects of the one or more additional therapies is reduced relative to the one or more side effects observed after administration with an equivalent dose of intravenous racemic ketamine, or a pharmaceutically acceptable salt thereof. In some embodiments, one or more side effects of the one or more additional therapies is reduced relative to the one or more side effects observed after administration with an equivalent dose of (S)-ketamine, or a pharmaceutically acceptable salt thereof. In some embodiments, one or more side effects of both the ketamine, or a pharmaceutically acceptable salt thereof, and the one or more additional therapies are reduced. In some embodiments, the total number of side effects is reduced. In some embodiments, the magnitude of one or more side effects is reduced. In some embodiments, both the total number of side effects is reduced and the magnitude of one or more remaining side effects is also reduced.

In some embodiments, the one or more side effects of ketamine comprise cognitive impairment, motor impairment, vertigo, nausea, vomiting, sweating, increased blood pressure, ulcerative cystitis, or interstitial cystitis. In some embodiments, the one or more side effects of ketamine consist of cognitive impairment, motor impairment, vertigo, nausea, vomiting, sweating, increased blood pressure, ulcerative cystitis, or interstitial cystitis.

In some embodiments, the cognitive impairment comprises one or more of psychotomimetic effects, dizziness, dysgeusia, sedation, dissociation, euphoria, changes in hearing, changes in vision, and hallucinations. In some embodiments, the cognitive impairment consists of one or more of psychotomimetic effects, dizziness, dysgeusia, sedation, dissociation, euphoria, changes in hearing, changes in vision, and hallucinations. In some embodiments, the cognitive impairment comprises sedation. In some embodiments, the cognitive impairment is sedation. In some embodiments, the motor impairment comprises tremors, issues with balance, or dystonic movements. In some embodiments, the motor impairment consists of one or more of tremors, issues with balance, and dystonic movements.

Many methods can be used to assess side effects associated with ketamine. Non-limiting examples of such methods include the Modified Observer's Assessment of Alertness/Sedation Scale (MOAA/S), Bowdle Visual Analog Scale (VAS), the Clinician Administered Dissociative States Scale (CADSS), the Profile of Mood States (POMS), Choice Reaction Time Test, Sternberg Short-Term Memory Task, and the Subject-Rated Assessment of Intranasal Irritation (SRAII©) (for intranasal administration of ketamine).

In some embodiments, the MOAA/S can be used to measure sedation in a subject. See, e.g., Kim et al., Br J Anaesth, Vol. 115, No. 4, pp. 569-577 (2015), which is incorporated by reference herein in its entirety. The MOAA/S is a scale from 0 to 5, where 0 indicates the patient has no response after a painful trapezius squeeze; 1 indicates the subject responds only after a painful trapezius squeeze; 2 indicates the patient responds only after mild prodding or shaking; 3 indicates the subject responds only after name is called loudly and/or repeatedly; 4 indicates the subject has a lethargic response to name spoken in normal tone; and 5 indicates the subject readily responds to name spoken in normal tone.

In some embodiments, the MOAA/S of the subject is 5 or 6 prior to intranasal administration of racemic ketamine, or a pharmaceutically acceptable salt thereof, as described herein. In some embodiments, the MOAA/S score of the subject is measured at about 5 minutes to about 24 hours prior to intranasal administration of the racemic ketamine, or a pharmaceutically acceptable salt thereof. For example, about 5 minutes to 1 hour, about 5 minutes to 6 hours, about 5 minutes to 12 hours, about 5 minutes to 18 hours, about 18 hours to 24 hours, about 12 hours to 24 hours, or about 6 hours to 24 hours prior to intranasal administration of the racemic ketamine, or a pharmaceutically acceptable salt thereof. In some embodiments, the MOAA/S score of the subject is as described herein about 1 hour to about 4 hours, about 1.5 hours to about 5 hours, about 2 hours to about 6 hours, about 5 hours to about 10 hours, or about 45 minutes to about 24 hours prior to intranasal administration of the racemic ketamine, or a pharmaceutically acceptable salt thereof.

In some embodiments, the MOAA/S of the subject is 5 or 6 after intranasal administration of racemic ketamine, or a pharmaceutically acceptable salt thereof, as described herein. In some embodiments, the MOAA/S score of the subject is measured at about 5 minutes to about 24 hours after intranasal administration of the racemic ketamine, or a pharmaceutically acceptable salt thereof. For example, about 5 minutes to 1 hour, about 5 minutes to 6 hours, about 5 minutes to 12 hours, about 5 minutes to 18 hours, about 18 hours to 24 hours, about 12 hours to 24 hours, or about 6 hours to 24 hours after intranasal administration of the racemic ketamine, or a pharmaceutically acceptable salt thereof. In some embodiments, the MOAA/S score of the subject is as described herein about 1 hour to about 4 hours, about 1.5 hours to about 5 hours, about 2 hours to about 6 hours, about 5 hours to about 10 hours, or about 45 minutes to about 24 hours after intranasal administration of the racemic ketamine, or a pharmaceutically acceptable salt thereof.

In some embodiments, the MOAA/S of the subject is 5 or 6 prior to intranasal administration of racemic ketamine, or a pharmaceutically acceptable salt thereof, and the MOAA/S of the subject is 5 or 6 after intranasal administration of racemic ketamine, or a pharmaceutically acceptable salt thereof. In some embodiments, the MOAA/S score of the subject is measured at about 5 minutes to about 24 hours prior to intranasal administration of the racemic ketamine, or a pharmaceutically acceptable salt thereof, and about 5 minutes to about 24 hours after to intranasal administration of the racemic ketamine, or a pharmaceutically acceptable salt thereof. For example, about 5 minutes to 1 hour, about 5 minutes to 6 hours, about 5 minutes to 12 hours, about 5 minutes to 18 hours, about 18 hours to 24 hours, about 12 hours to 24 hours, or about 6 hours to 24 hours prior to intranasal administration of the racemic ketamine, or a pharmaceutically acceptable salt thereof, and about 5 minutes to 1 hour, about 5 minutes to 6 hours, about 5 minutes to 12 hours, about 5 minutes to 18 hours, about 18 hours to 24 hours, about 12 hours to 24 hours, or about 6 hours to 24 hours after intranasal administration of the racemic ketamine, or a pharmaceutically acceptable salt thereof. In some embodiments, the MOAA/S score of the subject is 5 or 6 at about 1 hour to about 4 hours, about 1.5 hours to about 5 hours, about 2 hours to about 6 hours, about 5 hours to about 10 hours, or about 45 minutes to about 24 hours prior to intranasal administration of the racemic ketamine, or a pharmaceutically acceptable salt thereof, and the MOAA/S score of the subject is 5 or 6 at about 1 hour to about 4 hours, about 1.5 hours to about 5 hours, about 2 hours to about 6 hours, about 5 hours to about 10 hours, or about 45 minutes to about 24 hours after intranasal administration of the racemic ketamine, or a pharmaceutically acceptable salt thereof.

In some embodiments, the MOAA/S score of the subject is substantially the same prior to and after intranasal administration of the racemic ketamine, or a pharmaceutically acceptable salt thereof. For example, the MOAA/S score of the subject does not change (i.e., does not increase or decrease) after intranasal administration of the racemic ketamine, or a pharmaceutically acceptable salt thereof, relative to prior to intranasal administration of the racemic ketamine, or a pharmaceutically acceptable salt thereof. In some embodiments, the MOAA/S score of the subject is substantially the same about 5 minutes to about 24 hours prior to intranasal administration of the racemic ketamine, or a pharmaceutically acceptable salt thereof, as about 5 minutes to about 24 hours after intranasal administration of the racemic ketamine, or a pharmaceutically acceptable salt thereof. For example, about 5 minutes to 1 hour, about 5 minutes to 6 hours, about 5 minutes to 12 hours, about 5 minutes to 18 hours, about 18 hours to 24 hours, about 12 hours to 24 hours, about 6 hours to 24 hours, 1 hour to about 4 hours, about 1.5 hours to about 5 hours, about 2 hours to about 6 hours, or about 5 hours to about 10 hours prior to intranasal administration of the racemic ketamine, or a pharmaceutically acceptable salt thereof, and about 5 minutes to 1 hour, about 5 minutes to 6 hours, about 5 minutes to 12 hours, about 5 minutes to 18 hours, about 18 hours to 24 hours, about 12 hours to 24 hours, about 6 hours to 24 hours, 1 hour to about 4 hours, about 1.5 hours to about 5 hours, about 2 hours to about 6 hours, or about 5 hours to about 10 hours after intranasal administration of the racemic ketamine, or a pharmaceutically acceptable salt thereof.

In some embodiments, the MOAA/S score of the subject is reduced by about 1 to about 5 after intranasal administration of the racemic ketamine, or a pharmaceutically acceptable salt thereof. For example, the MOAA/S score of the subject can be reduced by 1, 2, 3, 4, or 5 after intranasal administration of the racemic ketamine, or a pharmaceutically acceptable salt thereof, relative to administration of an equivalent dose of (S)-ketamine, or a pharmaceutically acceptable salt thereof, and/or intravenous administration of an equivalent dose of (S)-ketamine, or a pharmaceutically acceptable salt thereof. In some embodiments, the MOAA/S score of the subject is reduced as described herein about 5 minutes to about 24 hours after intranasal administration of the racemic ketamine, or a pharmaceutically acceptable salt thereof. For example, about 5 minutes to 1 hour, about 5 minutes to 6 hours, about 5 minutes to 12 hours, about 5 minutes to 18 hours, about 18 hours to 24 hours, about 12 hours to 24 hours, or about 6 hours to 24 hours after intranasal administration of the racemic ketamine, or a pharmaceutically acceptable salt thereof. In some embodiments, the MOAA/S score of the subject is as described herein about 1 hour to about 4 hours, about 1.5 hours to about 5 hours, about 2 hours to about 6 hours, or about 5 hours to about 10 hours, after intranasal administration of the racemic ketamine, or a pharmaceutically acceptable salt thereof, (e.g., relative to administration of an equivalent dose of (S)-ketamine, or a pharmaceutically acceptable salt thereof, and/or intravenous administration of an equivalent dose of (S)-ketamine, or a pharmaceutically acceptable salt thereof).

In some embodiments, the Bowdle Visual Analog Scale (VAS) can be used to measure psychedelic effects in a subject. See, e.g., Bowdle, et al. Anesthesiology, Vol. 88, No. 1, pp. 82-88 (1998), which is incorporated herein by reference in its entirety. The Bowdle VAS is a questionnaire where the subject is asked to rate his or her current feelings. For example, the questionnaire can include the following items: 1) my body or body parts seemed to change their shape or position; 2) my surroundings seemed to change in size, depth, or shape; 3) the passing of time was altered; 4) I had feelings of unreality; 5) it was difficult to control my thoughts; 6) the intensity of colors changed; 7) the intensity of sound changed; 8) I heard voices or sounds that were not real; 9) I had the idea that events, objects, or other people had particular meaning that was specific for me; 10) I had suspicious ideas or the belief that others were against me; 11) I felt anxious; 12) I felt high; and 13) I felt drowsy, for the subject to rate. Each item is scored from 0 to 100 by the subject, for a total score of up to 1300, which indicates the subject experiences significant side effects. A score of 0 reflects that the subject did not feel at all as described in the item (i.e., very few side effects) whereas a score of 100 reflects that the subject felt extremely like the item. Thus, lower individual and overall scores indicate fewer psychedelic effects.

In some embodiments, items 1, 2, 3, 5, 6, and 7 are combined to assess the derived variable “subjective external perception.” In some embodiments, items 4, 8, 9, 10, and 11 are combined to assess the derived variable “subjective internal perception.” In some embodiments, items 12 and 13 are assessed as individual VAS items.

In some embodiments, the Bowdle VAS of the subject is about 0 to about 50 prior to intranasal administration of racemic ketamine, or a pharmaceutically acceptable salt thereof, as described herein. In some embodiments, the Bowdle VAS of the subject is about 25 to about 75 prior to intranasal administration of racemic ketamine, or a pharmaceutically acceptable salt thereof, as described herein. In some embodiments, the Bowdle VAS of the subject is about 50 to about 100 prior to intranasal administration of racemic ketamine, or a pharmaceutically acceptable salt thereof, as described herein. In some embodiments, the Bowdle VAS of the subject is about 0 to about 10, about 0 to about 20, about 0 to about 30, about 0 to about 40, about 0 to about 50, about 0 to about 60, about 0 to about 70, about 0 to about 80, about 0 to about 90, about 90 to about 100, about 80 to about 100, about 70 to about 100, about 60 to about 100, about 50 to about 100, about 40 to about 100, about 30 to about 100, about 20 to about 100, or about 10 to about 100 prior to intranasal administration of racemic ketamine as described herein. In some embodiments, the Bowdle VAS of the subject is about 5 to about 20, about 15 to about 40, about 10 to about 50, or about 20 to about 60 prior to intranasal administration of racemic ketamine as described herein. In some embodiments, the Bowdle VAS score of the subject is measured at about 5 minutes to about 24 hours prior to intranasal administration of the racemic ketamine, or a pharmaceutically acceptable salt thereof. For example, about 5 minutes to 1 hour, about 5 minutes to 6 hours, about 5 minutes to 12 hours, about 5 minutes to 18 hours, about 18 hours to 24 hours, about 12 hours to 24 hours, or about 6 hours to 24 hours prior to intranasal administration of the racemic ketamine, or a pharmaceutically acceptable salt thereof. In some embodiments, the Bowdle VAS score of the subject is measured at about 1 hour to about 4 hours, about 1.5 hours to about 5 hours, about 2 hours to about 6 hours, about 5 hours to about 10 hours, or about 45 minutes to about 24 hours prior to intranasal administration of the racemic ketamine, or a pharmaceutically acceptable salt thereof.

In some embodiments, the Bowdle VAS of the subject is about 0 to about 50 after intranasal administration of racemic ketamine, or a pharmaceutically acceptable salt thereof, as described herein. In some embodiments, the Bowdle VAS of the subject is about 25 to about 75 after intranasal administration of racemic ketamine, or a pharmaceutically acceptable salt thereof, as described herein. In some embodiments, the Bowdle VAS of the subject is about 50 to about 100 after intranasal administration of racemic ketamine, or a pharmaceutically acceptable salt thereof, as described herein. In some embodiments, the Bowdle VAS of the subject is about 0 to about 10, about 0 to about 20, about 0 to about 30, about 0 to about 40, about 0 to about 50, about 0 to about 60, about 0 to about 70, about 0 to about 80, about 0 to about 90, about 90 to about 100, about 80 to about 100, about 70 to about 100, about 60 to about 100, about 50 to about 100, about 40 to about 100, about 30 to about 100, about 20 to about 100, or about 10 to about 100 after intranasal administration of racemic ketamine as described herein. In some embodiments, the Bowdle VAS of the subject is about 5 to about 20, about 15 to about 40, about 10 to about 50, or about 20 to about 60 after intranasal administration of racemic ketamine as described herein. In some embodiments, the Bowdle VAS score of the subject is measured at about 5 minutes to about 24 hours after intranasal administration of the racemic ketamine, or a pharmaceutically acceptable salt thereof. For example, about 5 minutes to 1 hour, about 5 minutes to 6 hours, about 5 minutes to 12 hours, about 5 minutes to 18 hours, about 18 hours to 24 hours, about 12 hours to 24 hours, or about 6 hours to 24 hours after intranasal administration of the racemic ketamine, or a pharmaceutically acceptable salt thereof. In some embodiments, the Bowdle VAS score of the subject is measured at about 1 hour to about 4 hours, about 1.5 hours to about 5 hours, about 2 hours to about 6 hours, about 5 hours to about 10 hours, or about 45 minutes to about 24 hours after intranasal administration of the racemic ketamine, or a pharmaceutically acceptable salt thereof.

In some embodiments, the Bowdle VAS of the subject is about 0 to about 50 prior to intranasal administration of racemic ketamine, or a pharmaceutically acceptable salt thereof, as described herein, and the Bowdle VAS of the subject is about 0 to about 50 after intranasal administration of racemic ketamine, or a pharmaceutically acceptable salt thereof. In some embodiments, the Bowdle VAS of the subject is about 25 to about 75 prior to intranasal administration of racemic ketamine, or a pharmaceutically acceptable salt thereof, as described herein, and the Bowdle VAS of the subject is about 25 to about 75 after intranasal administration of racemic ketamine, or a pharmaceutically acceptable salt thereof, as described herein. In some embodiments, the Bowdle VAS of the subject is about 50 to about 100 prior to intranasal administration of racemic ketamine, or a pharmaceutically acceptable salt thereof, as described herein and the Bowdle VAS of the subject is about 50 to about 100 after intranasal administration of racemic ketamine, or a pharmaceutically acceptable salt thereof, as described herein. In some embodiments, the Bowdle VAS of the subject is about 0 to about 10, about 0 to about 20, about 0 to about 30, about 0 to about 40, about 0 to about 50, about 0 to about 60, about 0 to about 70, about 0 to about 80, about 0 to about 90, about 90 to about 100, about 80 to about 100, about 70 to about 100, about 60 to about 100, about 50 to about 100, about 40 to about 100, about 30 to about 100, about 20 to about 100, or about 10 to about 100 prior to intranasal administration of racemic ketamine as described herein and about 0 to about 10, about 0 to about 20, about 0 to about 30, about 0 to about 40, about 0 to about 50, about 0 to about 60, about 0 to about 70, about 0 to about 80, about 0 to about 90, about 90 to about 100, about 80 to about 100, about 70 to about 100, about 60 to about 100, about 50 to about 100, about 40 to about 100, about 30 to about 100, about 20 to about 100, or about 10 to about 100 after intranasal administration of racemic ketamine as described herein. In some embodiments, the Bowdle VAS of the subject is about 5 to about 20, about 15 to about 40, about 10 to about 50, or about 20 to about 60 prior to intranasal administration of racemic ketamine as described herein and the Bowdle VAS of the subject is about 5 to about 20, about 15 to about 40, about 10 to about 50, or about 20 to about 60 after intranasal administration of racemic ketamine as described herein. In some embodiments, the Bowdle VAS score of the subject is measured at about 5 minutes to about 24 hours prior to intranasal administration of the racemic ketamine, or a pharmaceutically acceptable salt thereof, and the Bowdle VAS score of the subject is measured at about 5 minutes to about 24 hours after intranasal administration of the racemic ketamine, or a pharmaceutically acceptable salt thereof. For example, about 5 minutes to 1 hour, about 5 minutes to 6 hours, about 5 minutes to 12 hours, about 5 minutes to 18 hours, about 18 hours to 24 hours, about 12 hours to 24 hours, or about 6 hours to 24 hours prior to intranasal administration of the racemic ketamine, or a pharmaceutically acceptable salt thereof, and about 5 minutes to 1 hour, about 5 minutes to 6 hours, about 5 minutes to 12 hours, about 5 minutes to 18 hours, about 18 hours to 24 hours, about 12 hours to 24 hours, or about 6 hours to 24 hours after intranasal administration of the racemic ketamine, or a pharmaceutically acceptable salt thereof. In some embodiments, the Bowdle VAS score of the subject is measured at about 1 hour to about 4 hours, about 1.5 hours to about 5 hours, about 2 hours to about 6 hours, about 5 hours to about 10 hours, or about 45 minutes to about 24 hours prior to intranasal administration of the racemic ketamine, or a pharmaceutically acceptable salt thereof, and the Bowdle VAS score of the subject is measured at about 1 hour to about 4 hours, about 1.5 hours to about 5 hours, about 2 hours to about 6 hours, about 5 hours to about 10 hours, or about 45 minutes to about 24 hours after intranasal administration of the racemic ketamine, or a pharmaceutically acceptable salt thereof.

In some embodiments, the Bowdle VAS score of the subject is substantially the same prior to and after intranasal administration of the racemic ketamine, or a pharmaceutically acceptable salt thereof. For example, the Bowdle VAS score of the subject changes (i.e., increases or decreases) by about 0 to about 10 after intranasal administration of the racemic ketamine, or a pharmaceutically acceptable salt thereof, relative to the Bowdle VAS score of the subject prior to intranasal administration of the racemic ketamine, or a pharmaceutically acceptable salt thereof. In some embodiments, the Bowdle VAS score of the subject is substantially the same about 5 minutes to about 24 hours prior to intranasal administration of the racemic ketamine, or a pharmaceutically acceptable salt thereof, as about 5 minutes to about 24 hours after intranasal administration of the racemic ketamine, or a pharmaceutically acceptable salt thereof. For example, about 5 minutes to 1 hour, about 5 minutes to 6 hours, about 5 minutes to 12 hours, about 5 minutes to 18 hours, about 18 hours to 24 hours, about 12 hours to 24 hours, about 6 hours to 24 hours, 1 hour to about 4 hours, about 1.5 hours to about 5 hours, about 2 hours to about 6 hours, or about 5 hours to about 10 hours prior to intranasal administration of the racemic ketamine, or a pharmaceutically acceptable salt thereof, and about 5 minutes to 1 hour, about 5 minutes to 6 hours, about 5 minutes to 12 hours, about 5 minutes to 18 hours, about 18 hours to 24 hours, about 12 hours to 24 hours, about 6 hours to 24 hours, 1 hour to about 4 hours, about 1.5 hours to about 5 hours, about 2 hours to about 6 hours, or about 5 hours to about 10 hours after intranasal administration of the racemic ketamine, or a pharmaceutically acceptable salt thereof.

In some embodiments, the Bowdle VAS score of the subject is reduced by about 10 to about 1300 after intranasal administration of the racemic ketamine, or a pharmaceutically acceptable salt thereof. For example, the Bowdle VAS score of the subject can be reduced by about 10 to about 1300 after intranasal administration of the racemic ketamine, or a pharmaceutically acceptable salt thereof, relative to the score observed after administration of an equivalent dose of (S)-ketamine, or a pharmaceutically acceptable salt thereof, and/or intravenous administration of an equivalent dose of racemic ketamine, or a pharmaceutically acceptable salt thereof. In some embodiments, the Bowdle VAS score of the subject is reduced by about 10 to about 100, about 10 to about 200, about 10 to about 300, about 10 to about 400, about 10 to about 500, about 10 to about 600, about 10 to about 700, about 10 to about 800, about 10 to about 900, about 10 to about 1000, about 10 to about 1100, about 10 to about 1200, about 1200 to about 1300, about 1100 to about 1300, about 1000 to about 1300, about 900 to about 1300, about 800 to about 1300, about 700 to about 1300, about 600 to about 1300, about 500 to about 1300, about 400 to about 1300, about 300 to about 1300, about 200 to about 1300, or about 100 to about 1300 after intranasal administration of the racemic ketamine, or a pharmaceutically acceptable salt thereof. In some embodiments, the Bowdle VAS score of the subject is reduced as described herein about 5 minutes to about 24 hours after intranasal administration of the racemic ketamine, or a pharmaceutically acceptable salt thereof. For example, about 5 minutes to 1 hour, about 5 minutes to 6 hours, about 5 minutes to 12 hours, about 5 minutes to 18 hours, about 18 hours to 24 hours, about 12 hours to 24 hours, or about 6 hours to 24 hours after intranasal administration of the racemic ketamine, or a pharmaceutically acceptable salt thereof. In some embodiments, the Bowdle VAS score of the subject is measured at about 1 hour to about 4 hours, about 1.5 hours to about 5 hours, about 2 hours to about 6 hours, or about 5 hours to about 10 hours, after intranasal administration of the racemic ketamine, or a pharmaceutically acceptable salt thereof, (or after administration of an equivalent dose of (S)-ketamine, or a pharmaceutically acceptable salt thereof, or intravenous administration of an equivalent dose of racemic ketamine, or a pharmaceutically acceptable salt thereof).

In some embodiments, the Clinician Administered Dissociative States Scale (CADSS) can be used to measure dissociative states in a subject. See, e.g., Luckenbaugh, et al. J. Affect. Disord., Vol. 159, pp. 56-61 (2014), which is incorporated herein by reference in its entirety. The CADSS assessment includes, but are not limited to, statements such as things in slow motion, things seem unreal, feel separated from what is happening, out of body experience, feel as a spectator or observer, feel disconnected from the body, sense of body changed, people seem motionless/dead/mechanical, objects look different, colors are diminished in intensity, seeing things as if in a tunnel/wide-angle lens, things taking longer, things happening quickly, things happen that can't account for, losing track of what is going on, sounds change in intensity, special sense of clarity, as if looking through a fog, and colors seem brighter. Typically, CADSS will include 23 statements that the subject rates from 0-4, for a score ranging from 0 (no dissociation) to 92 (extreme dissociation). A score of 0 reflects that the subject did not feel at all as described in the item whereas a score of 4 reflects that the subject agreed with the question posed to the maximum level. e.g., 0 reflect not at all, 1 reflects mild agreement, 2 reflects moderate agreement, 3 reflects severe agreement, and 4 reflects the maximum level of agreement with the indicated question. Thus, lower individual and overall scores indicate less dissociation. In some embodiments, a portion of the scale is completed by the subject. In some embodiments, a portion of the scale is completed by a trained observer of the subject.

In some embodiments, the CADSS of the subject is about 0 to about 10 prior to intranasal administration of racemic ketamine, or a pharmaceutically acceptable salt thereof, as described herein. For example, about 0 to about 2, about 0 to about 3, about 0 to about 4, about 0 to about 5, about 0 to about 6, about 0 to about 7, about 0 to about 8, about 0 to about 9, about 9 to about 10, about 8 to about 10, about 7 to about 10, about 6 to about 10, about 5 to about 10, about 4 to about 10, about 3 to about 10, about 2 to about 10, or about 1 to about 10 prior to intranasal administration of racemic ketamine as described herein. In some embodiments, the CADSS of the subject is about 2 to about 6, about 3 to about 7, or about 4 to about 8 prior to intranasal administration of racemic ketamine as described herein. In some embodiments, the CADSS score of the subject is measured at about 5 minutes to about 24 hours prior to intranasal administration of the racemic ketamine, or a pharmaceutically acceptable salt thereof. For example, about 5 minutes to 1 hour, about 5 minutes to 6 hours, about 5 minutes to 12 hours, about 5 minutes to 18 hours, about 18 hours to 24 hours, about 12 hours to 24 hours, or about 6 hours to 24 hours prior to intranasal administration of the racemic ketamine, or a pharmaceutically acceptable salt thereof. In some embodiments, the CADSS Scale score of the subject is measured at about 1 hour to about 4 hours, about 1.5 hours to about 5 hours, about 2 hours to about 6 hours, about 5 hours to about 10 hours, or about 45 minutes to about 24 hours prior to intranasal administration of the racemic ketamine, or a pharmaceutically acceptable salt thereof.

In some embodiments, the CADSS of the subject is about 0 to about 10 after intranasal administration of racemic ketamine, or a pharmaceutically acceptable salt thereof, as described herein. For example, about 0 to about 2, about 0 to about 3, about 0 to about 4, about 0 to about 5, about 0 to about 6, about 0 to about 7, about 0 to about 8, about 0 to about 9, about 9 to about 10, about 8 to about 10, about 7 to about 10, about 6 to about 10, about 5 to about 10, about 4 to about 10, about 3 to about 10, about 2 to about 10, or about 1 to about 10 after intranasal administration of racemic ketamine as described herein. In some embodiments, the CADSS of the subject is about 2 to about 6, about 3 to about 7, or about 4 to about 8 after intranasal administration of racemic ketamine as described herein. In some embodiments, the CADSS score of the subject is measured at about 5 minutes to about 24 hours after intranasal administration of the racemic ketamine, or a pharmaceutically acceptable salt thereof. For example, about 5 minutes to 1 hour, about 5 minutes to 6 hours, about 5 minutes to 12 hours, about 5 minutes to 18 hours, about 18 hours to 24 hours, about 12 hours to 24 hours, or about 6 hours to 24 hours after intranasal administration of the racemic ketamine, or a pharmaceutically acceptable salt thereof. In some embodiments, the CADSS Scale score of the subject is measured at about 1 hour to about 4 hours, about 1.5 hours to about 5 hours, about 2 hours to about 6 hours, about 5 hours to about 10 hours, or about 45 minutes to about 24 hours after intranasal administration of the racemic ketamine, or a pharmaceutically acceptable salt thereof.

In some embodiments, the CADSS of the subject is about 0 to about 10 prior to intranasal administration of racemic ketamine, or a pharmaceutically acceptable salt thereof, and the CADSS of the subject is about 0 to about 10 after intranasal administration of racemic ketamine, or a pharmaceutically acceptable salt thereof. For example, about 0 to about 2, about 0 to about 3, about 0 to about 4, about 0 to about 5, about 0 to about 6, about 0 to about 7, about 0 to about 8, about 0 to about 9, about 9 to about 10, about 8 to about 10, about 7 to about 10, about 6 to about 10, about 5 to about 10, about 4 to about 10, about 3 to about 10, about 2 to about 10, or about 1 to about 10 prior to intranasal administration of racemic ketamine as described herein and about 0 to about 2, about 0 to about 3, about 0 to about 4, about 0 to about 5, about 0 to about 6, about 0 to about 7, about 0 to about 8, about 0 to about 9, about 9 to about 10, about 8 to about 10, about 7 to about 10, about 6 to about 10, about 5 to about 10, about 4 to about 10, about 3 to about 10, about 2 to about 10, or about 1 to about 10 after intranasal administration of racemic ketamine. In some embodiments, the CADSS of the subject is about 2 to about 6, about 3 to about 7, or about 4 to about 8 prior to intranasal administration of racemic ketamine as described herein and the CADSS of the subject is about 2 to about 6, about 3 to about 7, or about 4 to about 8 after intranasal administration of racemic ketamine as described herein. In some embodiments, the CADSS score of the subject is measured at about 5 minutes to about 24 hours prior to intranasal administration of the racemic ketamine, or a pharmaceutically acceptable salt thereof, and the CADSS score of the subject is measured at about 5 minutes to about 24 hours after intranasal administration of the racemic ketamine, or a pharmaceutically acceptable salt thereof. For example, about 5 minutes to 1 hour, about 5 minutes to 6 hours, about 5 minutes to 12 hours, about 5 minutes to 18 hours, about 18 hours to 24 hours, about 12 hours to 24 hours, or about 6 hours to 24 hours prior to intranasal administration of the racemic ketamine, or a pharmaceutically acceptable salt thereof, and about 5 minutes to 1 hour, about 5 minutes to 6 hours, about 5 minutes to 12 hours, about 5 minutes to 18 hours, about 18 hours to 24 hours, about 12 hours to 24 hours, or about 6 hours to 24 hours after intranasal administration of the racemic ketamine, or a pharmaceutically acceptable salt thereof. In some embodiments, the CADSS Scale score of the subject is measured at about 1 hour to about 4 hours, about 1.5 hours to about 5 hours, about 2 hours to about 6 hours, about 5 hours to about 10 hours, or about 45 minutes to about 24 hours prior to intranasal administration of the racemic ketamine, or a pharmaceutically acceptable salt thereof, and the CADSS Scale score of the subject is measured at about 1 hour to about 4 hours, about 1.5 hours to about 5 hours, about 2 hours to about 6 hours, about 5 hours to about 10 hours, or about 45 minutes to about 24 hours after intranasal administration of the racemic ketamine, or a pharmaceutically acceptable salt thereof.

In some embodiments, the CADSS score of the subject is substantially the same prior to and after intranasal administration of the racemic ketamine, or a pharmaceutically acceptable salt thereof. For example, the CADSS score of the subject changes (i.e., increases or decreases) by about 0 to about 5 after intranasal administration of the racemic ketamine, or a pharmaceutically acceptable salt thereof, relative to prior to intranasal administration of the racemic ketamine, or a pharmaceutically acceptable salt thereof. In some embodiments, the CADSS score of the subject is substantially the same about 5 minutes to about 24 hours prior to intranasal administration of the racemic ketamine, or a pharmaceutically acceptable salt thereof, as about 5 minutes to about 24 hours after intranasal administration of the racemic ketamine, or a pharmaceutically acceptable salt thereof. For example, about 5 minutes to 1 hour, about 5 minutes to 6 hours, about 5 minutes to 12 hours, about 5 minutes to 18 hours, about 18 hours to 24 hours, about 12 hours to 24 hours, about 6 hours to 24 hours, 1 hour to about 4 hours, about 1.5 hours to about 5 hours, about 2 hours to about 6 hours, or about 5 hours to about 10 hours prior to intranasal administration of the racemic ketamine, or a pharmaceutically acceptable salt thereof, and about 5 minutes to 1 hour, about 5 minutes to 6 hours, about 5 minutes to 12 hours, about 5 minutes to 18 hours, about 18 hours to 24 hours, about 12 hours to 24 hours, about 6 hours to 24 hours, 1 hour to about 4 hours, about 1.5 hours to about 5 hours, about 2 hours to about 6 hours, or about 5 hours to about 10 hours after intranasal administration of the racemic ketamine, or a pharmaceutically acceptable salt thereof.

In some embodiments, the CADSS score of the subject is reduced by about 1 to about 92 after intranasal administration of the racemic ketamine, or a pharmaceutically acceptable salt thereof. For example, the CADDS score of the subject can be reduced by about 10 to about 92 after intranasal administration of the racemic ketamine, or a pharmaceutically acceptable salt thereof, relative to the score observed after administration of an equivalent dose of (S)-ketamine, or a pharmaceutically acceptable salt thereof, and/or intravenous administration of an equivalent dose of racemic ketamine, or a pharmaceutically acceptable salt thereof. In some embodiments, the CADS S score of the subject is reduced by about 1 to about 90, about 1 to about 80, about 1 to about 70, about 1 to about 60, about 1 to about 50, about 1 to about 40, about 1 to about 30, about 1 to about 20, about 1 to about 10, about 80 to about 92, about 70 to about 92, about 60 to about 92, about 50 to about 92, about 40 to about 92, about 30 to about 92, about 20 to about 92, or about 10 to about 92 after intranasal administration of the racemic ketamine, or a pharmaceutically acceptable salt thereof. In some embodiments, the CADSS score of the subject is reduced about 5 minutes to about 24 hours after intranasal administration of the racemic ketamine, or a pharmaceutically acceptable salt thereof. For example, about 5 minutes to 1 hour, about 5 minutes to 6 hours, about 5 minutes to 12 hours, about 5 minutes to 18 hours, about 18 hours to 24 hours, about 12 hours to 24 hours, or about 6 hours to 24 hours after intranasal administration of the racemic ketamine, or a pharmaceutically acceptable salt thereof. In some embodiments, the CADDS score of the subject is measured at about 1 hour to about 4 hours, about 1.5 hours to about 5 hours, about 2 hours to about 6 hours, or about 5 hours to about 10 hours, after intranasal administration of the racemic ketamine, or a pharmaceutically acceptable salt thereof (or after administration of an equivalent dose of (S)-ketamine, or a pharmaceutically acceptable salt thereof, or intravenous administration of an equivalent dose of racemic ketamine, or a pharmaceutically acceptable salt thereof).

In some embodiments, Profile of Mood States (POMS) (e.g., POMS 2nd edition) can be used to measure transient feelings and mood in a subject. See, e.g., Lin, et al. W A Vol. 32, No. 3, pp. 273-277 (2014), which is incorporated herein by reference in its entirety. The Profile of Mood States can includes items to monitor mood change in the subject.

In some embodiments, the Profile of Mood States score of the subject is substantially the same prior to and after intranasal administration of the racemic ketamine, or a pharmaceutically acceptable salt thereof. In some embodiments, the Profile of Mood States score of the subject is substantially the same about 5 minutes to about 24 hours prior to intranasal administration of the racemic ketamine, or a pharmaceutically acceptable salt thereof, as about 5 minutes to about 24 hours after intranasal administration of the racemic ketamine, or a pharmaceutically acceptable salt thereof. For example, about 5 minutes to 1 hour, about 5 minutes to 6 hours, about 5 minutes to 12 hours, about 5 minutes to 18 hours, about 18 hours to 24 hours, about 12 hours to 24 hours, about 6 hours to 24 hours, 1 hour to about 4 hours, about 1.5 hours to about 5 hours, about 2 hours to about 6 hours, or about 5 hours to about 10 hours prior to intranasal administration of the racemic ketamine, or a pharmaceutically acceptable salt thereof, and about 5 minutes to 1 hour, about 5 minutes to 6 hours, about 5 minutes to 12 hours, about 5 minutes to 18 hours, about 18 hours to 24 hours, about 12 hours to 24 hours, about 6 hours to 24 hours, 1 hour to about 4 hours, about 1.5 hours to about 5 hours, about 2 hours to about 6 hours, or about 5 hours to about 10 hours after intranasal administration of the racemic ketamine, or a pharmaceutically acceptable salt thereof.

In some embodiments, the Choice Reaction Time (CRT) test can be used to measure psychomotor performance in a subject. See, e.g., Hindmarch, et al. Br. J. Clin. Pharmcol., Vol. 49, No. 2, pp. 118-125 (2000), which is incorporated herein by reference in its entirety. The choice reaction time test is administered using a computer, where the subject is presented with an onscreen equivalent of a numeric keypad. When a key is illuminated on the screen, the subject presses the corresponding button on a separate keypad. For a given trial, four to eight numbered squares will be illuminated on the computer screen that correspond spatially to the keys on the keypad. The sequence of key illumination can be random. In some embodiments, the sequence of key illumination follows a pattern that alternates between the center button and any button that is part of the stimuli set of buttons. In some embodiments, the stimulus set size progresses from 4 to 6 to 8 during the test. The number of alternative choices can increase over blocks of responses in each cycle. The CRT test can include three outcome variables: recognition reaction time (RRT) is the time it takes for a subject to notice the light (e.g., the time between stimulus onset and the subject lifting his or her finger from the start button); motor reaction time (MRT) is the time between the subject lifting his or her finger from the start button and touching the response button; and total reaction time (TRT) is the sum of RRT and MRT. The accuracy of responses can also be recorded.

In some embodiments, the CRT test score of the subject is substantially the same prior to and after intranasal administration of the racemic ketamine, or a pharmaceutically acceptable salt thereof. In some embodiments, the CRT test score of the subject is substantially the same about 5 minutes to about 24 hours prior to intranasal administration of the racemic ketamine, or a pharmaceutically acceptable salt thereof, as about 5 minutes to about 24 hours after intranasal administration of the racemic ketamine, or a pharmaceutically acceptable salt thereof. For example, about 5 minutes to 1 hour, about 5 minutes to 6 hours, about 5 minutes to 12 hours, about 5 minutes to 18 hours, about 18 hours to 24 hours, about 12 hours to 24 hours, about 6 hours to 24 hours, 1 hour to about 4 hours, about 1.5 hours to about 5 hours, about 2 hours to about 6 hours, or about 5 hours to about 10 hours prior to intranasal administration of the racemic ketamine, or a pharmaceutically acceptable salt thereof, and about 5 minutes to 1 hour, about 5 minutes to 6 hours, about 5 minutes to 12 hours, about 5 minutes to 18 hours, about 18 hours to 24 hours, about 12 hours to 24 hours, about 6 hours to 24 hours, 1 hour to about 4 hours, about 1.5 hours to about 5 hours, about 2 hours to about 6 hours, or about 5 hours to about 10 hours after intranasal administration of the racemic ketamine, or a pharmaceutically acceptable salt thereof.

In some embodiments, the Sternberg short-term memory task (SSTM) can be used to measure immediate memory in a subject. See, e.g., Sternberg, Science, Vol. 153, Issue. 3736, pp. 652-654 (1966), which is incorporated herein by reference in its entirety. The SSTM can include asking a subject to remember a series of digits that are rapidly presented on a computer screen. For example, the SSTM can include rapid presentation of target lists of 2, 4, and 6 stimulus digits (e.g., at 1.2 seconds/digit), and two seconds after presentation of each list of digits, a series of 24 probe digits is presented. The subject is to identify as quickly as possible whether or not each probe appeared in the target list by pressing buttons on a response box corresponding to "yes" or "no." Probes that appeared on the target list can be called "positive," while probes that did not appear on the target list can be called "negative." The SSTM can include three trials with digit sequence size lengths of 2, 4, and 6. Performance can be assessed by measures of response latency and accuracy.

In some embodiments, the SSTM score of the subject is substantially the same prior to and after intranasal administration of the racemic ketamine, or a pharmaceutically acceptable salt thereof. In some embodiments, the SSTM score of the subject is substantially the same about 5 minutes to about 24 hours prior to intranasal administration of the racemic ketamine, or a pharmaceutically acceptable salt thereof, as about 5 minutes to about 24 hours after intranasal administration of the racemic ketamine, or a pharmaceutically acceptable salt thereof. For example, about 5 minutes to 1 hour, about 5 minutes to 6 hours, about 5 minutes to 12 hours, about 5 minutes to 18 hours, about 18 hours to 24 hours, about 12 hours to 24 hours, about 6 hours to 24 hours, 1 hour to about 4 hours, about 1.5 hours to about 5 hours, about 2 hours to about 6 hours, or about 5 hours to about 10 hours prior to intranasal administration of the racemic ketamine, or a pharmaceutically acceptable salt thereof, and about 5 minutes to 1 hour, about 5 minutes to 6 hours, about 5 minutes to 12 hours, about 5 minutes to 18 hours, about 18 hours to 24 hours, about 12 hours to 24 hours, about 6 hours to 24 hours, 1 hour to about 4 hours, about 1.5 hours to about 5 hours, about 2 hours to about 6 hours, or about 5 hours to about 10 hours after intranasal administration of the racemic ketamine, or a pharmaceutically acceptable salt thereof.

In some embodiments, the subject-rated assessment of intranasal irritation (SRAII) can be used to determine intranasal irritation in a subject administered intranasal ketamine (e.g., racemic ketamine or (S)-ketamine), or a pharmaceutically acceptable salt thereof. For example, the SRAII can be used to assess subjective effects of intranasal administration a drug such as ketamine, or a pharmaceutically acceptable salt thereof, as described herein. The SRAII includes five categories for which a subject is asked to provide a rating. For example, the categories can include: 1) burning sensation; 2) need to blow nose/sneeze; 3) runny nose and/or nasal discharge; 4) facial pressure or pain; and 5) nasal congestion. In some embodiments, each item is scored on a 6-point scale. For example, 0 refers to no difficulty at all; 1 refers to very mild difficulty; 2 refers to mild/slight difficulty; 3 refers to moderate difficulty; 4 refers to severe difficulty; and 5 refers to very severe difficulty, e.g., the worst possible.

In some embodiments, the SRAII of the subject is about 0 to about 5 after intranasal administration of racemic ketamine, or a pharmaceutically acceptable salt thereof, as described herein. For example, about 0 to about 1, about 0 to about 2, about 0 to about 3, about 0 to about 4, about 4 to about 5, about 3 to about 5, or about 2 to about 5 after intranasal administration of racemic ketamine as described herein. In some embodiments, the SRAII of the subject is about 1, about 2, about 3, about 4, or about 5 after administration of ketamine, or a pharmaceutically acceptable salt thereof, as described herein. In some embodiments, the SRAII score of the subject is measured at about 5 minutes to about 24 hours after intranasal administration of the racemic ketamine, or a pharmaceutically acceptable salt thereof. For example, about 5 minutes to 1 hour, about 5 minutes to 6 hours, about 5 minutes to 12 hours, about 5 minutes to 18 hours, about 18 hours to 24 hours, about 12 hours to 24 hours, or about 6 hours to 24 hours after intranasal administration of the racemic ketamine, or a pharmaceutically acceptable salt thereof. In some embodiments, the SRAII score of the subject is measured at about 1 hour to about 4 hours, about 1.5 hours to about 5 hours, about 2 hours to about 6 hours, about 5 hours to about 10 hours, or about 45 minutes to about 24 hours after intranasal administration of the racemic ketamine, or a pharmaceutically acceptable salt thereof.

In some embodiments, the SRAII score of the subject is substantially the same prior to and after intranasal administration of the racemic ketamine, or a pharmaceutically acceptable salt thereof. For example, SRAII score of the subject changes (i.e., increases or decreases) by about 0 to about 5 after intranasal administration of the racemic ketamine, or a pharmaceutically acceptable salt thereof, relative to prior to intranasal administration of the racemic ketamine, or a pharmaceutically acceptable salt thereof. In some embodiments, the SRAII score of the subject is substantially the same about 5 minutes to about 24 hours prior to intranasal administration of the racemic ketamine, or a pharmaceutically acceptable salt thereof, as about 5 minutes to about 24 hours after intranasal administration of the racemic ketamine, or a pharmaceutically acceptable salt thereof. For example, about 5 minutes to 1 hour, about 5 minutes to 6 hours, about 5 minutes to 12 hours, about 5 minutes to 18 hours, about 18 hours to 24 hours, about 12 hours to 24 hours, about 6 hours to 24 hours, 1 hour to about 4 hours, about 1.5 hours to about 5 hours, about 2 hours to about 6 hours, or about 5 hours to about 10 hours prior to intranasal administration of the racemic ketamine, or a pharmaceutically acceptable salt thereof, and about 5 minutes to 1 hour, about 5 minutes to 6 hours, about 5 minutes to 12 hours, about 5 minutes to 18 hours, about 18 hours to 24 hours, about 12 hours to 24 hours, about 6 hours to 24 hours, 1 hour to about 4 hours, about 1.5 hours to about 5 hours, about 2 hours to about 6 hours, or about 5 hours to about 10 hours after intranasal administration of the racemic ketamine, or a pharmaceutically acceptable salt thereof.

In some embodiments, the SRAII score of the subject is reduced by about 5 to about 25 after intranasal administration of the racemic ketamine, or a pharmaceutically acceptable salt thereof, relative to intranasal administration of an equivalent dose of (S)-ketamine, or a pharmaceutically acceptable salt thereof. For example, the SRAII score of the subject can be reduced by about 5 to about 25 after intranasal administration of the racemic ketamine, or a pharmaceutically acceptable salt thereof, relative to the score observed after administration of an equivalent dose of (S)-ketamine, or a pharmaceutically acceptable salt thereof. In some embodiments, the SRAII score of the subject is reduced by about 5 to about 20, about 5 to about 15, about 5 to about 10, about 20 to about 25, about 15 to about 25, or about 10 to about 25 after intranasal administration of the racemic ketamine, or a pharmaceutically acceptable salt thereof. In some embodiments, the SRAII score of the subject is reduced as described herein about 5 minutes to about 24 hours after intranasal administration of the racemic ketamine, or a pharmaceutically acceptable salt thereof. For example, about 5 minutes to 1 hour, about 5 minutes to 6 hours, about 5 minutes to 12 hours, about 5 minutes to 18 hours, about 18 hours to 24 hours, about 12 hours to 24 hours, or about 6 hours to 24 hours after intranasal administration of the racemic ketamine, or a pharmaceutically acceptable salt thereof. In some embodiments, the SRAII score of the subject is measured at about 1 hour to about 4 hours, about 1.5 hours to about 5 hours, about 2 hours to about 6 hours, or about 5 hours to about 10 hours, after intranasal administration of the racemic ketamine, or a pharmaceutically acceptable salt thereof (or after administration of an equivalent dose of (S)-ketamine, or a pharmaceutically acceptable salt thereof).

In some embodiments, no clinically meaningful sedation is observed in the subject within about 24 hours after intranasal administration of the racemic ketamine, or a pharmaceutically acceptable salt thereof. In some embodiments, no clinically meaningful sedation is observed in the subject at about 4 hours after intranasal administration of the racemic ketamine, or a pharmaceutically acceptable salt thereof. In some embodiments, no clinically meaningful sedation is observed in the subject at about 1 hour after intranasal administration of the racemic ketamine, or a pharmaceutically acceptable salt thereof.

In some embodiments, no clinically meaningful dissociation is observed in the subject within about 24 hours after intranasal administration of the racemic ketamine, or a pharmaceutically acceptable salt thereof. In some embodiments, no clinically meaningful dissociation is observed in the subject at about 4 hours after intranasal administration of the racemic ketamine, or a pharmaceutically acceptable salt thereof. In some embodiments, no clinically meaningful dissociation is observed in the subject at about 1 hour after intranasal administration of the racemic ketamine, or a pharmaceutically acceptable salt thereof.

In some embodiments wherein the subject exhibits suicidal ideation, the subject has been previously diagnosed with one or more of: suicidality, suicidal ideation, major depressive disorder, treatment-resistant depression, and post-traumatic stress disorder. In some embodiments wherein the subject exhibits suicidal ideation, the subject is currently suffering from one or more of: suicidality, suicidal ideation, major depressive disorder, treatment-resistant depression, and post-traumatic stress disorder.

In some embodiments wherein the subject exhibits suicidality, the subject has been previously diagnosed with one or more of: suicidality, suicidal ideation, major depressive disorder, treatment-resistant depression, and post-traumatic stress disorder. In some embodiments wherein the subject exhibits suicidality, the subject is currently suffering from one or more of: suicidality, suicidal ideation, major depressive disorder, treatment-resistant depression, and post-traumatic stress disorder.

In some embodiments, the treatment-resistant depression is Stage I to Stage IV. In some embodiments, the treatment resistant depression is Stage V. In some embodiments, the subject exhibits one or more of the following characteristics: unwanted upsetting memories, nightmares, flashbacks, emotional distress after exposure to traumatic reminders, or physical reactivity after exposure to traumatic reminders; and one or more of trauma-related thoughts or feelings and trauma-related external reminders.

In some embodiments, the subject exhibits two or more of the following characteristics: inability to recall key features of a traumatic event, overly negative thoughts and assumptions about oneself or the world, exaggerated blame of self or others for causing a traumatic event, negative affect, decreased interest in activities, feeling isolated, and difficulty experiencing positive affect. In some embodiments, the subject exhibits one or more of the following characteristics: irritability or aggression, risky or destructive behavior, hypervigilance, heightened startle reaction, difficulty concentrating, and difficulty sleeping. In some embodiments, the characteristics are present for more than about 1 month, create distress and/or functional impairment in social or occupational situations, and are not due to medication or substance abuse. In some embodiments, the characteristics are present for at least about 1 month up to about 12 months.

In some embodiments, about 30 mg to about 90 mg of racemic ketamine, or a pharmaceutically acceptable salt thereof, is intranasally administered to the subject. For example, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, or any value in between. In some embodiments, about 30 mg to about 60 mg of racemic ketamine, or a pharmaceutically acceptable salt thereof, is intranasally administered to the subject. In some embodiments, about 45 mg to about 75 mg of racemic ketamine, or a pharmaceutically acceptable salt thereof, is intranasally administered to the subject. In some embodiments, about 60 mg to about 90 mg of racemic ketamine, or a pharmaceutically acceptable salt thereof, is intranasally administered to the subject. In some embodiments, about 30 mg, about 60 mg, about 75 mg, or about 90 mg of racemic ketamine, or a pharmaceutically acceptable salt thereof, is intranasally administered to the subject. In some embodiments, the formulation provides about 30 mg of racemic ketamine, or a pharmaceutically acceptable salt thereof, per dose. In some embodiments, the formulation provides about 60 mg of racemic ketamine, or a pharmaceutically acceptable salt thereof, per dose. In some embodiments, the formulation provides about 75 mg of racemic ketamine, or a pharmaceutically acceptable salt thereof, per dose. In some embodiments, the formulation provides about 90 mg of racemic ketamine, or a pharmaceutically acceptable salt thereof, per dose.

Some embodiments provide a method of treating suicidality in a subject in need thereof, the method comprising intranasally administering to the subject a therapeutically effective amount of racemic ketamine, or a pharmaceutically acceptable salt thereof, wherein intranasal administration of the racemic ketamine exhibits one or more of:

an $AUC_{0-t}$ of norketamine that is at least 1.5 times higher than the $AUC_{0-t}$ of norketamine exhibited by intravenous administration of an equivalent dose of racemic ketamine;

an $AUC_{0-inf}$ of norketamine that is at least 1.5 times higher than the $AUC_{0-inf}$ of norketamine exhibited by intravenous administration of an equivalent dose of racemic ketamine; and a $C_{max}$ of norketamine that is at least 2 times higher than the $C_{max}$ of norketamine exhibited by intravenous administration of an equivalent dose of racemic ketamine.

Some embodiments provide a method for treating suicidal ideation in a subject in need thereof, the method comprising intranasally administering to the subject a therapeutically effective amount of racemic ketamine, or a pharmaceutically acceptable salt thereof; wherein intranasal administration of the racemic ketamine exhibits one or more of:

an $AUC_{0-t}$ of norketamine that is at least 1.5 times higher than the $AUC_{0-t}$ of norketamine exhibited by intravenous administration of an equivalent dose of racemic ketamine;

an $AUC_{0-inf}$ of norketamine that is at least 1.5 times higher than the $AUC_{0-inf}$ of norketamine exhibited by intravenous administration of an equivalent dose of racemic ketamine; and a $C_{max}$ of norketamine that is at least 2 times higher than the $C_{max}$ of norketamine exhibited by intravenous administration of an equivalent dose of racemic ketamine.

Some embodiments provide a method for treating major depressive disorder in a subject in need thereof, the method comprising intranasally administering to the subject a therapeutically effective amount of racemic ketamine, or a pharmaceutically acceptable salt thereof; wherein intranasal administration of the racemic ketamine exhibits one or more of:

an $AUC_{0-t}$ of norketamine that is at least 1.5 times higher than the $AUC_{0-t}$ of norketamine exhibited by intravenous administration of an equivalent dose of racemic ketamine;

an $AUC_{0-inf}$ of norketamine that is at least 1.5 times higher than the $AUC_{0-inf}$ of norketamine exhibited by intravenous administration of an equivalent dose of racemic ketamine; and a $C_{max}$ of norketamine that is at least 2 times higher than the $C_{max}$ of norketamine exhibited by intravenous administration of an equivalent dose of racemic ketamine.

In some embodiments, intranasal administration of the racemic ketamine exhibits an $AUC_{0-t}$ of norketamine that is about 1.7 to about 2.5 times higher than the $AUC_{0-t}$ of norketamine exhibited by intravenous administration of an equivalent dose of racemic ketamine. In some embodiments, intranasal administration of the racemic ketamine exhibits an $AUC_{0-t}$ of norketamine that is about 1.9 to about 2.3 times higher than the $AUC_{0-t}$ of norketamine exhibited by intravenous administration of an equivalent dose of racemic ketamine. In some embodiments, intranasal administration of the racemic ketamine exhibits an $AUC_{0-t}$ of norketamine that is about 2.0 times higher than the $AUC_{0-t}$ of norketamine exhibited by intravenous administration of an equivalent dose of racemic ketamine.

In some embodiments, intranasal administration of the racemic ketamine exhibits an $AUC_{0-inf}$ of norketamine that is about 1.5 to about 2.5 times higher than the $AUC_{0-inf}$ of norketamine exhibited by intravenous administration of an equivalent dose of racemic ketamine. In some embodiments, intranasal administration of the racemic ketamine exhibits an $AUC_{0-inf}$ of norketamine that is about 1.8 to about 2.2 times higher than the $AUC_{0-inf}$ of norketamine exhibited by intravenous administration of an equivalent dose of racemic ketamine. In some embodiments, intranasal administration of the racemic ketamine exhibits an $AUC_{0-inf}$ of norketamine that is about 2.0 times higher than the $AUC_{0-inf}$ of norketamine exhibited by intravenous administration of an equivalent dose of racemic ketamine.

In some embodiments, intranasal administration of the racemic ketamine exhibits a $C_{max}$ of norketamine that is about 2.2 to about 3.5 times higher than the $C_{max}$ of norketamine exhibited by intravenous administration of an equivalent dose of racemic ketamine. In some embodiments, intranasal administration of the racemic ketamine exhibits a $C_{max}$ of norketamine that is about 2.4 to about 3.2 times higher than the $C_{max}$ of norketamine exhibited by intravenous administration of an equivalent dose of racemic ketamine. In some embodiments, intranasal administration of the racemic ketamine exhibits a $C_{max}$ of norketamine that is about 2.9 times higher than the $C_{max}$ of norketamine exhibited by intravenous administration of an equivalent dose of racemic ketamine.

In some embodiments, intranasal administration of the racemic ketamine exhibits a $T_{max}$ of norketamine that is about 80% to about 125% of the $T_{max}$ of norketamine exhibited by an intravenous administration of an equivalent dose of racemic ketamine. In some embodiments, intranasal administration of the racemic ketamine exhibits a $T_{max}$ of norketamine that is about 90% to about 110% of the $T_{max}$ of norketamine exhibited by an intravenous administration of an equivalent dose of racemic ketamine.

In some embodiments, one or more of the $AUC_{0-t}$, $AUC_{0-inf}$, $C_{max}$, and $T_{max}$ of norketamine is determined following one dose of racemic ketamine. In some embodiments, one or more of the $AUC_{0-t}$, $AUC_{0-inf}$, $C_{max}$, and $T_{max}$ of norketamine is determined following two doses of racemic ketamine. In some embodiments, one or more of the $AUC_{0-t}$, $AUC_{0-inf}$, $C_{max}$, and $T_{max}$ of norketamine is determined following three doses of racemic ketamine.

Some embodiments provide a method of treating suicidality in a subject in need thereof, the method comprising intranasally administering to the subject a therapeutically effective amount of racemic ketamine, or a pharmaceutically acceptable salt thereof, wherein intranasal administration of the racemic ketamine exhibits one or more of:

an $AUC_{0-t}$ of hydroxynorketamine that is at least 1.5 times higher than the $AUC_{0-t}$ of hydroxynorketamine exhibited by intravenous administration of an equivalent dose of racemic ketamine;

an $AUC_{0-inf}$ of hydroxynorketamine that is at least 1.2 times higher than the $AUC_{0-inf}$ of hydroxynorketamine exhibited by intravenous administration of an equivalent dose of racemic ketamine; and a $C_{max}$ of hydroxynorketamine that is at least 2 times higher than the $C_{max}$ of norketamine exhibited by intravenous administration of an equivalent dose of racemic ketamine.

Some embodiments provide a method for treating suicidal ideation in a subject in need thereof, the method comprising intranasally administering to the subject a therapeutically effective amount of racemic ketamine, or a pharmaceutically acceptable salt thereof, wherein intranasal administration of the racemic ketamine exhibits one or more of:

an $AUC_{0-t}$ of hydroxynorketamine that is at least 1.5 times higher than the $AUC_{0-t}$ of hydroxynorketamine exhibited by intravenous administration of an equivalent dose of racemic ketamine;

an $AUC_{0-inf}$ of hydroxynorketamine that is at least 1.2 times higher than the $AUC_{0-inf}$ of hydroxynorketamine exhibited by intravenous administration of an equivalent dose of racemic ketamine; and a $C_{max}$ of hydroxynorketamine that is at least 2 times higher than the $C_{max}$ of norketamine exhibited by intravenous administration of an equivalent dose of racemic ketamine.

Some embodiments provide a method for treating major depressive disorder in a subject in need thereof, the method comprising intranasally administering to the subject a therapeutically effective amount of racemic ketamine, or a pharmaceutically acceptable salt thereof, wherein intranasal administration of the racemic ketamine exhibits one or more of:

an $AUC_{0-t}$ of hydroxynorketamine that is at least 1.5 times higher than the $AUC_{0-t}$ of hydroxynorketamine exhibited by intravenous administration of an equivalent dose of racemic ketamine;

an $AUC_{0-inf}$ of hydroxynorketamine that is at least 1.2 times higher than the $AUC_{0-inf}$ of hydroxynorketamine exhibited by intravenous administration of an equivalent dose of racemic ketamine; and a $C_{max}$ of hydroxynorketamine that is at least 2 times higher than the $C_{max}$ of norketamine exhibited by intravenous administration of an equivalent dose of racemic ketamine.

In some embodiments, intranasal administration of the racemic ketamine exhibits an $AUC_{0-t}$ of hydroxynorketamine that is about 1.7 to about 2.5 times higher than the $AUC_{0-t}$ of hydroxynorketamine exhibited by intravenous administration of an equivalent dose of racemic ketamine. In some embodiments, intranasal administration of the racemic ketamine exhibits an $AUC_{0-t}$ of hydroxynorketamine that is about 1.9 to about 2.3 times higher than the $AUC_{0-t}$ of hydroxynorketamine exhibited by intravenous administration of an equivalent dose of racemic ketamine. In some embodiments, intranasal administration of the racemic ketamine exhibits an $AUC_{0-t}$ of hydroxynorketamine that is about 2.1 times higher than the $AUC_{0-t}$ of hydroxynorketamine exhibited by intravenous administration of an equivalent dose of racemic ketamine.

In some embodiments, intranasal administration of the racemic ketamine exhibits an $AUC_{0-inf}$ of hydroxynorketamine that is about 1.5 to about 2.5 times higher than the $AUC_{0-inf}$ of hydroxynorketamine exhibited by intravenous administration of an equivalent dose of racemic ketamine. In some embodiments, intranasal administration of the racemic ketamine exhibits an $AUC_{0-t}$ of hydroxynorketamine that is about 1.7 to about 2.1 times higher than the $AUC_{0-inf}$ of hydroxynorketamine exhibited by intravenous administration of an equivalent dose of racemic ketamine. In some embodiments, intranasal administration of the racemic ketamine exhibits an $AUC_{0-t}$ of hydroxynorketamine that is about 1.9 times higher than the $AUC_{0-inf}$ of hydroxynorketamine exhibited by intravenous administration of an equivalent dose of racemic ketamine.

In some embodiments, intranasal administration of the racemic ketamine exhibits a $C_{max}$ of hydroxynorketamine that is about 2.2 to about 3.2 times higher than the $C_{max}$ of hydroxynorketamine exhibited by intravenous administration of an equivalent dose of racemic ketamine. In some embodiments, intranasal administration of the racemic ketamine exhibits a $C_{max}$ of hydroxynorketamine that is about 2.4 to about 2.8 times higher than the $C_{max}$ of hydroxynorketamine exhibited by intravenous administration of an equivalent dose of racemic ketamine. In some embodiments, intranasal administration of the racemic ketamine exhibits a $C_{max}$ of hydroxynorketamine that is about 2.6 times higher than the $C_{max}$ of hydroxynorketamine exhibited by intravenous administration of an equivalent dose of racemic ketamine.

In some embodiments, intranasal administration of the racemic ketamine exhibits a $T_{max}$ of hydroxynorketamine that is about 80% to about 125% of the $T_{max}$ of hydroxynorketamine exhibited by an intravenous administration of an equivalent dose of racemic ketamine. In some embodiments intranasal administration of the racemic ketamine exhibits a $T_{max}$ of hydroxynorketamine that is about 90% to about 110% of the $T_{max}$ of hydroxynorketamine exhibited by an intravenous administration of an equivalent dose of racemic ketamine.

In some embodiments, the relative ratios and percentages described herein are measured from about 15 minutes to about 8 hours after intranasal administration of the racemic ketamine, or a pharmaceutically acceptable salt thereof. For example, in some embodiments, the ratios described herein are measured at about 15 minutes, about 20 minutes, about 25 minutes, about 30 minutes, about 35 minutes, about 40 minutes, about 45 minutes, about 50 minutes, about 55 minutes, about 60 minutes, about 75 minutes, about 90 minutes, about 105 minutes, about 2 hours, about 2.5 hours, about 3 hours, about 3.5 hours, about 4 hours, about 4.5 hours, about 5 hours, about 5.5 hours, about 6 hours, about 6.5 hours, about 7 hours, about 7.5 hours, about 8 hours, or any value in between. In some embodiments, the relative ratios and percentages described herein are measured for about 24 hours to about 1 month. In some embodiments, the relative ratios and percentages described herein are measured for about 24 hours to about 2 weeks. For example, about 24 hours, about 2 days, about 3 days, about 4 days, about 5 days, about 6 days, about 7 days, about 8 days, about 9 days, about 10 days, about 11 days, about 12 days, about 13 days, about 2 weeks, or any value in between. In some embodiments, the racemic ketamine, or a pharmaceutically acceptable salt thereof, is intranasally administered twice daily, once daily, once every other day, once every three days, once every four days, once every five days, once every six days, or once a week, or a combination thereof, for the measurement period (for example, about 24 hours to about 1 month).

In some embodiments, the $T_{max}$ of the ketamine is from about 20 minutes to about 120 minutes, following the intranasal administration of racemic ketamine, for example about 20 minutes, about 30 minutes, about 40 minutes, about 50 minutes, about 60 minutes, about 70 minutes, about 80 minutes, about 90 minutes, about 100 minutes, about 110 minutes, about 120 minutes, or any value in between. In some embodiments, the $T_{max}$ of the ketamine is from about 20 minutes to about 90 minutes, following the intranasal administration of racemic ketamine, for example about 20 minutes, about 30 minutes, about 40 minutes, about 50 minutes, about 60 minutes, about 70 minutes, about 80 minutes, about 90 minutes, or any value in between. In some embodiments, the $T_{max}$ of the ketamine is from about 30 minutes to about 90 minutes following the intranasal administration of racemic ketamine.

In some embodiments, the $T_{max}$ of norketamine is from about 45 minutes to about 360 minutes, following the intranasal administration of racemic ketamine, for example, about 45 minutes, about 60 minutes, about 75 minutes, about 90 minutes, about 105 minutes, about 120 minutes, about 135 minutes, about 150 minutes, about 165 minutes, about 180 minutes, about 195 minutes, about 210 minutes, about 225 minutes, about 240 minutes, about 255 minutes, about 270 minutes, about 285 minutes, about 300 minutes, about 315 minutes, about 315 minutes, about 330 minutes, about 345 minutes, about 360 minutes, or any value in between. In some embodiments, the $T_{max}$ of norketamine is from about 100 minutes to about 250 minutes following the intranasal administration of racemic ketamine In some embodiments, the $T_{max}$ of 6-hydroxynorketamine is from about 45 minutes to about 8 hours, following the intranasal administration of racemic ketamine, for example, about 45 minutes, about 1 hour, about 2 hours, about 3 hours, about 4 hours, about 5 hours, about 6 hours, about 7 hours, about 8 hours, about 9 hours, about 10 hours, or any value in between. In some embodiments, the $T_{max}$ of 6-hydroxynorketamine is from about 2 hours to about 4 hours, following the intranasal administration of racemic ketamine, for example, about 2 hours, about 2.5 hours, about 3 hours, about 3.5 hours, about 4 hours, or any value in between. In some embodiments, the $T_{max}$ of 6-hydroxynorketamine is from about 3 hours to about 4 hours following the intranasal administration of racemic ketamine.

In some embodiments, the $C_{max}$ of ketamine is from about 15 ng/mL to about 225 ng/mL, or any value in between, following the intranasal administration of racemic ketamine. In some embodiments, the $C_{max}$ of ketamine following the intranasal administration of racemic ketamine is from about 25 ng/mL to about 225 ng/mL, for example, about 25 ng/mL, about 35 ng/mL, about 45 ng/mL, about 55 ng/mL, about 65 ng/mL, about 75 ng/mL, about 85 ng/mL, about 95 ng/mL, about 105 ng/mL, about 115 ng/mL, about 125 ng/mL, about 135 ng/mL, about 145 ng/mL, about 155 ng/mL, about 165 ng/mL, about 175 ng/mL, about 185 ng/mL, about 195 ng/mL, about 205 ng/mL, about 215 ng/mL, about 225 ng/mL, or any value in between. In some embodiments, the $C_{max}$ of ketamine is from about 70 ng/mL to about 205 ng/mL, following the intranasal administration of racemic ketamine, for example, about 85 ng/mL, about 95 ng/mL, about 105 ng/mL, about 115 ng/mL, about 125 ng/mL, about 135 ng/mL, about 145 ng/mL, about 155 ng/mL, about 165 ng/mL, about 175 ng/mL, about 185 ng/mL, about 195 ng/mL, about 205 ng/mL, or any value in between. In some embodiments, the $C_{max}$ of ketamine is from about 75 ng/mL to about 175 ng/mL, following the intranasal administration of racemic ketamine, for example, about 75 ng/mL, about 100 ng/mL, about 125 ng/mL, about 150 ng/mL, about 175 ng/mL, or any value in between. In some embodiments, the $C_{max}$ of ketamine is from about 95 ng/mL to about 145 ng/mL, following the intranasal administration of racemic ketamine, for example, about 95 ng/mL, about 105 ng/mL, about 115 ng/mL, about 125 ng/mL, about 135 ng/mL, about 145 ng/mL, or any value in between.

In some embodiments, the $C_{max}$ of norketamine is from about 40 ng/mL to about 375 ng/mL, or any value in between, following the intranasal administration of racemic ketamine. In some embodiments, the $C_{max}$ of norketamine is from about 50 ng/mL to about 275 ng/mL, following the intranasal administration of racemic ketamine, for example, about 50 ng/mL, about 75 ng/mL, about 100 ng/mL, about 125 ng/mL, about 150 ng/mL, about 175 ng/mL, about 200 ng/mL, about 225 ng/mL, about 250 ng/mL, about 275 ng/mL, or any value in between. In some embodiments, the $C_{max}$ of norketamine is from about 90 ng/mL to about 180 ng/mL, following the intranasal administration of racemic ketamine, for example, about 90 ng/mL, about 100 ng/mL, about 110 ng/mL, about 120 ng/mL, about 130 ng/mL, about 140 ng/mL, about 150 ng/mL, about 160 ng/mL, about 170 ng/mL, about 180 ng/mL, or any value in between. In some embodiments, the $C_{max}$ of norketamine is from about 70 ng/mL to about 85 ng/mL following the intranasal administration of racemic ketamine. In some embodiments, the $C_{max}$ of norketamine is from about 90 ng/mL to about 130 ng/mL following the intranasal administration of racemic ketamine. In some embodiments, the $C_{max}$ of norketamine is from about 120 ng/mL to about 150 ng/mL following the intranasal administration of racemic ketamine. In some embodiments, the $C_{max}$ of norketamine is from about 160 ng/mL to about 195 ng/mL following the intranasal administration of racemic ketamine. In some embodiments, the $C_{max}$ of norketamine is from about 140 ng/mL to about 180 ng/mL following the intranasal administration of racemic ketamine. In some embodiments, the $C_{max}$ of norketamine is from about 215 ng/mL to about 225 ng/mL following the intranasal administration of racemic ketamine.

In some embodiments, the $C_{max}$ of 6-hydroxynorketamine is from about 15 ng/mL to about 275 ng/mL, or any value in between, following the intranasal administration of racemic ketamine. In some embodiments, the $C_{max}$ of 6-hydroxynorketamine is from about 40 ng/mL to about 275 ng/mL, or any value in between, following the intranasal administration of racemic ketamine. In some embodiments, the $C_{max}$ of 6-hydroxynorketamine is from about 55 ng/mL to about 245 ng/mL, following the intranasal administration of racemic ketamine, for example, about 55 ng/mL, about 65 ng/mL, about 75 ng/mL, about 85 ng/mL, about 95 ng/mL, about 105 ng/mL, about 115 ng/mL, about 125 ng/mL, about 135 ng/mL, about 145 ng/mL, about 155 ng/mL, about 165 ng/mL, about 175 ng/mL, about 185 ng/mL, about 195 ng/mL, about 205 ng/mL, about 215 ng/mL, about 225 ng/mL, about 235 ng/mL, about 245 ng/mL, or any value in between. In some embodiments, the $C_{max}$ of 6-hydroxynorketamine is from about 55 ng/mL to about 100 ng/mL following the intranasal administration of racemic ketamine. In some embodiments, the $C_{max}$ of 6-hydroxynorketamine is from about 95 ng/mL to about 135 ng/mL following the intranasal administration of racemic ketamine. In some embodiments, the $C_{max}$ of 6-hydroxynorketamine is from about 130 ng/mL to about 155 ng/mL following the intranasal administration of racemic ketamine. In some embodiments, the $C_{max}$ of 6-hydroxynorketamine is from about 150 ng/mL to about 185 ng/mL following the intranasal administration of racemic ketamine. In some embodiments, the $C_{max}$ of 6-hydroxynorketamine is from about 175 ng/mL to about 215 ng/mL following the intranasal administration of racemic ketamine. In some embodiments, the $C_{max}$ of 6-hydroxynorketamine is from about 210 ng/mL to about 245 ng/mL following the intranasal administration of racemic ketamine.

In some embodiments, the t½ for ketamine is about 2 hours to about 9 hours, following the intranasal administration of racemic ketamine, for example, about 2 hours, about 2.5 hours, about 3 hours, about 3.5 hours, about 4 hours, about 4.5 hours, about 5 hours, about 5.5 hours, about 6 hours, about 6.5 hours, about 7 hours, about 7.5 hours, about 8 hours, about 8.5 hours, about 9 hours, or any value in between. In some embodiments, the t½ for ketamine is about 4 hours to about 7 hours, following the intranasal administration of racemic ketamine, for example, about 4 hours, about 4.5 hours, about 5 hours, about 5.5 hours, about 6 hours, about 6.5 hours, about 7 hours, or any value in between.

In some embodiments, the t½ for norketamine is about 4.5 hours to about 12.5 hours, following the intranasal administration of racemic ketamine, for example, about 4.5 hours, about 5 hours, about 5.5 hours, about 6 hours, about 6.5 hours, about 7 hours, about 7.5 hours, about 8 hours, about 8.5 hours, about 9 hours, about 9.5 hours, about 10 hours, about 10.5 hours, about 11 hours, about 11.5 hours, about 12 hours, about 12.5 hours, or any value in between. In some embodiments, the t½ for norketamine is about 5 hours to about 10 hours, following the intranasal administration of racemic ketamine, for example, about 5 hours, about 5.5 hours, about 6 hours, about 6.5 hours, about 7 hours, about 7.5 hours, about 8 hours, about 8.5 hours, about 9 hours, about 0.5 hours, about 10 hours, or any value in between. In some embodiments, the t½ for norketamine is about 7 hours to about 8 hours, following the intranasal administration of racemic ketamine In some embodiments, the t½ for 6-hydroxynorketamine is about 5.5 hours to about 22.5 hours, following the intranasal administration of racemic ketamine, for example, about 5.5 hours, about 6 hours, about 6.5 hours, about 7 hours, about 7.5 hours, about 8 hours, about 8.5 hours, about 9 hours, about 9.5 hours, about 10 hours, about 10.5 hours, about 11 hours, about 11.5 hours, about 12 hours, about 12.5 hours, about 13 hours, about 13.5 hours, about 14 hours, about 14.5 hours, about 15 hours, about 15.5 hours, about 16 hours, about 16.5 hours, about 17 hours, about 18.5 hours, about 19 hours, about 19.5 hours, about 20 hours, about 20.5 hours, about 21 hours, about 21.5 hours, about 22 hours, about 22.5 hours, or any value in between. In some embodiments, the t½ for 6-hydroxynorketamine is about 8 hours and about 15 hours, following the intranasal administration of racemic ketamine, for example, about 8 hours, about 8.5 hours, about 9 hours, about 9.5 hours, about 10 hours, about 10.5 hours, about 11 hours, about 11.5 hours, about 12 hours, about 12.5 hours, about 13 hours, about 13.5 hours, about 14 hours, about 14.5 hours, about 15 hours, or any value in between. In some embodiments, the t½ for 6-hydroxynorketamine is about 10 hours and about 12 hours, following the intranasal administration of racemic ketamine In some embodiments, the apparent clearance for ketamine is from about 150 L/h to about 350 L/h, following the intranasal administration of racemic ketamine, for example, about 150 L/h, about 175 L/h, about 200 L/hr, about 225 L/h, about 250 L/h, about 275 L/h, about 300 L/hr, about 325 L/h, about 350 L/h, or any value in between. In some embodiments, the apparent clearance for ketamine is from about 200 L/h to about 300 L/h, following the intranasal administration of racemic ketamine, for example, about 200 L/hr, about 225 L/h, about 250 L/h, about 275 L/h, about 300 L/hr, or any value in between. In some embodiments, the apparent clearance for ketamine is from about 195 L/h to about 245 L/h, following the intranasal administration of racemic ketamine, for example, about 195 L/hr, about 200 L/hr, about 225 L/h, about 230 L/h, about 235 L/h, about 240 L/h, about 245 L/h, or any value in between.

In some embodiments, the apparent $V_d/F$ for ketamine is from about 2.5 L/kg to about 6 L/kg, or any value in between following the intranasal administration of racemic ketamine. In some embodiments, the apparent $V_d/F$ for ketamine is from about 1,000 L to about 2,500 L, following the intranasal administration of racemic ketamine, for example, about 1,000 L, about 1,250 L, about 1,500 L, about 1,750 L, about 2,000 L, about 2,250 L, about 2,500 L, or any value in between. In some embodiments, the apparent $V_d/F$ for ketamine is from about 1,250 L to about 1,750 L, following the intranasal administration of racemic ketamine, for example, about 1,250 L, about 1,300 L, about 1,350 L, about 1,400 L, about 1,450 L, about 1,500 L, about 1,550 L, about 1,600 L, about 1,650 L, about 1,700 L, about 1,750 L, or any value in between.

In some embodiments, the elimination rate constant ($K_{el}$ (l/h or $h^{-1}$)) for ketamine is from about 0.1 $h^{-1}$ to about 0.25 $h^{-1}$, following the intranasal administration of racemic ketamine, for example, about 0.1 $h^{-1}$, about 0.15 $h^{-1}$, about 0.2 $h^{-1}$, about 0.25 $h^{-1}$, or any value in between.

In some embodiments, the elimination rate constant ($K_{el}$ (l/h or $h^{-1}$)) for norketamine is from about 0.05$h^{-1}$ to about 0.15$h^{-1}$, following the intranasal administration of racemic ketamine, for example, about 0.05$h^{-1}$, about 0.1$h^{-1}$, about 0.15$h^{-1}$, or any value in between. In some embodiments, the elimination rate constant ($K_{el}$ (l/h or $h^{-1}$)) for norketamine is from about 0.09$h^{-1}$ to about 0.1$h^{-1}$, following the intranasal administration of racemic ketamine In some embodiments, the elimination rate constant ($K_{el}$ (l/h or $h^{-1}$)) for 6-hydroxynorketamine is from about 0.05 $h^{-1}$ to about 0.15 $h^{-1}$, following the intranasal administration of racemic ketamine, for example, about 0.05 $h^{-1}$, about 0.1 $h^{-1}$, about 0.15 $h^{-1}$, or any value in between. In some embodiments, the elimination rate constant ($K_{el}$ (l/h or $h^{-1}$)) for 6-hydroxynorketamine is from about 0.09 $h^{-1}$ to about 0.1 $h^{-1}$, following the intranasal administration of racemic ketamine In some embodiments, the $AUC_{0-t}$ for ketamine is from about 70 ng*h/mL to about 675 ng*h/mL, following the intranasal administration of racemic ketamine, for example, about 70 ng*h/mL, about 100 ng*h/mL, about 125 ng*h/mL, about 150 ng*h/mL, about 175 ng*h/mL, about 200 ng*h/mL, about 225 ng*h/mL, about 250 ng*h/mL, about 275 ng*h/mL, about 300 ng*h/mL, about 325 ng*h/mL, about 350 ng*h/mL, about 375 ng*h/mL, about 400 ng*h/mL, about 425 ng*h/mL, about 450 ng*h/mL, about 475 ng*h/mL, about 500 ng*h/mL, about 525 ng*h/mL, about 550 ng*h/mL, about 575 ng*h/mL, about 600, ng*h/mL, about 625 ng*h/mL, about 650 ng*h/mL, about 675 ng*h/mL, or any value in between. In some embodiments, the $AUC_{0-t}$ for ketamine is from about 70 ng*h/mL to about 250 ng*h/mL following the intranasal administration of racemic ketamine. In some embodiments, the $AUC_{0-t}$ for ketamine is from about 200 ng*h/mL to about 450 ng*h/mL following the intranasal administration of racemic ketamine. In some embodiments, the $AUC_{0-t}$ for ketamine is from about 400 ng*h/mL to about 675 ng*h/mL following the intranasal administration of racemic ketamine. In some embodiments, the $AUC_{0-t}$ for ketamine is from about 600 ng*h/mL to about 675 ng*h/mL following the intranasal administration of racemic ketamine.

In some embodiments, about 30 mg of racemic ketamine is intranasally administered and the $AUC_{0-t}$ for ketamine from about 70 ng*h/mL to about 350 ng*h/mL following the intranasal administration of racemic ketamine, for example, about 70 ng*h/mL, about 100 ng*h/mL, about 125 ng*h/mL about 150 ng*h/mL, about, 175 ng*h/mL, about 200 ng*h/mL, about 225 ng*h/mL, about 250 ng*h/mL, about 275 ng*h/mL, about 300 ng*h/mL, about 325 ng*h/mL, about 350 ng*h/mL, or any value in between. In some embodiments, about 30 mg of racemic ketamine is intranasally administered and the $AUC_{0-t}$ for ketamine from about 70 ng*h/mL to about 150 ng*h/mL. In some embodiments, about 30 mg of racemic ketamine is intranasally administered and the $AUC_{0-t}$ for ketamine from about 100 ng*h/mL to about 250 ng*h/mL. In some embodiments, about 30 mg of racemic ketamine is intranasally administered and the $AUC_{0-t}$ for ketamine from about 200 ng*h/mL to about 350 ng*h/mL.

In some embodiments, about 75 mg of racemic ketamine is intranasally administered and the $AUC_{0-t}$ for ketamine from about 225 ng*h/mL to about 525 ng*h/mL following the intranasal administration of racemic ketamine, for example, about 225 ng*h/mL, about 250 ng*h/mL, about 275 ng*h/mL about 300 ng*h/mL, about, 325 ng*h/mL, about 350 ng*h/mL, about 375 ng*h/mL, about 400 ng*h/mL, about 425 ng*h/mL, about 450 ng*h/mL, about 475 ng*h/mL, about 500 ng*h/mL, about 525 ng*h/mL, or any value in between. In some embodiments, about 75 mg of racemic ketamine is intranasally administered and the $AUC_{0-t}$ for ketamine from about 225 ng*h/mL to about 325 ng*h/mL. In some embodiments, about 75 mg of racemic ketamine is intranasally administered and the $AUC_{0-t}$ for ketamine from about 300. ng*h/mL to about 425 ng*h/mL. In some embodiments, about 75 mg of racemic ketamine is intranasally administered and the $AUC_{0-t}$ for ketamine from about 400 ng*h/mL to about 525 ng*h/mL.

In some embodiments, about 90 mg of racemic ketamine is intranasally administered and the $AUC_{0-t}$ for ketamine from about 220 ng*h/mL to about 675 ng*h/mL following the intranasal administration of racemic ketamine, for example, about 220 ng*h/mL, about 250 ng*h/mL, about 275 ng*h/mL about 300 ng*h/mL, about, 325 ng*h/mL, about 350 ng*h/mL, about 375 ng*h/mL, about 400 ng*h/mL, about 425 ng*h/mL, about 450 ng*h/mL, about 475 ng*h/mL, about 500 ng*h/mL, about 525 ng*h/mL, about 550 ng*h/mL, about 575 ng*h/mL, about 600 ng*h/mL, about 625 ng*h/mL, about 650 ng*h/mL, about 675 ng*h/mL, or any value in between. In some embodiments, about 90 mg of racemic ketamine is intranasally administered and the $AUC_{0-t}$ for ketamine from about 220 ng*h/mL to about 375 ng*h/mL. In some embodiments, about 90 mg of racemic ketamine is intranasally administered and the $AUC_{0-t}$ for ketamine from about 350 ng*h/mL to about 525 ng*h/mL. In some embodiments, about 90 mg of racemic ketamine is intranasally administered and the $AUC_{0-t}$ for ketamine from about 500 ng*h/mL to about 675 ng*h/mL.

In some embodiments, the $AUC_{0-t}$ for norketamine is from about 250 ng*h/mL to about 2,200 ng*h/mL, following the intranasal administration of racemic ketamine, for example, about 250 ng*h/mL, about 350 ng*h/mL, about 450 ng*h/mL, about 550 ng*h/mL, about 650 ng*h/mL, about 750 ng*h/mL, about 850 ng*h/mL, about 950 ng*h/mL, about 1,050 ng*h/mL, about 1,150 ng*h/mL, about 1,250 ng*h/mL, about 1,350 ng*h/mL, about 1,450 ng*h/mL, about 1,550 ng*h/mL, about 1,650 ng*h/mL, about 1750 ng*h/mL, about 1,850 ng*h/mL, about 1,950 ng*h/mL, about 2,050 ng*h/mL, about 2,200 ng*h/mL, or any value in between. In some embodiments, the $AUC_{0-t}$ for norketamine is from about 250 ng*h/mL to about 950 ng*h/mL following the intranasal administration of racemic ketamine. In some embodiments, the $AUC_{0-t}$ for norketamine is from about 900 ng*h/mL to about 1,550 ng*h/mL following the intranasal administration of racemic ketamine. In some embodiments, the $AUC_{0-t}$ for norketamine is from about 1,500 ng*h/mL to about 2,200 ng*h/mL following the intranasal administration of racemic ketamine.

In some embodiments, about 30 mg of racemic ketamine is intranasally administered and the $AUC_{0-t}$ for norketamine is from about 250 ng*h/mL to about 725 ng*h/mL, following the intranasal administration of racemic ketamine, for example, about 250 ng*h/mL, about 300 ng*h/mL, about 350 ng*h/mL, about 400 ng*h/mL, about 450 ng*h/mL, about 500 ng*h/mL, about 550 ng*h/mL, about 600 ng*h/mL, about 650 ng*h/mL, about 700 ng*h/mL, about 725 ng*h/mL, or any value in between. In some embodiments, about 30 mg of racemic ketamine is intranasally administered and the $AUC_{0-t}$ for norketamine is from about 250 ng*h/mL to about 400 ng*h/mL. In some embodiments, about 30 mg of racemic ketamine is intranasally administered and the $AUC_{0-t}$ for norketamine from about 375 ng*h/mL to about 550 ng*h/mL. In some embodiments, about 30 mg of racemic ketamine is intranasally administered and the $AUC_{0-t}$ for norketamine from about 500 ng*h/mL to about 725 ng*h/mL.

In some embodiments, about 75 mg of racemic ketamine is intranasally administered and the $AUC_{0-t}$ for norketamine is from about 675 ng*h/mL to about 1,800 ng*h/mL, following the intranasal administration of racemic ketamine, for example, about 675 ng*h/mL, about 800 ng*h/mL, about 900 ng*h/mL, about 1,000 ng*h/mL, about 1,100 ng*h/mL, about 1,200 ng*h/mL, about 1,300 ng*h/mL, about 1,400 ng*h/mL, about 1,500 ng*h/mL, about 1,600 ng*h/mL, about 1,700 ng*h/mL, about 1,800 ng*h/mL, or any value in between. In some embodiments, about 75 mg of racemic ketamine is intranasally administered and the $AUC_{0-t}$ for norketamine is from about 675 ng*h/mL to about 1,050 ng*h/mL. In some embodiments, about 75 mg of racemic ketamine is intranasally administered and the $AUC_{0-t}$ for norketamine from about 1,000 ng*h/mL to about 1,450 ng*h/mL. In some embodiments, about 75 mg of racemic ketamine is intranasally administered and the $AUC_{0-t}$ for norketamine from about 1,400 ng*h/mL to about 1,800 ng*h/mL.

In some embodiments, about 90 mg of racemic ketamine is intranasally administered and the $AUC_{0-t}$ for norketamine is from about 850 ng*h/mL to about 2,200 ng*h/mL, following the intranasal administration of racemic ketamine, for example, about 850 ng*h/mL, about 950 ng*h/mL, about 1,050 ng*h/mL, about 1,150 ng*h/mL, about 1,250 ng*h/mL, about 1,350 ng*h/mL, about 1,450 ng*h/mL, about 1,550 ng*h/mL, about 1,650 ng*h/mL, about 1,750 ng*h/mL, about 1850 ng*h/mL, about 1,950 ng*h/mL, about 2,050 ng*h/mL, about 2,200 ng*h/mL, or any value in between. In some embodiments, about 90 mg of racemic ketamine is intranasally administered and the $AUC_{0-t}$ for norketamine is from about 850 ng*h/mL to about 1,350 ng*h/mL. In some embodiments, about 90 mg of racemic ketamine is intranasally administered and the $AUC_{0-t}$ for norketamine from about 1,300 ng*h/mL to about 1,850 ng*h/mL. In some embodiments, about 90 mg of racemic ketamine is intranasally administered and the $AUC_{0-t}$ for norketamine from about 1,800 ng*h/mL to about 2,200 ng*h/mL.

In some embodiments, the $AUC_{0-t}$ for 6-hydroxynorketamine is from about 300 ng*h/mL to about 3,100 ng*h/mL, following the intranasal administration of racemic ketamine, for example, about 300 ng*h/mL, about 450 ng*h/mL, about 600 ng*h/mL, about 750 ng*h/mL, about 900 ng*h/mL, about 1,050 ng*h/mL, about 1,200 ng*h/mL, about 1,350 ng*h/mL, about 1,500 ng*h/mL, about 1,750 ng*h/mL, about 1,900 ng*h/mL, about 2,050 ng*h/mL, about 2,200 ng*h/mL, about 2,450 ng*h/mL, about 2,600 ng*h/mL, about 2,750 ng*h/mL, about 2,900 ng*h/mL, about 3,100 ng*h/mL, or any value in between. In some embodiments, the $AUC_{0-t}$ for 6-hydroxynorketamine is from about 300 ng*h/mL to about 700 ng*h/mL following the intranasal administration of racemic ketamine. In some embodiments, the $AUC_{0-t}$ for 6-hydroxynorketamine is from about 700 ng*h/mL to about 900 ng*h/mL following the intranasal administration of racemic ketamine. In some embodiments, the $AUC_{0-t}$ for 6-hydroxynorketamine is from about 850 ng*h/mL to about 950 ng*h/mL following the intranasal administration of racemic ketamine. In some embodiments, the $AUC_{0-t}$ for 6-hydroxynorketamine is from about 900 ng*h/mL to about 1,100 ng*h/mL following the intranasal administration of racemic ketamine. In some embodiments, the $AUC_{0-t}$ for 6-hydroxynorketamine is from about 1,100 ng*h/mL to about 1,300 ng*h/mL following the intranasal administration of racemic ketamine. In some embodiments, the $AUC_{0-t}$ for 6-hydroxynorketamine is from about 1,300 ng*h/mL to about 1,700 ng*h/mL following the intranasal administration of racemic ketamine. In some embodiments, the $AUC_{0-t}$ for 6-hydroxynorketamine is from about 1,700 ng*h/mL to about 2,400 ng*h/mL following the intranasal administration of racemic ketamine. In some embodiments, the $AUC_{0-t}$ for 6-hydroxynorketamine is from about 2,400 ng*h/mL to about 3,100 ng*h/mL following the intranasal administration of racemic ketamine.

In some embodiments, about 30 mg of racemic ketamine is intranasally administered and the $AUC_{0-t}$ for 6-hydroxynorketamine is from about 300 ng*h/mL to about 825 ng*h/mL, following the intranasal administration of racemic ketamine, for example, about 300 ng*h/mL, about 400 ng*h/mL, about 500 ng*h/mL, about 600 ng*h/mL, about 700 ng*h/mL, about 800 ng*h/mL, about 825 ng*h/mL, or any value in between. In some embodiments, about 30 mg of racemic ketamine is intranasally administered and the $AUC_{0-t}$ for 6-hydroxynorketamine is from about 300 ng*h/mL to about 450 ng*h/mL following the intranasal administration of racemic ketamine. In some embodiments, about 30 mg of racemic ketamine is intranasally administered and the $AUC_{0-t}$ for 6-hydroxynorketamine is from about 400 ng*h/mL to about 550 ng*h/mL following the intranasal administration of racemic ketamine. In some embodiments, about 30 mg of racemic ketamine is intranasally administered and the $AUC_{0-t}$ for 6-hydroxynorketamine is from about 500 ng*h/mL to about 825 ng*h/mL following the intranasal administration of racemic ketamine.

In some embodiments, about 75 mg of racemic ketamine is intranasally administered and the $AUC_{0-t}$ for 6-hydroxynorketamine is from about 650 ng*h/mL to about 1,900 ng*h/mL, following the intranasal administration of racemic ketamine, for example, about 650 ng*h/mL, about 750 ng*h/mL, about 850 ng*h/mL, about 950 ng*h/mL, about 1,050 ng*h/mL, about 1,150 ng*h/mL, about 1,250 ng*h/mL, about 1,350 ng*h/mL, about 1,450 ng*h/mL, about 1,550 ng*h/mL, about 1,650 ng*h/mL, about 1,750 ng*h/mL, about 1,900 ng*h/mL, or any value in between. In some embodiments, about 75 mg of racemic ketamine is intranasally administered and the $AUC_{0-t}$ for 6-hydroxynorketamine is from about 450 ng*h/mL to about 950 ng*h/mL following the intranasal administration of racemic ketamine. In some embodiments, about 75 mg of racemic ketamine is intranasally administered and the $AUC_{0-t}$ for 6-hydroxynorketamine is from about 900 ng*h/mL to about 1,400 ng*h/mL following the intranasal administration of racemic ketamine. In some embodiments, about 75 mg of racemic ketamine is intranasally administered and the $AUC_{0-t}$ for 6-hydroxynorketamine is from about 1,350 ng*h/mL to about 1,900 ng*h/mL following the intranasal administration of racemic ketamine.

In some embodiments, about 90 mg of racemic ketamine is intranasally administered and the $AUC_{0-t}$ for 6-hydroxynorketamine is from about 1,050 ng*h/mL to about 3,100 ng*h/mL, following the intranasal administration of racemic ketamine, for example, about 1,050 ng*h/mL, about 1,200 ng*h/mL, about 1,350 ng*h/mL, about 1,500 ng*h/mL, about 1,750 ng*h/mL, about 1,900 ng*h/mL, about 2,050 ng*h/mL, about 2,200 ng*h/mL, about 2,450 ng*h/mL, about 2,600 ng*h/mL, about 2,750 ng*h/mL, about 2,900 ng*h/mL, about 3100 ng*h/mL, or any value in between. In some embodiments, about 90 mg of racemic ketamine is intranasally administered and the $AUC_{0-t}$ for 6-hydroxynorketamine is from about 1,050 ng*h/mL to about 1,850 ng*h/mL following the intranasal administration of racemic ketamine. In some embodiments, about 90 mg of racemic ketamine is intranasally administered and the $AUC_{0-t}$ for 6-hydroxynorketamine is from about 1,800 ng*h/mL to about 2,600 ng*h/mL following the intranasal administration of racemic ketamine. In some embodiments, about 90 mg of racemic ketamine is intranasally administered and the $AUC_{0-t}$ for 6-hydroxynorketamine is from about 2,550 ng*h/mL to about 3,100 ng*h/mL following the intranasal administration of racemic ketamine.

In some embodiments, the $AUC_{0-t}$ for ketamine is from about 70 ng*h/mL to about 675 ng*h/mL, following the intranasal administration of racemic ketamine, for example, about 70 ng*h/mL, about 100 ng*h/mL, about 125 ng*h/mL, about 150 ng*h/mL, about 175 ng*h/mL, about 200 ng*h/mL, about 225 ng*h/mL, about 250 ng*h/mL, about 275 ng*h/mL, about 300 ng*h/mL, about 325 ng*h/mL, about 350 ng*h/mL, about 375 ng*h/mL, about 400 ng*h/mL, about 425 ng*h/mL, about 450 ng*h/mL, about 475 ng*h/mL, about 500 ng*h/mL, about 525 ng*h/mL, about 550 ng*h/mL, about 575 ng*h/mL, about 600, ng*h/mL, about 625 ng*h/mL, about 650 ng*h/mL, about 675 ng*h/mL, and the $C_{max}$ of ketamine is from about 15 ng/mL to about 225 ng/mL, or any value in between following the intranasal administration of racemic ketamine. In some embodiments, the $AUC_{0-t}$ for ketamine is from about 70 ng*h/mL to about 675 ng*h/mL, following the intranasal administration of racemic ketamine, for example, about 70 ng*h/mL, about 100 ng*h/mL, about 125 ng*h/mL, about 150 ng*h/mL, about 175 ng*h/mL, about 200 ng*h/mL, about 225 ng*h/mL, about 250 ng*h/mL, about 275 ng*h/mL, about 300 ng*h/mL, about 325 ng*h/mL, about 350 ng*h/mL, about 375 ng*h/mL, about 400 ng*h/mL, about 425 ng*h/mL, about 450 ng*h/mL, about 475 ng*h/mL, about 500 ng*h/mL, about 525 ng*h/mL, about 550 ng*h/mL, about 575 ng*h/mL, about 600, ng*h/mL, about 625 ng*h/mL, about 650 ng*h/mL, about 675 ng*h/mL, and the $C_{max}$ of ketamine is from about 70 ng/mL to about 205 ng/mL, following the intranasal administration of racemic ketamine, for example, about 70 ng/mL, about 85 ng/mL, about 95 ng/mL, about 105 ng/mL, about 115 ng/mL, about 125 ng/mL, about 135 ng/mL, about 145 ng/mL, about 155 ng/mL, about 165 ng/mL, about 185 ng/mL, about 205 ng/mL, or any value in between. In some embodiments, the $AUC_{0-t}$ for ketamine is from about 70 ng*h/mL to about 250 ng*h/mL, about 200 ng*h/mL to about 450 ng*h/mL, about 400 ng*h/mL to about 675 ng*h/mL, about 600 ng*h/mL to about 675 ng*h/mL following the intranasal administration of racemic ketamine, and the $C_{max}$ of ketamine is from about 75 ng/mL to about 1755 ng/mL, for example, about 75 ng/mL, about 100 ng/mL, about 125 ng/mL, about 150 ng/mL, about 175 ng/mL, or any value in between following the intranasal administration of racemic ketamine.

In some embodiments, the $AUC_{0-t}$ for norketamine is from about 250 ng*h/mL to about 2,200 ng*h/mL, following the intranasal administration of racemic ketamine, for example, about 250 ng*h/mL, about 350 ng*h/mL, about 450 ng*h/mL, about 550 ng*h/mL, about 650 ng*h/mL, about 750 ng*h/mL, about 850 ng*h/mL, about 950 ng*h/mL, about 1,050 ng*h/mL, about 1,150 ng*h/mL, about 1,250 ng*h/mL, about 1,350 ng*h/mL, about 1,450 ng*h/mL, about 1,550 ng*h/mL, about 1,650 ng*h/mL, about 1750 ng*h/mL, about 1,850 ng*h/mL, about 1,950 ng*h/mL, about 2,050 ng*h/mL, about 2,200 ng*h/mL, or any value in between, and the $C_{max}$ of norketamine is from about 40 ng/mL to about 375 ng/mL, or any value in between following the intranasal administration of racemic ketamine. In some embodiments, the $AUC_{0-t}$ for norketamine is from about 250 ng*h/mL to about 2,200 ng*h/mL, following the intranasal administration of racemic ketamine, for example, about 250 ng*h/mL, about 350 ng*h/mL, about 450 ng*h/mL, about 550 ng*h/mL, about 650 ng*h/mL, about 750 ng*h/mL, about 850 ng*h/mL, about 950 ng*h/mL, about 1,050 ng*h/mL, about 1,150 ng*h/mL, about 1,250 ng*h/mL, about 1,350 ng*h/mL, about 1,450 ng*h/mL, about 1,550 ng*h/mL, about 1,650 ng*h/mL, about 1,750 ng*h/mL, about 1,850 ng*h/mL, about 1,950 ng*h/mL, about 2,050 ng*h/mL, about 2,200 ng*h/mL, or any value in between, and the $C_{max}$ of norketamine is from about 50 ng/mL to about 275 ng/mL, following the intranasal administration of racemic ketamine, for example, about 50 ng/mL, about 75 ng/mL, about 100 ng/mL, about 125 ng/mL, about 150 ng/mL, about 175 ng/mL, about 200 ng/mL, about 225 ng/mL, about 250 ng/mL, about 275 ng/mL, or any value in between. In some embodiments, the $C_{max}$ of norketamine is from about 50 ng/mL to about 135 ng/mL, about 130 ng/mL to about 15 ng/mL, about 210 ng/mL to about 245 ng/mL, about 240 ng/mL to about 275 ng/mL, following the intranasal administration of racemic ketamine, and the $AUC_{0-t}$ for norketamine is from about 250 ng*h/mL to about 950 ng*h/mL, about 900 ng*h/mL to about 1,550 ng*h/mL, or about 1,500 ng*h/mL to about 2,200 ng*h/mL following the intranasal administration of racemic ketamine. In some embodiments, the $AUC_{0-t}$ for 6-hydroxynorketamine is from about 300 ng*h/mL to about 3,100 ng*h/mL, following the intranasal administration of racemic ketamine, for example, about 300 ng*h/mL, about 450 ng*h/mL, about 600 ng*h/mL, about 750 ng*h/mL, about 900 ng*h/mL, about 1,050 ng*h/mL, about 1,200 ng*h/mL, about 1,350 ng*h/mL, about 1,500 ng*h/mL, about 1,750 ng*h/mL, about 1,900 ng*h/mL, about 2,050 ng*h/mL, about 2,200 ng*h/mL, about 2,450 ng*h/mL, about 2,600 ng*h/mL, about 2,750 ng*h/mL, about 2,900 ng*h/mL, about 3100 ng*h/mL, or any value in between, and the $C_{max}$ of 6-hydroxynorketamine is from about 15 ng/mL to about 275 ng/mL, or any value in between following the intranasal administration of racemic ketamine. In some embodiments, the $AUC_{0-t}$ for 6-hydroxynorketamine is from about 300 ng*h/mL to about 3,100 ng*h/mL, following the intranasal administration of racemic ketamine, for example, about 300 ng*h/mL, about 450 ng*h/mL, about 600 ng*h/mL, about 750 ng*h/mL, about 900 ng*h/mL, about 1,050 ng*h/mL, about 1,200 ng*h/mL, about 1,350 ng*h/mL, about 1,500 ng*h/mL, about 1,750 ng*h/mL, about 1,900 ng*h/mL, about 2,050 ng*h/mL, about 2,200 ng*h/mL, about 2,450 ng*h/mL, about 2,600 ng*h/mL, about 2,750 ng*h/mL, about 2,900 ng*h/mL, about 3,100 ng*h/mL, or any value in between, following the intranasal administration of racemic ketamine, and the $C_{max}$ of 6-hydroxynorketamine is from about 55 ng/mL to about 245 ng/mL, for example, about 55 ng/mL, about 65 ng/mL, about 75 ng/mL, about 85 ng/mL, about 95 ng/mL, about 105 ng/mL, about 115 ng/mL, about 125 ng/mL, about 135 ng/mL, about 145 ng/mL, about 155 ng/mL, about 165 ng/mL, about 175 ng/mL, about 185 ng/mL, about 195 ng/mL, about 205 ng/mL, about 215 ng/mL, about 225 ng/mL, about 235 ng/mL, about 245 ng/mL, or any value in between following the intranasal administration of racemic ketamine. In some embodiments, the $AUC_{0-t}$ for 6-hydroxynorketamine is from about 700 ng*h/mL to about 1,550 ng*h/mL, about 1,500 ng*h/mL to about 2,050 ng*h/mL, about 2,000 ng*h/mL to about 2,550 ng*h/mL, about 2,500 ng*h/mL to about 3,100 ng*h/mL following the intranasal administration of racemic ketamine, and the $C_{max}$ of 6-hydroxynorketamine is from about 55 ng/mL to about 125 ng/mL, about 120 ng/mL to about 180 ng/mL, or about 175 ng/mL to about 245 ng/mL following the intranasal administration of racemic ketamine.

In some embodiments, the $AUC_{0-inf}$ for ketamine is from about 80 ng*h/mL to about 675 ng*h/mL, following the intranasal administration of racemic ketamine, for example, about 80 ng*h/mL, about 125 ng*h/mL, about 175 ng*h/mL, about 225 ng*h/mL, about 275 ng*h/mL, about 325 ng*h/mL, about 475 ng*h/mL, about 525 ng*h/mL, about 575 ng*h/mL, about 625 ng*h/mL, about 675 ng*h/mL, or any value in between. In some embodiments, the $AUC_{0-inf}$ for ketamine is from about 80 ng*h/mL to about 175 ng*h/mL following the intranasal administration of racemic ketamine. In some embodiments, the $AUC_{0-inf}$ for ketamine is from about 150 ng*h/mL to about 275 ng*h/mL following the intranasal administration of racemic ketamine. In some embodiments, the $AUC_{0-inf}$ for ketamine is from about 250 ng*h/mL to about 375 ng*h/mL following the intranasal administration of racemic ketamine. In some embodiments, the $AUC_{0-inf}$ for ketamine is from about 350 ng*h/mL to about 475 ng*h/mL following the intranasal administration of racemic ketamine. In some embodiments, the $AUC_{0-inf}$ for ketamine is from about 450 ng*h/mL to about 575 ng*h/mL following the intranasal administration of racemic ketamine. In some embodiments, the $AUC_{0-inf}$ for ketamine is from about 550 ng*h/mL to about 675 ng*h/mL following the intranasal administration of racemic ketamine.

In some embodiments, the $AUC_{0-inf}$ for norketamine is from about 250 ng*h/mL to about 875 ng*h/mL, following the intranasal administration of racemic ketamine, for example, about 250 ng*h/mL, about 275 ng*h/mL, about 300 ng*h/mL, about 325 ng*h/mL, about 350 ng*h/mL, about 375 ng*h/mL, about 400 ng*h/mL, about 425 ng*h/mL, about 450 ng*h/mL, about 475 ng*h/mL, about 500 ng*h/mL, about 525 ng*h/mL, about 550 ng*h/mL, about 575 ng*h/mL, about 600 ng*h/mL, about 625 ng*h/mL, about 650 ng*h/mL, about 675 ng*h/mL, about 700 ng*h/mL, about 725 ng*h/mL, about 750 ng*h/mL, about 775 ng*h/mL, about 800 ng*h/mL, about 825 ng*h/mL, about 850 ng*h/mL, about 875 ng*h/mL or any value in between. In some embodiments, the $AUC_{0-inf}$ for norketamine is from about 250 ng*h/mL to about 475 ng*h/mL following the intranasal administration of racemic ketamine. In some embodiments, the $AUC_{0-inf}$ for norketamine is from about 450 ng*h/mL to about 675 ng*h/mL following the intranasal administration of racemic ketamine. In some embodiments, the $AUC_{0-inf}$ for norketamine is from about 650 ng*h/mL to about 875 ng*h/mL following the intranasal administration of racemic ketamine.

In some embodiments, the $AUC_{0-inf}$ for 6-hydroxynorketamine is from about 375 ng*h/mL to about 3,700 ng*h/mL, following the intranasal administration of racemic ketamine, for example, about 375 ng*h/mL, about 500 ng*h/mL, about 650 ng*h/mL, about 900 ng*h/mL, about 1,050 ng*h/mL, about 1,200 ng*h/mL, about 1,350 ng*h/mL, about 1,500 ng*h/mL, about 1,650 ng*h/mL, about 1,800 ng*h/mL, about 1,950 ng*h/mL, about 2,100 ng*h/mL, about 2,250 ng*h/mL, about 2,400 ng*h/mL, about 2,550 ng*h/mL, about 2,700 ng*h/mL, about 2,850 ng*h/mL, about 3,000 ng*h/mL, about 3,150 ng*h/mL, about 3,300 ng*h/mL, about 3,450 ng*h/mL, about 3,600 ng*h/mL, about 3,700 ng*h/mL, or any value in between. In some embodiments, the $AUC_{0-inf}$ for 6-hydroxynorketamine is from about 375 ng*h/mL to about 1,250 ng*h/mL following the intranasal administration of racemic ketamine. In some embodiments, the $AUC_{0-inf}$ for 6-hydroxynorketamine is from about 1,200 ng*h/mL to about 1,400 ng*h/mL following the intranasal administration of racemic ketamine. In some embodiments, the $AUC_{0-inf}$ for 6-hydroxynorketamine is from about 1,350 ng*h/mL to about 2,700 ng*h/mL following the intranasal administration of racemic ketamine. In some embodiments, the $AUC_{0-inf}$ for 6-hydroxynorketamine is from about 2,600 ng*h/mL to about 3,700 ng*h/mL following the intranasal administration of racemic ketamine.

In some embodiments, the residual area for ketamine is about 2.5% to about 8%, for example, about 2.5%, about 3%, about 3.5%, about 4%, about 4.5%, about 5%, about 5.5%, about 6%, about 6.5%, about 7%, about 7.5%, about 8%, or any value in between following the intranasal administration of racemic ketamine. In some embodiments, the residual area for ketamine is about 2.5% to about 5%, following the intranasal administration of racemic ketamine. In some embodiments, the residual area for ketamine is about 4% to about 6% following the intranasal administration of racemic ketamine. In some embodiments, the residual area for ketamine is about 5% to about 8% following the intranasal administration of racemic ketamine.

In some embodiments, the residual area for norketamine is about 6% to about 15%, following the intranasal administration of racemic ketamine, for example, about 6%, about 6.5%, about 7%, about 7.5%, about 8%, about 8.5%, about 9%, about 9.5%, about 10%, about 10.5%, about 11%, about 11.5%, about 12%, about 12.5%, about 13%, about 13.5%, about 14%, about 14.5%, about 15%, or any value in between. In some embodiments, the residual area for norketamine is about 2.5% to about 5% following the intranasal administration of racemic ketamine. In some embodiments, the residual area for norketamine is about 4% to about 6% following the intranasal administration of racemic ketamine. In some embodiments, the residual area for norketamine is about 5% to about 8% following the intranasal administration of racemic ketamine.

In some embodiments, the residual area for 6-hydroxynorketamine is about 16% to about 34%, following the intranasal administration of racemic ketamine, for example, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, or any value in between. In some embodiments, the residual area for 6-hydroxynorketamine is about 16% to about 24% following the intranasal administration of racemic ketamine. In some embodiments, the residual area for 6-hydroxynorketamine is about 20% to about 30% following the intranasal administration of racemic ketamine. In some embodiments, the residual area for 6-hydroxynorketamine is about 26% to about 34% following the intranasal administration of racemic ketamine.

In some embodiments, the $AUC_{0-t}$ for the intranasal racemic ketamine is about 80% to about 125% of the $AUC_{0-t}$ for an equivalent dose of intravenous racemic ketamine. For example, about 80%, about 85%, about 90%, about 95%, about 100%, about 105%, about 110%, about 115%, about 120%, about 125%, or any value in between. In some embodiments, the $AUC_{0-t}$ for the intranasal racemic ketamine is about 80% to about 95% of the $AUC_{0-t}$ for an equivalent dose of intravenous racemic ketamine. In some embodiments, the $AUC_{0-inf}$ for the intranasal racemic ketamine is about 80% to about 125% of the $AUC_{0-inf}$ for an equivalent dose of intravenous racemic ketamine. For example, about 80%, about 85%, about 90%, about 95%, about 100%, about 105%, about 110%, about 115%, about 120%, about 125%, or any value in between. In some embodiments, the $AUC_{0-inf}$ for the intranasal racemic ketamine is about 80% to about 95% of the $AUC_{0-inf}$ for an equivalent dose of intravenous racemic ketamine.

In some embodiments, the $AUC_{0-t}$ of norketamine after administration of the intranasal racemic ketamine is about 1.1 to about 4.0 times greater than the $AUC_{0-t}$ of norketamine after administration of an equivalent dose of intravenous racemic ketamine. In some embodiments, the $AUC_{0-inf}$ of norketamine after administration of the intranasal racemic ketamine is about 1.1 to about 4.0 times greater than the $AUC_{0-inf}$ of norketamine after administration of an equivalent dose of intravenous racemic ketamine. For example, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, or about 4.0, times greater, or any value in between.

In some embodiments, the $AUC_{0-t}$ of 6-hydroxynorketamine after administration of the intranasal racemic ketamine is about 1.3 to about 3.6 times greater than the $AUC_{0-t}$ of norketamine after administration of an equivalent dose of intravenous racemic ketamine. For example, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, or about 3.6, times greater, or any value in between. In some embodiments, the $AUC_{0-inf}$ of 6-hydroxynorketamine after administration of the intranasal racemic ketamine is about 1.1 to about 3.1 times greater than the $AUC_{0-inf}$ of norketamine after administration of an equivalent dose of intravenous racemic ketamine. For example, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, or about 3.1, times greater, or any value in between.

In some embodiments, the $C_{max}$ for the intranasal racemic ketamine is about 25% to about 125% of the $C_{max}$ for an equivalent dose of intravenous racemic ketamine. For example, about 25%, about 30%, about 35%, about 40%, about 45%, about 50%, about 55%, about 60%, about 65%, about 70%, about 75%, about 80%, about 85%, about 90%, about 95%, about 100%, about 105%, about 110%, about 115%, about 120%, about 125%, or any value in between. In some embodiments, the $C_{max}$ for the intranasal racemic ketamine is about 25% to about 100% of the $C_{max}$ for an equivalent dose of intravenous racemic ketamine. In some embodiments, the $C_{max}$ for the intranasal racemic ketamine is about 30% to about 75% of the $C_{max}$ for an equivalent dose of intravenous racemic ketamine. In some embodiments, the $C_{max}$ for the intranasal racemic ketamine is about 50% to about 70% of the $C_{max}$ for an equivalent dose of intravenous racemic ketamine.

In some embodiments, the $C_{max}$ of norketamine after administration of the intranasal racemic ketamine is about 1.5 to about 6.0 times greater than the $C_{max}$ of norketamine after administration of an equivalent dose of intravenous racemic ketamine. For example, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, or about 6.0 times greater, or any value in between.

In some embodiments, the $C_{max}$ of 6-hydroxynorketamine after administration of the intranasal racemic ketamine is about 1.4 to about 5.0 times greater than the $C_{max}$ of 6-hydroxynorketamine after administration of an equivalent dose of intravenous racemic ketamine. For example, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, or about 5.0 times greater, or any value in between.

In some embodiments, the $T_{max}$ for the intranasal racemic ketamine is about 1.6 to about 6.0 times greater than the $T_{max}$ for an equivalent dose of intravenous racemic ketamine. For example, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, or about 6.0 times greater, or any value in between.

In some embodiments, the $T_{max}$ of norketamine after administration of the intranasal racemic ketamine is about 30% to about 550% of the $T_{max}$ of norketamine after administration of an equivalent dose of intravenous racemic ketamine. For example, about 30%, about 45%, about 60%, about 75%, about 90%, about 105%, about 120%, about 140%, about 155%, about 170%, about 185%, about 200%, about 215%, about 230%, about 245%, about 260%, about 275%, about 290%, about 305%, about 320%, about 340%, about 355%, about 370%, about 385%, about 400%, about 415%, about 430%, about 445%, about 460%, about 475%, about 490%, about 505%, about 520%, about 540%, about 550%, or any value in between. In some embodiments, the $T_{max}$ of norketamine after administration of the intranasal racemic ketamine is about 80% to about 240% of the $T_{max}$ of norketamine after administration of an equivalent dose of intravenous racemic ketamine. For example, about 80%, about 100%, about 120%, about 140%, about 160%, about 180%, about 200%, about 220%, about 240%, or any value in between. In some embodiments, the $T_{max}$ of norketamine after administration of the intranasal racemic ketamine is about 90% to about 180% of the $T_{max}$ of norketamine after administration of an equivalent dose of intravenous racemic ketamine. For example, about 90%, about 100%, about 110%, about 120%, about 130%, about 140%, about 150%, about 160%, about 170%, about 180%, or any value in between.

In some embodiments, the $T_{max}$ of 6-hydroxynorketamine after administration of the intranasal racemic ketamine is about 20% to about 200% of the $T_{max}$ of 6-hydroxynorketamine after administration of an equivalent dose of intravenous racemic ketamine. For example, about 20%, about 30%, about 40%, about 50%, about 60%, about 70%, about 80%, about 90%, about 100%, about 110%, about 120%, about 130%, about 140%, about 150%, about 160%, about 170%, about 180%, about 190%, about 200%, or any value in between. In some embodiments, the $T_{max}$ of 6-hydroxynorketamine after administration of the intranasal racemic ketamine is about 50% to about 100% of the $T_{max}$ of 6-hydroxynorketamine after administration of an equivalent dose of intravenous racemic ketamine. For example, about 50%, about 60%, about 70%, about 80%, about 90%, about 100%, or any value in between. In some embodiments, the $T_{max}$ of 6-hydroxynorketamine after administration of the intranasal racemic ketamine is about 65% to about 85% of the $T_{max}$ of 6-hydroxynorketamine after administration of an equivalent dose of intravenous racemic ketamine. For example, about 65%, about 70%, about 75%, about 80%, about 85%, or any value in between.

In some embodiments, administration of intranasal racemic ketamine provides higher exposure and/or higher plasma concentrations of one or more active metabolites of ketamine relative to an equivalent dose of intravenous racemic ketamine. In some embodiments, the one or more active metabolites are selected from norketamine, 6-hydroxynorketamine, and a combination thereof.

In some embodiments, administration of intranasal racemic ketamine provides higher exposure and/or higher plasma concentrations of norketamine, relative to an equivalent dose of intravenous racemic ketamine. In some embodiments, administration of intranasal racemic ketamine provides higher exposure and/or higher plasma concentrations of 6-hydroxynorketamine, relative to an equivalent dose of intravenous racemic ketamine. In some embodiments, administration of intranasal racemic ketamine provides higher exposure and/or higher plasma concentrations of norketamine and 6-hydroxynorketamine, relative to an equivalent dose of intravenous racemic ketamine.

In some embodiments, "equivalent" doses of intranasal racemic ketamine and intravenous racemic ketamine and/or intravenous (S)-ketamine, or a pharmaceutically acceptable salt of any of the foregoing, is determined by the equivalence of the $AUC_{0-inf}$ values.

In some embodiments, intranasal administration of the racemic ketamine exhibits one or more of:

- an $AUC_{0-t}$ of norketamine that is at least 1.5 times higher than the $AUC_{0-t}$ of norketamine exhibited by intravenous administration of an equivalent dose of racemic ketamine;
- an $AUC_{0-inf}$ of norketamine that is at least 1.5 times higher than the $AUC_{0-inf}$ of norketamine exhibited by intravenous administration of an equivalent dose of racemic ketamine; and
- a $C_{max}$ of norketamine that is at least 2 times higher than the $C_{max}$ of norketamine exhibited by intravenous administration of an equivalent dose of racemic ketamine.

In some embodiments, intranasal administration of the racemic ketamine exhibits an $AUC_{0-t}$ of norketamine that is about 1.7 to about 2.5 times higher than the $AUC_{0-t}$ of norketamine exhibited by intravenous administration of an equivalent dose of racemic ketamine. In some embodiments, intranasal administration of the racemic ketamine exhibits an $AUC_{0-t}$ of norketamine that is about 1.9 to about 2.3 times higher than the $AUC_{0-t}$ of norketamine exhibited by intravenous administration of an equivalent dose of racemic ketamine. In some embodiments, intranasal administration of the racemic ketamine exhibits an $AUC_{0-t}$ of norketamine that is at least 1.8 times higher (e.g., at least 1.9 times higher or at least 2 times higher) than the $AUC_{0-t}$ of norketamine exhibited by intravenous administration of an equivalent dose of racemic ketamine.

In some embodiments, intranasal administration of the racemic ketamine exhibits an $AUC_{0-inf}$ of norketamine that is about 1.5 to about 2.5 times higher than the $AUC_{0-inf}$ of norketamine exhibited by intravenous administration of an equivalent dose of racemic ketamine. In some embodiments, intranasal administration of the racemic ketamine exhibits an $AUC_{0-t}$ of norketamine that is about 1.8 to about 2.2 times higher than the $AUC_{0-inf}$ of norketamine exhibited by intravenous administration of an equivalent dose of racemic ketamine. In some embodiments, intranasal administration of the racemic ketamine exhibits an $AUC_{0-t}$ of norketamine that is at least 1.7 time higher (e.g., at least 1.8 times higher, at least 1.9 times higher, or at least 2 times higher) than the $AUC_{0-inf}$ of norketamine exhibited by intravenous administration of an equivalent dose of racemic ketamine.

In some embodiments, intranasal administration of the racemic ketamine exhibits a $C_{max}$ of norketamine that is about 2.2 to about 3.5 times higher than the $C_{max}$ of norketamine exhibited by intravenous administration of an equivalent dose of racemic ketamine. In some embodiments, intranasal administration of the racemic ketamine exhibits a $C_{max}$ of norketamine that is about 2.4 to about 3.2 times higher than the $C_{max}$ of norketamine exhibited by intravenous administration of an equivalent dose of racemic ketamine. In some embodiments, intranasal administration of the racemic ketamine exhibits a $C_{max}$ of norketamine that is at least 2.5 times higher (e.g., at least 2.8 times higher or at least 3 times higher) than the $C_{max}$ of norketamine exhibited by intravenous administration of an equivalent dose of racemic ketamine. In some embodiments, intranasal administration of the racemic ketamine exhibits a $T_{max}$ of norketamine that is about 80% to about 125% of the $T_{max}$ of norketamine exhibited by an intravenous administration of an equivalent dose of racemic ketamine. In some embodiments, intranasal administration of the racemic ketamine exhibits a $T_{max}$ of norketamine that is about 90% to about 110% of the $T_{max}$ of norketamine exhibited by an intravenous administration of an equivalent dose of racemic ketamine. In some embodiments, intranasal administration of the racemic ketamine exhibits a $T_{max}$ of norketamine that is about 95% to about 105% of the $T_{max}$ of norketamine exhibited by an intravenous administration of an equivalent dose of racemic ketamine.

In some embodiments, one or more of the $AUC_{0-t}$, $AUC_{0-inf}$, $C_{max}$, and $T_{max}$ of norketamine is determined following one dose of racemic ketamine. In some embodiments, one or more of the $AUC_{0-t}$, $AUC_{0-inf}$, $C_{max}$, and $T_{max}$ of norketamine is determined following two doses of racemic ketamine. In some embodiments, one or more of the $AUC_{0-t}$, $AUC_{0-inf}$, $C_{max}$, and $T_{max}$ of norketamine is determined following three doses of racemic ketamine.

In some embodiments, intranasal administration of the racemic ketamine exhibits one or more of:

- an $AUC_{0-t}$ of hydroxynorketamine that is at least 1.5 times higher than the $AUC_{0-t}$ of hydroxynorketamine exhibited by intravenous administration of an equivalent dose of racemic ketamine;
- an $AUC_{0-inf}$ of hydroxynorketamine that is at least 1.2 times higher than the $AUC_{0-inf}$ of hydroxynorketamine exhibited by intravenous administration of an equivalent dose of racemic ketamine; and a $C_{max}$ of hydroxynorketamine that is at least 2 times higher than the $C_{max}$ of norketamine exhibited by intravenous administration of an equivalent dose of racemic ketamine.

In some embodiments, intranasal administration of the racemic ketamine exhibits an $AUC_{0-t}$ of hydroxynorketamine that is about 1.7 to about 2.5 times higher than the $AUC_{0-t}$ of hydroxynorketamine exhibited by intravenous administration of an equivalent dose of racemic ketamine. In some embodiments, intranasal administration of the racemic ketamine exhibits an $AUC_{0-t}$ of hydroxynorketamine that is about 1.9 to about 2.3 times higher than the $AUC_{0-t}$ of hydroxynorketamine exhibited by intravenous administration of an equivalent dose of racemic ketamine. In some embodiments, intranasal administration of the racemic ketamine exhibits an $AUC_{0-t}$ of hydroxynorketamine that is at least 1.9 times higher (e.g., at least 2 times higher or at least 2.1 times higher) than the $AUC_{0-t}$ of hydroxynorketamine exhibited by intravenous administration of an equivalent dose of racemic ketamine.

In some embodiments, intranasal administration of the racemic ketamine exhibits an $AUC_{0-inf}$ of hydroxynorketamine that is about 1.5 to about 2.5 times higher than the $AUC_{0-inf}$ of hydroxynorketamine exhibited by intravenous administration of an equivalent dose of racemic ketamine. In some embodiments, intranasal administration of the racemic ketamine exhibits an $AUC_{0-t}$ of hydroxynorketamine that is about 1.7 to about 2.1 times higher than the $AUC_{0-inf}$ of hydroxynorketamine exhibited by intravenous administration of an equivalent dose of racemic ketamine. In some embodiments, intranasal administration of the racemic ketamine exhibits an $AUC_{0-t}$ of hydroxynorketamine that is at least 1.7 times higher (e.g., at least 1.8 times higher or at least 1.9 times higher) than the $AUC_{0-inf}$ of hydroxynorketamine exhibited by intravenous administration of an equivalent dose of racemic ketamine.

In some embodiments, intranasal administration of the racemic ketamine exhibits a $C_{max}$ of hydroxynorketamine that is about 2.2 to about 3.2 times higher than the $C_{max}$ of hydroxynorketamine exhibited by intravenous administration of an equivalent dose of racemic ketamine. In some embodiments, intranasal administration of the racemic ketamine exhibits a $C_{max}$ of hydroxynorketamine that is about 2.4 to about 2.8 times higher than the $C_{max}$ of hydroxynorketamine exhibited by intravenous administration of an equivalent dose of racemic ketamine. In some embodiments, intranasal administration of the racemic ketamine exhibits a $C_{max}$ of hydroxynorketamine that is at least 2.4 times higher (e.g., at least 2.5 times higher or at least 2.6 times higher) than the $C_{max}$ of hydroxynorketamine exhibited by intravenous administration of an equivalent dose of racemic ketamine.

In some embodiments, intranasal administration of the racemic ketamine exhibits a $T_{max}$ of hydroxynorketamine that is about 80% to about 125% of the $T_{max}$ of hydroxynorketamine exhibited by an intravenous administration of an equivalent dose of racemic ketamine. In some embodiments, intranasal administration of the racemic ketamine exhibits a $T_{max}$ of hydroxynorketamine that is about 90% to about 110% of the $T_{max}$ of hydroxynorketamine exhibited by an intravenous administration of an equivalent dose of racemic ketamine. In some embodiments, intranasal administration of the racemic ketamine exhibits a $T_{max}$ of hydroxynorketamine that is about 95% to about 105% of the $T_{max}$ of hydroxynorketamine exhibited by an intravenous administration of an equivalent dose of racemic ketamine.

In some embodiments, one or more of the $AUC_{0-t}$, $AUC_{0-inf}$, $C_{max}$, and $T_{max}$ of hydroxynorketamine is determined following one dose of racemic ketamine. In some embodiments, one or more of the $AUC_{0-t}$, $AUC_{0-inf}$, $C_{max}$, and $T_{max}$ of hydroxynorketamine is determined following two doses of racemic ketamine. In some embodiments, one or more of the $AUC_{0-t}$, $AUC_{0-inf}$, $C_{max}$, and $T_{max}$ of hydroxynorketamine is determined following three doses of racemic ketamine.

In some embodiments, the Montgomery-Asberg Depression Rating Scale (MADRS) Total Score of the subject is from 20-60 units prior to intranasal administration of the racemic ketamine, or a pharmaceutically acceptable salt thereof.

In some embodiments, the MADRS Total Score of the subject is from 30-60 units prior to intranasal administration of the racemic ketamine, or a pharmaceutically acceptable salt thereof. In some embodiments, the MADRS Total Score of the subject is reduced by at least 50% 24 hours after intranasal administration of the racemic ketamine, or a pharmaceutically acceptable salt thereof. In some embodiments, the MADRS Total Score of the subject is less than or equal to 15 units 24 hours after intranasal administration of the racemic ketamine, or a pharmaceutically acceptable salt thereof. In some embodiments, the MADRS Total Score of the subject is less than or equal to 12 units 48 hours after intranasal administration of the racemic ketamine, or a pharmaceutically acceptable salt thereof.

In some embodiments, the MADRS Item 10 Score of the subject is 4, 5, or 6 units prior to intranasal administration of the racemic ketamine, or a pharmaceutically acceptable salt thereof. In some embodiments, the MADRS Item 10 Score of the subject is 5 or 6 units prior to intranasal administration of the racemic ketamine, or a pharmaceutically acceptable salt thereof. In some embodiments, the MADRS Item 10 Score of the subject is reduced by at least 1 unit 4 hours administration of the racemic ketamine, or a pharmaceutically acceptable salt thereof.

In some embodiments, the Clinical Global Impression of Severity for Suicide Ideation and Behavior (CGIS-SI/B) score of the subject is 4 or 5 units prior to intranasal administration of the racemic ketamine, or a pharmaceutically acceptable salt thereof. In some embodiments, the CGIS-SI/B score of the subject is 1 or 2 units 24 hours after intranasal administration of the racemic ketamine, or a pharmaceutically acceptable salt thereof.

In some embodiments, the Sheehan—Suicidality Tracking Scale (S-STS) Clinically Meaningful Change Measure (CMCM) score of the subject is from 15-52 units prior to intranasal administration of the racemic ketamine, or a pharmaceutically acceptable salt thereof. In some embodiments, the S-STS CMCM score of the subject is from 20-52 units prior to intranasal administration of the racemic ketamine, or a pharmaceutically acceptable salt thereof. In some embodiments, the STS CMCM score of the subject is reduced by at least 50% 24 hours after intranasal administration of the racemic ketamine, or a pharmaceutically acceptable salt thereof. In some embodiments, the -STS CMCM score of the subject is from 1-3 units 24 hours after intranasal administration of the racemic ketamine, or a pharmaceutically acceptable salt thereof.

In some embodiments, the Sheehan—Suicidality Tracking Scale (S-STS) Clinically Meaningful Change Measure (CMCM) Risk of Suicide at Within the Next 7 Days score of the subject is from 5 to 10 units prior to intranasal administration of the racemic ketamine, or a pharmaceutically acceptable salt thereof. In some embodiments, the S-STS CMCM Risk of Suicide at Within the Next 7 Days score of the subject is reduced by at least 50% 24 hours after intranasal administration of the racemic ketamine, or a pharmaceutically acceptable salt thereof. In some embodiments, the S-STS CMCM Risk of Suicide at Within the Next 7 Days score of the subject is from 0-2 units 24 hours after intranasal administration of the racemic ketamine, or a pharmaceutically acceptable salt thereof. In some embodiments, the S-STS CMCM Risk of Suicide at Within the Next 7 Days score of the subject is 0 or 1 unit 96 hours after intranasal administration of the racemic ketamine, or a pharmaceutically acceptable salt thereof.

In some embodiments, the Modified Observer's Assessment of Alertness/Sedation (MOAA/S) score of the subject is 5 units prior to intranasal administration of the racemic ketamine, or a pharmaceutically acceptable salt thereof. In some embodiments, the MOAA/S score of the subject is 4 or 5 units from 15 minutes to 6 hours after intranasal administration of the racemic ketamine, or a pharmaceutically acceptable salt thereof.

In some embodiments, the Clinician Administered Dissociative States Scale (CADSS) score of the subject is zero units prior to intranasal administration of the racemic ketamine, or a pharmaceutically acceptable salt thereof. In some embodiments, the CADSS score of the subject is zero units from 1 hour to 6 hours after intranasal administration of the racemic ketamine, or a pharmaceutically acceptable salt thereof.

In some embodiments, the C-SSRS score of the subject is from 2 units to 9 units prior to intranasal administration of the racemic ketamine, or a pharmaceutically acceptable salt thereof. In some embodiments, the C-SSRS score of the subject is from 2 units to 5 units prior to intranasal administration of the racemic ketamine, or a pharmaceutically acceptable salt thereof. In some embodiments, the CSSR-S score of the subject is zero units 24 hours after intranasal administration of the racemic ketamine, or a pharmaceutically acceptable salt thereof.

Some embodiments provide a method of treating suicidality in a subject in need thereof, comprising intranasally administering to the subject a therapeutically effective amount of racemic ketamine, or a pharmaceutically acceptable salt thereof; wherein no clinically meaningful sedation is observed in the subject within about 24 hours after intranasal administration of the racemic ketamine, or a pharmaceutically acceptable salt thereof. In some embodiments, no clinically meaningful sedation is observed in the subject at about 4 hours after intranasal administration of the racemic ketamine, or a pharmaceutically acceptable salt thereof. In some embodiments, no clinically meaningful sedation is observed in the subject at about 1 hour after intranasal administration of the racemic ketamine, or a pharmaceutically acceptable salt thereof.

Some embodiments provide a method of treating suicidality in a subject in need thereof, comprising intranasally administering to the subject a therapeutically effective amount of racemic ketamine, or a pharmaceutically acceptable salt thereof; wherein no clinically meaningful dissociation is observed in the subject within about 24 hours after intranasal administration of the racemic ketamine, or a pharmaceutically acceptable salt thereof. In some embodiments, no clinically meaningful dissociation is observed in the subject at about 4 hours after intranasal administration of the racemic ketamine, or a pharmaceutically acceptable salt thereof. In some embodiments, no clinically meaningful dissociation is observed in the subject at about 1 hour after intranasal administration of the racemic ketamine, or a pharmaceutically acceptable salt thereof.

Some embodiments provide a method of treating suicidal ideation in a subject in need thereof, comprising intranasally administering to the subject a therapeutically effective amount of racemic ketamine, or a pharmaceutically acceptable salt thereof; wherein no clinically meaningful sedation is observed in the subject within about 24 hours after intranasal administration of the racemic ketamine, or a pharmaceutically acceptable salt thereof. In some embodiments, no clinically meaningful sedation is observed in the subject at about 4 hours after intranasal administration of the racemic ketamine, or a pharmaceutically acceptable salt thereof. In some embodiments, no clinically meaningful sedation is observed in the subject at about 1 hour after intranasal administration of the racemic ketamine, or a pharmaceutically acceptable salt thereof.

Some embodiments provide a method of treating suicidal ideation in a subject in need thereof, comprising intranasally administering to the subject a therapeutically effective amount of racemic ketamine, or a pharmaceutically acceptable salt thereof; wherein no clinically meaningful dissociation is observed in the subject within about 24 hours after intranasal administration of the racemic ketamine, or a pharmaceutically acceptable salt thereof. In some embodiments, no clinically meaningful dissociation is observed in the subject at about 4 hours after intranasal administration of the racemic ketamine, or a pharmaceutically acceptable salt thereof. In some embodiments, no clinically meaningful dissociation is observed in the subject at about 1 hour after intranasal administration of the racemic ketamine, or a pharmaceutically acceptable salt thereof.

Some embodiments provide a method of treating major depressive disorder in a subject in need thereof, comprising intranasally administering to the subject a therapeutically effective amount of racemic ketamine, or a pharmaceutically acceptable salt thereof; wherein no clinically meaningful sedation is observed in the subject within about 24 hours after intranasal administration of the racemic ketamine, or a pharmaceutically acceptable salt thereof. In some embodiments, no clinically meaningful sedation is observed in the subject at about 4 hours after intranasal administration of the racemic ketamine, or a pharmaceutically acceptable salt thereof. In some embodiments, no clinically meaningful sedation is observed in the subject at about 1 hour after intranasal administration of the racemic ketamine, or a pharmaceutically acceptable salt thereof.

Some embodiments provide a method of treating major depressive disorder in a subject in need thereof, comprising intranasally administering to the subject a therapeutically effective amount of racemic ketamine, or a pharmaceutically acceptable salt thereof wherein no clinically meaningful dissociation is observed in the subject within about 24 hours after intranasal administration of the racemic ketamine, or a pharmaceutically acceptable salt thereof. In some embodiments, no clinically meaningful dissociation is observed in the subject at about 4 hours after intranasal administration of the racemic ketamine, or a pharmaceutically acceptable salt thereof. In some embodiments, no clinically meaningful dissociation is observed in the subject at about 1 hour after intranasal administration of the racemic ketamine, or a pharmaceutically acceptable salt thereof.

In some embodiments, no clinically meaningful sedation and no clinically meaningful dissociation is observed in the subject within about 24 hours after intranasal administration of the racemic ketamine, or a pharmaceutically acceptable salt thereof. In some embodiments, no clinically meaningful sedation and no clinically meaningful dissociation is observed in the subject at about 4 hours after intranasal administration of the racemic ketamine, or a pharmaceutically acceptable salt thereof. In some embodiments, no clinically meaningful sedation and no clinically meaningful dissociation is observed in the subject at about 1 hour after intranasal administration of the racemic ketamine, or a pharmaceutically acceptable salt thereof.

Some embodiments provide a method of treating suicidality in a subject in need thereof, comprising:

(a) determining if the subject has one or more of:
(i) a MADRS Total Score of at least 20 units;
(ii) a MADRS Item 10 Score of 4, 5, or 6 units;
(iii) a CGIS-SI/B score of 4 or 5 units;
(iv) a S-STS CMCM score of at least 15 units;
(v) a S-STS CMCM Risk of Suicide at Within the Next 7 Days score of at least 5 units; and
(vi) a C-SSRS score of at least 2; and
(b) intranasally administering to the subject a therapeutically effective amount of racemic ketamine, or a pharmaceutically acceptable salt thereof;

wherein intranasal administration of the racemic ketamine exhibits one or more of:

an $AUC_{0-t}$ of norketamine that is at least 1.5 times higher than the $AUC_{0-t}$ of norketamine exhibited by intravenous administration of an equivalent dose of racemic ketamine;

an $AUC_{0-inf}$ of norketamine that is at least 1.5 times higher than the $AUC_{0-inf}$ of norketamine exhibited by intravenous administration of an equivalent dose of racemic ketamine; and a $C_{max}$ of norketamine that is at least 2 times higher than the $C_{max}$ of norketamine exhibited by intravenous administration of an equivalent dose of racemic ketamine.

Some embodiments provide a method of treating suicidal ideation in a subject in need thereof, comprising:

(a) determining if the subject has one or more of:
(i) a MADRS Total Score of at least 20 units;
(ii) a MADRS Item 10 Score of 4, 5, or 6 units;
(iii) a CGIS-SI/B score of 4 or 5 units;
(iv) a S-STS CMCM score of at least 15 units;
(v) a S-STS CMCM Risk of Suicide at Within the Next 7 Days score of at least 5 units; and
(vi) a C-SSRS score of at least 2; and
(b) intranasally administering to the subject a therapeutically effective amount of racemic ketamine, or a pharmaceutically acceptable salt thereof;

wherein intranasal administration of the racemic ketamine exhibits one or more of:

an $AUC_{0-t}$ of norketamine that is at least 1.5 times higher than the $AUC_{0-t}$ of norketamine exhibited by intravenous administration of an equivalent dose of racemic ketamine;

an $AUC_{0-inf}$ of norketamine that is at least 1.5 times higher than the $AUC_{0-inf}$ of norketamine exhibited by intravenous administration of an equivalent dose of racemic ketamine; and a $C_{max}$ of norketamine that is at least 2 times higher than the $C_{max}$ of norketamine exhibited by intravenous administration of an equivalent dose of racemic ketamine.

Some embodiments provide a method of treating major depressive disorder in a subject in need thereof, comprising:

(a) determining if the subject has one or more of:
(i) a MADRS Total Score of at least 20 units;
(ii) a MADRS Item 10 Score of 4, 5, or 6 units;
(iii) a CGIS-SI/B score of 4 or 5 units;
(iv) a S-STS CMCM score of at least 15 units;
(v) a S-STS CMCM Risk of Suicide at Within the Next 7 Days score of at least 5 units; and
(vi) a C-SSRS score of at least 2; and
(b) intranasally administering to the subject a therapeutically effective amount of racemic ketamine, or a pharmaceutically acceptable salt thereof;

wherein intranasal administration of the racemic ketamine exhibits one or more of:

an $AUC_{0-t}$ of norketamine that is at least 1.5 times higher than the $AUC_{0-t}$ of norketamine exhibited by intravenous administration of an equivalent dose of racemic ketamine;

an $AUC_{0-inf}$ of norketamine that is at least 1.5 times higher than the $AUC_{0-inf}$ of norketamine exhibited by intravenous administration of an equivalent dose of racemic ketamine; and a $C_{max}$ of norketamine that is at least 2 times higher than the $C_{max}$ of norketamine exhibited by intravenous administration of an equivalent dose of racemic ketamine.

Some embodiments provide a method of treating suicidality in a subject in need thereof, comprising:

(a) determining if the subject has one or more of:
(i) a MADRS Total Score of at least 20 units;
(ii) a MADRS Item 10 Score of 4, 5, or 6 units;
(iii) a CGIS-SI/B score of 4 or 5 units;
(iv) a S-STS CMCM score of at least 15 units;
(v) a S-STS CMCM Risk of Suicide at Within the Next 7 Days score of at least 5 units; and
(vi) a C-SSRS score of at least 2; and
(b) intranasally administering to the subject a therapeutically effective amount of racemic ketamine, or a pharmaceutically acceptable salt thereof;

wherein intranasal administration of the racemic ketamine exhibits one or more of:

an $AUC_{0-t}$ of hydroxynorketamine that is at least 1.5 times higher than the $AUC_{0-t}$ of hydroxynorketamine exhibited by intravenous administration of an equivalent dose of racemic ketamine;

an $AUC_{0-inf}$ of hydroxynorketamine that is at least 1.2 times higher than the $AUC_{0-inf}$ of hydroxynorketamine exhibited by intravenous administration of an equivalent dose of racemic ketamine; and a $C_{max}$ of hydroxynorketamine that is at least 2 times higher than the $C_{max}$ of norketamine exhibited by intravenous administration of an equivalent dose of racemic ketamine.

Some embodiments provide a method of treating suicidal ideation in a subject in need thereof, comprising:

(a) determining if the subject has one or more of:
(i) a MADRS Total Score of at least 20 units;
(ii) a MADRS Item 10 Score of 4, 5, or 6 units;
(iii) a CGIS-SI/B score of 4 or 5 units;
(iv) a S-STS CMCM score of at least 15 units;
(v) a S-STS CMCM Risk of Suicide at Within the Next 7 Days score of at least 5 units; and
(vi) a C-SSRS score of at least 2; and
(b) intranasally administering to the subject a therapeutically effective amount of racemic ketamine, or a pharmaceutically acceptable salt thereof;

wherein intranasal administration of the racemic ketamine exhibits one or more of:

an $AUC_{0-t}$ of hydroxynorketamine that is at least 1.5 times higher than the $AUC_{0-t}$ of hydroxynorketamine exhibited by intravenous administration of an equivalent dose of racemic ketamine;

an $AUC_{0-inf}$ of hydroxynorketamine that is at least 1.2 times higher than the $AUC_{0-inf}$ of hydroxynorketamine exhibited by intravenous administration of an equivalent dose of racemic ketamine; and a $C_{max}$ of hydroxynorketamine that is at least 2 times higher than the $C_{max}$ of norketamine exhibited by intravenous administration of an equivalent dose of racemic ketamine.

Some embodiments provide a method of treating major depressive disorder in a subject in need thereof, comprising:

(a) determining if the subject has one or more of:

(i) a MADRS Total Score of at least 20 units;

(ii) a MADRS Item 10 Score of 4, 5, or 6 units;

(iii) a CGIS-SI/B score of 4 or 5 units;

(iv) a S-STS CMCM score of at least 15 units;

(v) a S-STS CMCM Risk of Suicide at Within the Next 7 Days score of at least 5 units; and (vi) a C-SSRS score of at least 2; and (b) intranasally administering to the subject a therapeutically effective amount of racemic ketamine, or a pharmaceutically acceptable salt thereof;

wherein intranasal administration of the racemic ketamine exhibits one or more of:

an $AUC_{0-t}$ of hydroxynorketamine that is at least 1.5 times higher than the $AUC_{0-t}$ of hydroxynorketamine exhibited by intravenous administration of an equivalent dose of racemic ketamine;

an $AUC_{0-inf}$ of hydroxynorketamine that is at least 1.2 times higher than the $AUC_{0-inf}$ of hydroxynorketamine exhibited by intravenous administration of an equivalent dose of racemic ketamine; and a $C_{max}$ of hydroxynorketamine that is at least 2 times higher than the $C_{max}$ of norketamine exhibited by intravenous administration of an equivalent dose of racemic ketamine.

Some embodiments provide a method of treating suicidality in a subject in need thereof, comprising:

(a) determining if the subject has one or more of:

(i) a MADRS Total Score of at least 20 units;

(ii) a MADRS Item 10 Score of 4, 5, or 6 units;

(iii) a CGIS-SI/B score of 4 or 5 units;

(iv) a S-STS CMCM score of at least 15 units;

(v) a S-STS CMCM Risk of Suicide at Within the Next 7 Days score of at least 5 units; and (vi) a C-SSRS score of at least 2; and (b) intranasally administering to the subject a therapeutically effective amount of racemic ketamine, or a pharmaceutically acceptable salt thereof;

wherein intranasal administration of the racemic ketamine exhibits one or more of:

an $AUC_{0-t}$ of norketamine that is at least 1.5 times higher than the $AUC_{0-t}$ of norketamine exhibited by intravenous administration of an equivalent dose of racemic ketamine;

an $AUC_{0-inf}$ of norketamine that is at least 1.5 times higher than the $AUC_{0-inf}$ of norketamine exhibited by intravenous administration of an equivalent dose of racemic ketamine; and a $C_{max}$ of norketamine that is at least 2 times higher than the $C_{max}$ of norketamine exhibited by intravenous administration of an equivalent dose of racemic ketamine.

Some embodiments provide a method of treating suicidal ideation in a subject in need thereof, comprising:

(a) determining if the subject has one or more of:

(i) a MADRS Total Score of at least 20 units;

(ii) a MADRS Item 10 Score of 4, 5, or 6 units;

(iii) a CGIS-SI/B score of 4 or 5 units;

(iv) a S-STS CMCM score of at least 15 units;

(v) a S-STS CMCM Risk of Suicide at Within the Next 7 Days score of at least 5 units; and (vi) a C-SSRS score of at least 2; and (b) intranasally administering to the subject a therapeutically effective amount of racemic ketamine, or a pharmaceutically acceptable salt thereof;

wherein intranasal administration of the racemic ketamine exhibits one or more of:

an $AUC_{0-t}$ of norketamine that is at least 1.5 times higher than the $AUC_{0-t}$ of norketamine exhibited by intravenous administration of an equivalent dose of racemic ketamine;

an $AUC_{0-inf}$ of norketamine that is at least 1.5 times higher than the $AUC_{0-inf}$ of norketamine exhibited by intravenous administration of an equivalent dose of racemic ketamine; and a $C_{max}$ of norketamine that is at least 2 times higher than the $C_{max}$ of norketamine exhibited by intravenous administration of an equivalent dose of racemic ketamine.

Some embodiments provide a method of treating major depressive disorder in a subject in need thereof, comprising:

(a) determining if the subject has one or more of:

(i) a MADRS Total Score of at least 20 units;

(ii) a MADRS Item 10 Score of 4, 5, or 6 units;

(iii) a CGIS-SI/B score of 4 or 5 units;

(iv) a S-STS CMCM score of at least 15 units;

(v) a S-STS CMCM Risk of Suicide at Within the Next 7 Days score of at least 5 units; and (vi) a C-SSRS score of at least 2; and (b) intranasally administering to the subject a therapeutically effective amount of racemic ketamine, or a pharmaceutically acceptable salt thereof;

wherein intranasal administration of the racemic ketamine exhibits one or more of:

an $AUC_{0-t}$ of norketamine that is at least 1.5 times higher than the $AUC_{0-t}$ of norketamine exhibited by intravenous administration of an equivalent dose of racemic ketamine;

an $AUC_{0-inf}$ of norketamine that is at least 1.5 times higher than the $AUC_{0-inf}$ of norketamine exhibited by intravenous administration of an equivalent dose of racemic ketamine; and a $C_{max}$ of norketamine that is at least 2 times higher than the $C_{max}$ of norketamine exhibited by intravenous administration of an equivalent dose of racemic ketamine.

Some embodiments provide a method of treating suicidality in a subject in need thereof, comprising:

(a) determining if the subject has one or more of:

(i) a MADRS Total Score of at least 20 units;

(ii) a MADRS Item 10 Score of 4, 5, or 6 units;

(iii) a CGIS-SI/B score of 4 or 5 units;

(iv) a S-STS CMCM score of at least 15 units;

(v) a S-STS CMCM Risk of Suicide at Within the Next 7 Days score of at least 5 units; and (vi) a C-SSRS score of at least 2; and (b) intranasally administering to the subject a therapeutically effective amount of racemic ketamine, or a pharmaceutically acceptable salt thereof;

wherein no clinically meaningful sedation is observed in the subject within about 24 hours after intranasal administration of the racemic ketamine, or a pharmaceutically acceptable salt thereof. In some embodiments, no clinically meaningful sedation is observed in the subject at about 4 hours after intranasal administration of the racemic ketamine, or a pharmaceutically acceptable salt thereof. In some embodiments, no clinically meaningful sedation is observed in the subject at about 1 hour after intranasal administration of the racemic ketamine, or a pharmaceutically acceptable salt thereof.

Some embodiments provide a method of treating suicidality in a subject in need thereof, comprising:

(a) determining if the subject has one or more of:
(i) a MADRS Total Score of at least 20 units;
(ii) a MADRS Item 10 Score of 4, 5, or 6 units;
(iii) a CGIS-SI/B score of 4 or 5 units;
(iv) a S-STS CMCM score of at least 15 units;
(v) a S-STS CMCM Risk of Suicide at Within the Next 7 Days score of at least 5 units; and
(vi) a C-SSRS score of at least 2; and
(b) intranasally administering to the subject a therapeutically effective amount of racemic ketamine, or a pharmaceutically acceptable salt thereof;

wherein no clinically meaningful dissociation is observed in the subject within about 24 hours after intranasal administration of the racemic ketamine, or a pharmaceutically acceptable salt thereof. In some embodiments, no clinically meaningful dissociation is observed in the subject at about 4 hours after intranasal administration of the racemic ketamine, or a pharmaceutically acceptable salt thereof. In some embodiments, no clinically meaningful dissociation is observed in the subject at about 1 hour after intranasal administration of the racemic ketamine, or a pharmaceutically acceptable salt thereof.

Some embodiments provide a method of treating suicidality in a subject in need thereof, comprising:

(a) determining if the subject has one or more of:
(i) a MADRS Total Score of at least 20 units;
(ii) a MADRS Item 10 Score of 4, 5, or 6 units;
(iii) a CGIS-SI/B score of 4 or 5 units;
(iv) a S-STS CMCM score of at least 15 units;
(v) a S-STS CMCM Risk of Suicide at Within the Next 7 Days score of at least 5 units; and
(vi) a C-SSRS score of at least 2; and
(b) intranasally administering to the subject a therapeutically effective amount of racemic ketamine, or a pharmaceutically acceptable salt thereof;

wherein no clinically meaningful sedation and no clinically meaningful dissociation is observed in the subject within about 24 hours after intranasal administration of the racemic ketamine, or a pharmaceutically acceptable salt thereof. In some embodiments, no clinically meaningful sedation and no clinically meaningful dissociation is observed in the subject at about 4 hours after intranasal administration of the racemic ketamine, or a pharmaceutically acceptable salt thereof. In some embodiments, no clinically meaningful sedation and no clinically meaningful dissociation is observed in the subject at about 1 hour after intranasal administration of the racemic ketamine, or a pharmaceutically acceptable salt thereof.

Some embodiments provide a method of treating suicidal ideation in a subject in need thereof, comprising:

(a) determining if the subject has one or more of:
(i) a MADRS Total Score of at least 20 units;
(ii) a MADRS Item 10 Score of 4, 5, or 6 units;
(iii) a CGIS-SI/B score of 4 or 5 units;
(iv) a S-STS CMCM score of at least 15 units;
(v) a S-STS CMCM Risk of Suicide at Within the Next 7 Days score of at least 5 units; and
(vi) a C-SSRS score of at least 2; and
(b) intranasally administering to the subject a therapeutically effective amount of racemic ketamine, or a pharmaceutically acceptable salt thereof;

wherein no clinically meaningful sedation is observed in the subject within about 24 hours after intranasal administration of the racemic ketamine, or a pharmaceutically acceptable salt thereof. In some embodiments, no clinically meaningful sedation is observed in the subject at about 4 hours after intranasal administration of the racemic ketamine, or a pharmaceutically acceptable salt thereof. In some embodiments, no clinically meaningful sedation is observed in the subject at about 1 hour after intranasal administration of the racemic ketamine, or a pharmaceutically acceptable salt thereof.

Some embodiments provide a method of treating suicidal ideation in a subject in need thereof, comprising:

(a) determining if the subject has one or more of:
(i) a MADRS Total Score of at least 20 units;
(ii) a MADRS Item 10 Score of 4, 5, or 6 units;
(iii) a CGIS-SI/B score of 4 or 5 units;
(iv) a S-STS CMCM score of at least 15 units;
(v) a S-STS CMCM Risk of Suicide at Within the Next 7 Days score of at least 5 units; and
(vi) a C-SSRS score of at least 2; and
(b) intranasally administering to the subject a therapeutically effective amount of racemic ketamine, or a pharmaceutically acceptable salt thereof;

wherein no clinically meaningful dissociation is observed in the subject within about 24 hours after intranasal administration of the racemic ketamine, or a pharmaceutically acceptable salt thereof. In some embodiments, no clinically meaningful dissociation is observed in the subject at about 4 hours after intranasal administration of the racemic ketamine, or a pharmaceutically acceptable salt thereof. In some embodiments, no clinically meaningful dissociation is observed in the subject at about 1 hour after intranasal administration of the racemic ketamine, or a pharmaceutically acceptable salt thereof.

Some embodiments provide a method of treating suicidal ideation in a subject in need thereof, comprising:

(a) determining if the subject has one or more of:
(i) a MADRS Total Score of at least 20 units;
(ii) a MADRS Item 10 Score of 4, 5, or 6 units;
(iii) a CGIS-SI/B score of 4 or 5 units;
(iv) a S-STS CMCM score of at least 15 units;
(v) a S-STS CMCM Risk of Suicide at Within the Next 7 Days score of at least 5 units; and
(vi) a C-SSRS score of at least 2; and
(b) intranasally administering to the subject a therapeutically effective amount of racemic ketamine, or a pharmaceutically acceptable salt thereof;

wherein no clinically meaningful sedation and no clinically meaningful dissociation is observed in the subject within about 24 hours after intranasal administration of the racemic ketamine, or a pharmaceutically acceptable salt thereof. In some embodiments, no clinically meaningful sedation and no clinically meaningful dissociation is observed in the subject at about 4 hours after intranasal administration of the racemic ketamine, or a pharmaceutically acceptable salt thereof. In some embodiments, no clinically meaningful sedation and no clinically meaningful dissociation is observed in the subject at about 1 hour after intranasal administration of the racemic ketamine, or a pharmaceutically acceptable salt thereof.

Some embodiments provide a method of treating major depressive disorder in a subject in need thereof, comprising:

(a) determining if the subject has one or more of:

(i) a MADRS Total Score of at least 20 units;

(ii) a MADRS Item 10 Score of 4, 5, or 6 units;

(iii) a CGIS-SI/B score of 4 or 5 units;

(iv) a S-STS CMCM score of at least 15 units;

(v) a S-STS CMCM Risk of Suicide at Within the Next 7 Days score of at least 5 units; and (vi) a C-SSRS score of at least 2; and (b) intranasally administering to the subject a therapeutically effective amount of racemic ketamine, or a pharmaceutically acceptable salt thereof;

wherein no clinically meaningful sedation is observed in the subject within about 24 hours after intranasal administration of the racemic ketamine, or a pharmaceutically acceptable salt thereof. In some embodiments, no clinically meaningful sedation is observed in the subject at about 4 hours after intranasal administration of the racemic ketamine, or a pharmaceutically acceptable salt thereof. In some embodiments, no clinically meaningful sedation is observed in the subject at about 1 hour after intranasal administration of the racemic ketamine, or a pharmaceutically acceptable salt thereof.

Some embodiments provide a method of treating major depressive disorder in a subject in need thereof, comprising:

(a) determining if the subject has one or more of:

(i) a MADRS Total Score of at least 20 units;

(ii) a MADRS Item 10 Score of 4, 5, or 6 units;

(iii) a CGIS-SI/B score of 4 or 5 units;

(iv) a S-STS CMCM score of at least 15 units;

(v) a S-STS CMCM Risk of Suicide at Within the Next 7 Days score of at least 5 units; and (vi) a C-SSRS score of at least 2; and (b) intranasally administering to the subject a therapeutically effective amount of racemic ketamine, or a pharmaceutically acceptable salt thereof;

wherein no clinically meaningful dissociation is observed in the subject within about 24 hours after intranasal administration of the racemic ketamine, or a pharmaceutically acceptable salt thereof. In some embodiments, no clinically meaningful dissociation is observed in the subject at about 4 hours after intranasal administration of the racemic ketamine, or a pharmaceutically acceptable salt thereof. In some embodiments, no clinically meaningful dissociation is observed in the subject at about 1 hour after intranasal administration of the racemic ketamine, or a pharmaceutically acceptable salt thereof.

Some embodiments provide a method of treating major depressive disorder in a subject in need thereof, comprising:

(a) determining if the subject has one or more of:

(i) a MADRS Total Score of at least 20 units;

(ii) a MADRS Item 10 Score of 4, 5, or 6 units;

(iii) a CGIS-SI/B score of 4 or 5 units;

(iv) a S-STS CMCM score of at least 15 units;

(v) a S-STS CMCM Risk of Suicide at Within the Next 7 Days score of at least 5 units; and (vi) a C-SSRS score of at least 2; and (b) intranasally administering to the subject a therapeutically effective amount of racemic ketamine, or a pharmaceutically acceptable salt thereof;

wherein no clinically meaningful sedation and no clinically meaningful dissociation is observed in the subject within about 24 hours after intranasal administration of the racemic ketamine, or a pharmaceutically acceptable salt thereof. In some embodiments, no clinically meaningful sedation and no clinically meaningful dissociation is observed in the subject at about 4 hours after intranasal administration of the racemic ketamine, or a pharmaceutically acceptable salt thereof. In some embodiments, no clinically meaningful sedation and no clinically meaningful dissociation is observed in the subject at about 1 hour after intranasal administration of the racemic ketamine, or a pharmaceutically acceptable salt thereof.

In some embodiments, one or more of the MADRS Total, MADRS Item 10, CGIS-SI/B, S-STS CMCM, S-STS CMCM Risk of Suicide at Within the Next 7 Days, and C-SSRS scores is reduced by at least 50% 24 hours after intranasal administration of racemic ketamine, or a pharmaceutically acceptable salt thereof.

In some embodiments, one or more of the MADRS Total, MADRS Item 10, CGIS-SI/B, S-STS CMCM, S-STS CMCM Risk of Suicide at Within the Next 7 Days, and C-SSRS scores is reduced by at least 50% 48 hours after intranasal administration of racemic ketamine, or a pharmaceutically acceptable salt thereof.

In some embodiments, one or more of the MADRS Total, MADRS Item 10, CGIS-SI/B, S-STS CMCM, S-STS CMCM Risk of Suicide at Within the Next 7 Days, and C-SSRS scores is reduced by at least 50% 96 hours after intranasal administration of racemic ketamine, or a pharmaceutically acceptable salt thereof.

In some embodiments, one or more of the MADRS Total, MADRS Item 10, CGIS-SI/B, S-STS CMCM, S-STS CMCM Risk of Suicide at Within the Next 7 Days, and C-SSRS scores is below the standard for remission 24 hours after intranasal administration of racemic ketamine, or a pharmaceutically acceptable salt thereof.

In some embodiments, one or more of the MADRS Total, MADRS Item 10, CGIS-SI/B, S-STS CMCM, S-STS CMCM Risk of Suicide at Within the Next 7 Days, and C-SSRS scores is below the standard for remission 48 hours after intranasal administration of racemic ketamine, or a pharmaceutically acceptable salt thereof.

In some embodiments, one or more of the MADRS Total, MADRS Item 10, CGIS-SI/B, S-STS CMCM, S-STS CMCM Risk of Suicide at Within the Next 7 Days, and C-SSRS scores is below the standard for remission 96 hours after intranasal administration of racemic ketamine, or a pharmaceutically acceptable salt thereof.

In some embodiments, the subject has a MADRS Total Score of at least 20 units. In some embodiments, the subject has a MADRS Item 10 Score of 4, 5, or 6 units. In some embodiments, the subject has a CGIS-SI/B score of 4 or 5 units. In some embodiments, the subject has a S-STS CMCM score of at least 15 units. In some embodiments, the subject has a S-STS CMCM Risk of Suicide at Within the Next 7 Days score of at least 5 units. In some embodiments, the subject has a C-SSRS score of at least 2. In some embodiments, the subject has a MADRS Total Score of at least 20 units and a CGIS-SI/B score of 4 or 5 units. In some embodiments, the subject has a MADRS Total Score of at least 20 units and a S-STS CMCM score of at least 15 units. In some embodiments, the subject has a MADRS Total Score of at least 20 units; a CGIS-SI/B score of 4 or 5 units; and a S-STS CMCM score of at least 15 units.

In some embodiments, the racemic ketamine, or a pharmaceutically acceptable salt thereof, is intranasally administered from about once per day to about once per month, for example, once per day, once every other day, twice per week, or once per week. In some embodiments, the racemic ketamine, or a pharmaceutically acceptable salt thereof, is intranasally administered from about once per day to about once every two weeks. In some embodiments, the racemic ketamine, or a pharmaceutically acceptable salt thereof, is intranasally administered from about once per day to about once per week. In some embodiments, the racemic ketamine, or a pharmaceutically acceptable salt thereof, is intranasally administered from about once per week to about twice per week. In some embodiments, the racemic ketamine, or a pharmaceutically acceptable salt thereof, is intranasally administered twice per week. In some embodiments, the racemic ketamine, or a pharmaceutically acceptable salt thereof, is intranasally administered once per day, once every other day, three times per week, twice per week, or once per week. In some embodiments, the racemic ketamine, or a pharmaceutically acceptable salt thereof, is intranasally administered every four days (e.g., on day 1, day 4, day 8, day 12, day 16, etc.).

Some embodiments described herein provide a comparison between intranasal administration of racemic ketamine, or a pharmaceutically acceptable salt thereof, intravenous administration of racemic ketamine, or a pharmaceutically acceptable salt thereof, and/or administration (e.g., intravenous or intranasal administration) of (S)-ketamine, or a pharmaceutically acceptable salt thereof.

In some embodiments, the intranasal (S)-ketamine is Spravato®. In some embodiments, the intranasal (S)-ketamine is a solution consisting essentially of 32.3 mg of (S)-ketamine hydrochloride (equivalent to 28 mg of (S)-ketamine), citric acid monohydrate, edetate disodium, sodium hydroxide, and water. In some embodiments, the intranasal (S)-ketamine is a clear, colorless aqueous solution with a pH of 4.5. See the Spravato® ((S)-ketamine) Package Insert dated Feb. 11, 2020; www.accessdata.fda.gov/drugsatfda_docs/label/2020/211243s003lbl.pdf, which is hereby incorporated by reference in its entirety.

Some embodiments reference a time "prior to" administration of the intranasal racemic ketamine, or a pharmaceutically acceptable salt thereof. The time prior to administration may be a particular time or range of time as indicated (e.g., about 30 minutes, about 1 hour, from about 1 day to about 1 week, 6 months, etc.), or it may be any time prior to administration if no particular time or range is specified.

Combination Therapy

The methods of the present disclosure also contemplate treatments comprising administering ketamine, or a pharmaceutically acceptable salt thereof, as described in any of the embodiments of the disclosure, in combination with one or more additional therapies (such as an antidepressant). Accordingly, ketamine, or a pharmaceutically acceptable salt thereof, as described anywhere herein can be administered alone or in combination with one or more additional therapies. When administered in combination with one or more additional therapies, separate dosage forms can be administered to the subject. If administered as a separate dosage form, the one or more additional therapies may be administered simultaneously with the intranasal ketamine dosage form of the present disclosure or sequentially with the ketamine dosage form of the present disclosure, in either order. In some embodiments, the intranasal ketamine dosage form and the one or more additional therapies are administered sequentially on the same or different days. For example, the racemic ketamine, or a pharmaceutically acceptable salt thereof, is intranasally administered twice per week and the one or more additional therapies are administered once per day.

In some embodiments, the methods described herein further comprise administering one or more additional therapies consist of typical antipsychotics, atypical antipsychotics, antidepressants, electroconvulsive therapy, transcranial magnetic stimulation, benzodiazepines, mood stabilizers, and pramipexole.

In some embodiments, the methods described herein further comprise providing cognitive behavior therapy to the subject.

In some embodiments, the one or more additional therapies is a standard of care treatment for major depressive disorder. In some embodiments, the one or more additional therapies is a standard of care treatment for suicidality. In some embodiments, the one or more additional therapies is a standard of care treatment for suicidal ideation. In some embodiments, the one or more additional therapies is a standard of care treatment for treatment resistant depression. In some embodiments, the one or more additional therapies is a standard of care treatment for post-traumatic stress disorder.

In some embodiments, the one or more additional therapies is pramipexole.

In some embodiments, the one or more additional therapies is a typical antipsychotic. Representative typical antipsychotics include, but are not limited to chlorpromazine, chlorprothixene, levomepromazine, mesoridazine, periciazine, promazine, loxapine, molindone, perphenazine, thiothixene, droperidol, flupentixol, fluphenazine, haloperidol, pimozide, prochlorperazine, thioproperazine, trifluoperazine, and zuclopenthixol.

In some embodiments, the one or more additional therapies is an atypical antipsychotic. Representative atypical antipsychotics include, but are not limited to aripiprazole, risperidone, olanzapine, quetiapine, asenapine, paliperidone, ziprasidone, or lurasidone.

In some embodiments, the one or more additional therapies is an antidepressant. In some embodiments, the antidepressant is an atypical antidepressant, a selective serotonin reuptake inhibitor, a selective serotonin and norepinephrine reuptake inhibitor, a monoamine oxidase inhibitor, or a selective norepinephrine reuptake inhibitor.

In some embodiments, the antidepressant is an atypical antidepressant. Representative atypical antidepressants include, but are not limited to mirtazapine, mianserin, bupropion, trazodone, nefazodone, tianeptine, opipramol, agomelatine, vilazodone, and vortioxetine.

In some embodiments, the antidepressant is a selective serotonin reuptake inhibitor. Representative selective serotonin reuptake inhibitors include, but are not limited to citalopram, escitalopram, fluoxetine, fluvoxamine, paroxetine, and sertraline.

In some embodiments, the antidepressant is a selective serotonin and norepinephrine reuptake inhibitor. Representative selective serotonin and norepinephrine reuptake inhibitors include, but are not limited to atomoxetine, desvenlafaxine, duloxetine, levomilnacipran, milnacipran, sibutramine, tramadol, and venlafaxine.

In some embodiments, the antidepressant is a monoamine oxidase inhibitor. Representative monoamine oxidase inhibitors include, but are not limited to moclobemide, rasagiline, selegiline, or safinamide.

In some embodiments, the antidepressant is a selective norepinephrine reuptake inhibitor. Representative selective norepinephrine reuptake inhibitors include, but are not limited to reboxetine.

In some embodiments, the one or more additional therapies is a benzodiazepine. Representative benzodiazepines include, but are not limited to alprazolam, bromazepam, chlordiazepoxide, clonazepam, clorazepate, diazepam, flurazepam, lorazepam, oxazepam, temazepam, or triazolam.

In some embodiments, the one or more additional therapies is a mood stabilizer. Representative mood stabilizers include, but are not limited to lithium, valproic acid, lamotrigine, or carbamazepine. In some embodiments, the one or more additional therapies is electroconvulsive therapy or transcranial magnetic stimulation.

In some embodiments, the one or more additional therapies is sertraline. In some embodiments, the one or more additional therapies is venlafaxine.

In some embodiments, the one or more additional therapies is one additional therapy. In some embodiments, the one or more additional therapies is two, three, or four additional therapies.

In some embodiments, the subject has previously been administered one or more additional therapies consist of typical antipsychotics, atypical antipsychotics, antidepressants, electroconvulsive therapy, transcranial magnetic stimulation, benzodiazepines, mood stabilizers, and pramipexole; wherein the subject was not responsive to the previous one or more therapies.

In some embodiments, the subject has previously been administered a standard of care treatment for major depressive disorder and the subject was not responsive to the previous therapy. In some embodiments, the subject has previously been administered a standard of care treatment for suicidality and the subject was not responsive to the previous therapy. In some embodiments, the subject has previously been administered a standard of care treatment for suicidal ideation and the subject was not responsive to the previous therapy. In some embodiments, the subject has previously been administered a standard of care treatment for treatment resistant depression and the subject was not responsive to the previous therapy. In some embodiments, the subject has previously been administered a standard of care treatment for post-traumatic stress disorder and the subject was not responsive to the previous therapy.

In some embodiments, the subject has previously been administered one or more additional therapies consist of typical antipsychotics, atypical antipsychotics, antidepressants, electroconvulsive therapy, transcranial magnetic stimulation, benzodiazepines, mood stabilizers, and pramipexole, and was not responsive to the previous therapy.

In some embodiments, the subject has previously been administered pramipexole and was not responsive to the previous therapy.

In some embodiments, the subject has previously been administered one or more typical antipsychotics such as chlorpromazine, chlorprothixene, levomepromazine, mesoridazine, periciazine, promazine, loxapine, molindone, perphenazine, thiothixene, droperidol, flupentixol, fluphenazine, haloperidol, pimozide, prochlorperazine, thioproperazine, trifluoperazine, and zuclopenthixol, and was not responsive to the previous therapy.

In some embodiments, the subject has previously been administered one or more atypical antipsychotics, such as aripiprazole, risperidone, olanzapine, quetiapine, asenapine, paliperidone, ziprasidone, or lurasidone, and was not responsive to the previous therapy.

In some embodiments, the subject has previously been administered one or more antidepressants and was not responsive to the previous therapy. In some embodiments, the antidepressant is an atypical antidepressant, a selective serotonin reuptake inhibitor, a selective serotonin and norepinephrine reuptake inhibitor, a monoamine oxidase inhibitor, or a selective norepinephrine reuptake inhibitor, and was not responsive to the previous therapy.

In some embodiments, the subject has previously been administered one or more atypical antidepressants, such as mirtazapine, mianserin, bupropion, trazodone, nefazodone, tianeptine, opipramol, agomelatine, vilazodone, and vortioxetine, and was not responsive to the previous therapy.

In some embodiments, the subject has previously been administered one or more selective serotonin reuptake inhibitors, such as citalopram, escitalopram, fluoxetine, fluvoxamine, paroxetine, and sertraline, and was not responsive to the previous therapy.

In some embodiments, the subject has previously been administered one or more selective serotonin and norepinephrine reuptake inhibitors, such as atomoxetine, desvenlafaxine, duloxetine, levomilnacipran, milnacipran, sibutramine, tramadol, and venlafaxine, and was not responsive to the previous therapy.

In some embodiments, the subject has previously been administered one or more monoamine oxidase inhibitors, such as moclobemide, rasagiline, selegiline, or safinamide, and was not responsive to the previous therapy.

In some embodiments, the subject has previously been administered one or more selective norepinephrine reuptake inhibitors, such as reboxetine, and was not responsive to the previous therapy.

In some embodiments, the subject has previously been administered one or more benzodiazepines, such as alprazolam, bromazepam, chlordiazepoxide, clonazepam, clorazepate, diazepam, flurazepam, lorazepam, oxazepam, temazepam, or triazolam, and was not responsive to the previous therapy.

In some embodiments, the subject has previously been administered one or more mood stabilizers, such as lithium, valproic acid, lamotrigine, or carbamazepine, and was not responsive to the previous therapy.

In some embodiments, the one or more additional therapies is electroconvulsive therapy or transcranial magnetic stimulation, and was not responsive to the previous therapy.

In some embodiments, the subject has previously been administered sertraline, and was not responsive to the previous therapy. In some embodiments, the subject has previously been administered venlafaxine, and was not responsive to the previous therapy.

In some embodiments, the one or more additional therapies previously administered to the subject is one additional therapy. In some embodiments, the one or more additional therapies previously administered to the subject is two additional therapies. In some embodiments, the one or more additional therapies previously administered to the subject is three additional therapies. In some embodiments, the one or more additional therapies previously administered to the subject is four additional therapies. In some embodiments, the one or more additional therapies previously administered to the subject is five, six, seven, eight, nine, or ten additional therapies.

In some embodiments, the racemic ketamine, or a pharmaceutically acceptable salt thereof, is intranasally administered acutely. For example, in a suicidal subject, the racemic ketamine, or a pharmaceutically acceptable salt thereof, can be administered from one to four weeks, or until the suicidality resolves. In some embodiments, the racemic ketamine, or a pharmaceutically acceptable salt thereof, is intranasally administered chronically. For example, in a subject suffering from major depressive disorder, the racemic ketamine, or a pharmaceutically acceptable salt thereof, can be administered for several months to several years, or until the depression resolves.

In some embodiments described herein, the (S)-ketamine is administered intravenously. In some embodiments described herein, the (S)-ketamine is administered intranasally.

Some embodiments provide an intranasally administering composition, comprising a therapeutically effective amount of racemic ketamine, or a pharmaceutically acceptable salt thereof, and a pharmaceutically acceptable carrier.

Some embodiments provide the use of racemic ketamine, or a pharmaceutically acceptable salt thereof, in the preparation of an intranasally administering medicament for treating suicidality in a subject in need thereof.

Some embodiments provide the use of racemic ketamine, or a pharmaceutically acceptable salt thereof, in the preparation of an intranasally administering medicament for treating suicidal ideation in a subject in need thereof.

Some embodiments provide the use of racemic ketamine, or a pharmaceutically acceptable salt thereof, in the preparation of an intranasally administering medicament for treating major depressive disorder in a subject in need thereof.

Some embodiments provide the use of racemic ketamine, or a pharmaceutically acceptable salt thereof, in the preparation of an intranasally administering medicament for reducing one or more side effects of ketamine in a subject in need thereof.

Intranasal Delivery

In some embodiments, the racemic ketamine, or a pharmaceutically acceptable salt thereof, is intranasally administered. The administration can be accomplished via a suitable intranasal delivery device.

In some embodiments, a device (e.g., an intranasal device) can administer one or more doses of racemic ketamine to a nasal cavity of a subject. In some embodiments, the device is designed for a nostril of a subject. In some embodiments, the device is designed to measure a particular amount or a particular dose of racemic ketamine. In some embodiments, the device is designed to be actuated for operation by the breath of the subject. In some embodiments, the device is designed to deliver more than one dose to the nasal cavity of the subject. In some embodiments, the device can spray racemic ketamine into the nostril cavity of the subject.

In some embodiments, the device comprises a nozzle for providing an aerosol through a nosepiece. The nozzle comprises a head which is located, in some embodiments coaxially within the nosepiece, and a delivery tube, which is fluidly connected to the head. In some embodiments, the nozzle can be configured to provide a jet of a substance through the nosepiece. In some embodiments, the device further comprises a substance supply unit for delivering a metered dose of racemic ketamine to the nozzle. In some embodiments, the substance supply unit comprises a mechanical delivery pump, which is fluidly connected to the nozzle and which is configured, on actuation thereof, to deliver a metered dose of racemic ketamine to the nozzle, which nozzle generates an aerosol. The delivery pump is movable relative to the nozzle from a first, non-actuated position to a second, actuated position to deliver a metered dose of racemic ketamine to the nozzle, and hence generate an aerosol.

In some embodiments, the mechanical delivery pump comprises a liquid delivery pump for delivering a metered volume of a liquid comprising racemic ketamine, for example, as a suspension or a solution, to the nozzle on actuation thereof.

In some embodiments, the substance supply unit further comprises a biasing element, in this embodiment a resilient element, particularly a compression spring, for biasing the delivery pump in an actuating direction when in the non-actuated position, and a loading mechanism, and in some embodiments, comprising first and second levers, for loading the biasing element such as to bias the delivery pump, when in the non-actuated position, with an actuation force. In some embodiments, the loading mechanism is movable between a first, rest position in which the biasing element is not loaded thereby, and a second, operative position in which the biasing element, when restrained by the delivery pump, loads the delivery pump with the actuation force.

In some embodiments, the device further comprises a trigger mechanism, which is configured to be actuatable to cause the actuation of the substance supply unit. In some embodiments, the trigger mechanism is configured to be actuatable to cause the actuation of the substance supply unit on the generation of a predetermined pressure in the chamber in the housing. In some embodiments, the trigger mechanism could be configured to be actuatable to cause the actuation of the substance supply unit on the generation of a predetermined flow rate through a mouthpiece.

In some embodiments, the trigger mechanism comprises first and second stop members, and first and second biasing elements, which comprise resilient elements, such as compression springs, which act to bias respective ones of the first and second stop members inwardly to a stop position in which the first and second stop members act to prevent movement of the delivery pump from the non-actuated position to the actuated position.

In some embodiments, the trigger mechanism further comprises first and second arms which are pivotable about respective pivots and coupled at one end thereof to respective ones of the first and second stop members such that pivoting of the arms to a release position causes the respective ones of the stop members, to which the arms are coupled, to be moved outwardly against the bias of the first and second biasing elements to a release position in which the stop members are disposed outwardly of the head of the delivery pump, such that the delivery pump, when biased by the biasing element, is driven to the actuated position. In being driven to the actuated position, a metered dose of racemic ketamine is delivered from the delivery pump to the nozzle, with the nozzle acting to generate an aerosol.

In some embodiments, the trigger mechanism further comprises a diaphragm as the resilient member, which defines a part of the wall of the chamber in the housing. The diaphragm is configured such as, on generation of a predetermined actuation pressure within the chamber in the housing, to be deflected such as to engage the other, distal ends of the arms, and cause the same to be pivoted to the release position. This actuation pressure cannot be achieved until the nosepiece is sufficiently inserted in a nostril of a subject for effective operation of the device, in which position the escape of exhaled air from the exhalation breath of the subject directly to the atmosphere is prevented. While the nosepiece is not sufficiently inserted into a nostril of a subject as to provide for effective operation of the device, exhaled air from the exhalation breath of the subject escapes to the atmosphere, thereby preventing the development of the actuation pressure within the chamber in the housing.

With this configuration, the device, in being pre-primed and actuatable by the oral exhalation breath of a subject, does not require the application of an actuation force by the subject at the instance of actuation, and provides for the closure of the oropharyngeal velum of the subject.

In some embodiments, the device comprises mechanical liquid delivery pump operated by the manual compression of a chamber containing a volume of liquid to expel a flow of a metered volume of liquid.

In some embodiments, the device further comprises one or more of a filter, a flow meter, a flow regulator, and a nebulizer.

In some embodiments, the nozzle can be configured to deliver an aerosol spray with an asymmetric spray profile, with the aerosol spray having a significantly greater spray angle in the vertical, sagittal plane than in the horizontal plane. Such an aerosol spray has been found to be particularly advantageous in the delivery of substance to posterior regions of the nasal cavities, in particular the olfactory region.

In some embodiments, the spray angle in the vertical, sagittal plane is greater than about 35°, greater than about 40°, greater than about 45°, or greater than about 50°. In some embodiments, the spray angle in the horizontal plane is not more than about 35°, not more than about 30°, not more than about 25°, not more than about 20°, or not more than about 15°.

In some embodiments, the aerosol spray can present an elliptical spray zone. In some embodiments, the aerosol spray can present a substantially rectangular spray zone. In some embodiments, the device further comprises a substance supply unit for delivering metered doses of a composition comprising racemic ketamine, which is fluidly connected to the nozzle to deliver the composition from the nosepiece as an aerosol spray. In some embodiments, the substance supply unit is a multi-dose unit for delivering a plurality of metered doses of the composition. In some embodiments, the substance supply unit is a single-dose unit for delivering a single metered dose of the composition. In some embodiments, the substance supply unit is pre-primeable, by loading a resilient element, which, when released, the resilient element actuates the substance supply unit to deliver a metered dose of the composition through the nozzle. In some embodiments, the device comprises a piston to deliver a metered dose of the composition through the nozzle.

In some embodiments, the device comprises one or more indicators, for example, to indicate a first dose and a second dose. In some embodiments, the indicator can be a color change or a number change. For example, after a dose has been dispensed, the indicator comes to be positioned behind a viewing window such that it is viewable by the subject. In some embodiments, the device comprises one or two viewing windows. In some embodiments, after a first dose has been dispensed, a first viewing window can become red, whereas a second viewing window can remain blank. After a second dose has been dispensed, both viewing windows can be red. Thus, the subject will have no difficulty in quickly determining whether or not the first and/or the second dose has/have been dispensed, and thus does not risk over-dosing and/or under-dosing.

In some embodiments, the device is primeless and can be actuated with one hand. In some embodiments, the device is disposable. In some embodiments, each device provides one or two doses of racemic ketamine. In some embodiments, the device comprises a reservoir containing one or two doses of racemic ketamine, and a dispenser member (such as a piston), mounted to slide into the reservoir. Movement of the dispenser member results in dispensing of a dose of the racemic ketamine. In a dual-dose device, the piston is moved in two successive actuation strokes, thereby dispensing separate first and second doses. In some embodiments, the device further comprises an indicator such that the user can visually determine if (i) no dose has been dispensed; (ii) if only the first dose has been delivered; and (ii) if both the first dose and the second dose have been dispensed. For example, a colored indication zone within a viewing window in the device may change color after the first dose has been dispensed, and change color again (or another colored indication zone, if present, may change color) after the second dose has been dispensed. Similarly, actuation of the dispenser member may cause a first colored indication zone to be obscured after the first dose is dispensed, and may cause a second colored indication zone to be obscured after the second dose is dispensed.

In some embodiments, the device is the Aptar Biodose (BDS) system.

Figure 14B:
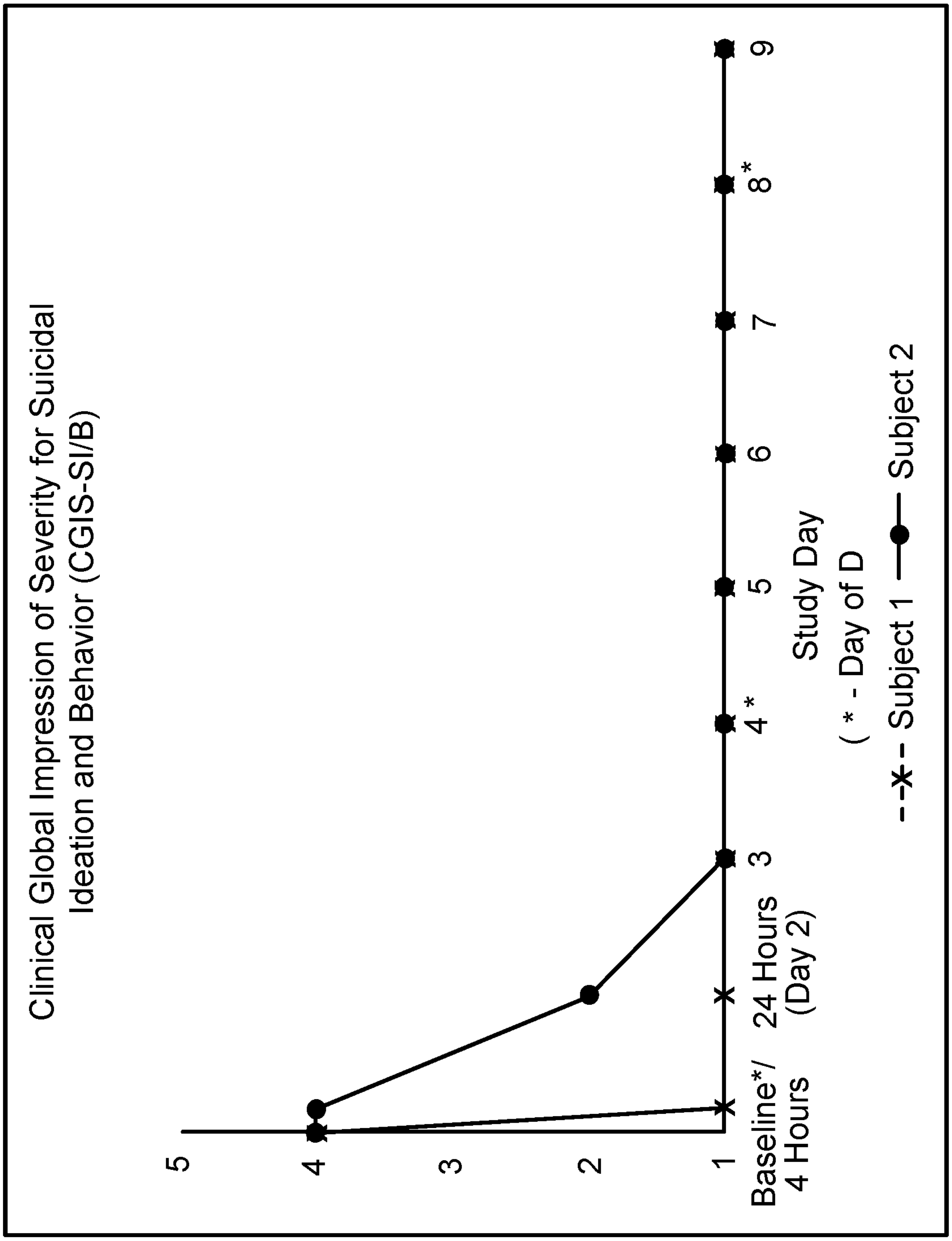
Figure 15B:
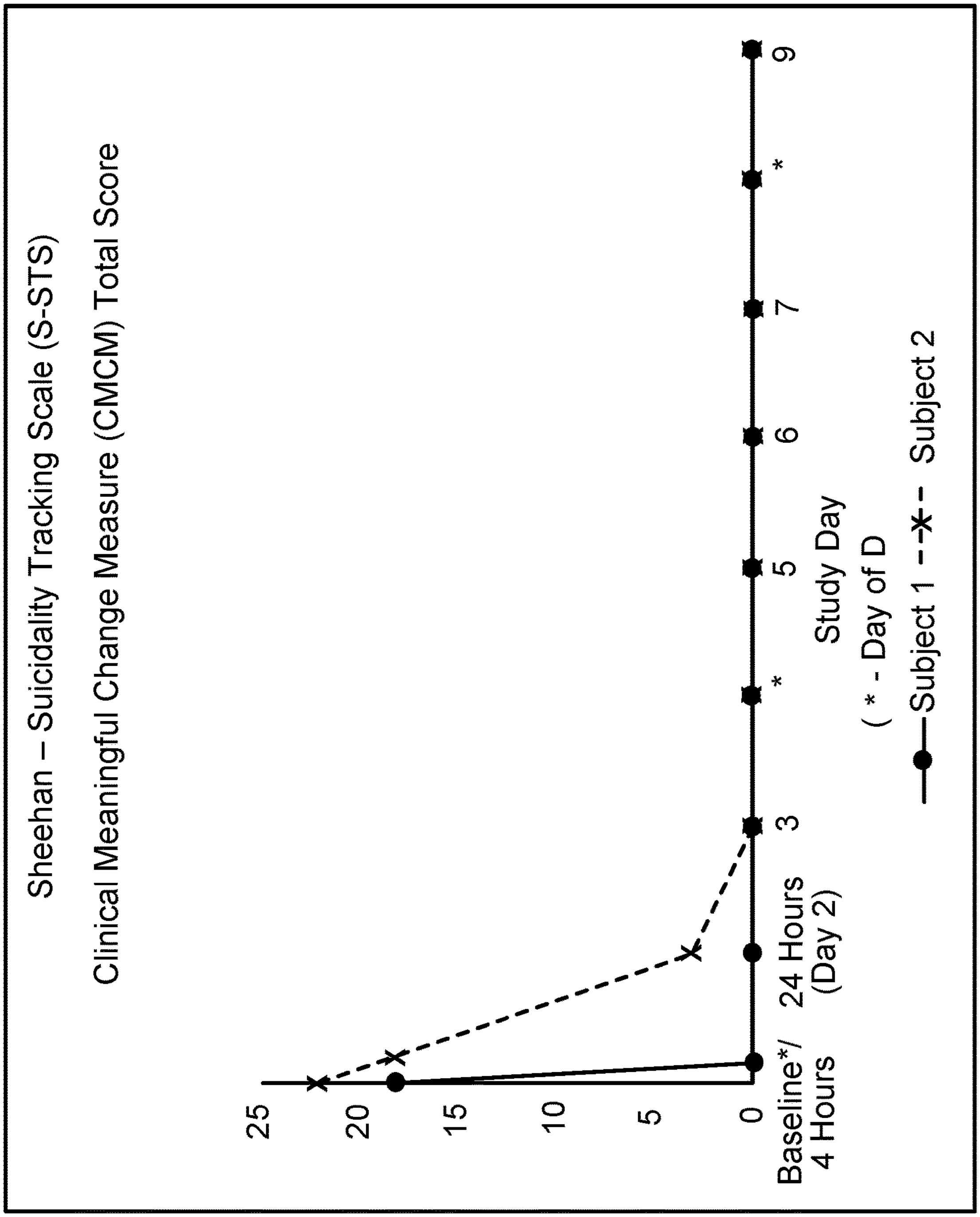
Figure 16B:
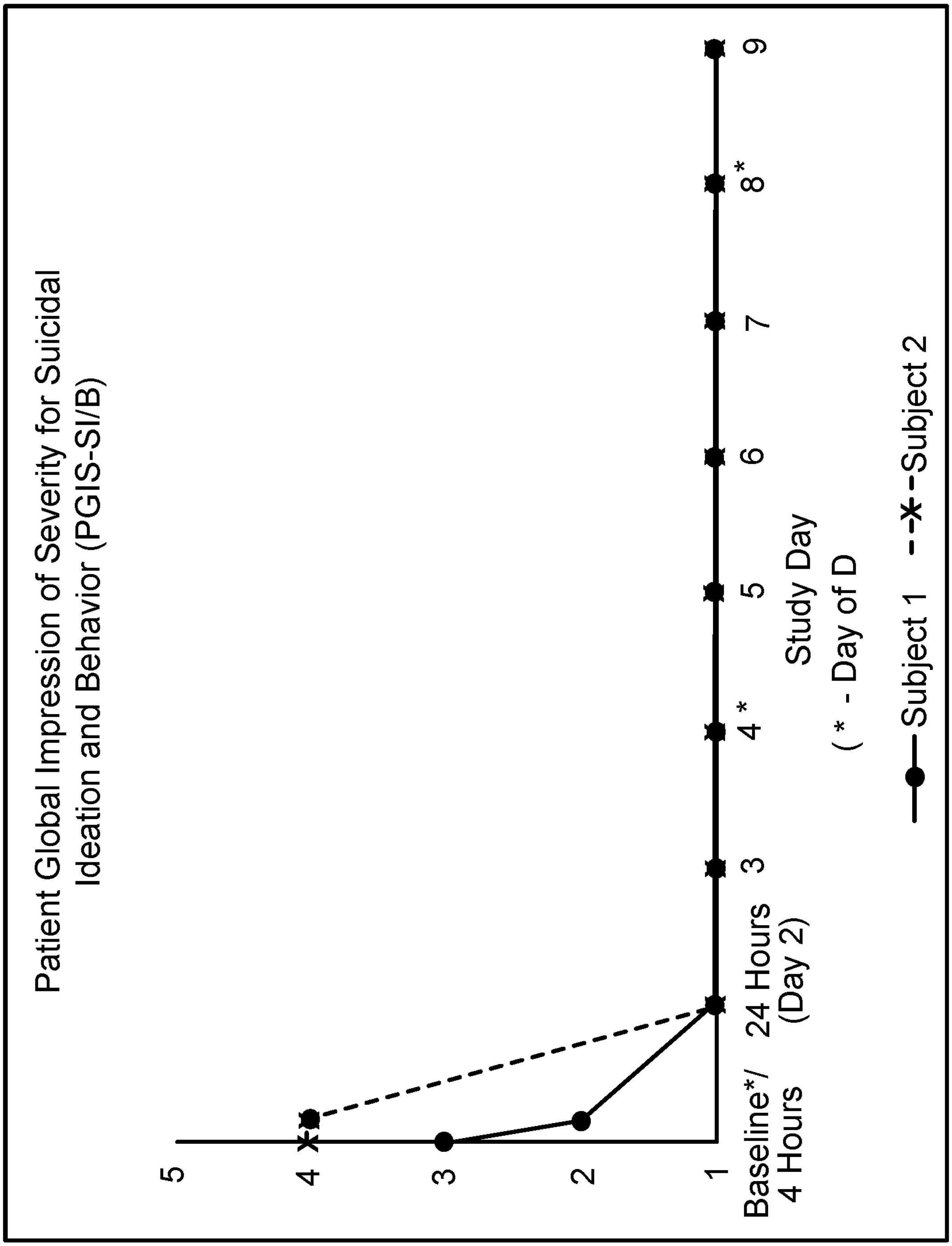
Figure 19B:
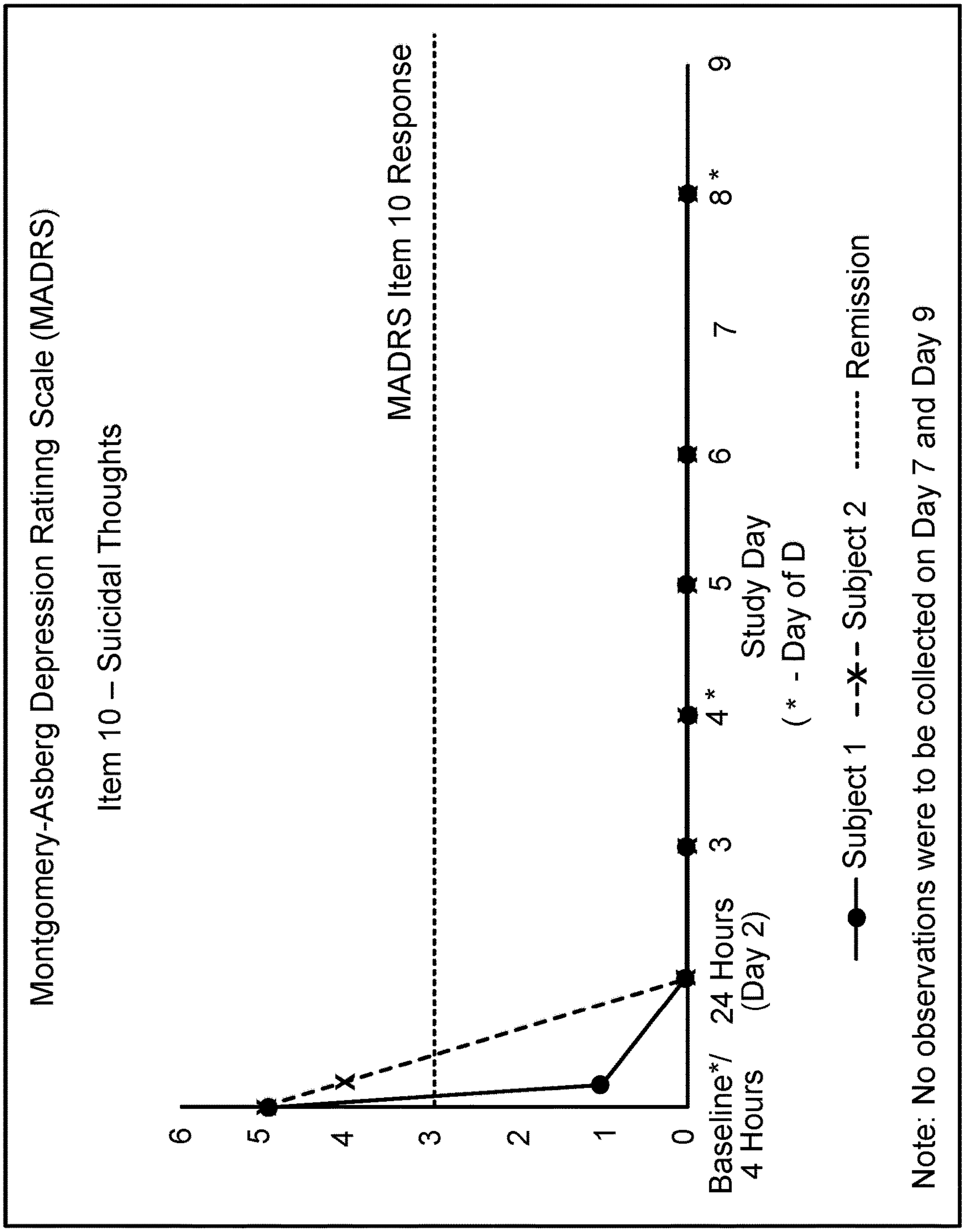
Figure 20B:
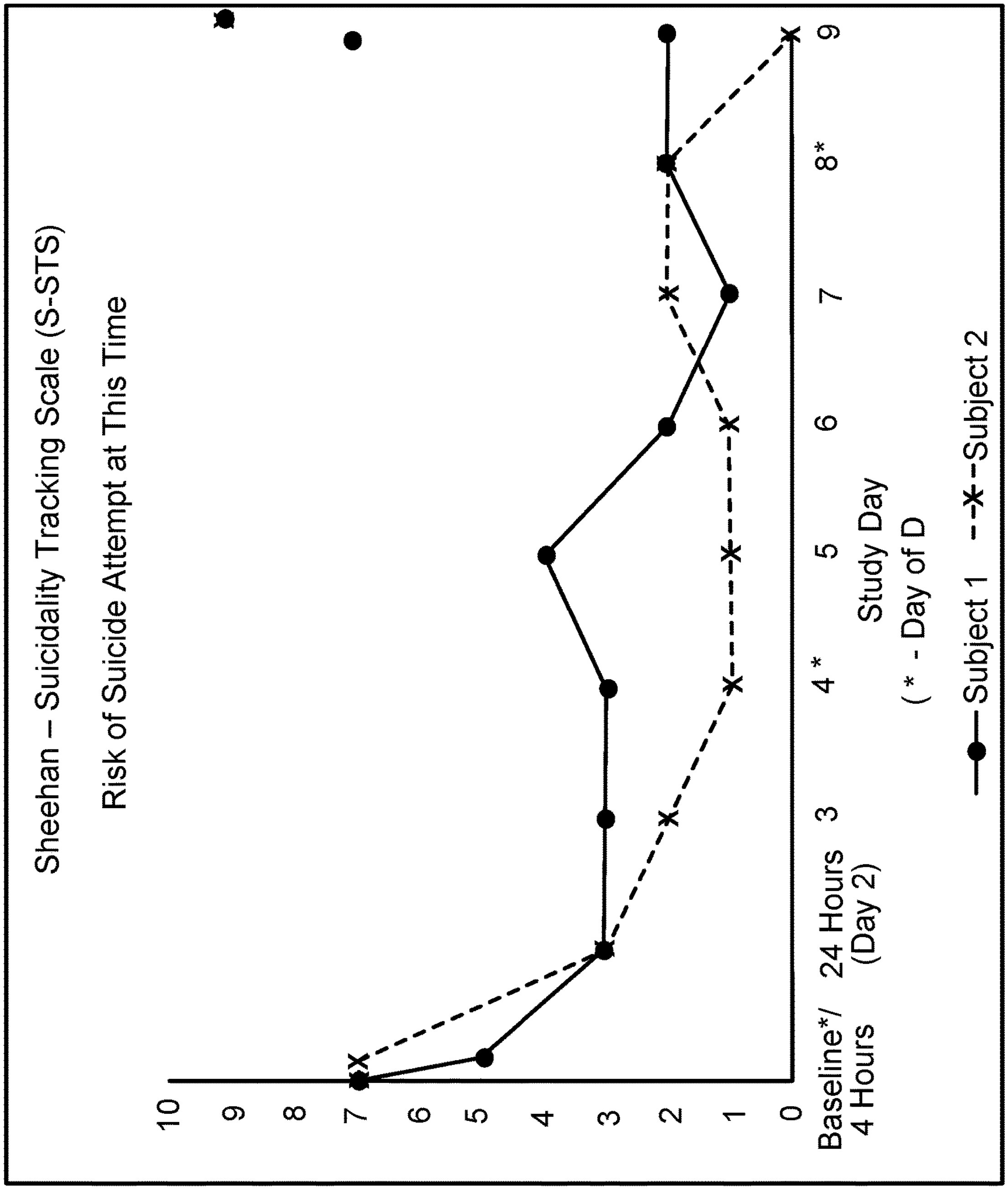
Figure 21B:
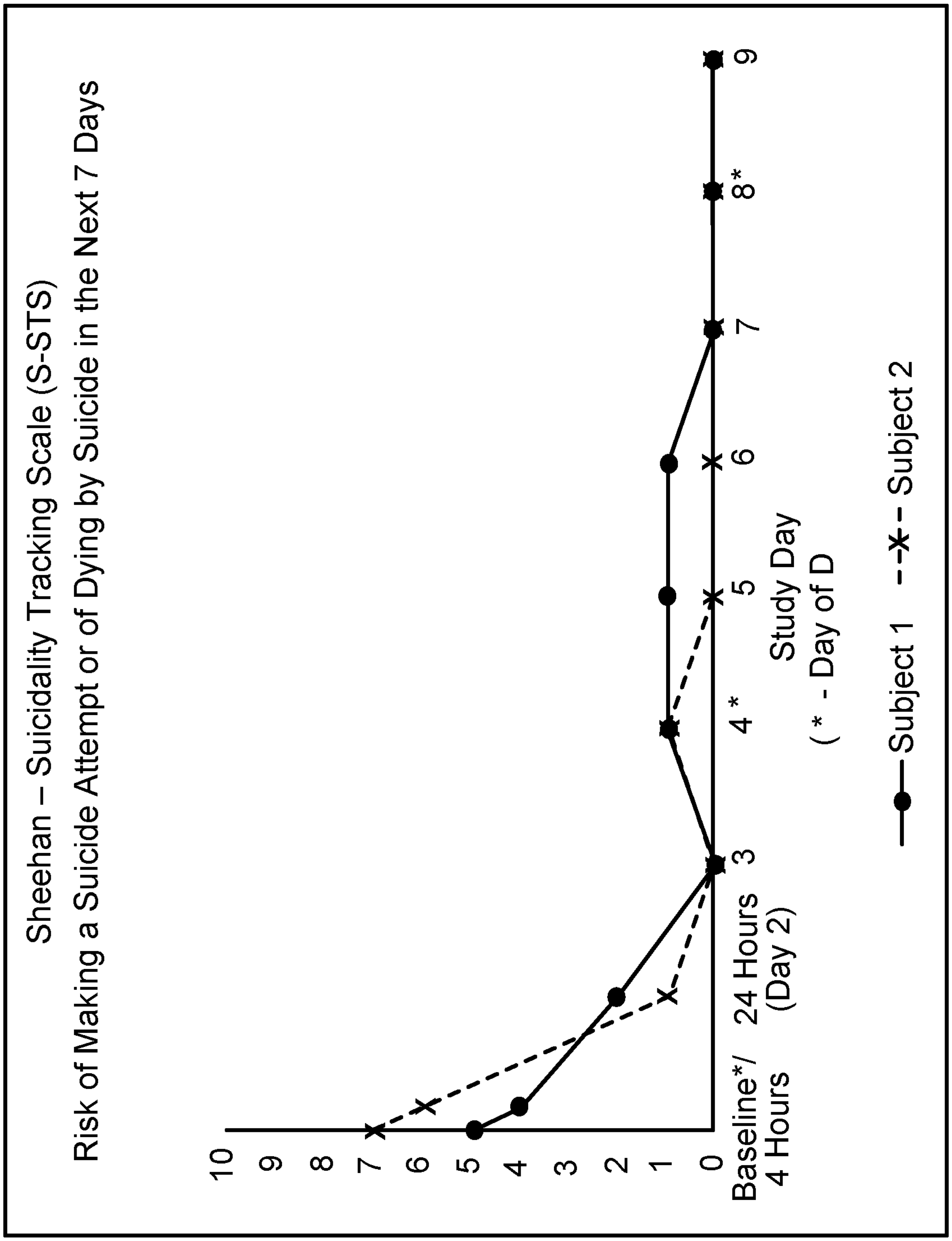

Other suitable intranasal delivery devices are described in U.S. Pat. No. 7,299,949 (see, e.g., FIGS. 1-3); U.S. Pat. No. 9,555,950 (see, e.g., FIGS. 1-3); U.S. Pat. No. 10,099,019 (see, e.g., FIGS. 1-41); U.S. Pat. No. 10,179,216 (see, e.g., FIGS. 1-5); U.S. Pat. No. 10,525,218 (see, e.g., FIGS. 1-26); U.S. Pat. No. 10,549,052 (see, e.g., FIGS. 1-19); U.S. Pat. No. 7,784,460 (see, e.g., FIGS. 1-8); U.S. Pat. No. 8,146,589 (see, e.g., FIGS. 1-5); U.S. Pat. No. 8,875,711 (see, e.g., FIG. 1); and U.S. Pat. No. 8,985,116 (see, e.g., FIG. 1); and U.S. Publ. Nos. 20040039352; 20090054923; 20120000459; 20120017902; 20130245560; 20140018295; 20150190268; 20170020383; 20170151397; 20170216540; 20180256836; 20180256867; 20180272085; 20180361085; 20190054016; 20190070372; 20190083722; 20190117916; 20190117918; 20190143054; 20190269867; 20190290863; 20190290864; 20190314588; 20190358078; 20190358417; 20200023146; 20200054843; 20200060972; 20200206012; 20200206441; and 20200206547, each of which is incorporated by reference in its entirety, including any drawings.

It is understood that the examples and embodiments described herein are for illustrative purposes only and that various modifications or changes in light thereof will be suggested to persons skilled in the art and are to be included within the spirit and purview of this application and scope of the appended claims. All publications, patents, patent applications, and sequence accession numbers cited herein are hereby incorporated by reference in their entirety for all purposes.

The disclosure will be more fully understood by reference to the following examples. They should not, however, be construed as limiting the scope of the disclosure. It is understood that the examples and embodiments described herein are for illustrative purposes only and that various modifications or changes in light thereof will be suggested to persons skilled in the art and are to be included within the spirit and purview of this application and scope of the appended claims.

EXAMPLES

Example 1. A Two-Part Randomized, Double-Blind, Placebo-Controlled, Parallel-Design and Partial Crossover Study Regarding the Pharmacodynamics, Pharmacokinetics, and Safety of Multiple Doses of Intranasal and Intravenous Ketamine in Normal Healthy Volunteers This example describes a two-part randomized, double-blind, placebo-controlled, parallel-design and partial crossover study to determine the pharmacodynamics, pharmacokinetics, and safety of multiple doses of intranasal and intravenous ketamine in normal healthy volunteers.

Study Overview

This protocol encompasses two parts. Part A is a randomized, double-blind, placebo-controlled, multiple-dose, parallel-design cohorts to evaluate the psychotomimetic effects, pharmacokinetics, and safety of various doses of intranasal racemic ketamine administered 3 times within 8 days. This part consists of a screening visit, a treatment phase, and a follow-up visit. Within 30 days of screening, eligible subjects are enrolled and randomized into the treatment phase. Subjects are admitted to the clinic 1 day prior to dosing (Day −1) and remain as an inpatient in the research clinic for 10 days (9 nights).

Part A consists of repeated single doses of racemic ketamine or placebo administered intranasally on Days 1, 4, and 8. There are 4 dose levels:

Treatment W: Placebo intranasal

Treatment X: racemic ketamine 30 mg intranasal

Treatment Y: racemic ketamine 75 mg intranasal

Treatment Z: racemic ketamine 90 mg intranasal

The trials included six sequential cohorts, consisting of 8 subjects each. Subjects in each cohort were randomized such that there was an even distribution of subjects per dose level (i.e., 2 subjects received placebo, 2 subjects received 30 mg, 2 subjects received 75 mg, and 2 subjects received 90 mg). After treatment of each cohort, the Safety Review Team assessed the feasibility of continuing with any dose level based on the available safety information.

The pharmacodynamic, pharmacokinetic, and safety assessments were performed up to 24 hours postdose. At the discretion of the investigator, subjects were discharged approximately 24 hours after the last dosing. Subjects return for a safety follow-up visit 12 days (±1 day) following the first drug administration. In case of early withdrawal, study exit procedures were completed at the time of withdrawal (or soon after) and subjects may be asked to return for a safety follow-up visit 12 days (±1 day) following the first drug administration, as per investigator's judgment.

Part B was a randomized, double-blind, double-dummy, placebo-controlled, 2-period partial crossover to evaluate the psychotomimetic effects, PK, and safety of a single dose of intranasal vs IV ketamine administered 3 times within 8 days. Within 30 days of screening, eligible subjects were enrolled and randomized into the treatment phase. Subjects participate in two 10-day (9 nights) inpatient stays in the research clinic separated by a washout of at least 4 days.

Part B consists of a single dose level of 60 mg, randomly administered as racemic ketamine intranasal on Days 1, 4, and 8 in one treatment period and as 0.3 mg/kg IV on Days 1, 4, and 8 in the other period. The IV dose of ketamine 0.3 mg/kg was considered to be equivalent to racemic ketamine 60 mg dose on the basis of anticipated plasma exposure. Subjects were randomized to receive the treatments listed below, such that 2 subjects received placebo and 12 subjects receive the active treatment. To maintain the blind, each study treatment was administered as intranasal and IV.

Treatment A: Placebo (intranasal+IV)

Treatment B: racemic ketamine 60 mg intranasal+placebo IV

Treatment C: Ketamine IV 0.3 mg/kg (dose equivalent to 60 mg intranasal)+placebo intranasal The PD, PK, and safety assessments were performed up to approximately 24 hours postdose. At the discretion of the investigator, subjects were discharged approximately 24 hours after the last dosing in each treatment period. Subjects returned for a safety follow-up visit 12 days (±1 day) following the first drug administration in treatment period 2. In case of early withdrawal, study exit procedures were completed at the time of withdrawal (or soon after) and subjects were asked to return for a safety follow-up visit 12 days (±1 day) following the last drug administration, as per investigator's judgment.

Objectives

The primary objective of this study was:

(1) to determine the pharmacodynamic (PD) effects of racemic ketamine (intranasal ketamine HCl) and IV ketamine following multiple doses (repeated single doses), as assessed by rating scales and psychomotor tests for psychotomimetic and dissociative effects.

The secondary objectives were:

(2) to assess the pharmacokinetic (PK) parameters of ketamine and its metabolites (norketamine and 6-hydroxynorketamine) following single and multiple intranasal and IV doses of ketamine;

(3) to compare the bioavailability of racemic ketamine 60 mg and 0.3 mg/kg ketamine IV after single and multiple doses;

(4) to assess the correlation between ketamine plasma concentrations and electrocardiogram parameters; and (5) to assess the safety of single and multiple intranasal and IV doses of ketamine.

The exploratory objectives were:

(6) to explore the dose proportionality of ketamine and norketamine after intranasal racemic ketamine administration; and (7) to examine the correlation between PK parameters and various PD effects for ketamine and its metabolites.

Number of Subjects

A sufficient number of healthy subjects were screened and randomized to the treatment phase in order to ensure evaluable data from at least 9 subjects per dose level in Part A (a total of 36 subjects) and at least 11 subjects in Part B.

Subjects who participated in Part A may be eligible to participate in Part B.

Criteria for Inclusion

The following were the inclusion criteria. Subjects must meet each of the following inclusion criteria to be eligible:

(1) healthy male or female subjects 20 to 55 years of age, inclusive;

(2) body mass index (BMI) within the range of 18.0 to 35.0 kg/$m^2$, inclusive, and a minimum weight of at least 50.0 kg;

(3) nonsmoker for at least 3 months and tests negative on a urine cotinine test;

(4) female subjects of childbearing potential with male sexual partners must be using and willing to continue using medically acceptable contraception for at least 1 month prior to Screening (at least 3 months for oral and transdermal contraceptives) and for at least 1 month after the last study drug administration;

(5) female subjects of non-childbearing potential must be surgically sterile (hysterectomy and/or bilateral oophorectomy/salpingo-oophorectomy, as determined by subject medical history) or congenitally sterile, or must be postmenopausal, where postmenopausal is defined as being amenorrheic for at least 1 year without another cause and an FSH level ≥26 IU/L.6;

(6) resting heart rate between 50 and 100 beats per minute inclusive;

(7) able to speak, read, and understand English or French sufficiently to understand the nature of the study, to provide written informed consent, and to allow completion of all study assessments; and (8) must provide written informed consent prior to the initiation of any protocol-specific procedures.

Exclusion Criteria

The following were the exclusion criteria. Subjects were not considered eligible to participate in this study if any one of the following exclusion criteria was satisfied at screening:

(1) self-reported substance or alcohol dependence or abuse (excluding nicotine and caffeine) in their lifetime, and/or has ever participated or plans to participate in a substance or alcohol rehabilitation program to treat their substance or alcohol dependence;

(2) self-reported abuse of ketamine or phencyclidine (PCP) in their lifetime;

(3) clinically significant abnormalities as assessed by physical examination, medical history, 12-lead electrocardiogram, vital signs, or laboratory values, as judged by the investigator or designee;

(4) history or presence of any clinically significant illness (e.g., cardiac, pulmonary, hepatic, renal, hematologic, gastrointestinal, endocrine, immunologic, dermatologic, oncologic, or musculoskeletal) or any condition, which in the opinion of the investigator or designee, would jeopardize the safety of the subject or the validity of the study results;

(5) personal or first-degree family history of psychosis, personal history of any one of: mood disorder, anxiety disorder, obsessive-compulsive disorder, somatoform disorder, and behavior disorder;

(6) personal history of neurologic disorder in relation to the central nervous system (CNS): congenital malformation of the brain, brain tumor, multiple sclerosis, degenerative disease of the CNS, or inflammatory disease of the CNS within the past year or having resulted in sequelae;

(7) history or present diagnosis of glaucoma;

(8) known hypertension or blood pressure above 140/90 mmHg (blood pressure may be repeated as per the site's SOPs);

(9) presence or history of cardiac disorder, including congenital heart disease, ischemic heart disease, cardiac insufficiency, supraventricular and ventricular heart rhythm disorder, prolonged QT syndrome (i.e., QTcF>450 msec) and associated risk factors (i.e., hypokalemia, family history of long QT syndrome);

(10) any history of suicidal ideation or suicidal behavior (lifetime), as assessed by the Columbia-Suicide Severity Rating Scale (C-SSRS; baseline version);

(11) current (i.e., within the last 3 months) treatment with any psychotropic medications;

(12) color blindness (for Bowdle VAS perception of color intensity) based on subject self-report;

(13) presence of piercing or any medical condition that could interfere with the absorption or pharmacokinetics of intranasal racemic ketamine (e.g., nasal polyps, clinically significant deviated septum [corrected or persistent], or other physical abnormalities of the nose);

(14) any history of epilepsy or seizures, excluding childhood febrile seizures;

(15) history of severe allergic reaction (including anaphylaxis) to ketamine or related drugs (other NMDA receptor antagonists) or to any food, medication, or bee sting, or previous status asthmaticus;

(16) use of a prohibited medication;

(17) use of soft drugs (such as marijuana) within 3 months prior to the screening visit or hard drugs (such as cocaine, crack, opioid derivatives including heroin, and amphetamine derivatives) within 1 year prior to screening;

(18) positive urine drug screen (UDS);

(19) regular use of alcohol within 6 months prior to the screening visit (more than 14 units of alcohol per week where 1 unit=150 mL of wine, 360 mL of beer, or 45 mL of 40% alcohol);

(20) positive breath alcohol test, but subjects may be rescheduled at the discretion of the investigator or designee;

(21) difficulty with venous access or unsuitable or unwilling to undergo catheter insertion;

(22) female subjects who have a positive pregnancy test, were currently pregnant or lactating, or who were planning to become pregnant within 30 days of last study drug administration;

(23) donation of plasma within 7 days prior to dosing or donation or loss of blood (excluding volume drawn at screening) of 50 mL to 499 mL of blood within 30 days, or more than 499 mL within 56 days prior to the first dosing;

(24) positive for hepatitis B, hepatitis C, or human immunodeficiency virus (HIV);

(25) treatment with an investigational drug within 5 times the elimination half-life, if known (e.g., a marketed product) or within 30 days (if the elimination half-life was unknown), or within 90 days for a biologic, prior to first drug administration or was concurrently enrolled in any research judged not to be scientifically or medically compatible with this study;

(26) an employee of the sponsor, clinical research organization, or research site personnel directly affiliated with this study or their immediate family member defined as a spouse, parent, child or sibling, whether biological or legally adopted;

(27) a subject who, in the opinion of the investigator or designee, was considered unsuitable or unlikely to comply with the study protocol for any reason; or

(28) a subject who has pending legal charges or was on probation.

Dietary and Other Restrictions

Aside from the inclusion and exclusion criteria, the subject must agree to abide by each of the following restrictions for the specified time:

(1) subjects were required to abstain from alcohol for 24 hours prior to each study visit and abstinence were confirmed with a breath alcohol test;

(2) subjects were required to abstain from recreational drug use throughout the study, from screening until after the follow-up visit;

(3) subjects were required to fast (abstain from food) for at least 8 hours prior to dosing and for at least 4 hours postdose, water was permitted ad libitum except for at least 1 hour prior to dosing and for at least 1 hour postdose;

(4) subjects were asked to abstain from the following foods from 1 week prior to the treatment phase until after the follow-up visit: grapefruit or grapefruit-containing products, pomegranate, pomelo, star fruit juice/products, foods containing poppy seeds, Seville oranges, and orange juice (5) subjects were asked not to consume more than 450 mg of caffeine per day (e.g., approximately 5 cups of tea or 3 cups of regular coffee or 8 cans of cola or 2 energy drinks) from 1 week prior to the treatment phase until after the follow-up visit, and subjects were not be permitted to consume caffeine-containing beverages while housed at the research site;

(6) subjects were asked to refrain from driving, operating machinery, or engaging in hazardous activities until they and the investigator were sure the study drug was not impairing their judgment and/or ability to perform skilled tasks, and subjects were informed that driving under the influence was a criminal offense and that if they were caught driving under the influence, they may be prosecuted to the fullest extent of the law;

(7) subjects were asked to abstain from strenuous physical activity for 48 hours prior to each study visit, subjects were not be permitted to engage in strenuous exercise during the in-subject stay at the research site, and for safety reasons, subjects were required to remain seated or semi-reclined in bed for the first 4 hours after drug administration;

(8) subjects were required to abstain from blood donation during the study and for 30 days following the follow-up visit; and (9) subjects were required to follow the informed consent form (ICF) and the clinic code of conduct.

Test Product(s), Dose, and Mode of Administration:

In Part A, subjects were randomized to receive either placebo or racemic ketamine (30 mg, 75 mg, or 90 mg), with an even distribution of subjects per dose level. The study drug (placebo and active) was administered intranasally following an overnight fast of at least 8 hours on Days 1, 4, and 8.

In Part B, the following study treatments were given in a double-dummy fashion, such that each subject will receive the study drug (placebo and/or active) as intranasal and IV:

Treatment A: Placebo intranasal+Placebo IV

Treatment B: racemic ketamine 60 mg intranasal+placebo IV

Treatment C: Ketamine 0.3 mg/kg IV+placebo intranasal

The study treatment was administered on Days 1, 4, and 8 of both treatment periods following an overnight fast of at least 8 hours.

Time of study drug administration was set as the first spray administration in Part A and was set at the start of the infusion in Part B.

Intranasal Administration

There was a total of 6 sprays per subject per day on dosing days. The subjects were instructed to gently blow their nose prior to drug administration. The start of dosing was considered time zero. The drug was administered by trained study personnel as 2 sprays (0.1 mL per spray), one in each nostril, from each bi-dose device. The study-specific procedure details the required standard position of the subject's head during drug administration and the instructions given to subjects regarding sniffing following administration of the sprays. Nasal cavity check was be done after each dosing in order to confirm proper inhalations.

The administration of drug from each bi-dose device was separated by approximately 5 minutes to ensure optimal absorption of the drug in the nasal cavity due to the 2-fold increase in the volume of spray relative to prior studies. Subjects may not blow their nose for 1 hour following dosing. A smell/taste evaluation was performed on Day 9, approximately 24 hours after administration of the last intranasal drug. Time of study drug administration was set as the first spray administration.

Effort was made to administer the 6 sprays in Part B during the IV infusion period, therefore the first spray was administered after the start of infusion and the last spray would be administered before the end of infusion.

Intravenous Administration

In Part B, the dose of ketamine IV was based on the subject's weight at admission time. The IV study drugs were administered as an IV infusion administered over approximately 10 minutes. The subject's actual times of the start and end of the infusion were recorded in the source documents. Time of study drug administration was set as the start of study drug infusion.

Criteria for Evaluation: Pharmacodynamic

The primary pharmacodynamic endpoints were the maximum (peak) effect ($E_{max}$), maximum change from baseline ($CFB_{max}$), and time-averaged were a under the effect curve (TA_AUE), as applicable, for:

(1) Bowdle visual analog scale (VAS); and $E_{max}$ for internal and external perceptions and TA_AUE (2) Clinician Administered Dissociative State Scale (CADSS)

$E_{max}$ and $CFB_{max}$ for total score.

The secondary endpoints include: $E_{max}$, minimum effect ($E_{min}$), $CFB_{max}$, minimum change from baseline ($CFB_{min}$), and TA_AUE, as applicable, for:

(3) Choice Reaction Time (CRT);

$CFB_{max}$ and baseline-adjusted TA_AUE of motor reaction time (MRT), recognition reaction time (RRT), and total reaction time (TRT));

$CFB_{min}$ and baseline-adjusted TA_AUE of percentage correct;

(4) Sternberg Short-Term Memory (SSTM) task; and $E_{min}$ and $CFB_{min}$ for d' pooled;

$E_{max}$ and $CFB_{max}$ for mean reaction time pooled for all valid responses;

(5) POMS 2 (for Treatment B and Treatment C in Part B only);

$CFB_{max}$ Total Mood Disturbance;

(6) Subject-Rated Assessment of Intranasal Irritation (SRAII);

$E_{max}$ and $CFB_{max}$

Criteria for Evaluation: Pharmacokinetic

The PK parameters that were evaluated in this study for ketamine, norketamine and 6-hydroxynorketamine, (as applicable) include:

(1) time to maximum observed plasma concentration ($T_{max}$);

(2) maximum observed plasma concentration ($C_{max}$);

(3) area under the plasma concentration-time curve from time zero to the last measurable concentration ($AUC_{0-t}$);

(4) area under the plasma concentration-time curve extrapolated to infinity ($AUC_{0-inf}$);

(5) first-order rate constant associated with the terminal (log-linear) portion of the curve (λ);

(6) terminal elimination half-life (t½);

(7) apparent clearance (ketamine only) (CL/F); and (8) apparent volume of distribution (ketamine only) ($V_d$/F);

Criteria for Evaluation: Safety

Safety endpoints include:

(1) Holter monitor to determine whether there was a correlation between electrocardiogram parameters and the PK concentration of intranasal racemic ketamine in plasma;

(2) adverse events including type, incidence, and severity;

(3) vital signs (blood pressure, respiratory rate, heart rate, oxygen saturation, and oral temperature);

(4) 12-lead electrocardiogram (ventricular heart rate and the PR, QRS, QT, and QTc intervals);

(5) clinical laboratory tests;

(6) physical examination;

(7) nasal cavity examination; and (8) Columbia-Suicide Severity Rating Scale (C-SSRS).

Subject Discontinuation

Any subject who voluntarily withdraws consent or was discontinued (e.g., because of an adverse event) from the study prior to completion was considered as withdrawn from the study. Subjects may be discontinued from the study under any of the following circumstances:

(1) occurrence of intolerable AE, as assessed by the investigator or designee;

(2) clinically significant abnormality on vital signs, electrocardiogram, clinical laboratory, or physical examination assessments, as assessed by the investigator or designee;

(3) withdrawal of consent;

(4) lost to follow-up;

(5) administrative reasons;

(6) sponsor decision;

(7) major violation of the protocol;

(8) if, in the opinion of the qualified investigator, it was in the best interest of the subject;

(9) pregnancy;

(10) noncompliance with study requirements and restrictions (e.g., positive urine cotinine test at any study visit, use of a concomitant medication); and

(11) termination of the study,

When an event such as a family emergency, a transient intercurrent illness (such as a cold) unrelated to study drug, or a remediable act of noncompliance prevents a subject from participating in a scheduled visit, but the subject wishes to continue in the study, with the agreement of the investigator, the research site staff may attempt to reschedule the visit if feasible for the study and retain the subject in the study.

If a subject was prematurely discontinued from participation in the study for any reason after drug administration, the investigator or designee must make every effort to perform the assessments scheduled for the Follow-up visit. Replacement subjects may be added at the sponsor's discretion, in agreement with the principal investigator.

Statistical Methods

Treatment Population Definitions:

The following analysis populations were used for Part A:

Part A Randomized Population: All subjects who were randomized into the study.

Part A Safety Population: All randomized subjects who receive any study treatment.

Part A Pharmacodynamic (PD) Population: All subjects in the Part A Safety Population who receive any study treatment and who have no protocol deviations or other circumstances that would exclude them from PD analysis.

Part A Pharmacokinetic (PK) Population: All subjects in the Part A Safety Population who receive at least 1 dose of the study drug, have evaluable PK data who have no protocol deviations or other circumstances that would exclude them from PK analysis.

The following analysis populations were used for Part B:

Part B Randomized Population: All subjects who were randomized into the study.

Part B Safety Population: All randomized subjects who receive any study treatment.

Part B Completers Population: All subjects in the Part B Safety Population who receive both study treatments (e.g., ketamine 60 mg intranasal and IV), and complete both treatment periods regardless of whether they have protocol deviations.

Part B Pharmacokinetic (PK) Population: All subjects in the Part B Safety Population who receive at least 1 dose of the study drug, have evaluable PK data and who have no protocol deviations or other circumstances that would exclude them from PK analysis.

Part B Bioavailability Population: All subjects in the Part B PK Population who receive both study treatments (e.g., ketamine 60 mg intranasal and IV), and complete both treatment periods.

Pharmacodynamics and Pharmacokinetics:

PK and PD statistical analyses were performed using SAS® (release 9.4 or higher). PK parameter derivation were performed using Phoenix WinNonlin (version 8.0 or higher on the Windows 7 platform or higher).

For Part A, descriptive statistics were provided for the Part A PD Population. PD data at each time point were summarized by summary statistics including n, mean, standard error (SE), minimum, first quartile ($Q_1$), median, third quartile ($Q_3$) and maximum. PD derived endpoints were summarized by treatment using descriptive statistics. PD data were presented graphically (where appropriate), and listed for the Part A Randomized Population.

For Part B, descriptive statistics and inferential analysis were done on the Part B Completers Population. Listings for each PD parameter and endpoint were provided for the Part B Randomized Population.

PD data at each time point was summarized by descriptive statistics including n, mean, standard error (SE), minimum, first quartile ($Q_1$), median, third quartile ($Q_3$) and maximum. Derived endpoints were summarized by treatment and paired difference using descriptive statistics. PD data were presented graphically (where appropriate), and listed for the Part B Randomized Population.

For Part A and Part B, PK descriptive statistics were done using the Part A and Part B PK Populations. Descriptive statistics, including n, arithmetic mean, standard deviation (SD), CV %, median, minimum, and maximum, were calculated and presented for each time point by treatment for plasma concentrations of the following analytes: ketamine, norketamine, and 6-hydroxynorketamine. Mean (SD) and individual time course plots of the concentrations (original and log transformed) vs time were generated.

PK parameters for all analytes were calculated using noncompartmental analysis (Phoenix WinNonlin®, version 8.0) and were summarized by treatment using descriptive statistics, including n, arithmetic mean, SD, CV %, median, minimum, maximum, geometric mean, and geometric CV % except $T_{max}$, t½, and λ. $T_{max}$ data were summarized with minimum, $Q_1$, median, $Q_3$, and maximum. The t½ and λ data were summarized with n, mean, SD, CV, minimum, median, and maximum. The PK blood sampling collected at follow-up visit for both Part A and Part B will not be used for PK parameters calculation.

Results

The results of Part A of the clinical study described in Example 1 are shown in FIGS. 1-9. FIGS. 1-3 describe the pharmacokinetic parameters for ketamine on Days 1, 4, and 8 (FIG. 1, FIG. 2, and FIG. 3, respectively). FIGS. 4-6 describe the pharmacokinetic parameters for norketamine on Days 1, 4, and 8 (FIG. 4, FIG. 5, and FIG. 6, respectively). FIGS. 7-9 describe the pharmacokinetic parameters for hydroxynorketamine on Days 1, 4, and 8 (FIG. 7, FIG. 8, and FIG. 9, respectively).

The results of Part B of the clinical study described in Example 1 are shown in FIGS. 10A-10C, FIGS. 11A-11C, and FIGS. 12A-12C.

Example 2. An Open-Label Study Regarding Drug-Drug Interactions of Multiple Doses of Oral Sertraline or Venlafaxine Coadministered with Intranasal Ketamine in Healthy Adult Volunteers This example describes an open-label study to determine the drug-drug interaction of multiple doses of oral sertraline or venlafaxine coadministered with intranasal ketamine in healthy adult volunteers.

Study Overview

This is a single-center, open-label study in healthy subjects. Each subject participates in a medical screening visit, a treatment period, and a follow-up visit. The total duration of this study is approximately 7 weeks. Within 30 days of screening, eligible subjects are randomized into 1 of 2 arms:

Arm 1: racemic ketamine (60 mg)+venlafaxine extended release (Effexor® XR)

Arm 2: racemic ketamine (60 mg)+sertraline (Zoloft®)

Subjects are admitted on Day −1 and are confined in the clinical research unit for 13 days (12 nights). On Day 1, subjects are given a single dose of racemic ketamine 60 mg, followed by PK sampling and PD and safety assessments. There are approximately 44 hours between the racemic ketamine and venlafaxine/sertraline doses. On Day 3, subjects are given single oral doses of either venlafaxine or sertraline for 9 consecutive days (Day 3 to Day 11), starting with a lower dose (75 mg venlafaxine, 50 mg sertraline) then increasing to a higher dose (150 mg venlafaxine, 100 mg sertraline) to achieve steady-state concentrations for venlafaxine and sertraline.

The second dose of racemic ketamine 60 mg is intranasally administered 4 hours after venlafaxine or sertraline on Day 11 to correspond with the time of maximum concentration of venlafaxine/sertraline, which would allow for the detection of any drug interaction. Racemic ketamine, or a pharmaceutically acceptable salt thereof, is intranasally administered at least 3 hours after a meal due to the food effect for sertraline and to mimic the fasted conditions implemented in previous studies.

Ketamine PK samples are taken on Day 1 and Day 2 following the first dose, as well as on Day 11 and Day 12 following the second dose of ketamine. Serial PK sampling for venlafaxine or sertraline is performed at the expected steady state, beginning on Day 10 without ketamine and on Day 11 in the presence of ketamine, accompanied by PD and safety assessments. Predose PK samples for venlafaxine or sertraline from Day 3 to Day 10 is used to verify if steady state is achieved for these drugs.

Subjects are discharged on Day 12, with a follow-up visit on Day 15.

Objectives:

The primary objective of this study is to determine the effect of coadministration of sertraline or venlafaxine on the PK and metabolism of a single dose of racemic ketamine (IN ketamine HCl).

The secondary objectives are:

(1) to assess the effect of a single dose of racemic ketamine and its metabolites on the PK of sertraline or venlafaxine;

(2) to assess the PD interaction (BP) between racemic ketamine and sertraline or venlafaxine; and (3) to assess the safety and tolerability of racemic ketamine coadministered with either sertraline or venlafaxine.

Number of Subjects

Approximately 48 healthy subjects (24 subjects per arm) are randomized into one of the 2 study treatment arms with the intent to ensure complete data from at least 14 subjects per treatment arm (total of 28 subjects).

Criteria for Inclusion:

Subjects are considered eligible to participate in this study if each one of the following inclusion criteria is satisfied at screening:

(1) healthy male or female subjects 20 to 55 years of age, inclusive;

(2) body mass index (BMI) within the range of 18.0 to 35.0 kg/m2, inclusive, and a minimum weight of at least 50.0 kg;

(3) nonsmoker for at least 3 months and tests negative on a urine cotinine test;

(4) female subjects of childbearing potential with male sexual partners must be using and willing to continue using medically acceptable contraception for at least 1 month prior to Screening (at least 3 months for oral and transdermal contraceptives) and for at least 1 month after the last study drug administration;

(5) female subjects of non-childbearing potential must be surgically sterile (hysterectomy and/or bilateral oophorectomy/salpingo-oophorectomy, as determined by subject medical history) or congenitally sterile, or must be postmenopausal, where postmenopausal is defined as being amenorrheic for at least 1 year without another cause and an FSH level ≥26 IU/L.6;

(6) male subjects with female partners of childbearing potential must be using and willing to continue using medically acceptable contraception from Screening and for at least 90 days after the last study drug administration;

(7) resting heart rate between 50 beats per minute and 100 beats per minute, inclusive, and heart rate measurements may be repeated as per the site's standard operating procedure (SOP);

(8) able to speak, read, and understand English or French sufficiently to understand the nature of the study, to provide written informed consent, and to allow completion of all study assessments;

(9) must provide written informed consent prior to the initiation of any protocol-specific procedures; and

(10) must be willing and able to abide by all study requirements and restrictions.

Exclusion Criteria

Subjects are not considered eligible to participate in this study if any one of the following exclusion criteria is satisfied at screening:

(1) self-reported substance or alcohol dependence or abuse (excluding nicotine and caffeine) in their lifetime, and/or has ever participated or plans to participate in a substance or alcohol rehabilitation program to treat their substance or alcohol dependence;

(2) self-reported abuse of ketamine or phencyclidine (PCP) in their lifetime;

(3) clinically significant abnormalities as assessed by physical examination, medical history, electrocardiogram, vital signs, or laboratory values as judged by the investigator or designee;

(4) history or presence of any clinically significant illness (e.g., cardiac, pulmonary, hepatic, renal, hematologic, gastrointestinal, endocrine, immunologic, dermatologic, oncologic, or musculoskeletal) or any condition, which in the opinion of the investigator or designee would jeopardize the safety of the subject or the validity of the study results;

(5) personal or first-degree family history of psychosis, personal history of mood disorder, anxiety disorder, obsessive-compulsive disorder, somatoform disorder, behavior disorder;

(6) personal history of neurologic disorder in relation to the CNS: congenital malformation of the brain, brain tumor, multiple sclerosis, degenerative disease of the CNS, or inflammatory disease of the CNS within the past year or having resulted in sequelae;

(7) history or present diagnosis of glaucoma;

(8) known hypertension or blood pressure above 140/90 mmHg (blood pressure may be repeated as per the site's SOPs);

(9) presence or history of cardiac disorder, including congenital heart disease, ischemic heart disease, cardiac insufficiency, supraventricular and ventricular heart rhythm disorder, prolonged QT syndrome (i.e., QTc>450 msec) and associated risk factors (i.e., hypokalemia, family history of long QT syndrome);

(10) any history of suicidal ideation or suicidal behavior (lifetime), as assessed by the Columbia-Suicide Severity Rating Scale (C-SSRS; baseline version);

(11) current (i.e., within the last 3 months) treatment with any psychotropic medications;

(12) presence of piercing or any medical condition that could interfere with the absorption or PK of IN ketamine (e.g., nasal polyps, clinically significant deviated septum [corrected or persistent], or other physical abnormalities of the nose);

(13) any history of epilepsy or seizures (except childhood febrile seizures);

(14) history of severe allergic reaction (including anaphylaxis) to ketamine or related drugs (other NMDA receptor antagonists), venlafaxine or related drugs (other SNRIs), or sertraline or related drugs (other SSRIs) or to any food, medication, or bee sting, or previous status asthmaticus;

(15) use of a prohibited medication.;

(16) use of soft drugs (such as marijuana) within 3 months prior to the screening visit or hard drugs (such as cocaine, crack, opioid derivatives including heroin, and amphetamine derivatives) within 1 year prior to screening;

(17) positive urine drug screen (UDS);

(18) regular use of alcohol within 6 months prior to the screening visit (more than 14 units of alcohol per week [1 unit=150 mL of wine, 360 mL of beer, or 45 mL of 40% alcohol]);

(19) positive breath alcohol test, however, subjects may be rescheduled at the discretion of the investigator or designee;

(20) difficulty with venous access or unsuitable or unwilling to undergo catheter insertion;

(21) female subjects who are currently pregnant (have a positive pregnancy test), lactating, breastfeeding, or who are planning to become pregnant within 30 days of last study drug administration;

(22) positive for hepatitis B, hepatitis C, or human immunodeficiency virus (HIV);

(23) donation of plasma within 7 days prior to dosing or donation or loss of blood (excluding volume drawn at screening) of 50 mL to 499 mL of blood within 30 days, or more than 499 mL within 56 days prior to the first dosing;

(24) treatment with an investigational drug within 5 times the elimination half-life, if known (e.g., a marketed product), or within 30 days (if the elimination half-life is unknown), or within 90 days for a biologic prior to first drug administration or is concurrently enrolled in any research judged not to be scientifically or medically compatible with this study;

(25) an employee of the sponsor, clinical research organization, or research site personnel directly affiliated with this study or their immediate family member defined as a spouse, parent, child, or sibling, whether biological or legally adopted;

(26) a subject who, in the opinion of the investigator or designee, is considered unsuitable or unlikely to comply with the study protocol for any reason; and

(27) a subject who has pending legal charges or is on probation.

Dietary and Other Restrictions

Aside from the inclusion and exclusion criteria, the subject must agree to abide by each of the following restrictions for the specified time:

(1) subjects are required to abstain from alcohol for 24 hours prior to each study visit and abstinence are confirmed with a breath alcohol test;

(2) subjects are required to abstain from recreational drug use throughout the study, from screening until after the follow-up visit;

(3) subjects are required to fast (abstain from food) for at least 3 hours prior to ketamine dosing and at least 1 hour after ketamine dosing;

(4) except for water given with venlafaxine or sertraline and fluids provided with the meal, no fluids are allowed from 1 hour before until 1 hour after venlafaxine or sertraline dosing, however, water is provided ad libitum at all other times;

(5) subjects are asked to abstain from the following foods from 1 week prior to the treatment phase until after the follow-up visit: grapefruit or grapefruit-containing products, pomegranate, pomelo, star fruit juice/products, foods containing poppy seeds, Seville oranges, and orange juice (6) subjects are asked not to consume more than 450 mg of caffeine per day (e.g., approximately 5 cups of tea or 3 cups of regular coffee or 8 cans of cola or 2 energy drinks) from 1 week prior to the treatment phase until after the follow-up visit, and subjects are not be permitted to consume caffeine-containing beverages while housed at the research site;

(7) subjects are asked to refrain from driving, operating machinery, or engaging in hazardous activities until they and the investigator are sure the study drug is not impairing their judgment and/or ability to perform skilled tasks, and subjects are informed that driving under the influence is a criminal offense and that if they are caught driving under the influence, they may be prosecuted to the fullest extent of the law;

(8) subjects are asked to abstain from strenuous physical activity for 48 hours prior to each study visit, subjects are not be permitted to engage in strenuous exercise during the in-subject stay at the research site, and for safety reasons, subjects are required to remain seated or semi-reclined in bed for the first 4 hours after intranasal racemic ketamine administration on Day 1 and Day 11, as well as after the first venlafaxine or sertraline administration on Day 3 and after dose increment of venlafaxine or sertraline on Day 7 or Day 5, respectively;

(9) subjects are required to abstain from blood donation during the study and for 30 days following the follow-up visit; and

(10) subjects are required to follow the informed consent form (ICF) and the clinic code of conduct.

Test Product(s), Dose, and Mode of Administration:

Subjects are randomized into 1 of 2 arms:

Arm 1: racemic ketamine 60 mg with venlafaxine

Arm 2: racemic ketamine 60 mg with sertraline

On Day 1, racemic ketamine 60 mg is intranasally administered as 4 sprays (in total) using 2 disposable bi-dose devices. Two sprays (1 spray per nostril) are administered from the first device. After approximately 5 minutes, two additional sprays (1 spray per nostril) are administered from the second disposable device. Subjects may not blow their nose for 1 hour following dosing with racemic ketamine.

Subjects are instructed to gently blow their nose prior to intranasal racemic ketamine administration. Details, including the required standard position of the subject's head during drug administration and the instructions given to subjects regarding sniffing following administration of the sprays, are outlined in a study-specific procedure.

Arm 1

From Day 3 to Day 6, subjects are given single oral doses of 75 mg venlafaxine (1×75 mg venlafaxine capsule) and the venlafaxine dose is escalated to 150 mg (2×75 mg venlafaxine capsules) from Day 7 to Day 10.

Arm 2

On Day 3 and Day 4, subjects are administered a single oral dose of 50 mg sertraline (1×50 mg sertraline capsule) and the sertraline dose is escalated to 100 mg (2×50 mg sertraline capsules) from Day 5 to Day 10.

On each day from Day 3 to Day 11, venlafaxine or sertraline is administered approximately 45 minutes after starting a meal and subjects will have approximately 30 minutes to complete the whole meal. Any residual amount of food is recorded. Meals served on the morning of Day 10 and Day 11 are standardized and similar in composition. The study drug is administered with about 240 mL of water and must be swallowed whole within 5 minutes. Time of dosing is set as the first capsule administration, when applicable.

On Day 11, 150 mg venlafaxine or 100 mg sertraline is administered first and the second dose of racemic ketamine 60 mg is given at approximately the same time as on Day 1 (approximately 4 hours following venlafaxine or sertraline dosing), following the same procedure for administration of the nasal sprays. Time of racemic ketamine dosing is set as the first spray administration. Nasal cavity check is done after each racemic ketamine dosing in order to confirm proper inhalations.

Criteria for Evaluation: Pharmacokinetics

The PK parameters to be evaluated in this study for ketamine, norketamine, and hydroxyketamine, with and without sertraline or venlafaxine, as applicable, include the following:

(1) $C_{max}$: maximum observed plasma concentration;

(2) $AUC_{0-inf}$: area under the plasma concentration-time curve extrapolated to infinity;

(3) $AUC_{0-t}$: area under the plasma concentration-time curve from 0 to last measurable concentration (for doses 1 and 3);

(4) $T_{max}$: time to maximum observed plasma concentration;

(5) $k_{el}$: first-order rate constant associated with the terminal (log-linear) portion of the curve (for dose 3 with and without sertraline or venlafaxine);

(6) t½: apparent first-order terminal elimination half-life (calculated as 0.693/kel);

(7) CL/F: apparent clearance (total ketamine only); and (8) $V_d$/F: apparent volume of distribution (total ketamine only).

Other PK parameters for venlafaxine and sertraline and their corresponding metabolites will include the following:

(9) $C_{max}$;

(10) $AUC_\tau$: area under the plasma concentration-time curve for the dosing interval;

(11) $CL_{ss}$: steady-state clearance; and

(12) $T_{max}$.

Criteria for Evaluation: Pharmacodynamics

The PD parameters to be evaluated in this study include:

(13) blood pressure maximum change from baseline ($CFB_{max}$) in blood pressure time to $CFB_{max}$ in blood pressure Other PD endpoints may be evaluated as appropriate.

Criteria for Evaluation: Safety

Safety endpoints include:

(14) AEs (type, incidence, and severity);

(15) Vital signs (blood pressure, respiratory rate, heart rate, oxygen saturation, and oral temperature);

(16) 12-lead electrocardiogram (electrocardiogram; heart rate and the PR, QRS, QT, and QTc intervals);

(17) clinical laboratory tests;

(18) Columbia-Suicide Severity Rating Scale (C-SSRS);

(19) Clinician-Administered Dissociative State Scale (CADSS);

(20) physical examination; and

(21) nasal cavity examination.

Stopping Criteria

Any subject who voluntarily withdraws consent or is discontinued (e.g., because of an adverse event) from the study prior to completion is considered as withdrawn from the study. Subjects may be discontinued from the study under any of the following circumstances:

(1) occurrence of intolerable AE, as assessed by the investigator or designee;

(2) clinically significant abnormality on vital signs, electrocardiogram, clinical laboratory, or physical examination assessments, as assessed by the investigator or designee;

(3) withdrawal of consent;

(4) lost to follow-up;

(5) administrative reasons;

(6) sponsor decision;

(7) major violation of the protocol;

(8) if, in the opinion of the qualified investigator, it is in the best interest of the subject;

(9) pregnancy;

(10) noncompliance with study requirements and restrictions (e.g., positive urine cotinine test at any study visit, use of a concomitant medication); and

(11) termination of the study,

Subjects experiencing emesis after dosing with venlafaxine or sertraline may be withdrawn. An evaluation is done on a case-by-case basis.

When an event such as a family emergency, a transient intercurrent illness (such as a cold) unrelated to study drug, or a remediable act of noncompliance prevents a subject from participating in a scheduled visit, but the subject wishes to continue in the study, with the agreement of the investigator, the research site staff may attempt to reschedule the visit if feasible for the study and retain the subject in the study.

If a subject is prematurely discontinued from participation in the study for any reason after drug administration, the investigator or designee must make every effort to perform the assessments scheduled for the Follow-up visit. Replacement subjects may be added at the sponsor's discretion, in agreement with the principal investigator.

Statistical Methods

Treatment Population Definitions:

- Randomized Population: All subjects who are randomized into one of the treatment arms
- Safety Population: All randomized subjects who receive any study drug
- Pharmacokinetic (PK) Population: All subjects in the Safety Population who receive at least 1 dose of the study drug, have evaluable PK data and have not experienced any protocol deviations or other circumstances to exclude the subject from the PK population.
- Bioavailability Population: All subjects in the Safety Population who complete all treatments for at least one PK parameter. Subjects with more than 3 consecutive samples missing or more than 5 samples missing in total will not be included in the Bioavailability Population
- Pharmacodynamic (PD) Population: All subjects in the Safety Population who have any post-baseline BP measurements.

Analysis of Safety Assessments

Safety analysis is done using the Safety Population. The incidence of adverse events, adverse events resulting in discontinuation, and serious adverse events are summarized by treatment arm, showing the number and percentage of subjects who experienced at least 1 adverse event. These summaries are presented by system organ class and preferred term using the Medical Dictionary for Regulatory Activities (MedDRA, version 22.0 or higher), and by maximum severity and relationship to the study treatment.

Laboratory data are summarized by the laboratory panel, laboratory test, treatment arm and visit. Laboratory abnormalities are summarized by treatment arm and subject in a listing. For each laboratory panel, laboratory data are listed by treatment arm and subject. Vital signs (BP, respiratory rate, heart rate, oxygen saturation) are summarized at each time point by treatment for absolute values and change from baseline. Special consideration is given to blood pressure as this is a known factor in ketamine safety.

12-Lead electrocardiogram data (absolute values and change from baseline in ventricular heart rate and the PR, QRS, QT, and QTc intervals) are summarized by treatment and time point using descriptive statistics. Frequencies (numbers and percentages) are calculated for the overall evaluation by treatment and time point.

The Clinician-Administered Dissociative State Scale (CADSS) is summarized by treatment and time point for the following summary scores:

- Subject-rated subscale (sum of Item 1 to 19)
- Observer-rated subscale (sum of Item 20 to 23)
- Total score (sum of Item 1 to 23)

In addition, responses to the individual CADSS items and summary scores are listed.

The Columbia-Suicide Severity Rating Scale (C-SSRS).

Any finding or absence of finding relative to each subject's baseline physical examination and nasal cavity examination are documented. Any abnormal finding noted after dosing is documented as an adverse event if judged as a clinically significant change from baseline.

Analysis of Pharmacokinetics

Pharmacokinetic descriptive statistics are done using the PK Population. The Bioavailability Population are used for inferential analysis. Treatment is defined as Day 1 Ketamine 60 mg, Day 10 Venlafaxine 150 mg or Sertraline 100 mg, Day 11 Ketamine 60 mg, and Day 11 Venlafaxine 150 mg or Sertraline 100 mg.

Plasma concentration data for ketamine, norketamine, and hydroxyketamine are summarized using descriptive statistics for each treatment and time point. Pharmacokinetic parameters are derived using noncompartmental methods for all analytes. Similar analysis is performed for venlafaxine and sertraline and their metabolites (N-desmethylvenlafaxine and O-desmethylvenlafaxine, N-desmethylsertraline).

Descriptive statistics, including n, mean, standard deviation (SD), coefficient of variation (CV), minimum, median, and maximum are summarized by treatment and time point. PK parameters are summarized by treatment. Graphs of the concentration (original and log-transformed) versus time are generated. Concentrations below the limit of quantification (BLQ) are set to zero for the generation of summary statistics and mean concentration time plots For the calculation of the PK parameters, concentration time data is treated as follows: BLQ concentrations before the first quantifiable concentration is set to zero; BLQ concentrations after the first quantifiable concentration are treated as missing; and predose sampling times relative to dosing are set to zero. The PK blood sampling collected at follow-up visit will not be used for PK parameters calculation. Descriptive statistics, including n, mean, SD, geometric mean, geometric CV, minimum, median, and maximum are calculated by dose level for all PK parameters except $T_{max}$, t½, and λ. $T_{max}$ data are summarized with n, minimum, median, maximum, and quartiles 1 and 3. The t½ and λ data are summarized with n, mean, SD, CV, minimum, median, and maximum.

Pharmacokinetic profiles are analyzed for all subjects, even if some PK sampling time points are missed. The PK parameters are subject to quality control criteria. If quality control criteria are met, the PK parameters are used in analyses and models. Quality control criteria for PK are sufficient to eliminate unreliable data.

Comparison of $C_{max}$, $AUC_{0-inf}$, and CL/F is performed for ketamine alone and in combination with venlafaxine or sertraline. Comparison of $C_{max}$, $AUC_{\tau}$, and $CL_{ss}$ is performed for venlafaxine and sertraline with and without ketamine. The comparison is performed using a mixed-effect analysis of variance (ANOVA) model with the logarithm of the parameter as the outcome. Treatment is included as a fixed effect and subject as a random effect.

Metabolic ratios are calculated for ketamine conversion to norketamine and hydroxyketamine using molecular-weight-adjusted metabolite-to-parent ratios. Conversion of venlafaxine and sertraline to their corresponding metabolites, individually and in combination with ketamine, will also be evaluated to provide more insight into the metabolic interaction through different pathways.

Analysis of Pharmacodynamic Measures

The analysis of PD endpoints are performed using the PD Population. The PD endpoints will include $CFB_{max}$ and time $CFB_{max}$.

Blood pressure changes are analyzed as CFB on dosing Days 1, 10, and 11. Statistical models are used to compare effect of ketamine or venlafaxine/sertraline alone with the effect of drug combination for each time point and relevant parameters.

The possible PD interaction between ketamine and sertraline and between ketamine and venlafaxine is explored. Pharmacodynamic data at each time point is summarized by descriptive statistics and presented graphically (where appropriate). Derived endpoints are summarized using descriptive statistics.

Example 3. A 2-Part Phase 2 Study to Assess the Efficacy, Safety, and Tolerability of Intranasal Racemic Ketamine Administered to Adults with Major Depressive Disorder at Imminent Risk of Suicide This example describes a Phase 2, multicenter, 2-part study to determine the efficacy, safety, and tolerability of intranasally (IN) administered racemic ketamine plus SOC in adult subjects diagnosed with MDD at imminent risk of suicide.

Study Overview

This Phase 2, multicenter, 2-part study in adult subjects diagnosed with MDD at imminent risk of suicide will evaluate the efficacy, safety, and tolerability of intranasally (IN) administered racemic ketamine plus SOC. In Part 1, 16 subjects will receive open-label racemic ketamine (90 mg). Part 2 of the study is double-blind and 120 subjects will be randomized 1:1 to receive either racemic ketamine (90 mg) or matching placebo.

The study schedule is identical for Parts 1 and 2. After admission to the emergency room or hospital, each subject will participate in a 1 to 2 day screening phase, a 16-day treatment phase including SOC during which study drug will be administered 2 times per week, and a 2-week safety follow-up phase for a total of up to 5 weeks of study participation. Subjects will be treated as inpatients for approximately 7 days (including screening), and assuming the subject meets readiness for discharge criteria, will be discharged on Day 6 to continue the trial as outpatients, provided it is clinically appropriate to do so. Subjects will return to the clinic to receive study drug and to undergo study assessments 2 times per week until Day 16. Subjects will be evaluated for efficacy using multiple psychometric scales and for safety using clinical laboratory assessments, electrocardiograms (ECGs), vital signs, and physical examinations. After the last dose of study drug, subjects will continue to be monitored for safety for 2 weeks, including 4 in-person safety follow-up visits on Days 19, 22, 25/26, and 29/30.

Throughout the study, safety data will be reviewed on a regular basis by the Safety Review Committee (SRC). In addition, members of the SRC will confirm readiness for discharge from the inpatient unit.

Objectives:

The primary objective of this study is to evaluate the efficacy of racemic ketamine plus standard of care (SOC) on symptoms of depression in adults with major depressive disorder (MDD) who are at imminent risk of suicide The secondary objectives are:

(1) To evaluate the efficacy of racemic ketamine plus SOC on symptoms of suicidality in adults with MDD who are at imminent risk of suicide; and (2) To evaluate the safety and tolerability of racemic ketamine plus SOC in adults with MDD who are at imminent risk of suicide.

The exploratory objective is to evaluate the psychometric properties of the Sheehan-Suicidality Tracking Scale (S-STS)—Clinically Meaningful Change Measure (CMCM).

Number of Subjects

Part 1: 16 subjects are planned. Part 2: Approximately 120 randomized subjects are planned including 60 subjects per arm.

Criteria for Inclusion:

Subjects must fulfill all of the following requirements to enter the study:

(1) The subject is able to speak, read, and understand English and/or the language of the investigative staff to sufficiently understand the nature of the study, to provide written informed consent, and to allow the completion of all study assessments.

(2) Subject is 18 to 65 years of age at the time of informed consent.

(3) Male subjects who are sexually active must agree to abstain from sexual activity or be willing to use medically acceptable contraception if they become sexually active from time of consent and for 3 months after the last dose of study drug.

(4) Female subjects of childbearing potential must have a negative serum pregnancy test at screening, and must not be breastfeeding or lactating. Females must be willing to abstain from sexual activity or use medically accepted contraception if they are sexually active from time of consent and for 1 month after the last dose of study drug.

(5) The subject meets Diagnostic and Statistical Manual of Mental Disorders, Fifth Edition (DSM-5) criteria for a diagnosis of current MDD (unipolar without psychotic features), with symptoms present for at least 4 weeks, based on psychiatric intake and confirmed by the Mini International Psychiatric Interview Version 7.02 for Suicidality Disorders (MINI).

(6) The subject has a Montgomery Asberg Depression Ration Scale (MADRS) total score of ≥28 predose on Day 1.

(7) The subject has a score of 5 or 6 on item 10 of the MADRS.

(8) In the investigator's opinion, the subject requires psychiatric hospitalization due to significant risk of suicide, has ≥15 on the S-STS CMCM total score, and a score of 6-9 (inclusive) on the S-STS CMCM Clinician judgment of subject's risk of a suicide attempt or death by suicide at this time (p12 top).

(9) In the investigator's opinion, the subject has current suicidal ideation with intent, which is confirmed by the MINI Suicidality Module at screening and baseline, specifically a positive response related to present symptoms on Question B3, as well as a positive response related to symptoms within the past 24 hours on Question B10 or B11.

(10) In the investigator's opinion, if the imminent suicidality is based upon a precipitating event (i.e., a clearly identifiable situational stressor that contributes to initiation or exacerbation of the subject's current suicidality), the active suicidality must be present for >72 hours.

(11) The subject has a history of previous suicide attempt(s), as confirmed on the C-SSRS with a history of at least one actual attempt, or if the attempt was interrupted or aborted, is judged to have been serious in intent in the investigator's opinion.

(12) As part of SOC treatment, the subject agrees to be hospitalized voluntarily for a recommended period of approximately 7 days (screening to Day 6), and fully understands that the duration of hospitalization may be longer if clinically indicated (i.e., he/she is not safe to be discharged on Day 6).

(13) The subject is willing and able to take prescribed non-investigational antidepressant therapy(ies) at investigator's discretion for at least the duration of the study.

(14) The subject is willing and able to maintain other existing treatments and to avoid the use of alcohol and recreational drugs, as well as specific therapies prohibited by the protocol, from screening through the last study visit (Day 29/30). Subjects with acute alcohol intoxication should not be screened (but can be screened once sober); subjects suspected of intoxication can be confirmed by BAC or breathalyzer.

(15) The subject is able to complete IN administration of study drug.

Exclusion Criteria

The presence of any of the following criteria excludes a subject from participating in the study:

(1) Subjects who have ongoing sequelae from prior COVID illness, or subjects who have either documented COVID infection or symptoms suggestive of recent COVID infection within 1 month of screening.

(2) The subject has a lifetime diagnosis of bipolar disorder, any mood disorder with psychotic features, schizophrenia or other psychotic disorder, obsessive compulsive disorder, or antisocial personality disorder, as confirmed by the MINI. (Note subjects who have post-traumatic stress disorder and generalized anxiety disorder (GAD)/panic disorder are not necessarily excluded as long as MDD is the most prominent diagnosis.)

(3) In the investigator's opinion, the subject has chronic, refractory treatment-resistant depression from >4 adequate therapeutic trials of antidepressants (with or without adjuvants and/or electroconvulsive therapy [ECT]) as confirmed by ATRQ.

(4) In the investigator's opinion, the subject has a current diagnosis of borderline personality disorder or, if the subject has not met full diagnostic criteria for borderline personality disorder within the last 5 years, the subject has a history of recurrent non-suicidal self-injury, or self-mutilating behavior.

(5) The subject has a score of 10 on the S-STS CMCM Clinician judgment of subject's risk of a suicide attempt or death by suicide at this time (top of S-STS CMCM p12).

(6) The subject is diagnosed with intellectual disability, a neurocognitive disorder including dementia, or has a history of moderate or severe traumatic brain injury. Mild traumatic brain injuries are not necessarily exclusionary provided the investigator believes current symptoms would not interfere with conduct or interpretation of safety and/or efficacy assessments.

(7) The subject has a history or current finding of any clinically significant, hematological, hepatic, respiratory, renal, neurological, known positive human immunodeficiency virus (HIV) infection, gastrointestinal disorder, or other disease that might confound the results of safety assessments conducted in the study.

(8) The subject has a history of seizures (other than childhood febrile seizures).

(9) The subject has a body mass index (BMI)>40 or <18 at screening.

(10) The subject has known, uncontrolled hypertension or blood pressure (BP) that, in the investigator's judgment, should exclude the subject at screening or baseline (BP may be repeated as per the site's standard operating procedures [SOPs]).

(11) The subject has a known history or current finding of cardiovascular disease, advanced arteriosclerosis, structural cardiac abnormality, cardiomyopathy, serious heart rhythm abnormalities, coronary artery disease, congenital heart disease, ischemic heart disease, cardiac insufficiency, supraventricular and ventricular heart rhythm disorder, prolonged QT syndrome (i.e., QTcF>450 msec) and associated risk factors (i.e., hypokalemia, family history of long QT syndrome), syncope, cardiac conduction problems (e.g., clinically significant heart block), exercise-related cardiac events including syncope and pre-syncope, clinically significant bradycardia, or other serious cardiac problems.

(12) The subject has a known family history of sudden cardiac death or ventricular arrhythmia.

(13) The subject has any clinically significant abnormality on 12-lead ECG performed at screening or baseline such as serious arrhythmia, cardiac conduction problems, or other abnormalities deemed to be a potential safety issue.

(14) The subject has a concurrent chronic or acute illness, disability, or other condition (e.g., narcolepsy) that might confound the results of safety assessments conducted in the study.

(15) The subject has any medical condition that could interfere with the absorption of IN ketamine (e.g., nasal polyps, clinically significant deviated septum [corrected or persistent], or other physical abnormalities of the nose).

(16) The subject meets the DSM-5 criteria for moderate or severe substance use disorder in the 6 months prior to screening, OR in the investigator's opinion, is at risk of withdrawal from substance use (e.g., opiate or alcohol dependent), OR has a lifetime history of ketamine, phencyclidine, lysergic acid diethylamide, or 4-methylenedioxy-methamphetamine hallucinogen-related use disorders. Nicotine use disorder is permitted.

(17) The subject has a positive urine test for phencyclidine (PCP), cocaine, or amphetamines (inclusive of amphetamine, methamphetamine [mAMP], and 3, 4 methylenedioxy-methamphetamine [MDMA]) at screening.

(18) The subject has positive hepatitis B, hepatitis C, or HIV results at screening.

(19) The subject has any history of using ketamine or esketamine for any psychiatric treatment.

(20) The subject has known or suspected intolerance or hypersensitivity to the investigational product(s), closely related compounds, or any ingredients.

(21) In the investigator's opinion, the subject has any clinically significant laboratory abnormality including an abnormality that indicates clinically significant hematologic, hepatobiliary, or renal disease.

(22) The subject has received an investigational product, including vaccines, within 30 days prior to the first dose of study drug.

(23) The subject was previously enrolled in the current study. Subjects previously screened for, but not randomized in, the current study may be rescreened with approval from the study medical monitor.

(24) The subject does not meet or is not willing to comply with the requirements related to prohibited and restricted medications, as well as required washout periods prior to participation. Prohibited medications include, but are not limited to, monoamine oxidase inhibitors (MAOIs), opioids or drugs with activity at the opioid receptor, psychostimulants, lamotrigine, N-methyl-D-aspartate (NMDA) receptor modulators, magnesium, or any medication that might confound the results of safety assessments conducted in the study.

Subjects who have received any of these prohibited medications within 2 weeks of screening are excluded from the study. Potent CYP 3A4 inhibitors are not permitted within 1 week of first dose and until at least 1 day after the last dose. Potent CYP 3A4 inducers are not permitted within 30 days of first dose and until at least 1 day after the last dose. Subjects who have recently discontinued lithium or calcium channel blockers within 3 months prior to screening are also excluded.

(25) The subject is an employee of the sponsor, clinical research organization, or research site personnel directly affiliated with this study or their immediate family member defined as a spouse, parent, child, or sibling, whether biological or legally adopted.

(26) The subject has pending legal charges or is on probation.

(27) The subject, in the investigator's opinion, is considered unsuitable or unlikely to comply with the study protocol for any reason.

(28) The subject is legally incapacitated, has been involuntarily hospitalized in the past year, or has another significant mental health issue, physical issue, or life circumstance that could interfere with the conduct or interpretation of study evaluations.

Concomitant Treatment

SOC is required for all subjects during the study which should include evidence-/empirically based antidepressant options at the investigator's discretion. In addition, subjects are permitted to be participating in SOC psychotherapy, including behavioral therapy. Benzodiazepine (dose equivalent to <6 mg/day of lorazepam) medications may be taken on a limited basis as needed, as defined in the protocol restricted medications section, but may never be taken within 24 hours prior to study medication dosing and assessments. Short acting non-benzodiazepine hypnotics (e.g. zolpidem, zaleplon) are permitted.

Criteria for Evaluation:

Primary Efficacy Endpoint:

The primary efficacy endpoint will be the change from baseline in the MADRS total score at 24 hours following the initial dose.

Secondary Efficacy Endpoints:

The secondary endpoints will be the change from baseline at 24 hours, as well as at Day 16, in the following:

(1) S-STS total score (2) MADRS total score at Day 16 (only)

(3) Clinical Global Impression (CGI) of Severity for SI/B (CGIS-SI/B) and Change in SI/B (CGIC-SI/B)

(4) Patient Global Impression (PGI) of Severity for SI/B (PGIS-SI/B) and Change in SI/B (PGIC-SI/B (5) S-STS Clinician-Rated Global Severity of Suicidal Impulses, Thoughts, and Behaviors (6) S-STS Clinician judgment of subject's risk of a suicide attempt or death by suicide at this time (7) S-STS Clinician judgment of subject's likelihood (risk) of making a suicide attempt or of dying by suicide in the next 7 days (8) S-STS Subject-rated global severity of suicidal impulses, thoughts, and behavior (9) S-STS Subject-rated treatment needed score

(10) MADRS item 10 response rate (response ≤3)

(11) MADRS response (total score ≥50% reduction from baseline)

(12) MADRS remission (total score ≤12)

Exploratory Endpoint:

The exploratory endpoint is the analysis of the validity, reliability, and ability to detect change by the S-STS CMCM.

Safety Endpoints:

The safety and tolerability of IN racemic ketamine will be assessed by:

(1) The frequency and severity of treatment-emergent adverse events (TEAEs)

(2) Frequencies of new or worsening clinically significant laboratory, vital signs, ECGs, or physical examination abnormalities (3) Clinician-Administered Dissociative States Scale (CADSS)

(4) Modified Observer's Assessment of Alertness/Sedation (MOAA/S) Scale (5) Columbia Suicide Severity Rating Scale (C-SSRS)

Statistical Methods

Separate summaries will be prepared for the Part 1 and Part 2 results. Descriptive statistics will be used to summarize the results of Part 1. For the analysis of the Part 2 data, the primary efficacy endpoint, the change in the MADRS total score from baseline at 24 hours following the initial dose, will be analyzed using an ANCOVA model including baseline MADRS total score as a covariate, treatment as fixed effect and a random subject effect. A sensitivity analysis will be done using MADRS item 10 as a covariate. Further details of the statistical analyses, including secondary efficacy, safety, and sensitivity analyses, will be described in the protocol and/or the Statistical Analysis Plan (SAP).

Sample Size Determination

In Part 1, the sample size planned is 16 subjects and is viewed to be sufficient to provide meaningful assessments of variability of the efficacy endpoints which can be used in planning of future trials In Part 2, the sample size planned is calculated assuming an effect size of 0.50, a 2-sided significance level of 0.10, and assuming approximately a 15% dropout rate. Based on these assumptions, 60 subjects will need to be randomized to each treatment group to achieve 80% power. The treatment difference and standard deviation used in this calculation were based on results of previous ketamine studies and on clinical judgment.

Study and Treatment Duration

The sequence and maximum duration of the study periods will be as follows:

a 1- to 2-day screening phase a 16-day treatment phase a 2-week safety follow-up phase Therefore, the maximum study duration for each subject is approximately 5 weeks.

All subjects will be referred for follow up post study; this includes subjects who do not qualify for study, subjects who discontinue participation, and those subjects who complete the study.

Results

This study is currently underway. Data from the first eight days (of 16 total) in two subjects is described below and in FIGS. 13A-24.

Both subjects entered the trial with severe major depressive disorder (MDD) based on pre-dosing MADRS scores of 35 and 38 for Subjects 1 and 2, respectively. Scores of 35 and up are considered severe, and scores of 18-34 indicate moderate MDD.

The MADRS total score of Subject 1 decreased from the baseline score of 35 to 8 at 24 hours post-administration of intranasal racemic ketamine. Similarly, the MADRS total score of Subject 2 decreased from the baseline score of 38 to 15 at 24 hours post-administration of intranasal racemic ketamine. Thus, both subjects demonstrated an extremely rapid, clinically significant (>50% reduction) response, going from severe MDD to remission in only 24 hours based on the MADRS total score. Intranasal racemic ketamine also delivers a sustained response through the next dosing, and after receiving the second dose on Day 4, symptoms were further reduced, with Subject 2 having a MADRS total score of 16 on Day 8, just above a remission score. See FIGS. 13A-13B.

The MADRS item 10 (suicidality)(range 0-6) score of Subject 1 decreased from the baseline score of 5 to 0 at 24 hours post-administration of intranasal racemic ketamine. The MADRS item 10 score also decreased from the baseline score of 5 pre-dose to 0 at 24 hours post-administration of intranasal racemic ketamine. Thus, both subjects also demonstrated a rapid, clinically significant response (meets the definition of MADRS item 10 response; score ≤3) that was sustained through the next dosing. See FIGS. 19A-19B.

The CGIS-SI/B (range 1-5) score of Subject 1 decreased from a baseline of 4 to 1 ("not at all suicidal") 24 hours post-administration of intranasal racemic ketamine, and remained at 1 thereafter. The CGIS-SI/B score of Subject 2 decreased from a baseline of 4 down to 2 ("mildly suicidal") at 24 hours post-administration of intranasal racemic ketamine, and further decreased to 1 on Day 3. Thus, both subjects demonstrated remarkable clinical improvement. See FIGS. 14A-14B.

The S-STS CMCM score (range 0-52) of Subject 1 decreased from 18 to zero at 24 hours post-administration of intranasal racemic ketamine. The S-STS CMCM score of Subject 2 was similarly reduced from 22 to 3 at 24 hours post-administration of intranasal racemic ketamine. Consistent with the previous results, both subjects demonstrated rapid and clinically meaningful improvement. See FIGS. 15A-15B.

The PGIS-SI/B score (range 1-5) of Subject 1 decreased from a baseline of 3 to 1 ("not present") and the PGIS-SI/B score of Subject 2 decreased from 4 to 1, at 24 hours post-administration of intranasal racemic ketamine, and both subjects remained at a PGIS-SI/B score of 1 thereafter. This demonstrates rapid clinical improvement. See FIGS. 16A-16B.

The CGIC-SI/B score (range 1-7) of Subject 1 was a 1 at 4 hours post-administration of intranasal racemic ketamine and the CGIC-SI/B score of Subject 2 was a 1 at 24 hours post-administration of intranasal racemic ketamine, and both subjects remained at a CGIC-SI/B score of 1 thereafter. See FIG. 17.

The PGIC-SI/B score (range 1-5) of Subject 1 was reduced from 2 to 1 at 24 hours post-administration of intranasal racemic ketamine, and remained at a PGIC-SI/B score of 1 thereafter. The PGIC-SI/B score of Subject 2 was reduced from a 3 to 2 at 24 hours post-administration of intranasal racemic ketamine, and further decreased to 1 at Day 3. See FIG. 18.

The S-STS CMCM score (range 0-9) of Subject 1 decreased from a baseline of 7 to 3 at 24 hours post-administration of intranasal racemic ketamine. The S-STS CMCM score of Subject 2 decreased from 7 to 3 at 24 hours post-administration of intranasal racemic ketamine. These score decreased to 2 at Day 8; Subject 1 remained at 2 on Day 9, while Subject 2's score was zero at Day 9. Consistent with the previous results, both subjects demonstrated rapid and clinically meaningful improvement. See FIGS. 20A-20B.

The S-STS CMCM "Risk of Suicide at Within the Next 7 Days" score (range 1-10) of Subject 1 decreased from 5 to 2 at 24 hours post-administration of intranasal racemic ketamine. The S-STS CMCM "Risk of Suicide at Within the Next 7 Days" score of Subject 2 decreased from a baseline of 7 to 1 at 24 hours post-administration of intranasal racemic ketamine. The scores remained at 1 on Day 4 and further decreased to 0 on Day 8. Consistent with the previous results, both subjects demonstrated rapid and clinically meaningful improvement. See FIGS. 21A-21B.

The C-SSRS score ("yes" or "no") for suicidal ideation of Subject 1 improved from a baseline of yes to no at 24 hours post-administration of intranasal racemic ketamine, and the C-SSRS score for suicidal ideation of Subject 2 improved from a baseline of yes to no at 24 hours post-administration of intranasal racemic ketamine. The C-SSRS scores for suicidal ideation and suicidal behavior for both subjects remained a "no" throughout the remainder of the study. See FIG. 24.

The CADSS scale measures dissociation, a well-known adverse event with ketamine. Indeed, the Spravato® (intranasal (S)-ketamine) label carries a Black Box warning for risk of dissociation, in which patients must be monitored for at least 2 hours after dosing. The label also indicates that some 61%-69% of patients administered (S)-ketamine developed dissociative changes on the CADSS assessment (at 56 mg or 84 mg doses).

In contrast, intranasal racemic ketamine unexpectedly provides less dissociation, as shown in FIG. 23. Subject 1 never scored over zero on the CADSS scale (no dissociation) and Subject 2 scored a 2 at 40 minutes post-administration of intranasal racemic ketamine, which does not meet the clinical threshold for dissociation (a score ≥4). Subject 2 scored a zero on the CADSS scale at 1 hour post-administration. Thus, neither subject exhibited clinically relevant dissociation.

The MOAA/S scale is a measure of sedation in a patient. Intranasal (S)-ketamine also carries a Black Box warning for risk of sedation (patients must be monitored for at least 2 hours after dosing) due to 48-61% of subjects developed sedation at a 56 mg or 84 mg dose. Pre-dose, Subject 1 had a MOAA/S score of 5, which decreased to 4 at 15 minutes post-administration of intranasal racemic ketamine, but was a 5 at 30 minutes. Subject 2 remained at a MOAA/S score of 5 throughout the trial. Thus, in contrast to intranasal (S)-ketamine, subjects administered intranasal racemic ketamine unexpectedly exhibit little to no sedation at doses sufficient to provide rapid and clinically significant treatment. See FIG. 22.

The preliminary data indicates that intranasal racemic ketamine rapid, significant, and sustained improvements in depression and suicidality, with no meaningful sedation or dissociation. There is no anticipated loss of effect at day 16, (i.e., persistent effect), nor any change to the safety and tolerability of intranasal administration of intranasal racemic ketamine.

The contents of each of the references cited in the present disclosure are hereby incorporated by reference in their entirety.

A number of embodiments of the present disclosure have been described. Nevertheless, it will be understood that various modifications may be made without departing from the spirit and scope of the disclosure. Accordingly, other embodiments are within the scope of the following claims.

What is claimed is:

1. A method for reducing suicidality in a subject in need thereof, comprising:

(a) identifying the subject as having a Montgomery-Asberg Depression Rating Scale (MADRS) Total Score from 35-60 units; and (b) intranasally administering to the subject about 30 mg to about 90 mg of racemic ketamine, or a pharmaceutically acceptable salt thereof, once every 3 to 4 days for 15 days, wherein ketamine is the sole therapeutic agent administered during the 15 days, wherein intranasal administration of the racemic ketamine, or a pharmaceutically acceptable salt thereof, exhibits one or more of:

an $AUC_{0-24}$ of norketamine at day 1, 4, or 8 after the intranasal administration that is at least 1.5 times higher than the $AUC_{0-24}$ of norketamine exhibited by intravenous administration of an equivalent dose of racemic ketamine at day 1, 4, or 8 after the intravenous administration;

an $AUC_{0-inf}$ of norketamine at day 1, 4, or 8 after the intranasal administration that is at least 1.5 times higher than the $AUC_{0-inf}$ of norketamine exhibited by intravenous administration of an equivalent dose of racemic ketamine at day 1, 4, or 8 after the intravenous administration;

a $C_{max}$ of norketamine at day 1, 4, or 8 after the intranasal administration that is at least 2 times higher than the $C_{max}$ of norketamine exhibited by intravenous administration of an equivalent dose of racemic ketamine at day 1, 4, or 8 after the intravenous administration;

thereby reducing suicidality in the subject compared to suicidality in the subject prior to the administering of racemic ketamine, or a pharmaceutically acceptable salt thereof.

2. The method of claim 1, comprising intranasally administering to the subject about 30 mg of racemic ketamine, or a pharmaceutically acceptable salt thereof, once every 3 to 4 days for 15 days.

3. The method of claim 1, comprising intranasally administering to the subject about 60 mg of racemic ketamine, or a pharmaceutically acceptable salt thereof, once every 3 to 4 days for 15 days.

4. The method of claim 1, comprising intranasally administering to the subject about 75 mg of racemic ketamine, or a pharmaceutically acceptable salt thereof, once every 3 to 4 days for 15 days.

5. The method of claim 1, comprising intranasally administering to the subject about 90 mg of racemic ketamine, or a pharmaceutically acceptable salt thereof, once every 3 to 4 days for 15 days.

6. The method of claim 1, wherein the same amount of racemic ketamine, or a pharmaceutically acceptable salt thereof, is intranasally administered to the subject each day of administration.

7. The method of claim 1, comprising intranasally administering to the subject about 30 mg to about 90 mg of racemic ketamine, or a pharmaceutically acceptable salt thereof, once per day on Day 1, Day 4, Day 8, Day 11, and Day 15 of a 15-day cycle.

8. The method of claim 7, comprising intranasally administering to the subject about 30 mg of racemic ketamine, or a pharmaceutically acceptable salt thereof, once every 3 to 4 days for 15 days.

9. The method of claim 7, comprising intranasally administering to the subject about 60 mg of racemic ketamine, or a pharmaceutically acceptable salt thereof, once every 3 to 4 days for 15 days.

10. The method of claim 7, comprising intranasally administering to the subject about 75 mg of racemic ketamine, or a pharmaceutically acceptable salt thereof, once every 3 to 4 days for 15 days.

11. The method of claim 7, comprising intranasally administering to the subject about 90 mg of racemic ketamine, or a pharmaceutically acceptable salt thereof, once every 3 to 4 days for 15 days.

12. The method of claim 7, wherein the same amount of racemic ketamine, or a pharmaceutically acceptable salt thereof, is intranasally administered to the subject each day of administration.

13. The method of claim 1, wherein the MADRS Total Score of the subject is reduced by at least 50% 24 hours after intranasal administration of the racemic ketamine, or a pharmaceutically acceptable salt thereof.

14. The method of claim 1, wherein the MADRS Total Score of the subject is less than or equal to 12 units 48 hours after intranasal administration of the racemic ketamine, or a pharmaceutically acceptable salt thereof.

15. The method of claim 1, wherein the subject has a MADRS Item 10 Score of 4, 5, or 6 units prior to intranasal administration of the racemic ketamine, or a pharmaceutically acceptable salt thereof.

16. The method of claim 1, wherein the subject has a MADRS Item 10 Score that is reduced by at least 1 unit 4 hours after administration of the racemic ketamine, or a pharmaceutically acceptable salt thereof.

17. The method of claim 7, wherein the MADRS Total Score of the subject is reduced by at least 50% 24 hours after intranasal administration of the racemic ketamine, or a pharmaceutically acceptable salt thereof.

18. The method of claim 7, wherein the MADRS Total Score of the subject is less than or equal to 12 units 48 hours after intranasal administration of the racemic ketamine, or a pharmaceutically acceptable salt thereof.

19. The method of claim 7, wherein the subject has a MADRS Item 10 Score of 4, 5, or 6 units prior to intranasal administration of the racemic ketamine, or a pharmaceutically acceptable salt thereof.

20. The method of claim 7, wherein the subject has a MADRS Item 10 Score that is reduced by at least 1 unit 4 hours after administration of the racemic ketamine, or a pharmaceutically acceptable salt thereof.

21. The method of claim 1, wherein no clinically meaningful dissociation is observed in the subject at about 1 hour after intranasal administration of the racemic ketamine, or a pharmaceutically acceptable salt thereof.

22. The method of claim 1, wherein no clinically meaningful sedation is observed in the subject at about 1 hour after intranasal administration of the racemic ketamine, or a pharmaceutically acceptable salt thereof.

23. The method of claim 15, wherein no clinically meaningful dissociation is observed in the subject at about 1 hour after intranasal administration of the racemic ketamine, or a pharmaceutically acceptable salt thereof.

24. The method of claim 15, wherein no clinically meaningful sedation is observed in the subject at about 1 hour after intranasal administration of the racemic ketamine, or a pharmaceutically acceptable salt thereof.

25. The method of claim 1, wherein the MADRS Total Score 24 hours after administering is reduced by at least 50% compared to the MADRS Total Score prior to administering.

26. The method of claim 1, wherein MADRS Total Score 24 hours after administering is less than 12 units.

* * * * *